(12) United States Patent
Schwabacher et al.

(10) Patent No.: US 11,275,071 B2
(45) Date of Patent: Mar. 15, 2022

(54) SENSOR DYES FOR REAL-TIME SENSING OF METAL IONS IN AQUEOUS ENVIRONMENTS

(71) Applicant: UWM Research Foundation, Inc., Milwaukee, WI (US)

(72) Inventors: Alan Schwabacher, Shorewood, WI (US); Peter Geissinger, Shorewood, WI (US); Trevor Hagemann, Milwaukee, WI (US); Sarah Oehm, Milwaukee, WI (US); Tyler G. Fenske, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 604 days.

(21) Appl. No.: 15/767,175

(22) PCT Filed: Oct. 14, 2016

(86) PCT No.: PCT/US2016/057182
§ 371 (c)(1),
(2) Date: Apr. 10, 2018

(87) PCT Pub. No.: WO2017/066672
PCT Pub. Date: Apr. 20, 2017

(65) Prior Publication Data
US 2020/0033314 A1    Jan. 30, 2020

Related U.S. Application Data

(60) Provisional application No. 62/241,479, filed on Oct. 14, 2015.

(51) Int. Cl.
*G01N 33/00* (2006.01)
*G01N 33/18* (2006.01)
(Continued)

(52) U.S. Cl.
CPC ..... *G01N 33/1813* (2013.01); *C09B 29/0048* (2013.01); *C09B 29/3621* (2013.01);
(Continued)

(58) Field of Classification Search
CPC .................................................. G01N 33/1813
(Continued)

(56) References Cited

U.S. PATENT DOCUMENTS

| 5,512,490 A | 4/1996 | Walt et al. |
| 7,244,572 B1 | 7/2007 | Schwabacher et al. |

FOREIGN PATENT DOCUMENTS

| CN | 103293135 A | 9/2013 |
| CN | 103644845 A | 3/2014 |
| WO | WO2004053467 A1 | 6/2004 |

OTHER PUBLICATIONS

Ensafi et al. "Development of a mercury optical sensor based on immobilization of 4-(2-pyridylazo)-resorcinol on a triacetylcellulose membrane" Sensors and Actuators B 113 (2006) 88-93 (Year: 2006).*

(Continued)

*Primary Examiner* — Lyle Alexander
*Assistant Examiner* — Emily R. Berkeley
(74) *Attorney, Agent, or Firm* — Michael Best & Friedrich LLP

(57) ABSTRACT

Sensors for detecting and distinguishing metals in a sample comprise phenol group-containing azo dyes, the phenol group having one hydroxy involved in reversible metal ion binding and a second hydroxy alkylated to an optically transparent substrate. The sensors have utility for detecting chromium, calcium, magnesium, copper, mercury, nickel, zinc, cobalt, manganese, cadmium, lead, tin, aluminum, potassium, sodium, or arsenic ions in a sample.

12 Claims, 43 Drawing Sheets

(51) Int. Cl.
  C09B 29/036  (2006.01)
  C09B 29/42   (2006.01)
  C09B 29/44   (2006.01)
  G01N 21/64   (2006.01)
  G01N 21/78   (2006.01)

(52) U.S. Cl.
  CPC ....... *C09B 29/3643* (2013.01); *G01N 21/643* (2013.01); *G01N 21/78* (2013.01); *G01N 2021/6439* (2013.01)

(58) Field of Classification Search
  USPC .......................................................... 436/80
  See application file for complete search history.

(56) References Cited

OTHER PUBLICATIONS

Tavallali et al. "Developing a new method of 4-(2-pyridylazo)-resorcinol immobilization on triacetylcellulose membrane for selective determination of Ga3+ in water samples" Sensors and Actuators B 159 (2011) 154-158 (Year: 2011).*
Morishima et al. "Spectroscopic Studies of Competitive Binding of Thallium and Alkaline-Earth Metal Cations onto Poly(sodium acrylate-co-acrylamide) Tagged with Optical Probes" Macromolecules 1996, 29, 3960-3964 (Year: 1996).*
A. Maxwell Burroughs, et al., "Structural and Functional Characterization of MppR, an Enduracididine Biosynthetic Enzyme from Streptomyces hygroscopicus: Functional Diversity in the Acetoacetate Decarboxylase-like Superfamily" Biochemistry, 52, 4492-4506, 2013.
Alan W. Schwabacher et al, "Fourier Transform Analysis for Periodic Combinatorial Arrays," Measurement Science and Technology, 16, 144-152, 2005.
Alan W. Schwabacher et al., Synthesis of a New Ligand for Metal Assembly to a Selective Receptor. J. Org. Chem. 64: 1784-1788, 1999.
Alan W. Schwabacher et al., "Linear Combinatorial Synthesis with Fourier Transform Library Analysis. Macromolecular Rapid Communications," 25: 108-118, 2004.
Alan W. Schwabacher, Yixing Shen, Christopher W. Johnson. Fourier Transform Combinatorial Chemistry. J. Amer. Chem. Soc. 121: 8669-8670, 1999.
Albrecht, T.; Addai-Mensah, J.; Fornasiero, D., Effect of pH, Concentration and Temperature on Copper and Zinc Hydroxide Formation/Precipitation in Solution. In Chemica, Sydney Australia, 2011.
Anna Benko, Maureen Prince, Barry J. Price, Nadejda T. Kaltcheva, Peter Geissinger, and Alan W. Schwabacher. Chemically Stable Films for Combinatorial Fluorosensor Arrays. J. Comb. Chem. 8: 221-227, 2006.
Barry J. Prince, Alan W. Schwabacher, Peter Geissinger, A Readout Scheme for Closely Packed Fluorescent Chemosensors on Optical Fibers, Analytical Chemistry, 73, 1007-1015 (2001).
Barry J. Prince, Nadejda T. Kaltcheva, Alan W. Schwabacher, and Peter Geissinger. Fluorescent Fiber Optic Sensor Arrays Probed Utilizing Evanescent Fiber-Fiber Coupling. Applied Spectroscopy. 55: 1018-1024, 2001.
Busev, A.I.; Nemtseva, Z.I.; Ivanov, V.M., Spectrophotometric investigation of 4-(2-benzothiazolylazo)resorcinol, 4-(6-bromo-2-benzothiazolylazo)resorcinol, and 4-(8-quinolylazo)resorcinol. Vestnik Moskovskogo Universiteta. Seriya II, Khimiia. 1969, 24 (1), 35-39.
Carofiglio, T. et al., Optical sensor arrays: one-pot, multiparallel synthesis andcellulose immobilization of pH and metal ion sensitive azo-dyes, Tetrahedron, 2006, vol. 62, pp. 1502-1507 See abstract; Schemes 1-4; p. 1502, right column; p. 1503, right column; p. 1505, right column.
Dario, Stacchiola, Florencia Calaza, Luke Burkholder, Alan W. Schwabacher, Matthew Neurock, and Wilfred T. Tysoe. Elucidation of the mechanism of the palladium-catalyzed synthesis of vinyl acetate. Angew. Chem. Int. Ed. English. 44: 4572-4574, 2005.

Fen Wang, Alan W. Schwabacher. A Convenient Set of Bidentate Pyridine Ligands for Combinatorial Synthesis. Tetrahedron Lett., 40: 4779-4782, 1999.
Fen Wang, Alan W. Schwabacher. Metal Control of Non-Polar Binding Shape Selectivity. Tetrahedron Lett. 40: 7641-7644, 1999.
Fen Wang, Alan W. Schwabacher. Tuning of Binding Selectivity: Metal Control of Organic Guest Binding, and Allosteric Perturbation of Fluorescent Metal Sensor. J. Org. Chem. 64: 8922-8928, 1999.
Hadar, H. A. et al., Detection of heavy metals in water using dye nano-complexants and a polymeric film, Journal of Hazardous Materials, 2013, vol. 260, pp. 652-659 See figure 6.
Hannah E. Wagie, Peter Geissinger, Hole-Burning Spectroscopy as a Probe of Nano-Environments and Processes in Biomolecules: A Review, Applied Spectroscopy, 66(6), 609-627 (2012).
Hirose, K., A Practical Guide for the Determination of Binding Constants. Journal of Inclusion Phenomena 2001, 39 (3-4), 193-209.
Hunt, J.B.; Neece, S.J.; Ginsburg, A., The use of 4-(2-pyridylazo)resorcinol in studies of zinc release from *Escherichia coli* aspartate transcarbamoylase. Analytical Biochemistry 1985, 146 (1), 150-157.
Ivanov, V.M.; Busev, A.I.; Nemtseva, Z.I., Cobalt(II) complexing with 4-(2-benzothiazolylazo)resorcinol, 4-(6-bromo-2-benzothiazolylazo)resorcinol, and 4-(8-quinolylazo)resorcinol. Vestnik Moskovskogo Universiteta. Seriya II, Khimiia. 1969, 24 (5), 80-84.
M. Veronica Rigo, Peter Geissinger, Crossed-Optical Fiber Sensor Arrays for High-Spatial-Resolution Sensing: Application to Dissolved-Oxygen-Concentration Measurements, Journal of Sensors, 2012, 464092(10) (2012).
M. Veronica Rigo, Peter Geissinger, Measurement and Optimization of Metal-Nanoparticle-Induced Luminescence Enhancement Factors in a Crossed-Optical Fiber Configuration, Journal of Nanomaterials, 2010, 396214(11), doi: 10.1155/2010/396214 (2010).
M. Veronica Rigo, Robert J. Olsson, Peter Geissinger, Crossed-Fiber Sensors for Oxygen Measurement and Intensity Referencing for use in High Spatial Resolution Optical Fiber Sensor Arrays, Sensors and Transducers, 113(2), 18-32 (2010).
Masoud, M. S. et al., Chemical speciation and equilibria of some nucleic acid compounds and their iron (III) complexes, Spectrochimica Acta Part A: Molecular and biomolecular Spectroscopy, 2012, vol. 92, pp. 256-282 See page 257.
Paul E. Henning, Anna Benko, Robert J. Olsson, Alan W. Schwabacher, Peter Geissinger, Apparatus and Methods for Optical Time-of-Flight Discrimination in Combinatorial Library Analysis, Review of Scientific Instruments, 76, 062220 (2005)
Paul E. Henning, M. Veronica Rigo, Peter Geissinger, Fabrication of a Porous Fiber Cladding Material Using Microsphere Templating for Improved Response Time with Fiber Optic Sensor Arrays, The Scientific World Journal—Analytical Chemistry, 2012, 876106(7) (2012).
Paul E. Henning, Peter Geissinger, Application of Time-Correlated Single Photon Counting and Stroboscopic Detection Methods with an Evanescent-Wave Fibre-Optic Sensor for Fluorescence Lifetime-Based pH Measurements, Measurement Science & Technology (formerly Journal of Physics E, 23, 045104(11) (2012).
Peter Geissinger, Thomas Giering, Wolfgang Richter, Dietrich Haarer, Doped Rare Gas Solids as Model Systems for Chromophore-Matrix Interactions, Accounts of Chemical Research, 33, 131-38 (2000).
Szurdoki, F., Ren, D.; Walt, D.R., A combinatorial approach to discover new chelators for optical metal ion sensing. Analytical Chemistry 2000, 72 (21), 5250-5257.
Thordarson, P., Determining association constants from titration experiments in supramolecular chemistry. Chemical Society Reviews 2011, 40 (3), 1305-1323.
Yoshinori, I. et al., Synthesis of 2-(p-aminophenylazo)-1,3,5-triazine derivatives, Nippon Kagaku Kaishi, The Chemical Society of Japan, 1981, vol. 12, pp. 1922-1928 See scheme 1; table 5.
International Search Report and Written Opinion for Application No. PCT/US2016/057182 dated Jan. 26, 2017 (14 pages).
Chinese Patent Office Action for Application No. 201680073374.3 dated Apr. 1, 2019 (63 pages, English translation included).

(56) References Cited

OTHER PUBLICATIONS

European Patent Office Extended Search Report for Application No. 16856342.7 dated Jul. 15, 2019 (15 pages).
Ariza-Avidad et al., "Printed Disposable Colorimetric Array for Metal Ion Discrimination," Analytical Chemistry, 2014, 86(17):8634-8641.
Zhang et al., "Postage stamp-sized array sensor for the sensitive screening test of heavy-metal ions," Analyst, 2014, 139(19):4887-4893.
Tongge et al., "An inorganicorganic hybrid optical sensor for heavy metal ion detection based on immobilizing 4-(2-pyridylazo)-resorcinol on functionalized HMS," Journal of Hazardous Materials, 2011, 201(17)155-161.
Hrishikesan et al., "Azobenzene chemosensor based on nitrogen chelator for the detection of Cu (II) ion in aqueous medium," Inorganic Chemistry Communications, 2013, 37(19):21-25.
Wang et al., "Coumarin-coupled Receptor as a Membrane-permeable, Cu2+-selective Fluorescent Chemosensor for Imaging Copper(II) in HEPG-2 Cell," Chemistry Letters, 2008, 37(4):462-463.
Park et al., "Development of a microchip metal ion sensor using dinitro-azocalix[4]azacrown," Microchemical Journal, 2004, 80(2):139-144.
Sarkar et al., "Synthesis and characterization of rhenium(I) complexes based on O, N, N coordinating ligands: DFT/TDDFT studies on the electronic structures and spectral properties," Journal of Organometallic Chemistry, 2015, 779:1-13.
Zheng et al., "Simultaneous determination of copper, nickel, lead, cobalt and cadmium by adsorptive voltammetry," Analytica Chimica Acta, 1993, 272(2):227-232.
Li et al., "Synthesis of some quinolylazo derivatives and comparison of their analytical characteristics," Huaxue Shiji, 1984, 6(4):193-198.
Zhou et al., "Functionalized Ionic Microgel Sensor Array for Colorimetric Detection and Discrimination of Metal Ions," ACS Applied Materials & Interfaces, 2017, 9(24):20913-20921.
Chinese Patent Office Action for Application No. 201680073374.3 dated Mar. 31, 2020 (27 pages, English translation included).

\* cited by examiner

SENSOR DYES FOR REAL-TIME SENSING OF METAL IONS IN AQUEOUS ENVIRONMENTS

CROSS-REFERENCE TO RELATED APPLICATIONS

This patent application is the U.S. national stage entry, under 35 U.S.C. § 371, of international application number PCT/US2016/057182, filed Oct. 14, 2016, which claims priority to U.S. Provisional Patent Application No. 62/241,479, filed Oct. 14, 2015, the entire contents of which are hereby incorporated by reference.

STATEMENT REGARDING FEDERALLY SPONSORED RESEARCH

This invention was made with government support under Small Business Innovation Research (SBIR) grant 1621759 awarded by the National Science Foundation. The government has certain rights in the invention.

BACKGROUND

Real-time monitoring of environmental and industrial waters for metal pollutants of concern for public and environmental health via the standard methods of sampling followed by laboratory analysis is not possible with current technology. Toxic metal ions enter environmental waters, through industrial waste water, landfills, mine runoff, and ineffective industrial and municipal waste water treatment. Although many monitoring methods have been tried, there is no proven technology capable of reliably measuring low levels of pollutant concentrations in real-time, in the field. There is a critical need for a real-time monitoring system to ensure and enforce regulatory compliance and to warn of threats to public and environmental health.

SUMMARY

In some embodiments, the disclosure provides a sensor comprising at least one dye covalently bound to an optically transparent substrate; wherein the dye reversibly binds at least one metal ion.

In other embodiments the disclosure provides a panel for the detection of multiple metals in aqueous solution comprising more than one dye covalently bound to an optically transparent substrate; wherein the dye reversibly binds at least one metal ion.

The dye may be a compound of formula:

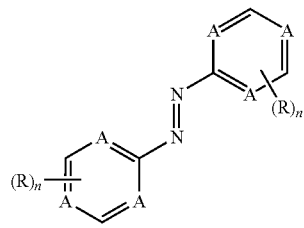

(II)

wherein each R is independently selected from the group consisting of OH, H, $OR_1$, $C_{1-4}$ alkyl, nitro, halo, $NR_{N1}R_{N2}$, $SO_3H$, $SO_2NHR_3$, $NHSO_2R_4$, carboxyl, amido, nitrile, —C(=N—OH)$R_3$, —C(=O)$NR_{N1}$OH, —$SR^5$, thioamido, phosphonate or two Rs may join together to form a 5, 6, or 7-membered ring, which may be aromatic or heteroaromatic, which may be substituted; each A is independently N, NO, CH, or $CR_5$; $R_{N1}$ and $R_{N2}$ are independently $C(O)R_2$, heteroaryl, aryl, $C_{1-4}$ alkyl,

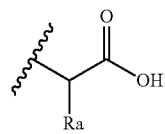

or H; $R^a$ is an amino acid side chain; each $R_1$ is independent $C_{1-4}$ alkyl, $C_{2-4}$ alkenyl, heteroaryl, or aryl; each $R_2$ is independently $C_{1-4}$ alkyl, $C_{2-4}$ alkenyl, heteroaryl, or aryl; each $R_3$ is independently H, $C_{1-4}$ alkyl, heteroaryl, aryl, cycloalkyl, or heterocyclyl; each $R_4$ is independently H, $C_{1-4}$ alkyl, heteroaryl, aryl, cycloalkyl, or heterocyclyl; each $R_5$ is independently H, $C_{1-4}$ alkyl, heteroaryl, aryl, cycloalkyl, or heterocyclyl; and each n is independently an integer from 1 to 5.

The dye may be a compound of formula:

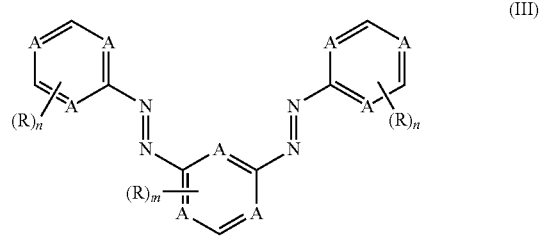

(III)

wherein each R is independently selected from the group consisting of OH, H, $OR_1$, $C_{1-4}$ alkyl, nitro, halo, $NR_{N1}R_{N2}$, $SO_3H$, $SO_2NHR_3$, $NHSO_2R_4$, carboxyl, amido, nitrile, —C(=N—OH)$R_3$, —C(=O)$NR_{N1}$OH, —$SR^5$, thioamido, phosphonate or two Rs may join together to form a 5, 6, or 7-membered ring, which may be aromatic or heteroaromatic, which may be substituted; each A is independently N, NO, CH, or $CR_5$; $R_{N1}$ and $R_{N2}$ are independently $C(O)R_2$, heteroaryl, aryl, $C_{1-4}$ alkyl,

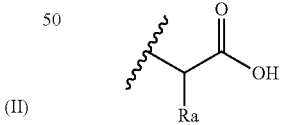

or H; $R^a$ is an amino acid side chain; each $R_1$ is independent $C_{1-4}$ alkyl, $C_{2-4}$ alkenyl, heteroaryl, or aryl; each $R_2$ is independently $C_{1-4}$ alkyl, $C_{2-4}$ alkenyl, heteroaryl, or aryl; each $R_3$ is independently H, $C_{1-4}$ alkyl, heteroaryl, aryl, cycloalkyl, or heterocyclyl; each $R_4$ is independently H, $C_{1-4}$ alkyl, heteroaryl, aryl, cycloalkyl, or heterocyclyl; each $R_5$ is independently H, $C_{1-4}$ alkyl, heteroaryl, aryl, cycloalkyl, or heterocyclyl; each n is independently an integer from 1 to 5; and each m is independent an integer from 1 to 4.

The dye may be a compound of formula: A-B (IV) wherein A is selected from the group consisting of:

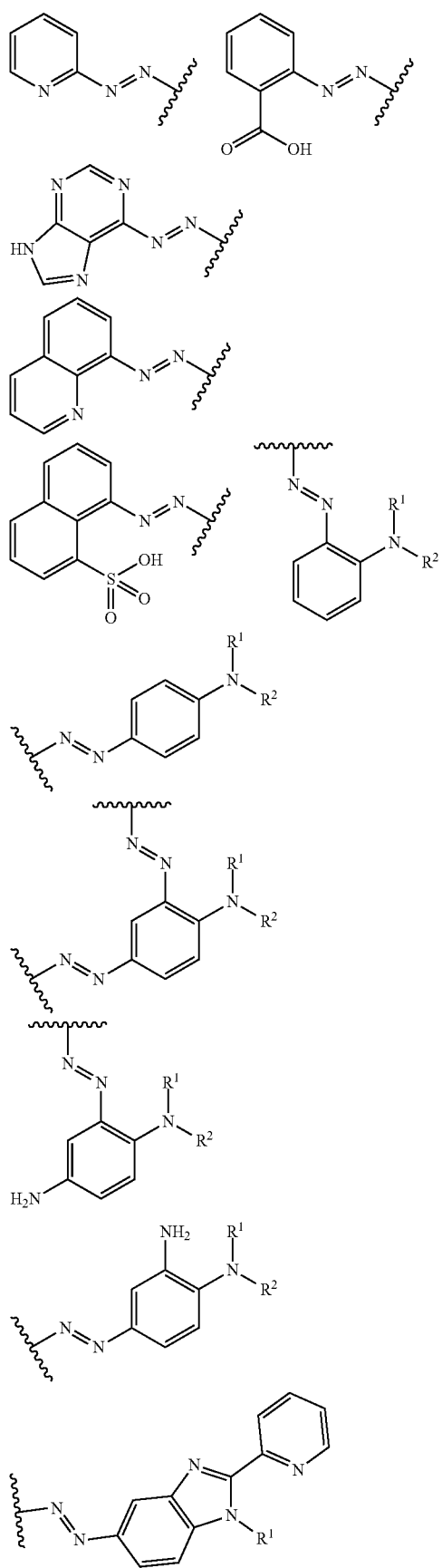
-continued
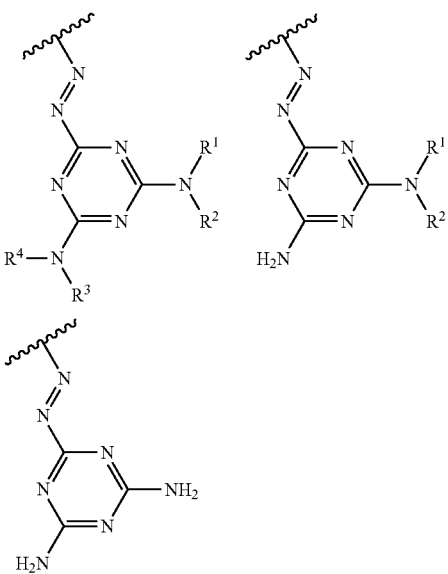
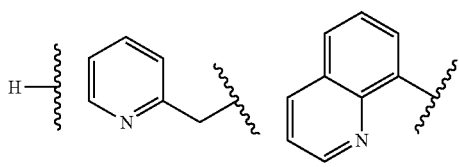
wherein $R^1$, $R^2$, $R^3$ and $R^4$ are independently selected from:
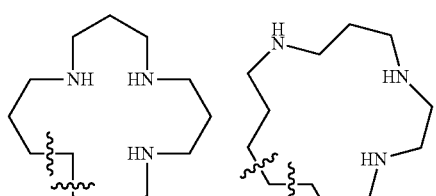
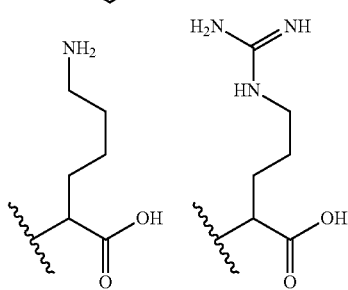
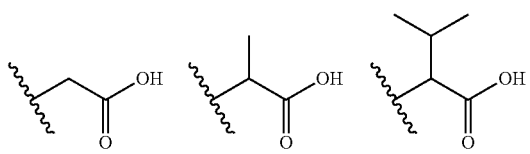
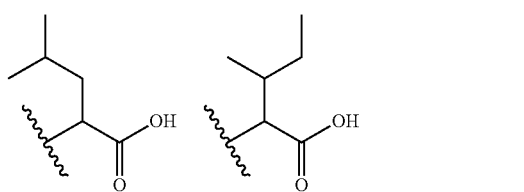

-continued
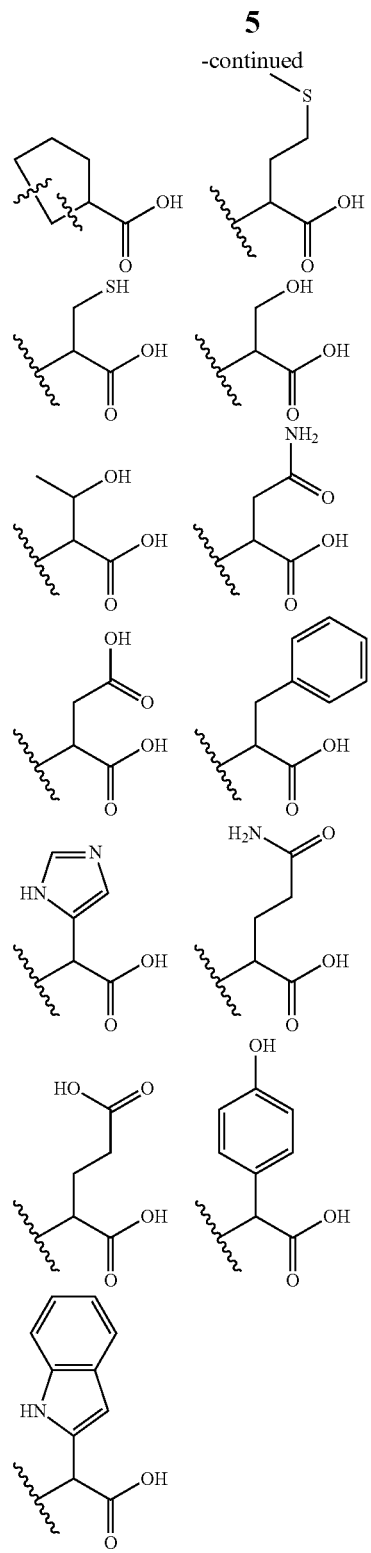
B may be selected from the group consisting of:
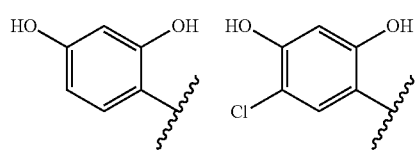
-continued
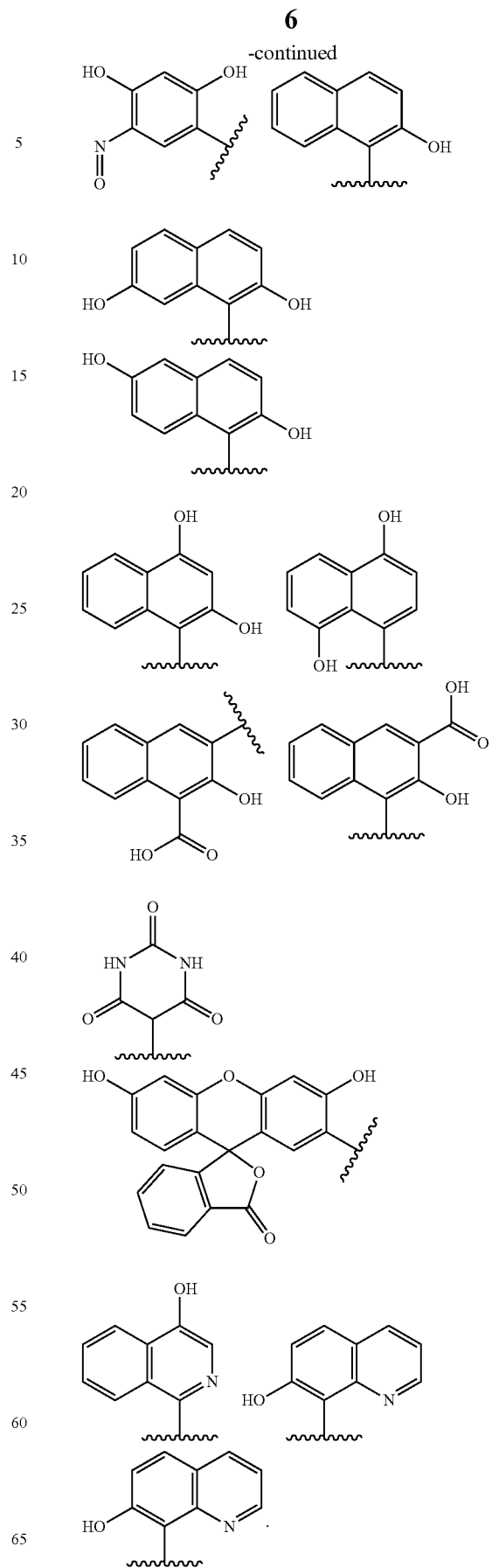

The dye may be selected from the group consisting of:
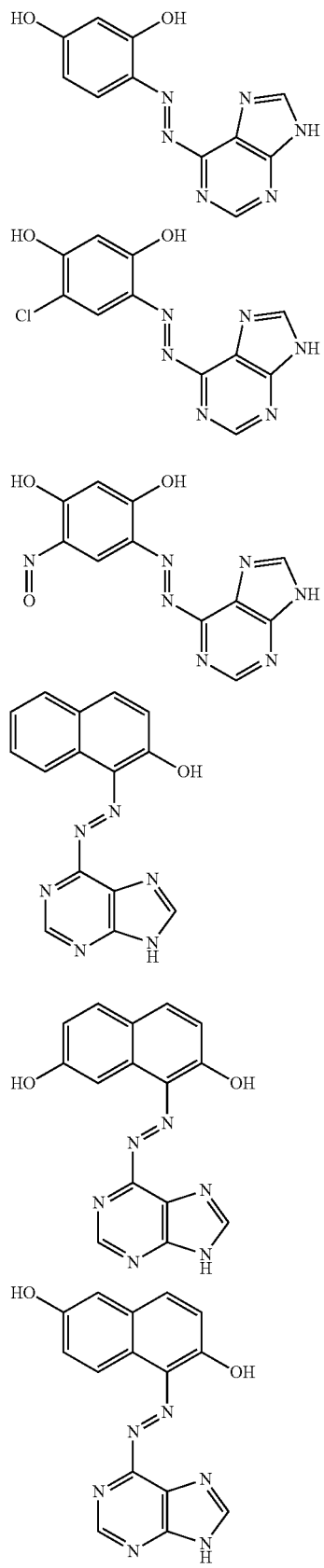
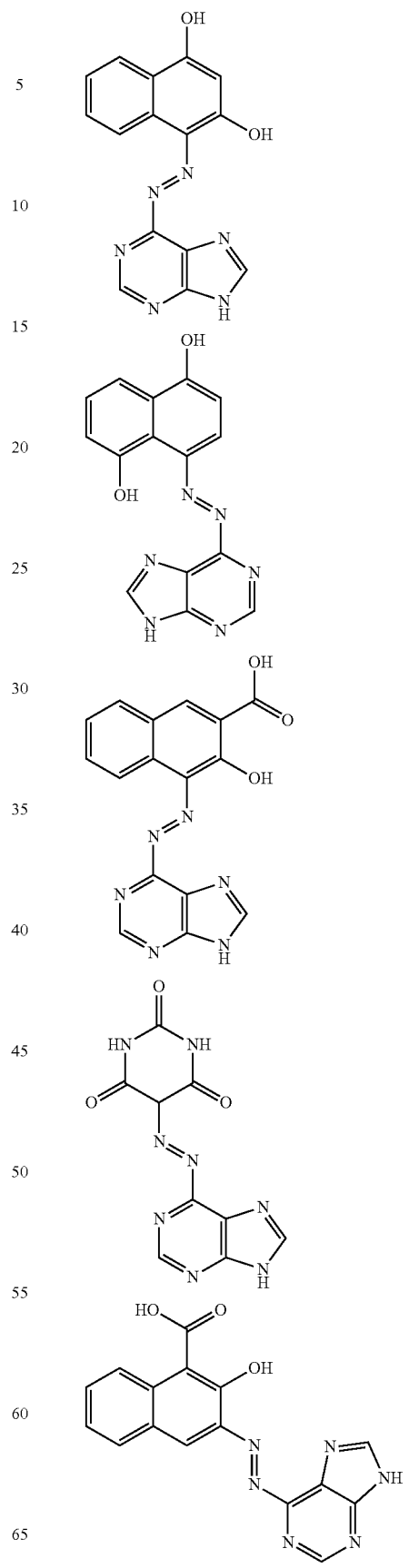

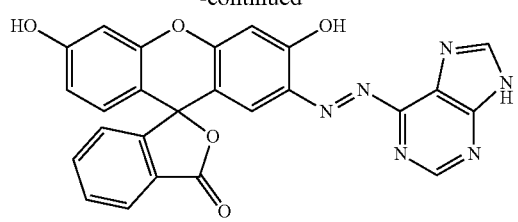
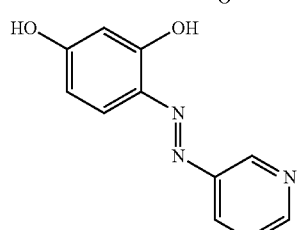
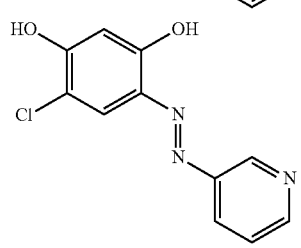
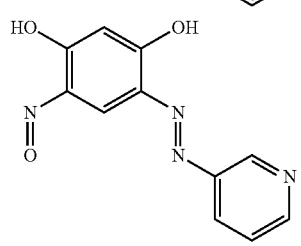
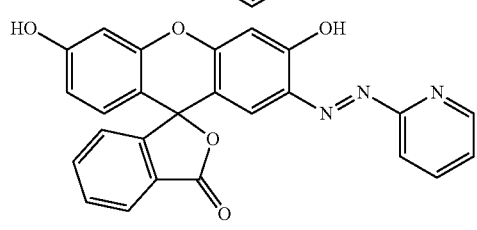
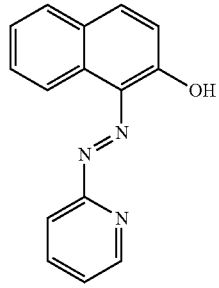
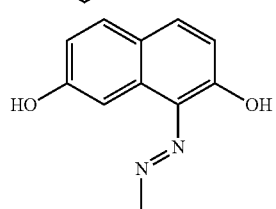
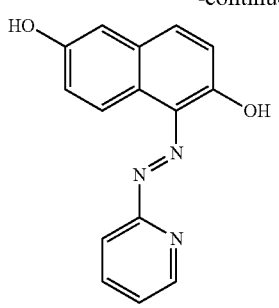
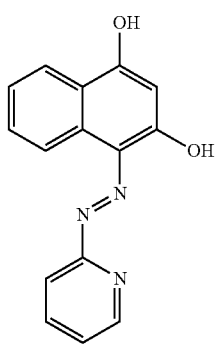
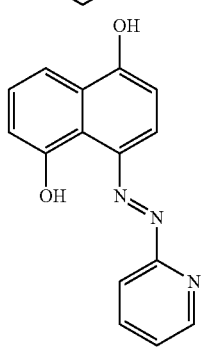
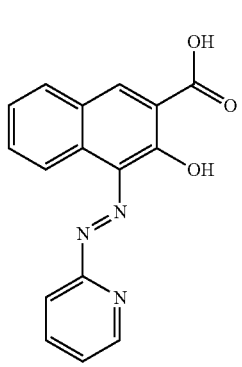
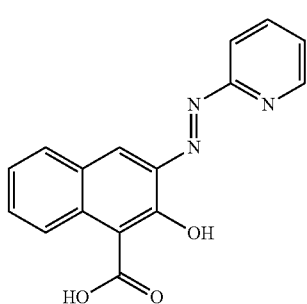

-continued
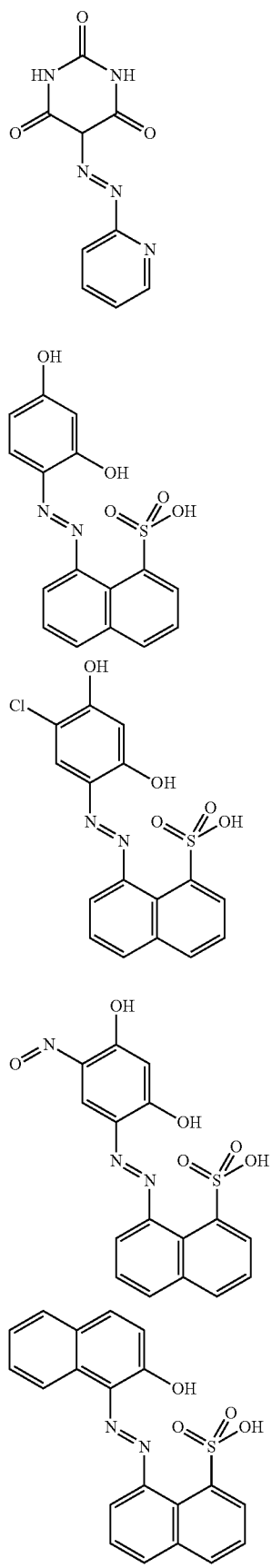
-continued
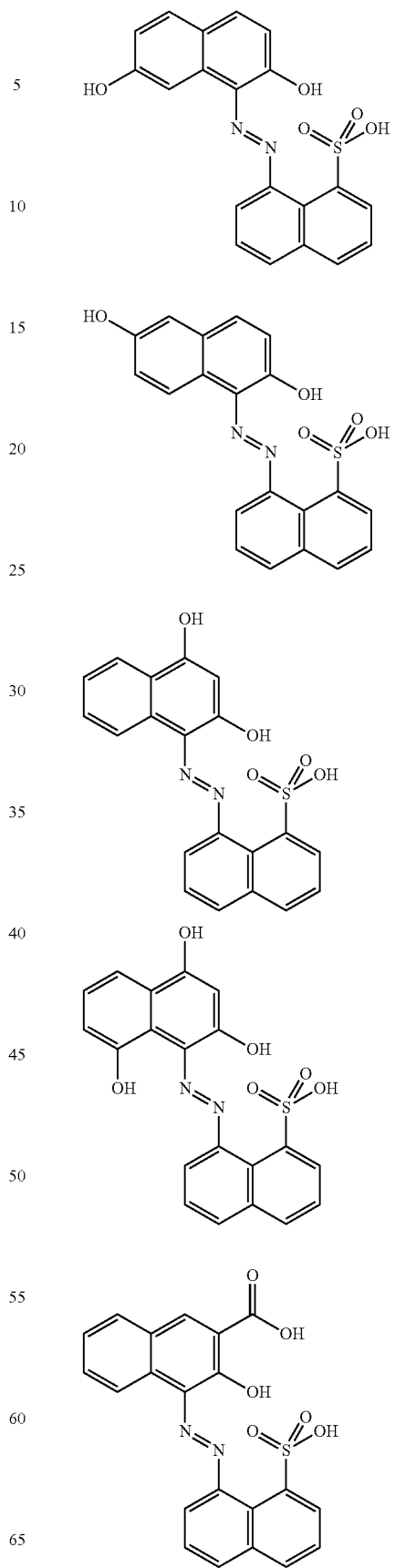

-continued
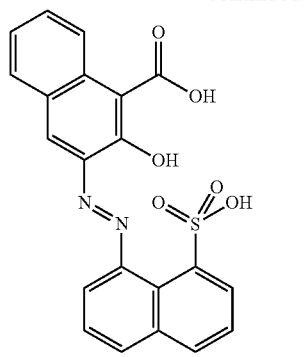
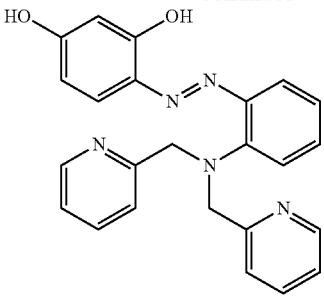
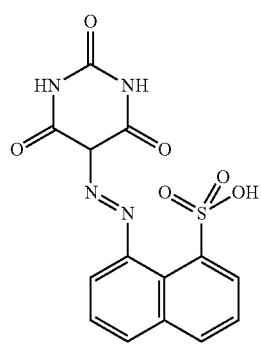
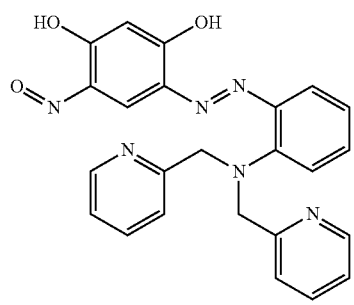

-continued
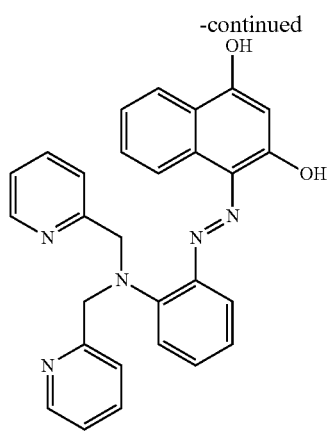
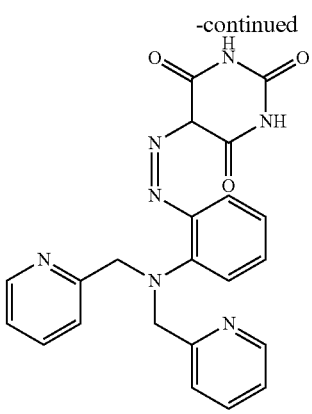
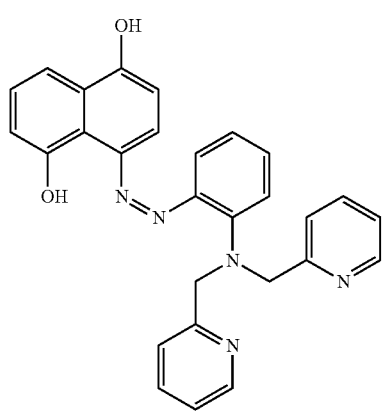
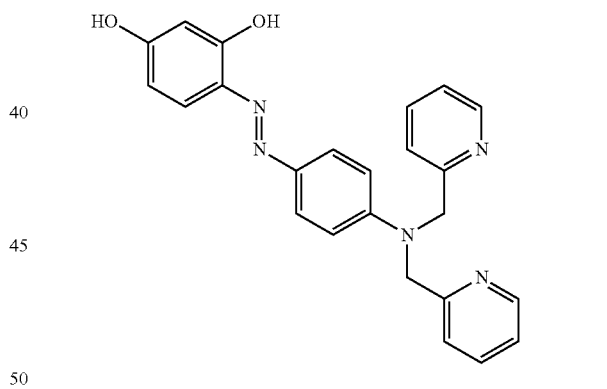
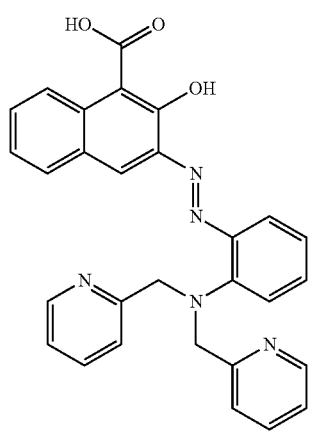
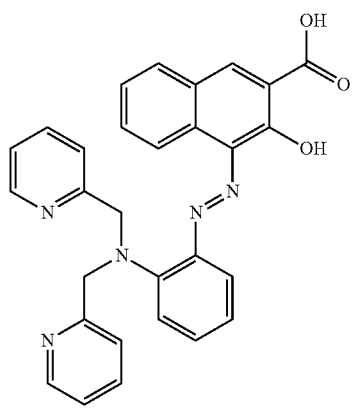
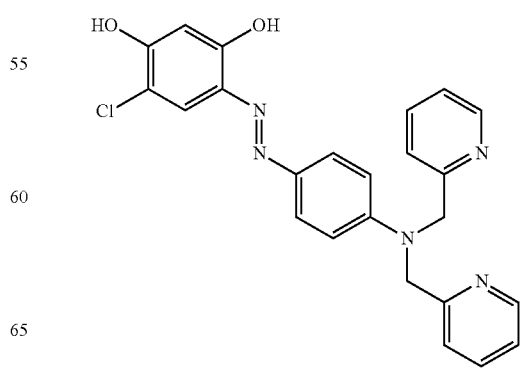

17
-continued
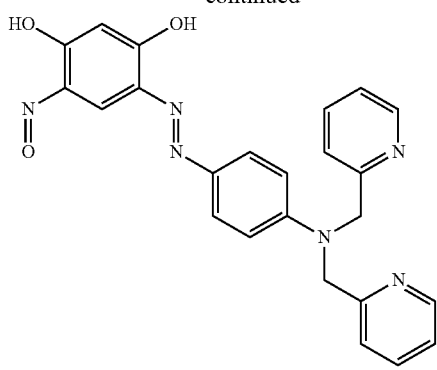
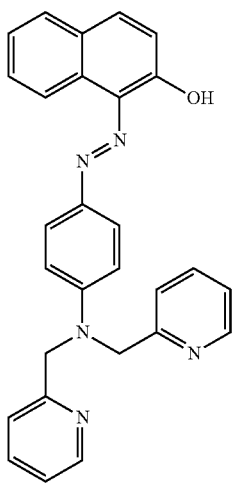
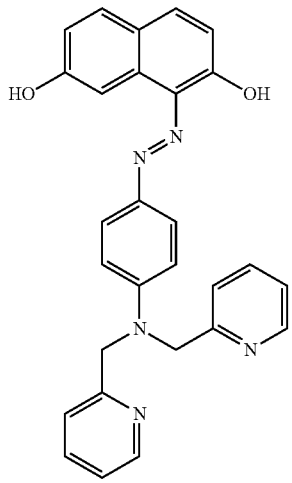
18
-continued
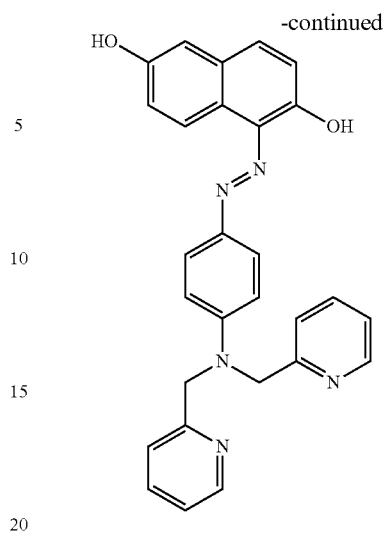
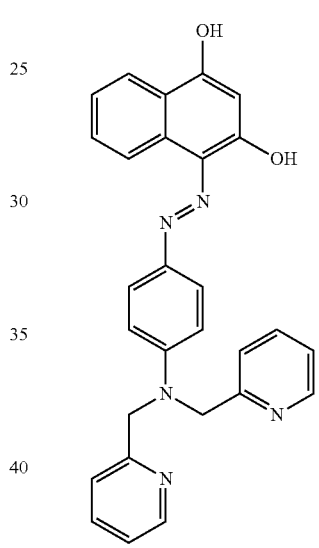
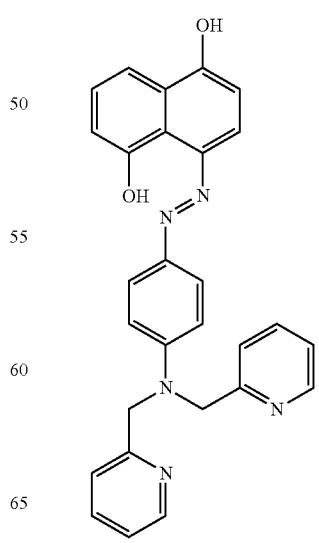

19
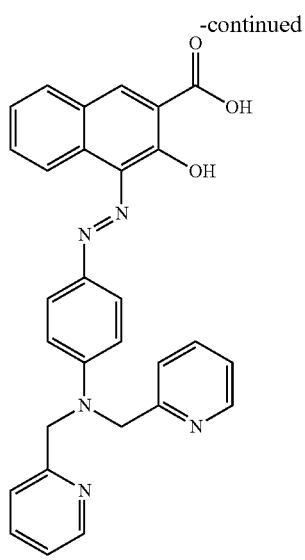
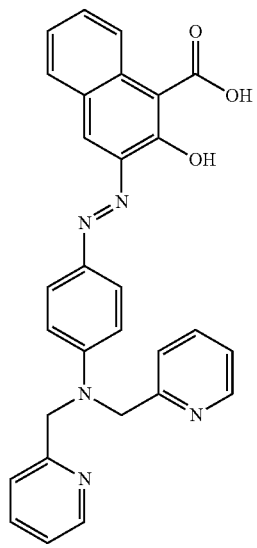
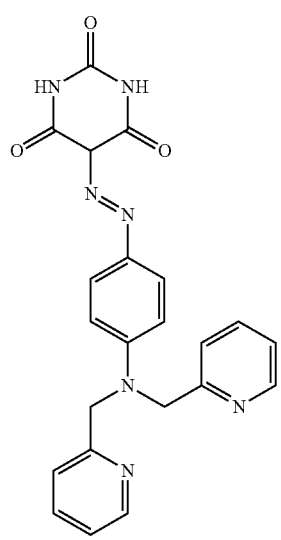
20
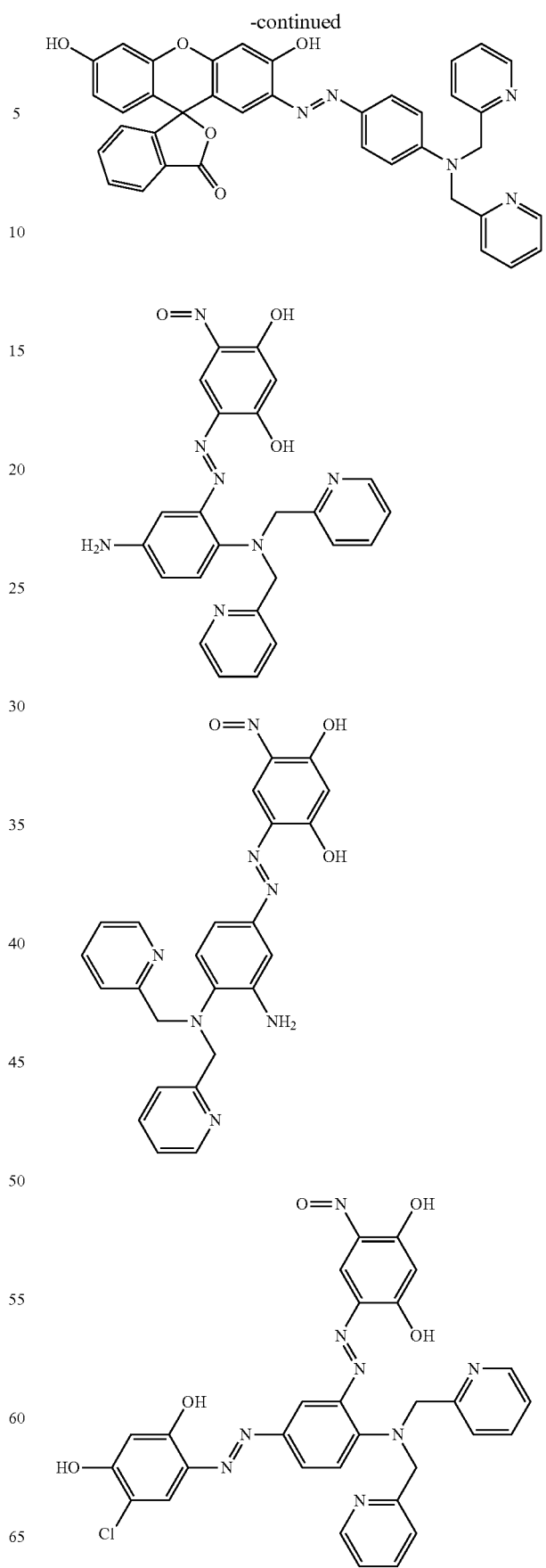

21
-continued
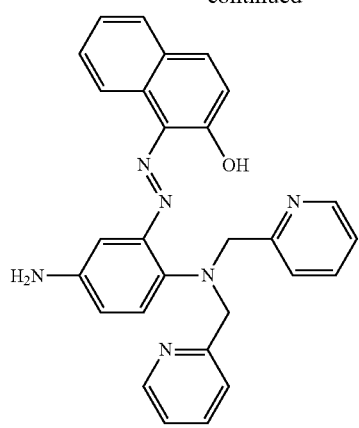
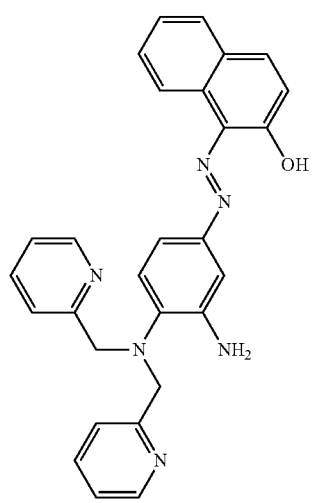
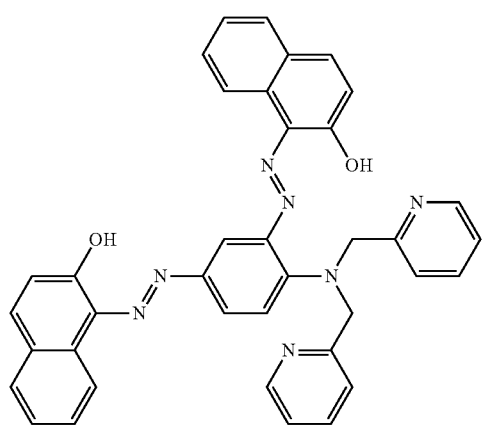
22
-continued
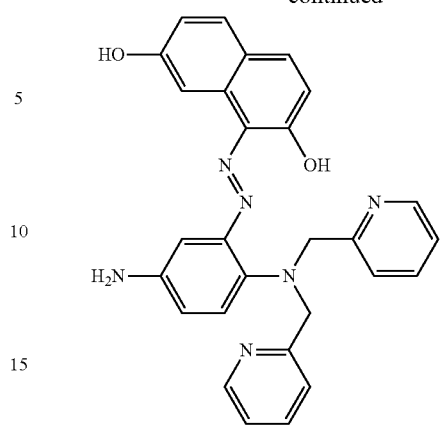
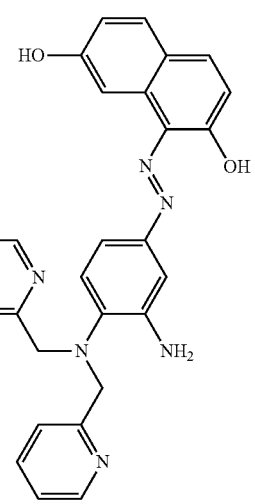
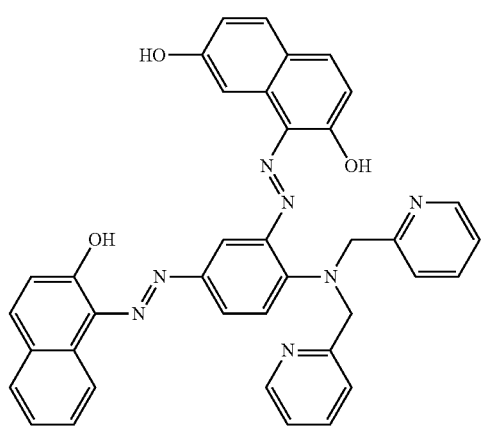

23
-continued
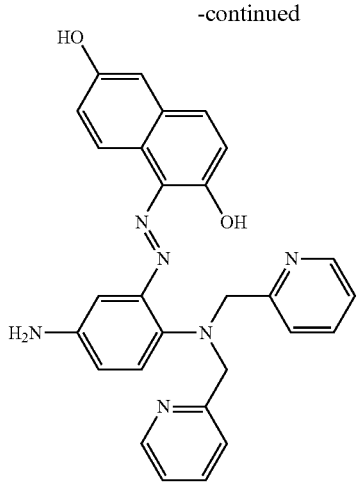
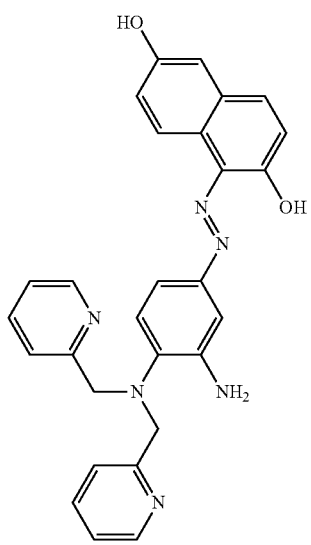
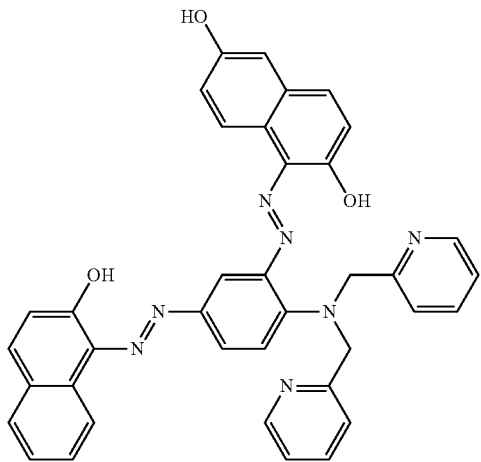
24
-continued
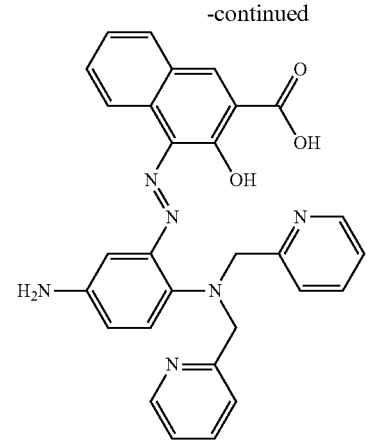
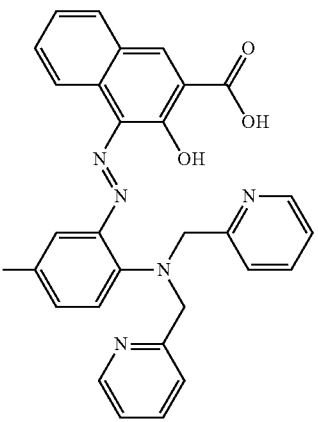

25
-continued
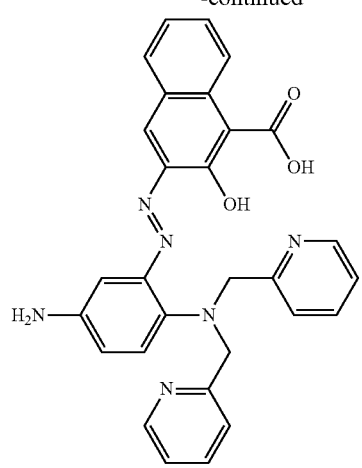
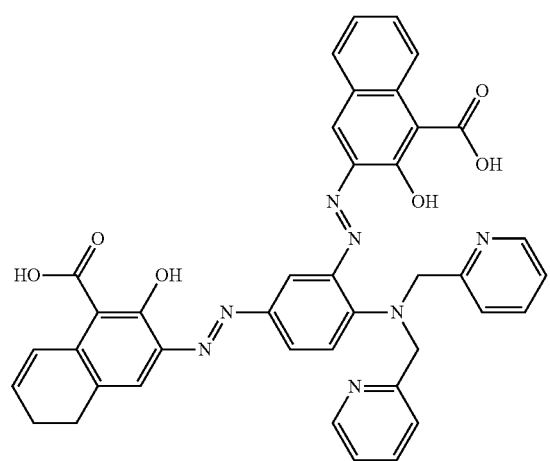
26
-continued
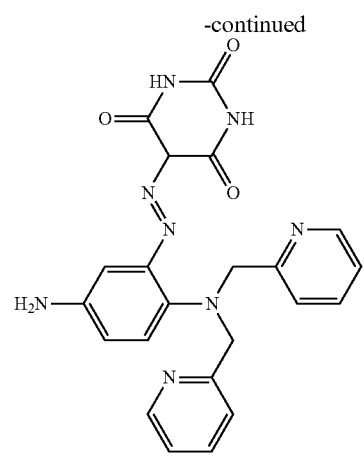
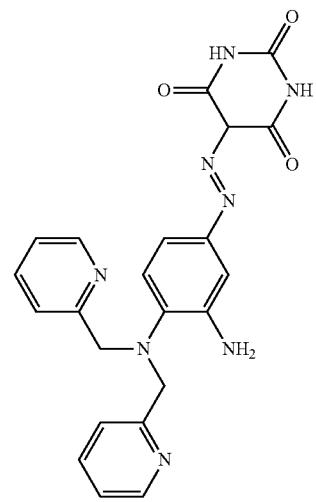
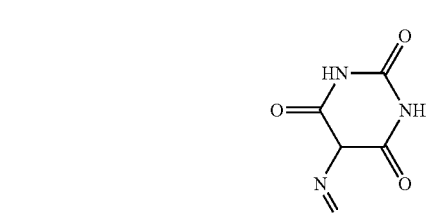
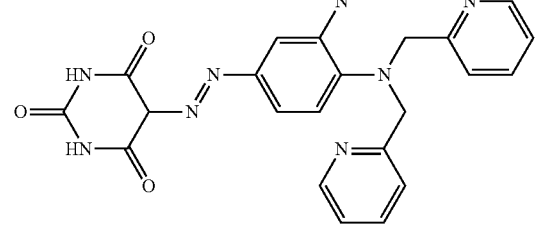
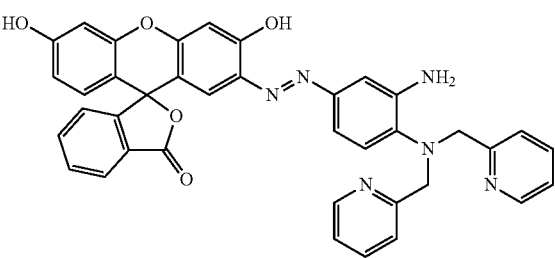

27
-continued
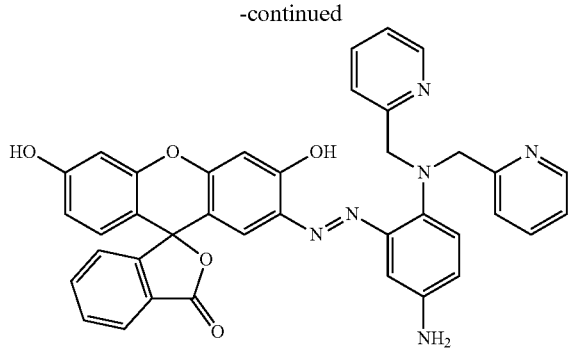
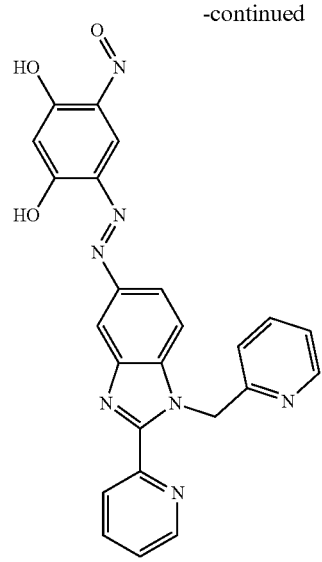
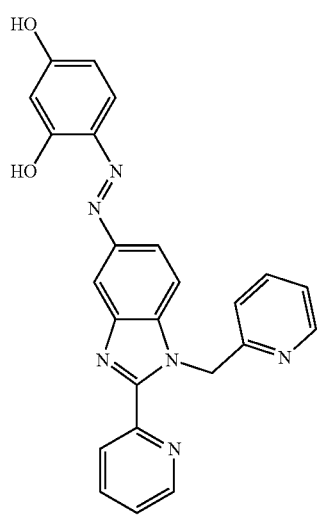
28
-continued
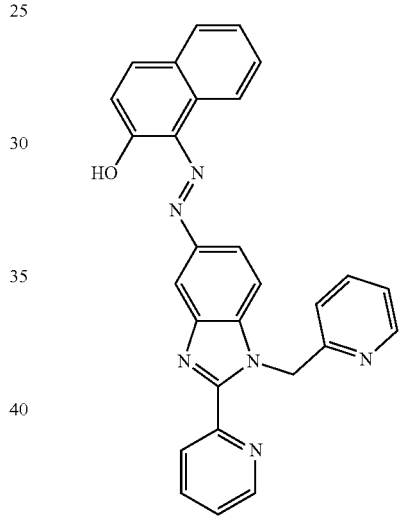
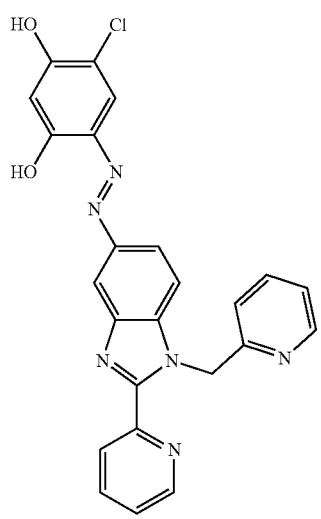
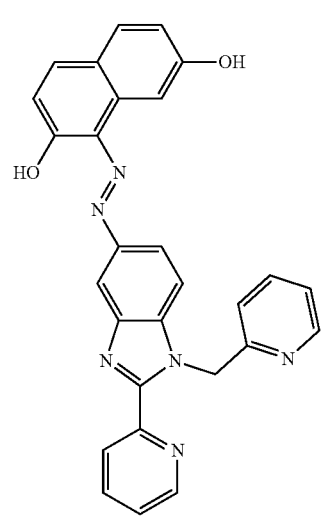

-continued
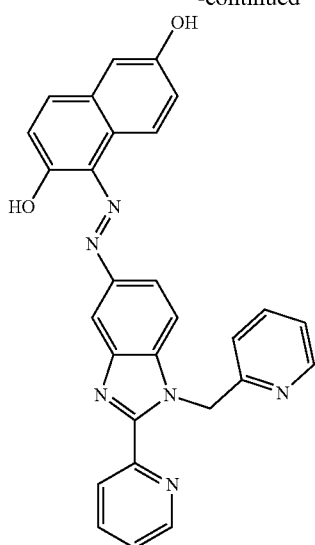
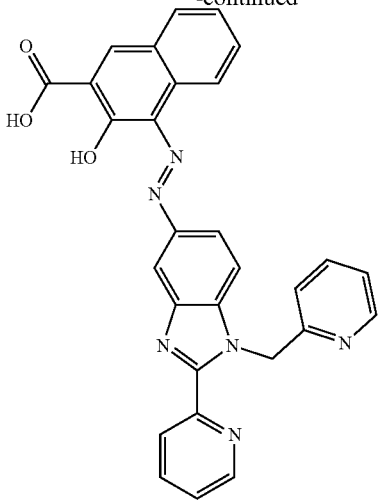
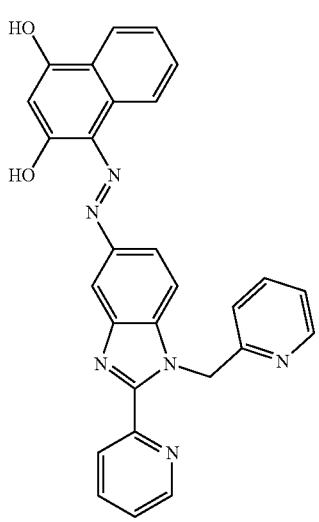
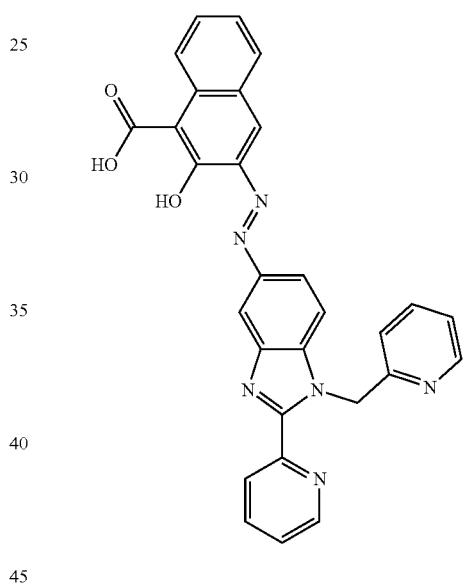
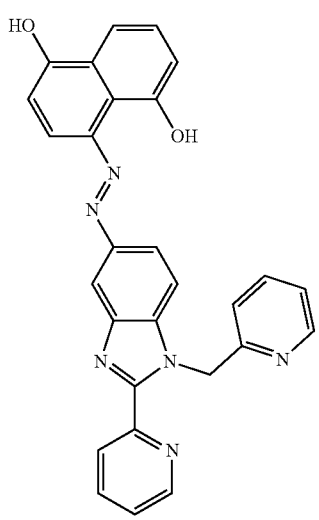
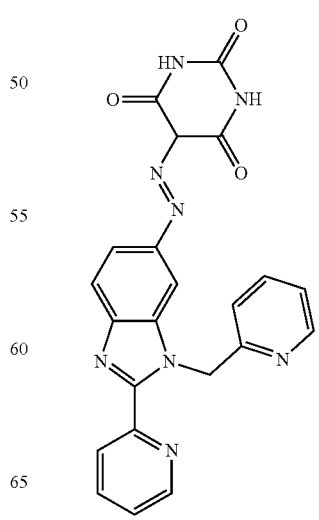

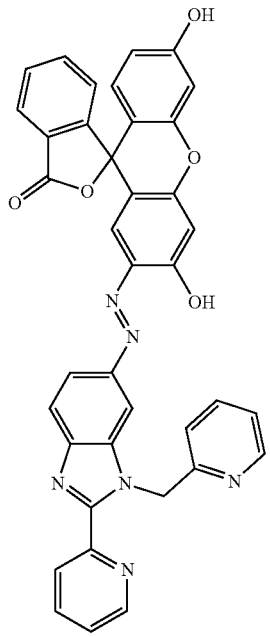
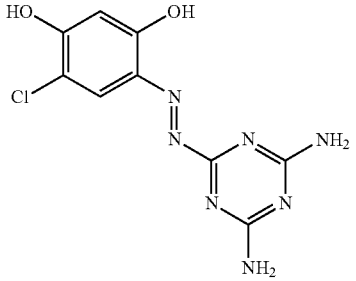
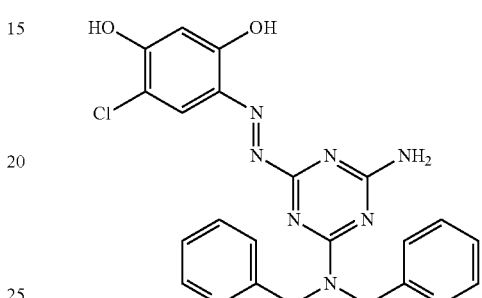
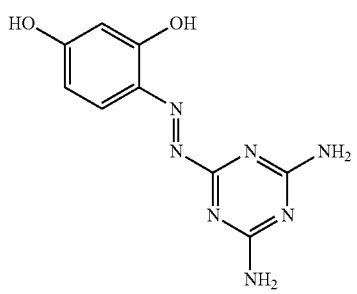
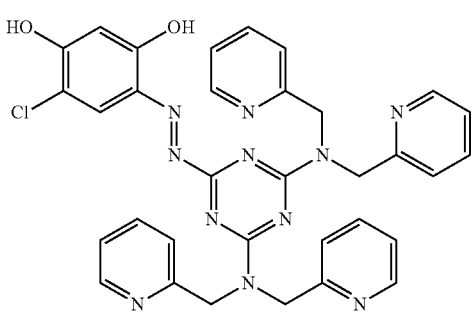
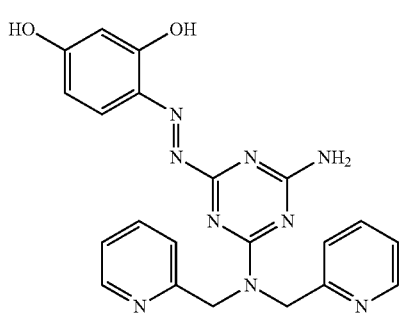
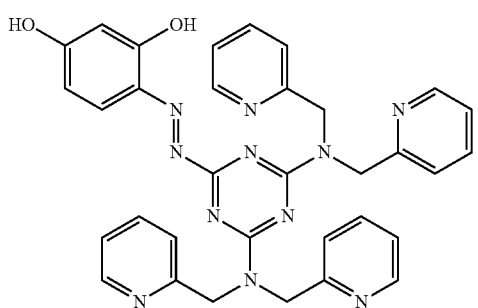
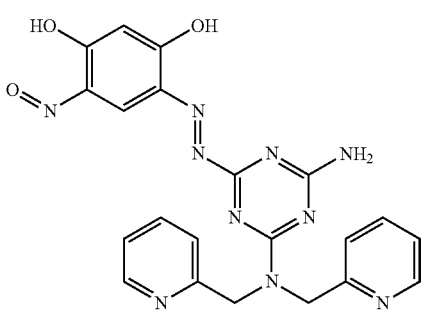

33
-continued
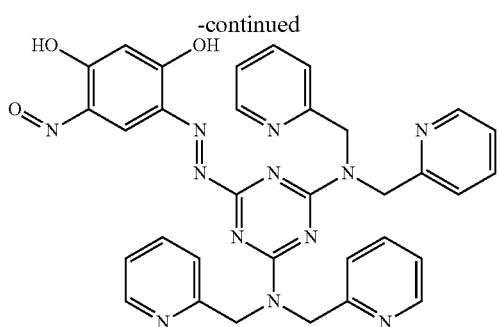
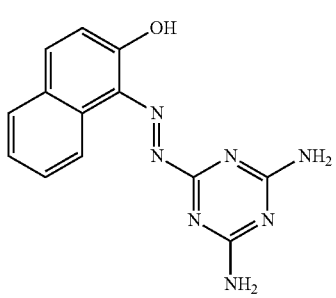
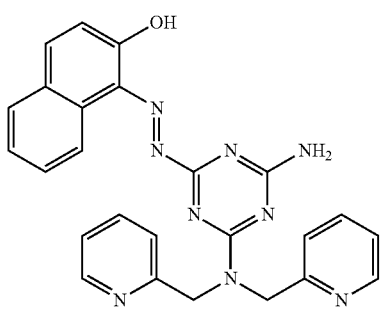
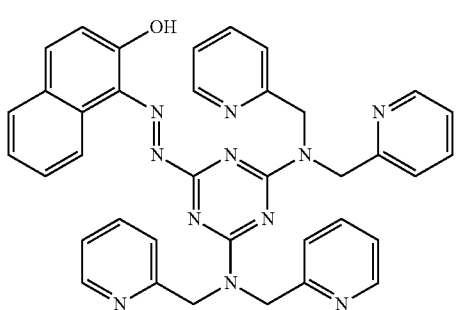
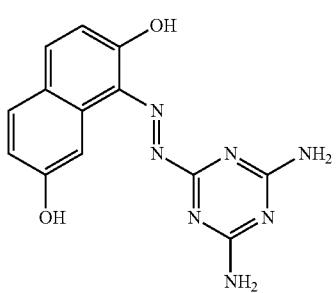
34
-continued
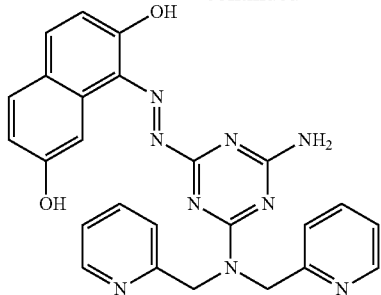
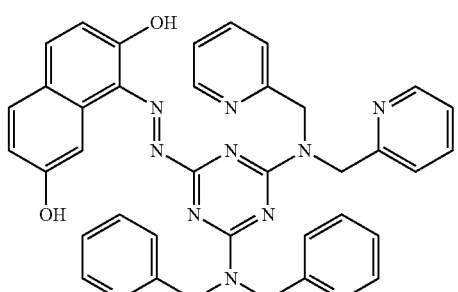
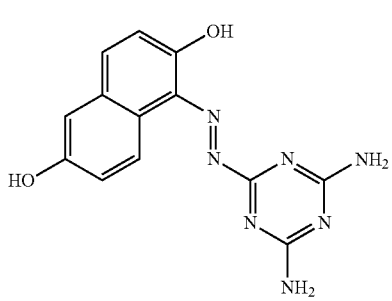
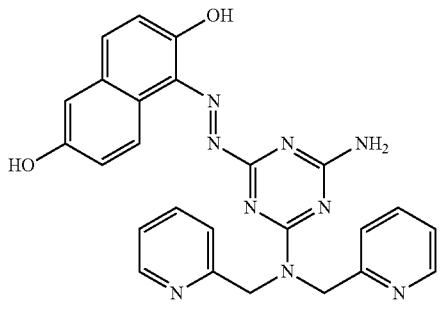
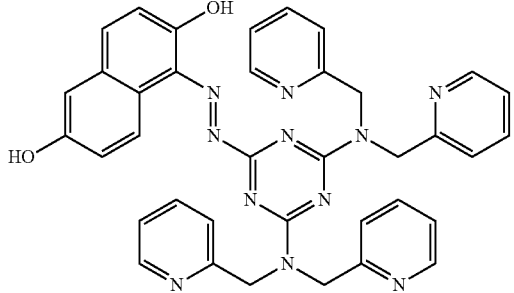

35
-continued
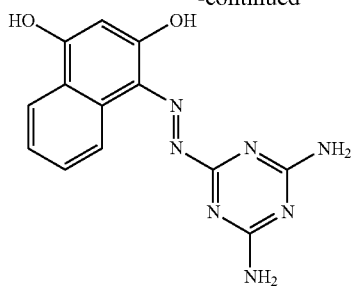
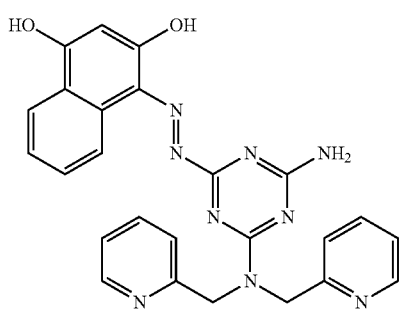
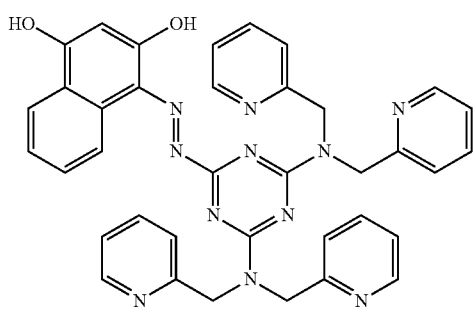
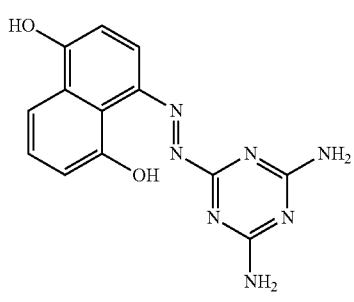
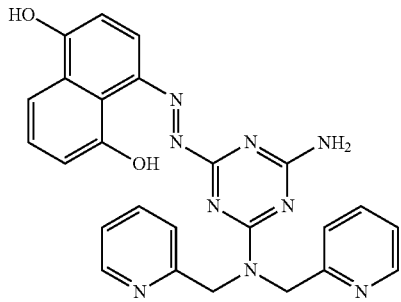
36
-continued
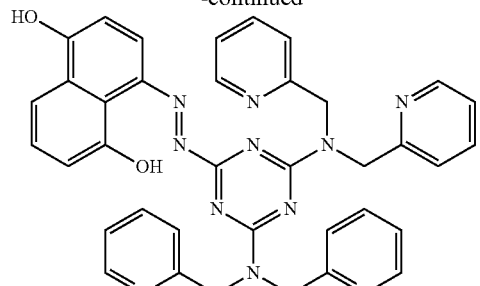
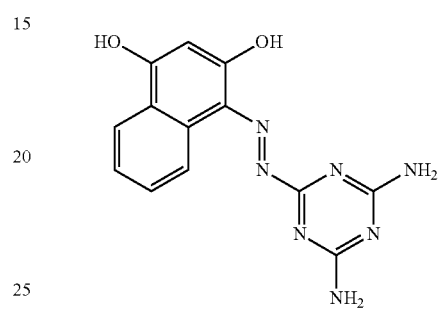
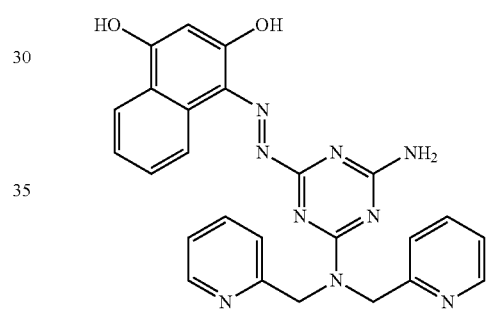
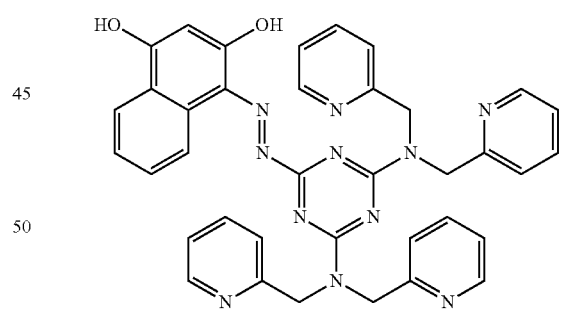
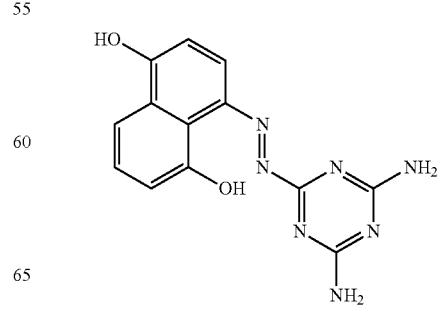

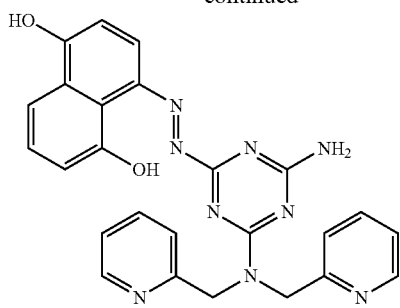

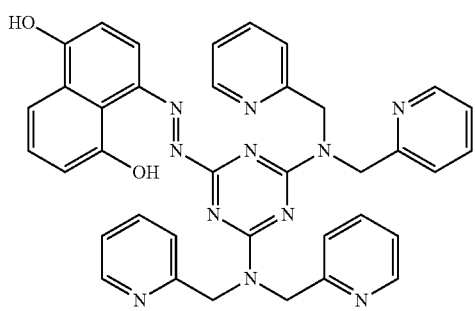

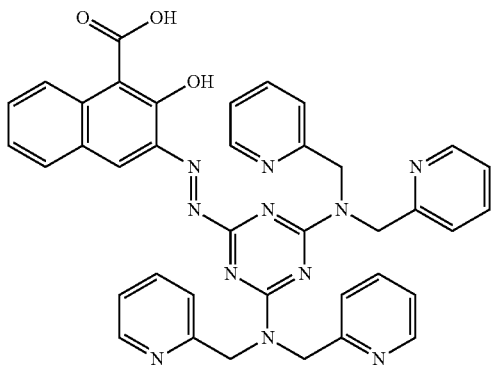 [SMILES: O=C(O)c1c(O)c(/N=N/c2nc(N(Cc3ccccn3)Cc3ccccn3)nc(N(Cc3ccccn3)Cc3ccccn3)n2)cc2ccccc12]

In some embodiments, the optically transparent substrate is a polymer. In some embodiments, the polymer comprises cellulose, crosslinked polymethacrylate ester, polyacrylamide, or crosslinked polyethylene glycol. In some embodiments, the optically transparent substrate further comprises a perturbation moiety. In some embodiments, the perturbation moiety is a cation, an anion or a zwitterion or a neutral species. In some embodiments, the cations comprise trialkylammonium groups. In some embodiments, the dyes are different. In some embodiments, the array comprises more than one optically transparent substrate, wherein each optically transparent substrate has a dye capable of sensing more than one metal covalently bound to the substrate. In some embodiments, the covalent bond is an ether bond, an amide bond, a sulfonamide bond, a urethane or an alkene.

In some embodiments, the dye covalently bound to the optically transparent substrate is a compound of formula:

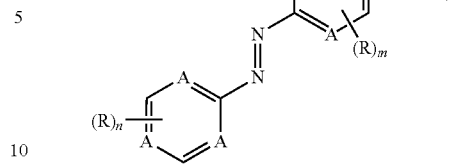

wherein each R is independently selected from the group consisting of OH, H, OR$_1$, C$_{1-4}$ alkyl, nitro, halo, NR$_{N1}$R$_{N2}$, SO$_3$H, SO$_2$NHR$_3$, NHSO$_2$R$_4$, carboxyl, amido, nitrile, —C(=N—OH)R$_3$, —C(=O)NR$_{N1}$OH, —SR$^5$, thioamido, phosphonate or two Rs may join together to form a 5, 6, or 7-membered ring, which may be aromatic or heteroaromatic, which may be substituted; each A is independently N, NO, CH, or CR$_5$; R$_{N1}$ and R$_{N2}$ are independently C(O)R$_2$, heteroaryl, aryl, C$_{1-4}$ alkyl,

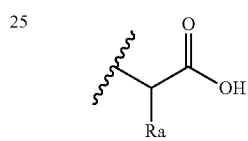

or H; R$^a$ is an amino acid side chain; each R$_1$ is independent C$_{1-4}$ alkyl, C$_{2-4}$ alkenyl, heteroaryl, or aryl; each R$_2$ is independently C$_{1-4}$ alkyl, C$_{2-4}$ alkenyl, heteroaryl, or aryl; each R$_3$ is independently H, C$_{1-4}$ alkyl, heteroaryl, aryl, cycloalkyl, or heterocyclyl; each R$_4$ is independently H, C$_{1-4}$ alkyl, heteroaryl, aryl, cycloalkyl, or heterocyclyl; each R$_5$ is independently H, C$_{1-4}$ alkyl, heteroaryl, aryl, cycloalkyl, or heterocyclyl; each n is independently an integer from 1 to 5; each me is independently an integer from 1 to 4 L is a linker; and X is an optically transparent substrate.

In some embodiments, the dye covalently bound to the optically transparent substrate is a compound of formula:

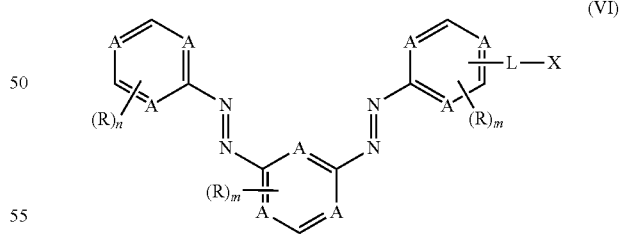

wherein each R is independently selected from the group consisting of OH, H, OR$_1$, C$_{1-4}$ alkyl, nitro, halo, NR$_{N1}$R$_{N2}$, SO$_3$H, SO$_2$NHR$_3$, NHSO$_2$R$_4$, carboxyl, amido, nitrile, —C(=N—OH)R$_3$, —C(=O)NR$_{N1}$OH, —SR$^5$, thioamido, phosphonate or two Rs may join together to form a 5, 6, or 7-membered ring, which may be aromatic or heteroaromatic, which may be substituted; each A is independently N, NO, CH, or CR$_5$; R$_{N1}$ and R$_{N2}$ are independently C(O)R$_2$, heteroaryl, aryl, C$_{1-4}$ alkyl,

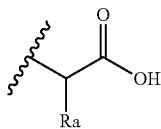

or H; $R^a$ is an amino acid side chain; each $R_1$ is independent $C_{1-4}$ alkyl, $C_{2-4}$ alkenyl, heteroaryl, or aryl; each $R_2$ is independently $C_{1-4}$ alkyl, $C_{2-4}$ alkenyl, heteroaryl, or aryl; each $R_3$ is independently H, $C_{1-4}$ alkyl, heteroaryl, aryl, cycloalkyl, or heterocyclyl; each $R_4$ is independently H, $C_{1-4}$ alkyl, heteroaryl, aryl, cycloalkyl, or heterocyclyl; each $R_5$ is independently H, $C_{1-4}$ alkyl, heteroaryl, aryl, cycloalkyl, or heterocyclyl; each n is independently an integer from 1 to 5; each m is independent an integer from 1 to 4; L is a linker; and X is an optically transparent substrate.

In some embodiments, the linker is selected from the group consisting of —O—$(CH_2)_p$—$C_6H_4$—, wherein p is an integer from 1 to 4; —$OCH_2C(O)NH$—$(CH_2O)_tCH_2CH_2$—$NHC(O)$—, wherein t is an integer from 1 to 10; —O—$(CH_2O)_r$—$C(O)NH$—, wherein r is an integer from 1 to 10; —$C(O)NH$—$(CH_2O)_q$—$CH_2CH_2NHC(O)$—$(OCH_2)_vOC(O)$—, wherein q and v are independently an integer from 1 to 10; and —O—$(CH_2O)_uC(O)$—, wherein u is an integer from 1 to 10. In other embodiments the disclosure provides a method of detecting at least one metal ion in an aqueous solution comprising contacting the aqueous solution with a sensor or a panel according to any one of the preceding claims; obtaining a signal for the sensor; analyzing the signal; and identifying at least one metal ion. In some embodiments, the method further comprises quantifying concentration of at least one metal ion.

In some embodiments, the metal ion is chromium, calcium, magnesium, copper, mercury, nickel, zinc, cobalt, manganese, cadmium, lead, tin, aluminum, potassium, sodium, or arsenic. In some embodiments, chromium is chromium(III). In some embodiments, iron is iron(II) or iron(III). In some embodiments, copper is copper(I) or copper(II). In some embodiments, cobalt is cobalt(II). In some embodiments, nickel is nickel(II). In some embodiments, zinc is zinc(II). In some embodiments, mercury is mercury(II). In some embodiments, calcium is calcium(II). In some embodiments, magnesium is magnesium(II). In some embodiments, aluminum is aluminum(III). In some embodiments, cadmium is cadmium(II). In some embodiments, potassium is potassium(I). In some embodiments, sodium is sodium(I). In some embodiments, lead is lead(II). In some embodiments, manganese is manganese (II). In some embodiments, tin is tin(II). In some embodiments, arsenic is arsenic(III) or arsenic(V). In some embodiments, the aqueous solution contains more than one metal ion. In some embodiments, the aqueous solution contains contaminants. In some embodiments, the signal is obtained and analyzed in real-time. In some embodiments, the method further comprises washing the sensor or panel to remove bound metal ions. In some embodiments, the method further comprises contacting a second aqueous solution with a sensor or array as detailed herein; obtaining a second signal for the sensor; analyzing the second signal; and identifying at least one metal ion.

In other embodiments the disclosure provides a kit comprising a sensor or panel as detailed herein and instructions for use.

In other embodiments the disclosure provides a compound of formula (II):

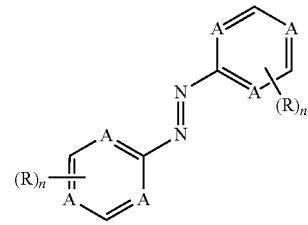

(II)

wherein each R is independently selected from the group consisting of OH, H, $OR_1$, $C_{1-4}$ alkyl, nitro, halo, $NR_{N1}R_{N2}$, $SO_3H$, $SO_2NHR_3$, $NHSO_2R_4$, carboxyl, amido, nitrile, —$C(=N-OH)R_3$, —$C(=O)NR_{N1}OH$, —$SR_5$, thioamido, phosphonate or two Rs may join together to form a 5, 6, or 7-membered ring, which may be aromatic or heteroaromatic, which may be substituted; each A is independently N, NO, CH, or $CR_5$; $R_{N1}$ and $R_{N2}$ are independently $C(O)R_2$, heteroaryl, aryl, $C_{1-4}$ alkyl,

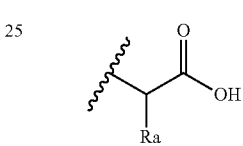

or H; $R^a$ is an amino acid side chain; each $R_1$ is independent $C_{1-4}$ alkyl, $C_{2-4}$ alkenyl, heteroaryl, or aryl; each $R_2$ is independently $C_{1-4}$ alkyl, $C_{2-4}$ alkenyl, heteroaryl, or aryl; each $R_3$ is independently H, $C_{1-4}$ alkyl, heteroaryl, aryl, cycloalkyl, or heterocyclyl; each $R_4$ is independently H, $C_{1-4}$ alkyl, heteroaryl, aryl, cycloalkyl, or heterocyclyl; each $R_5$ is independently H, $C_{1-4}$ alkyl, heteroaryl, aryl, cycloalkyl, or heterocyclyl; and each n is independently an integer from 1 to 5; wherein the compound of Formula (I) is not 4-(2-pyridylazo)resorcinol (PAR) or 4-(quinolin-8-yldiazenyl)benzene-1,3-diol (QAR).

In other embodiments the disclosure provides a compound according to formula (IV): A-B (IV) wherein A is selected from the group consisting of:

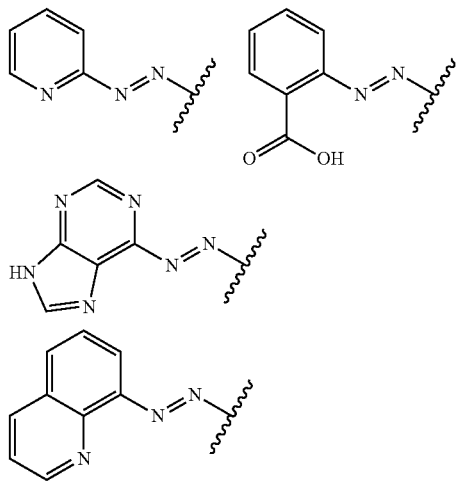

-continued
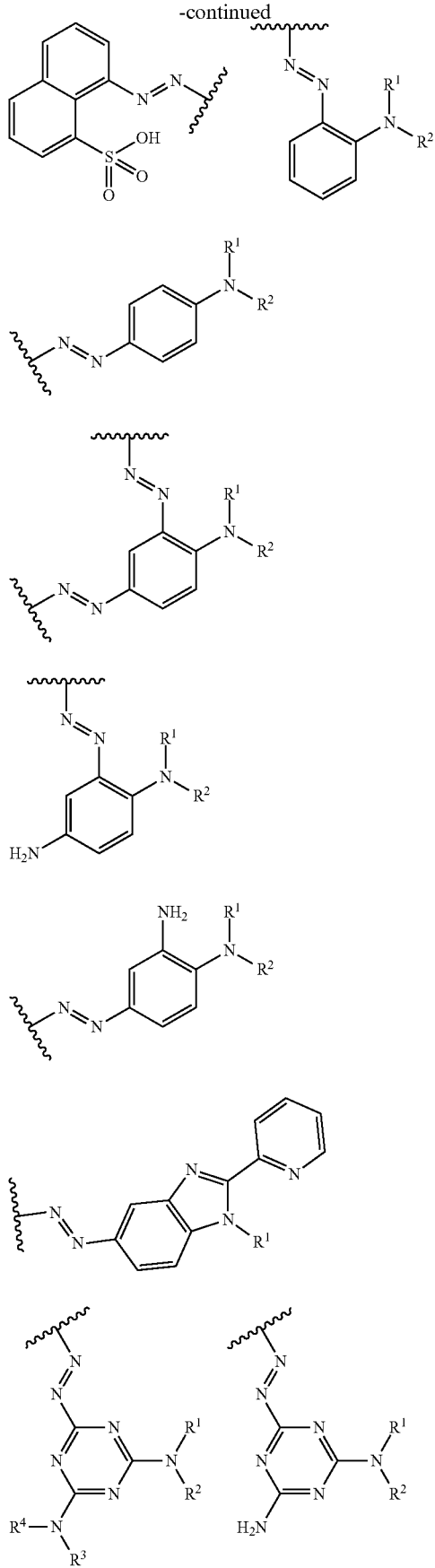
-continued
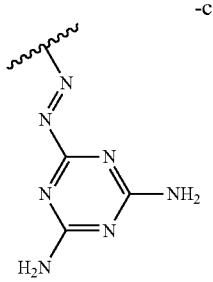
wherein R[1], R[2], R[3] and R[4] are independently selected from:
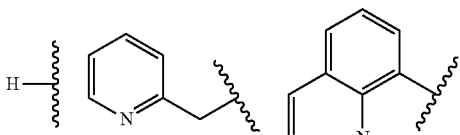
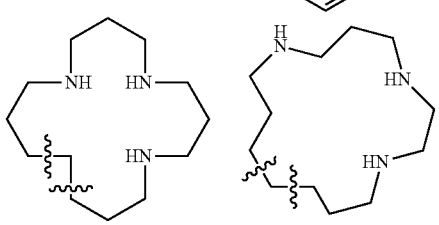
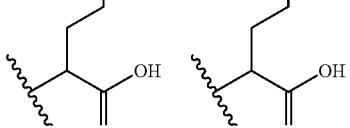
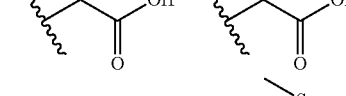
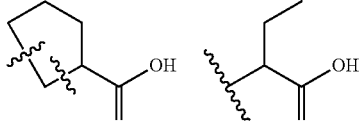
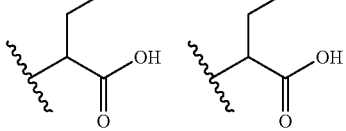

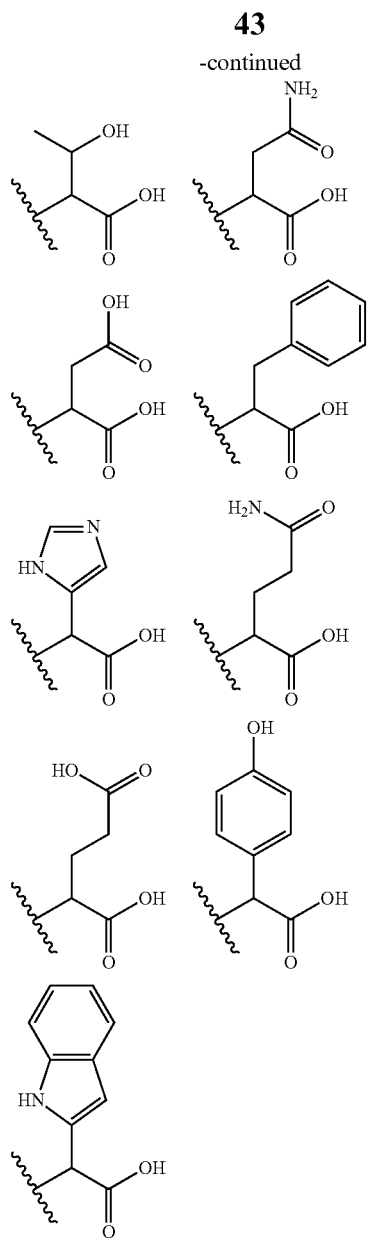
B is selected from the group consisting of:
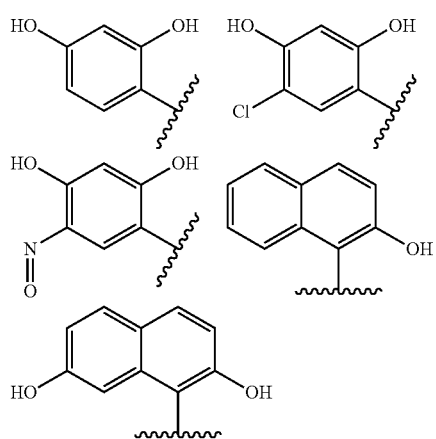
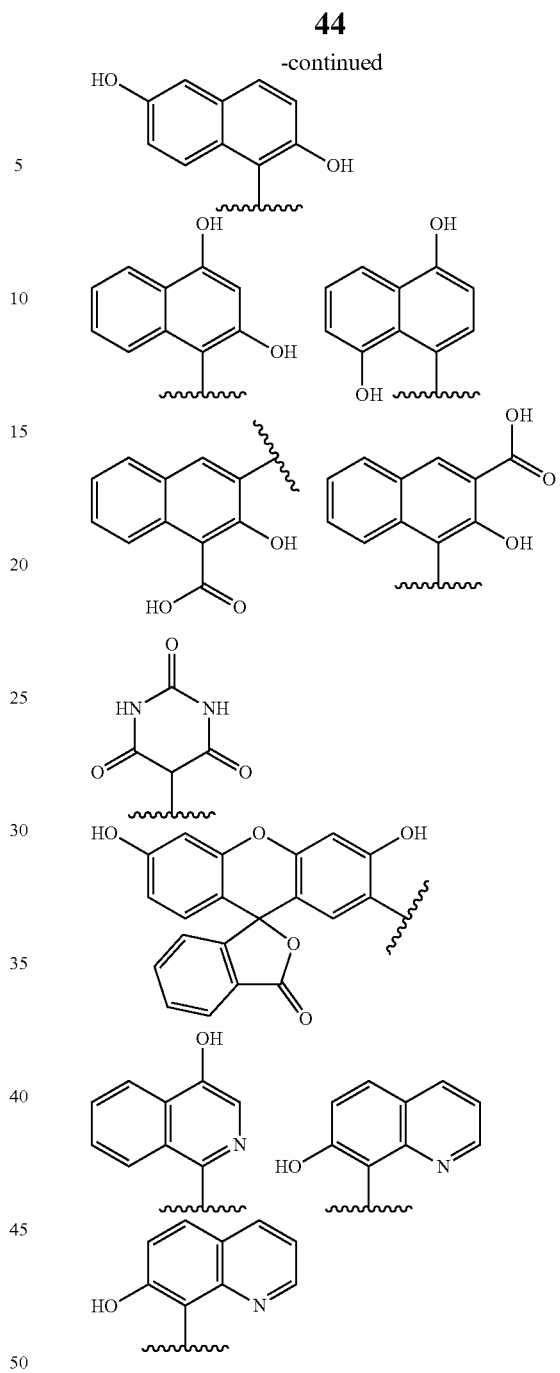
wherein the compound of Formula (IV) is not 4-(2-pyridylazo)resorcinol (PAR) or 4-(quinolin-8-yldiazenyl)benzene-1,3-diol (QAR).
In other embodiments the disclosure provides a compound selected from the group consisting of:
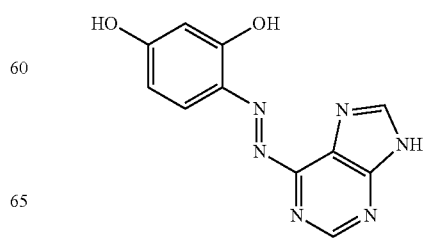

-continued
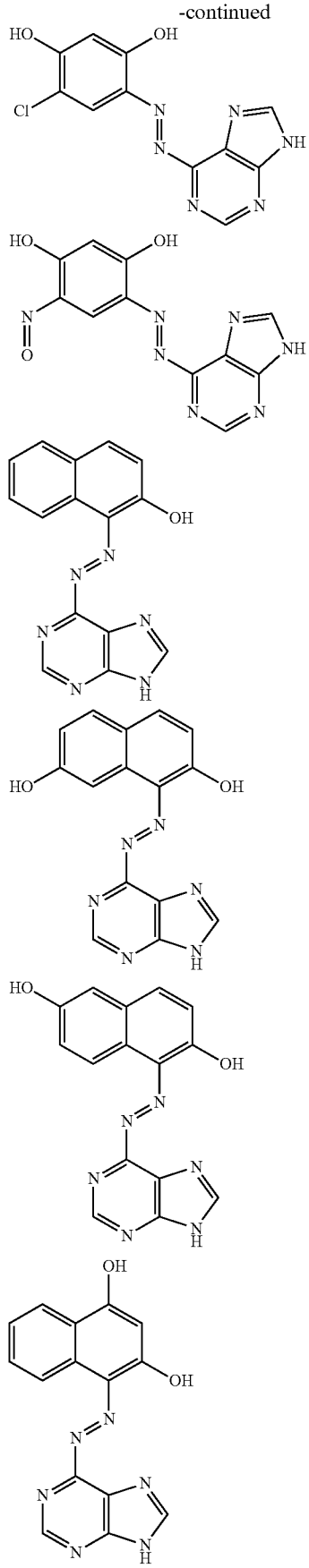
-continued
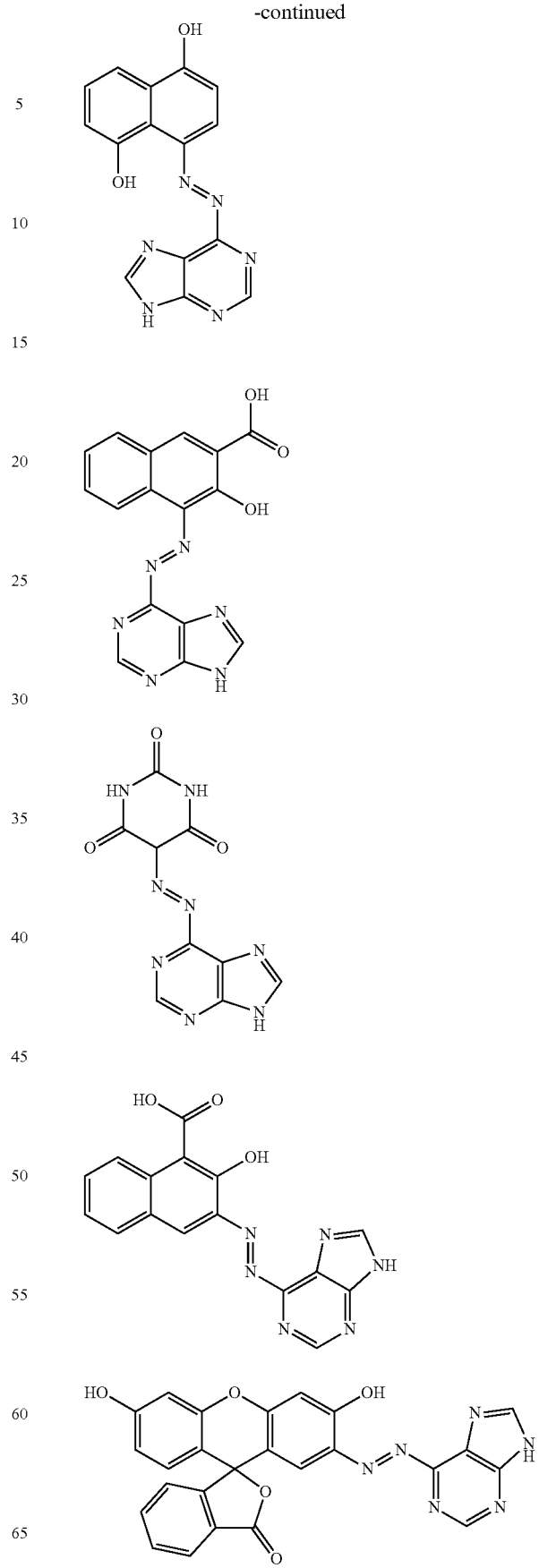

-continued
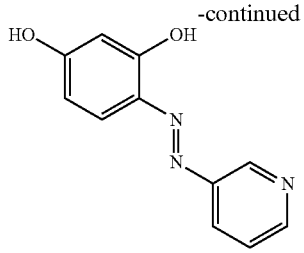
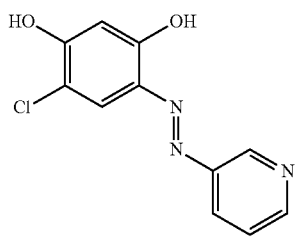
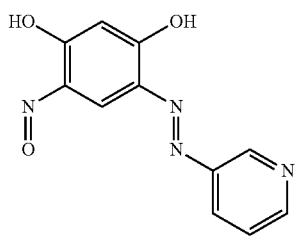
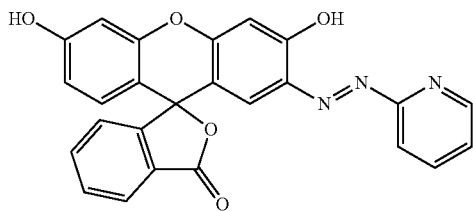
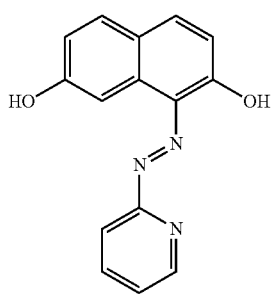
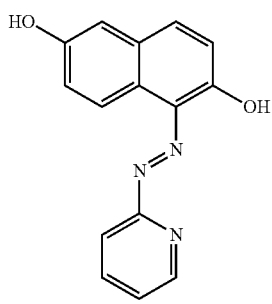
-continued
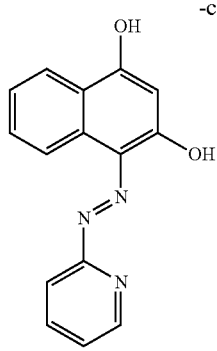
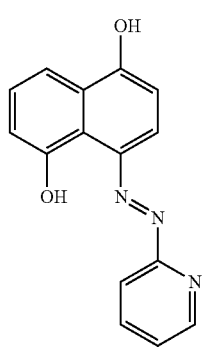
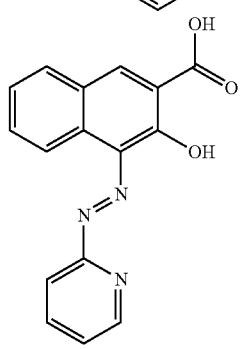
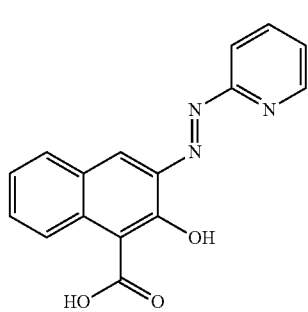
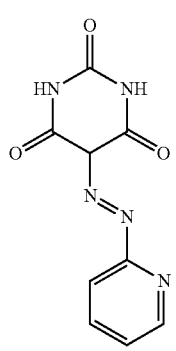

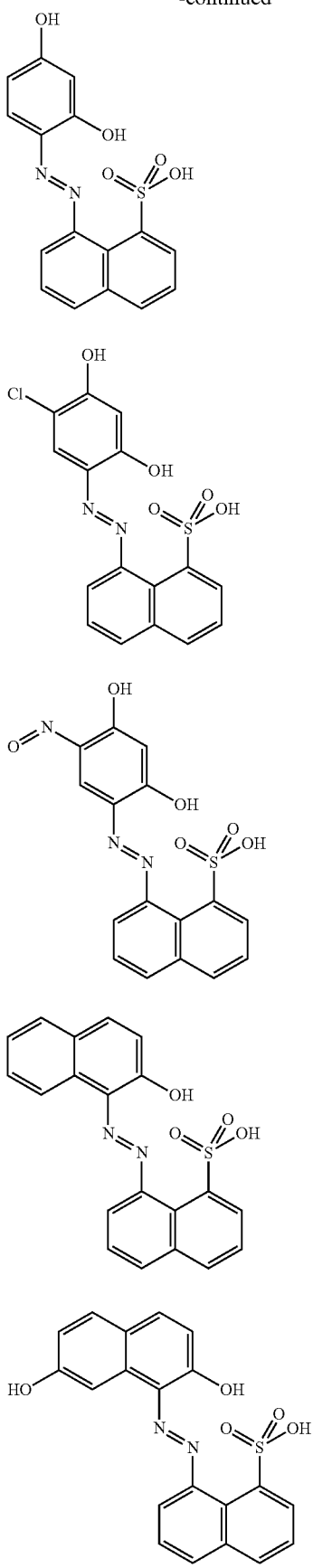
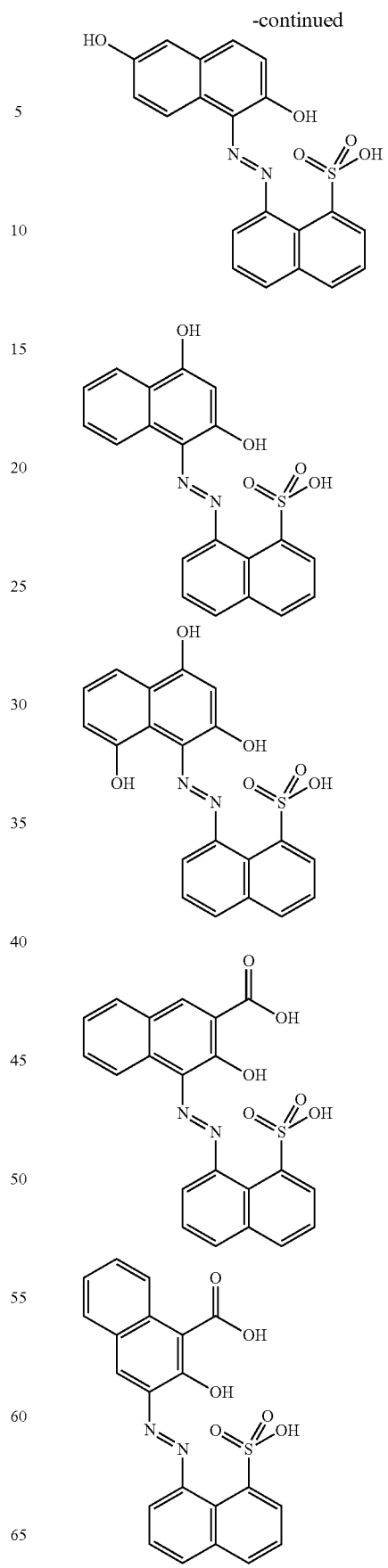

51
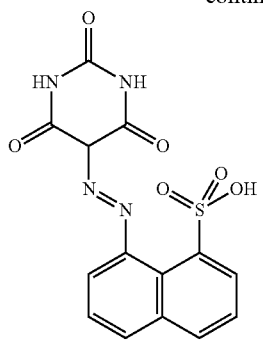
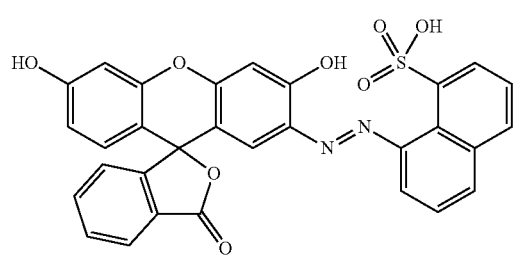
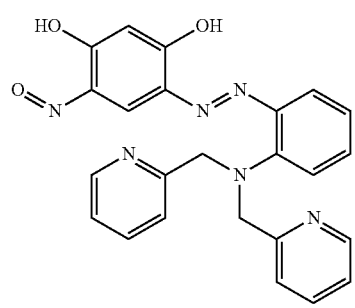
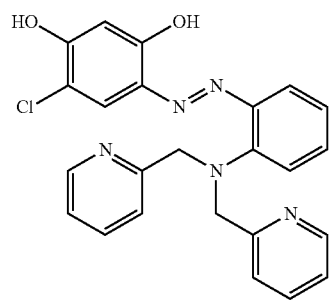
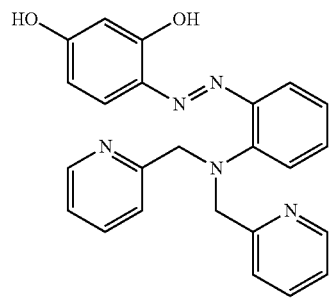
52
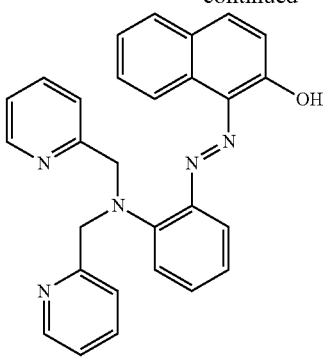
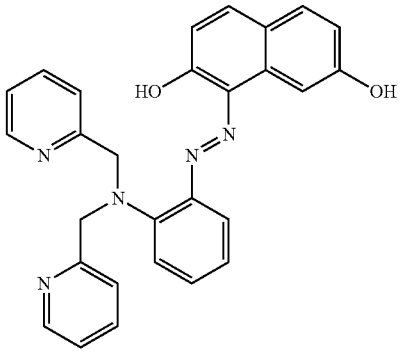
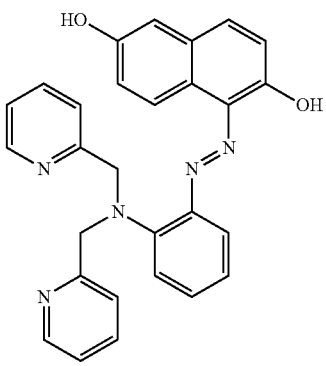
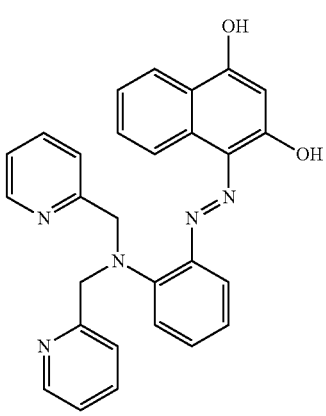

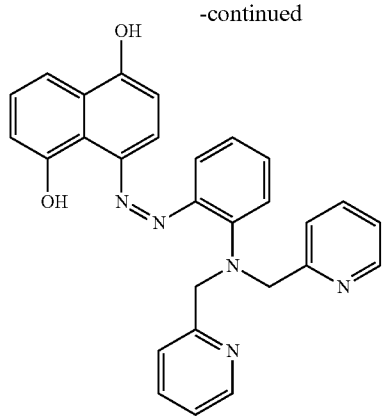
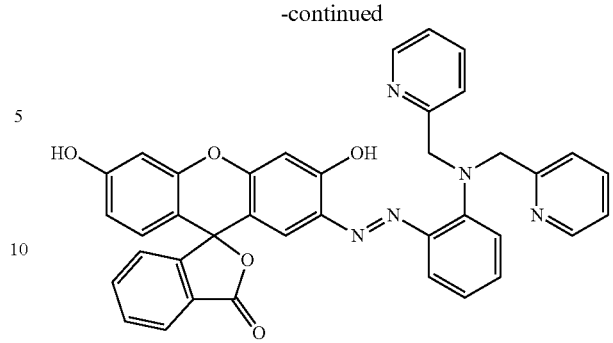
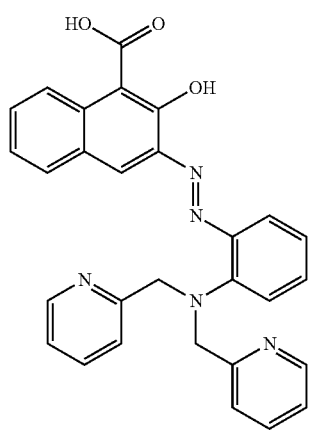
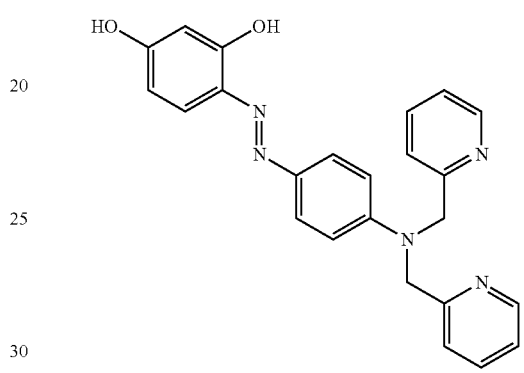
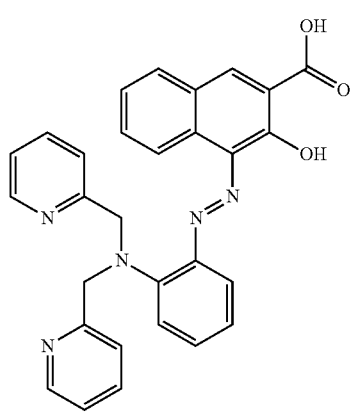
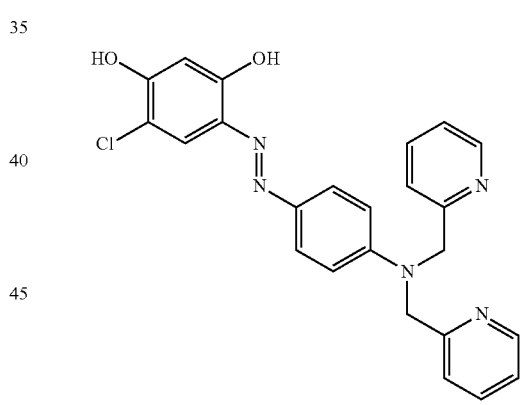
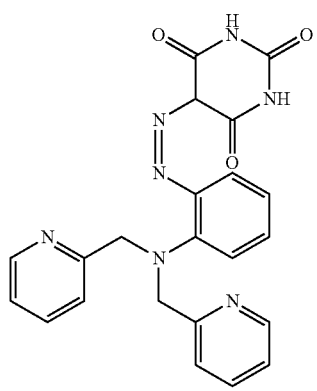
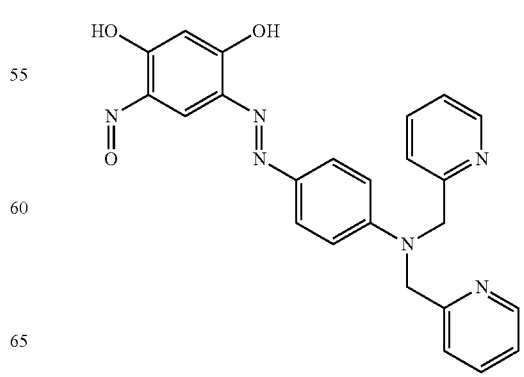

55
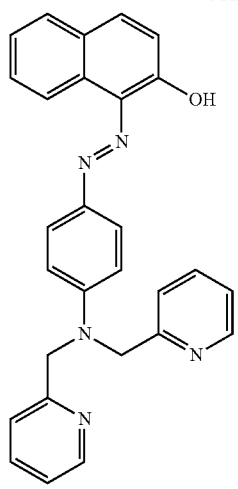
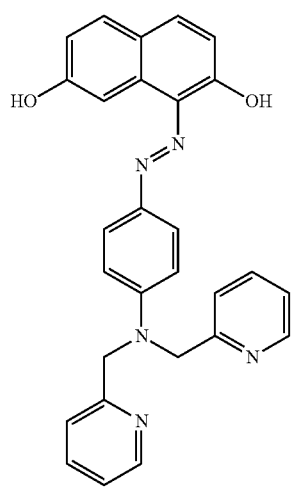
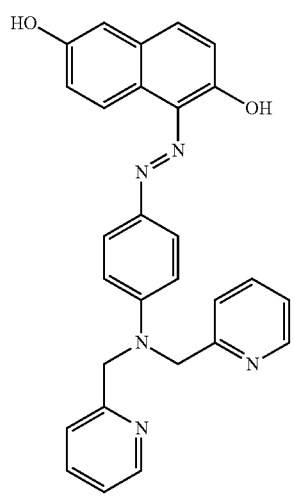
56
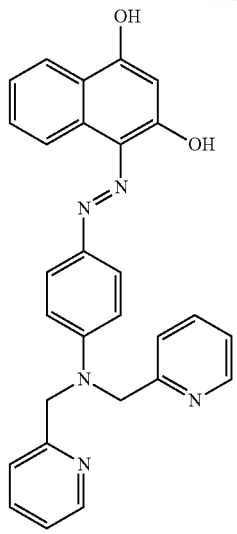
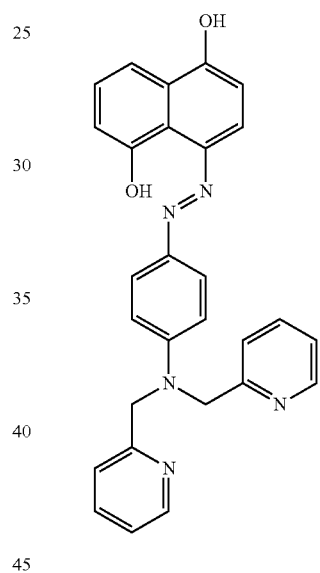
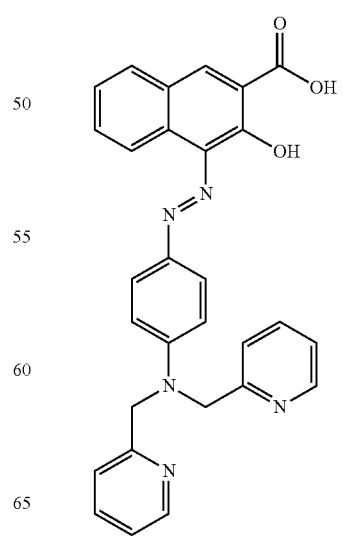

-continued
57
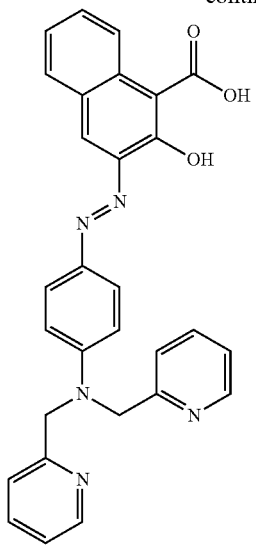
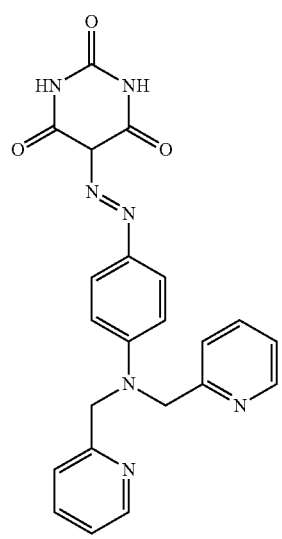
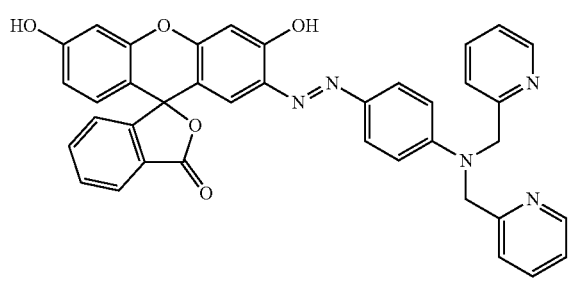
58
-continued
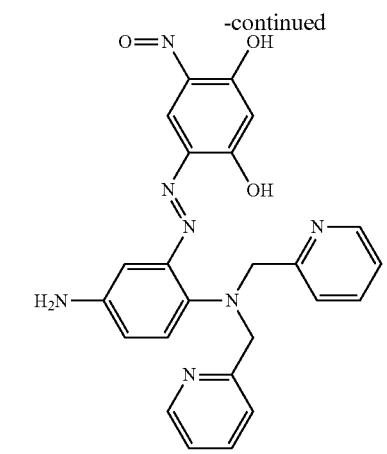
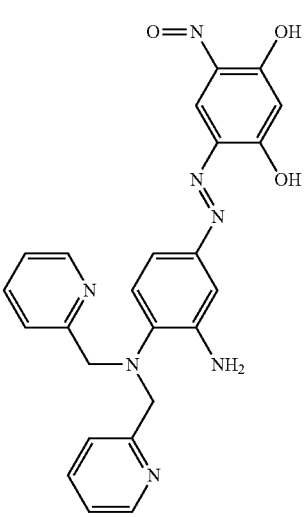
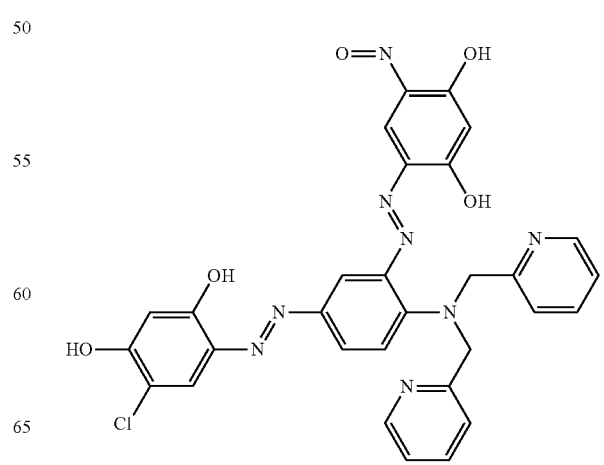

59
-continued
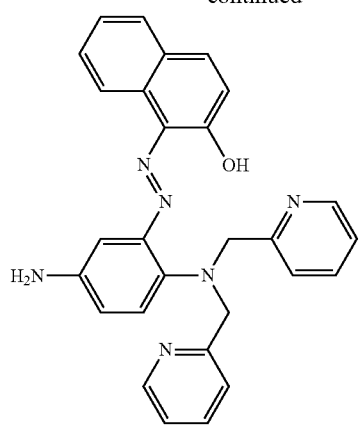
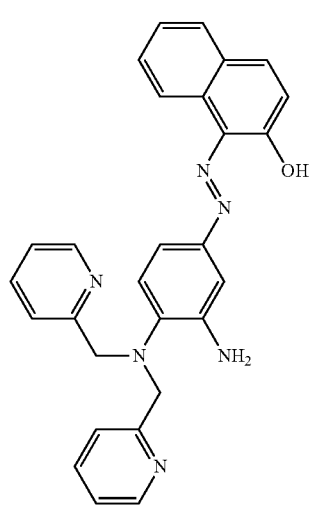
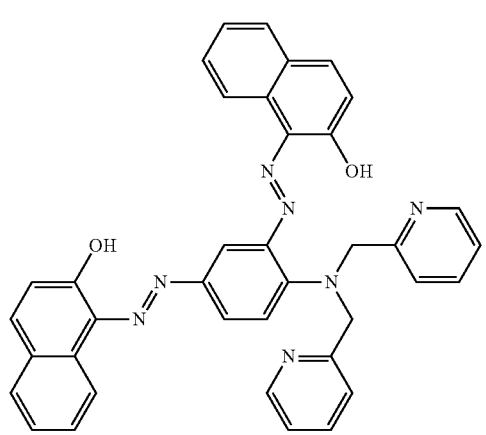
60
-continued
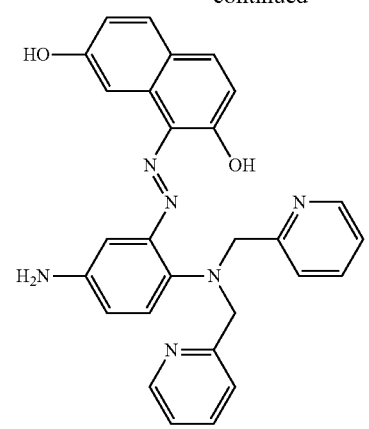
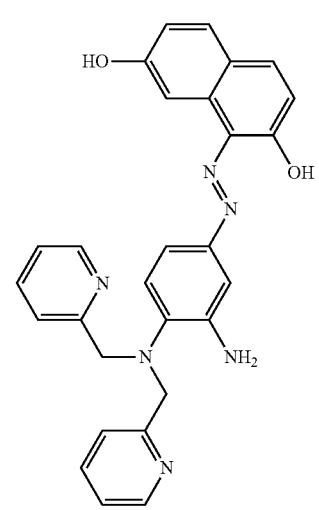
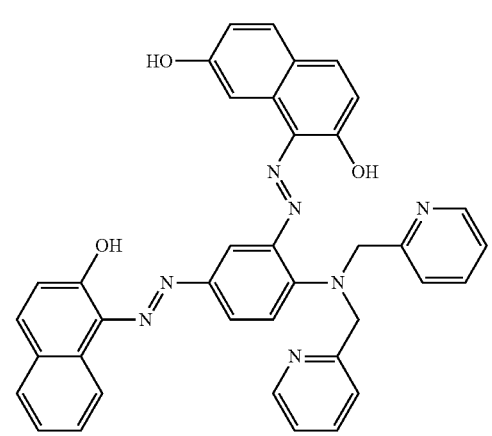

61
-continued
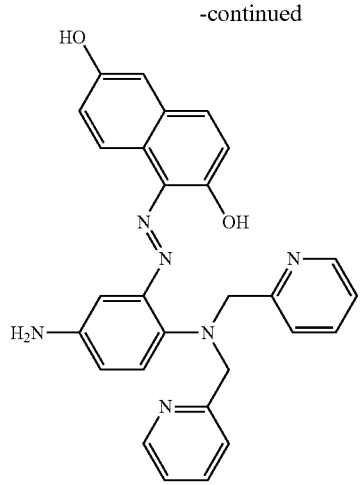
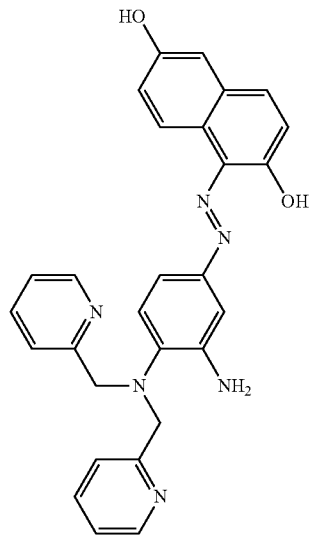
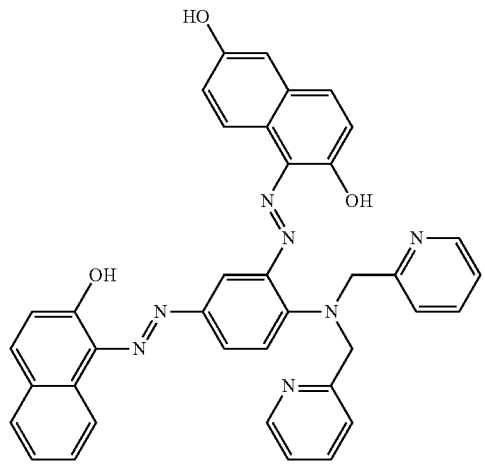
62
-continued
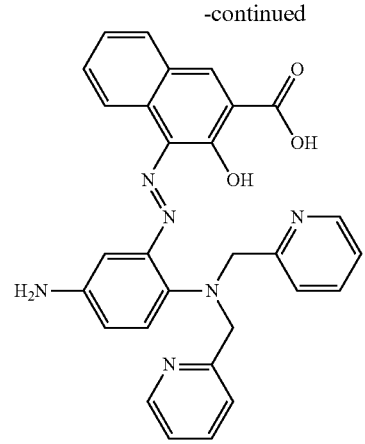
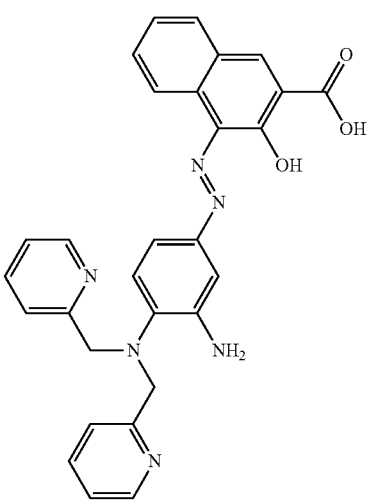
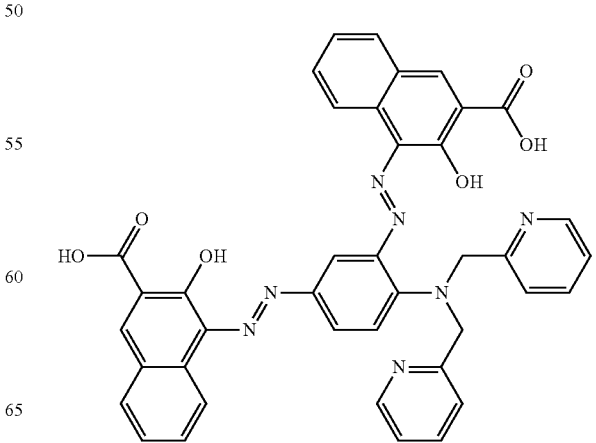

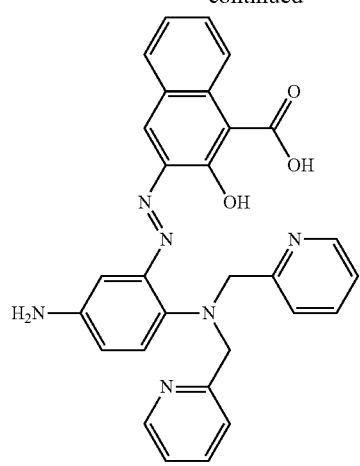
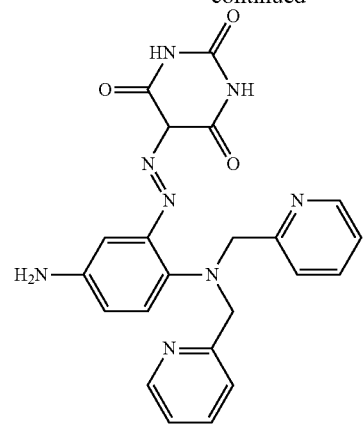
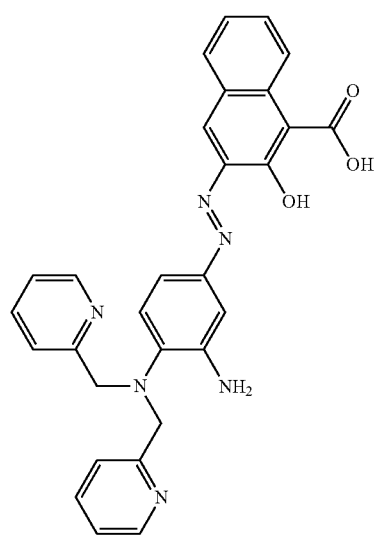
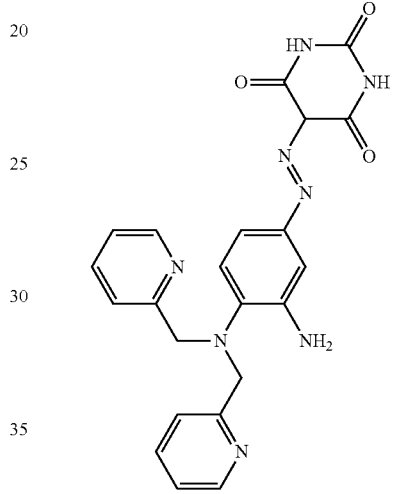
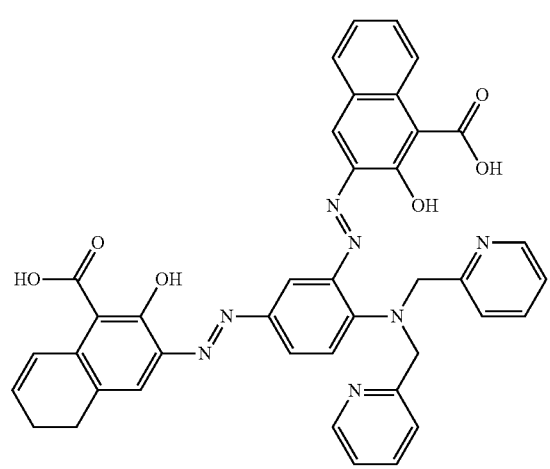
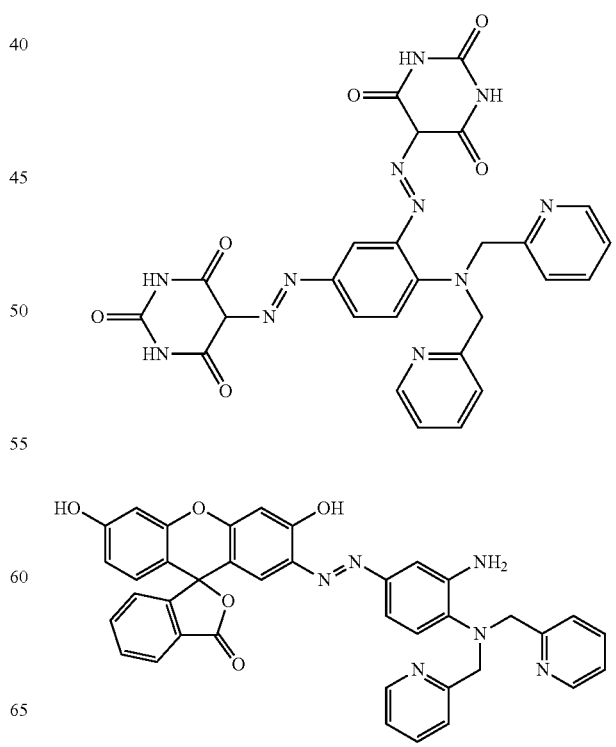

65
-continued
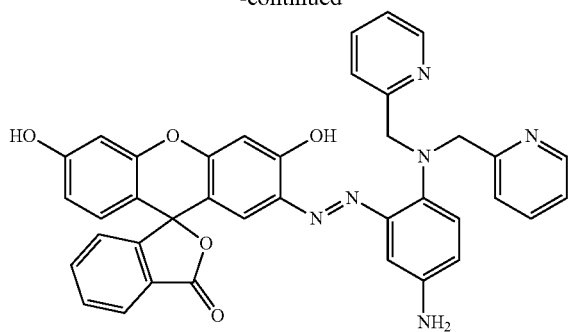
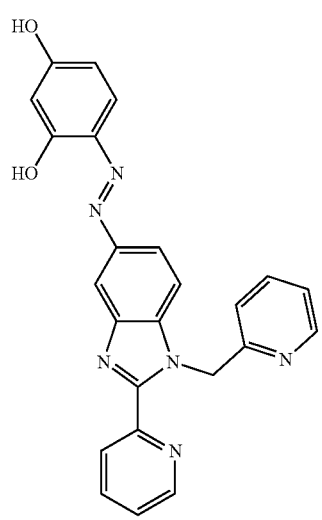
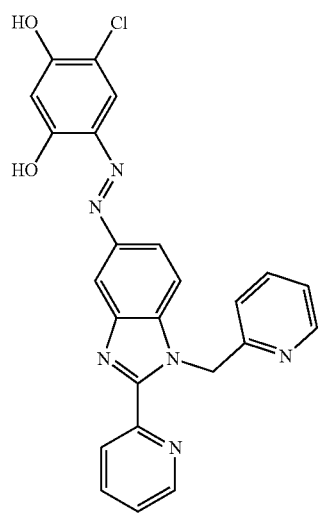
66
-continued
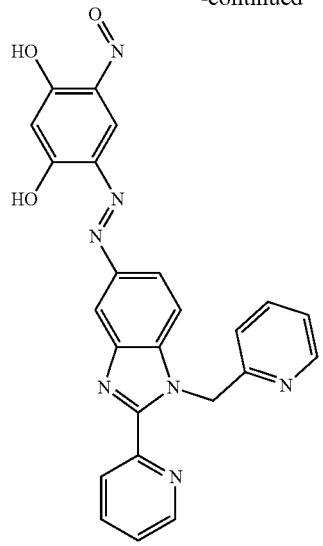
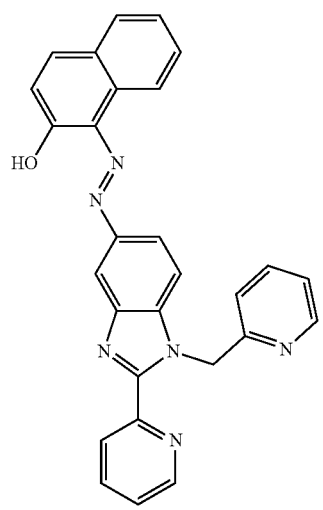
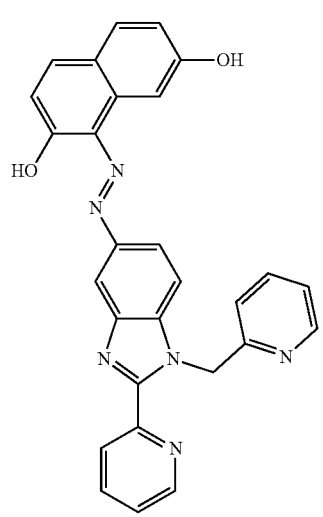

-continued
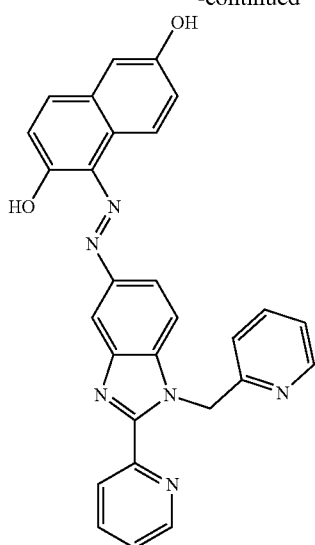
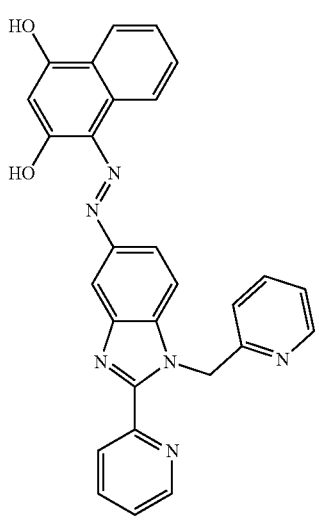
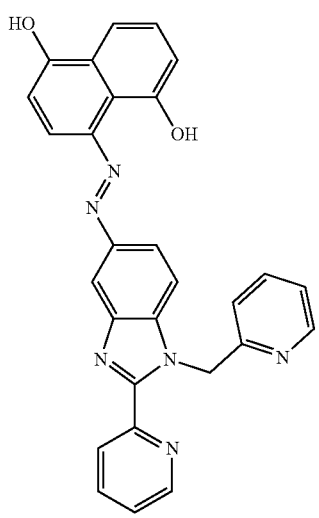
-continued
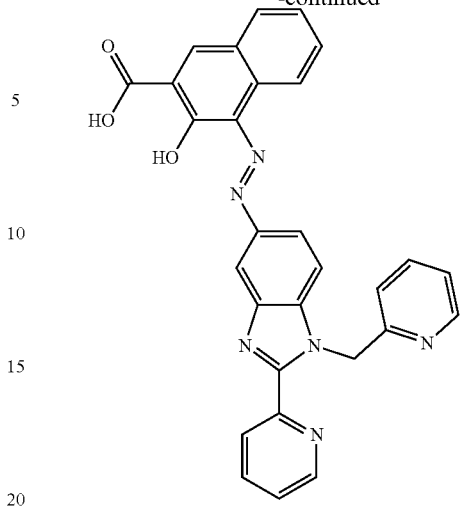
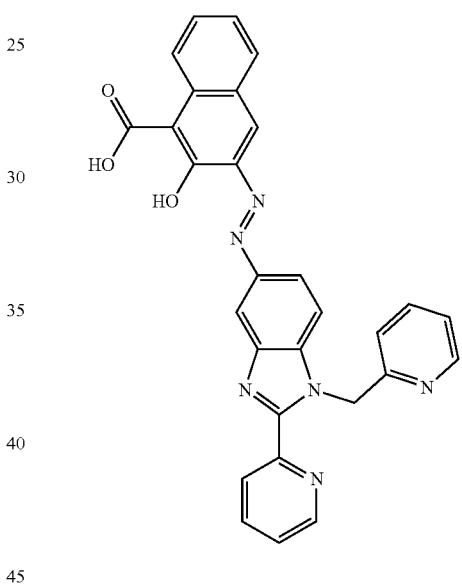
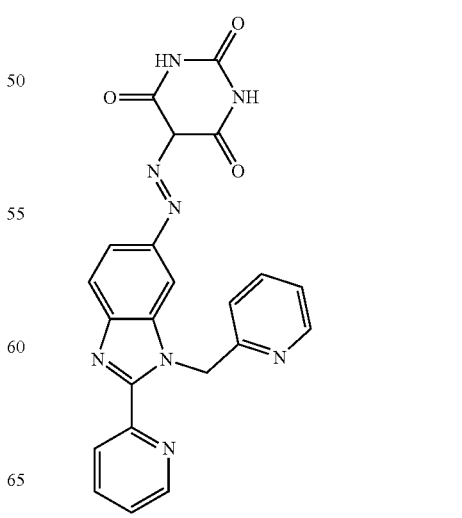

-continued
69
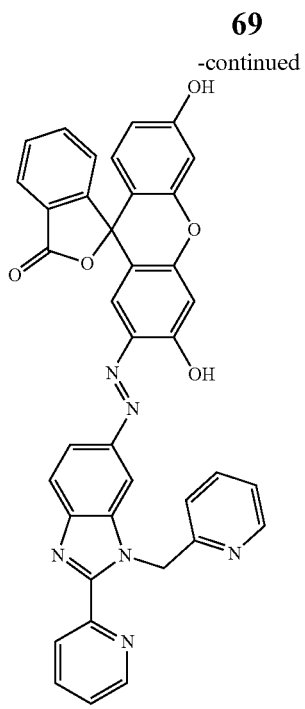
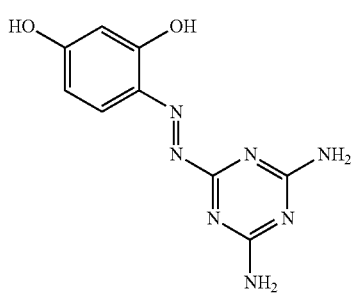
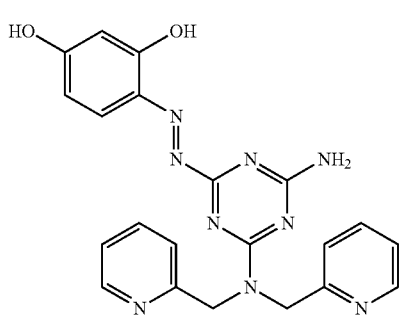
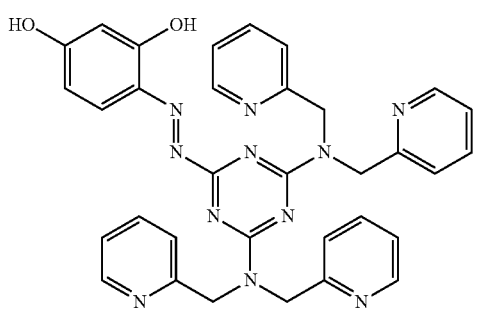
70
-continued
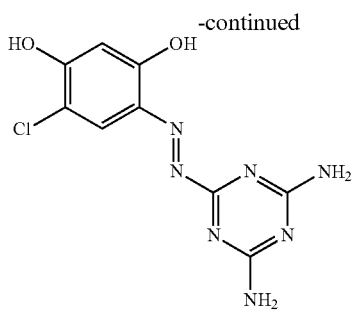
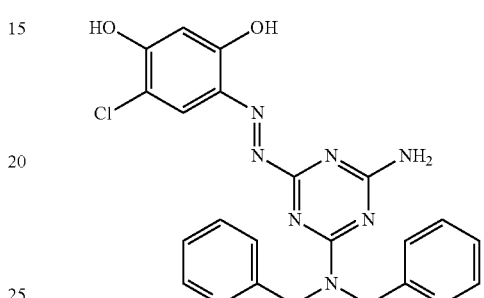
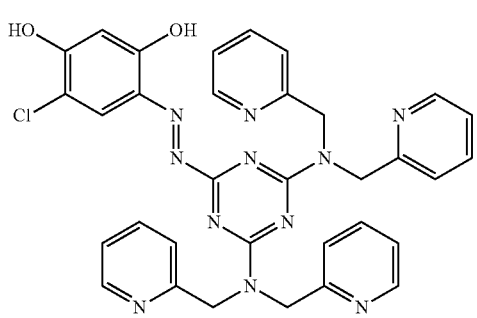
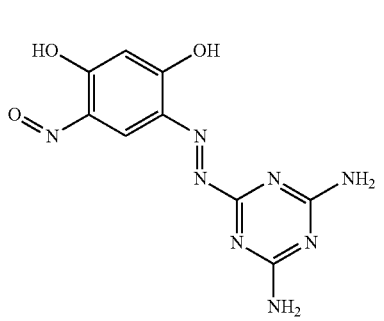
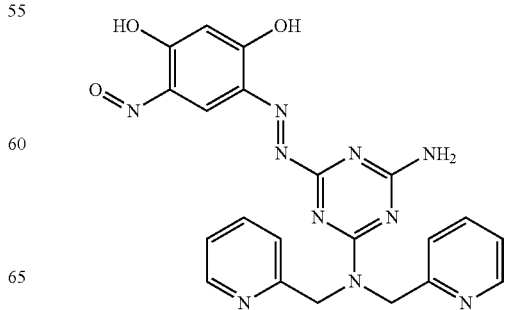

71
-continued
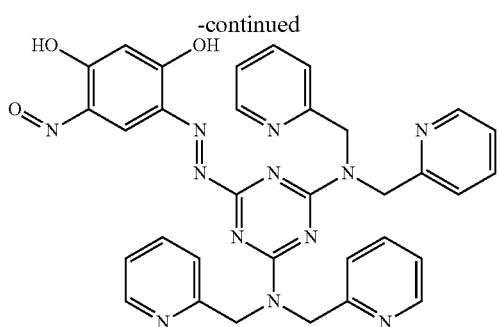
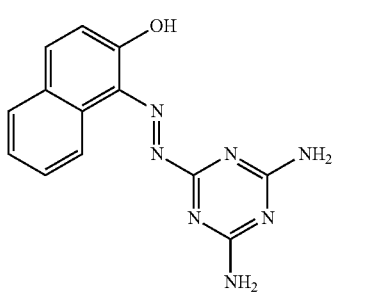
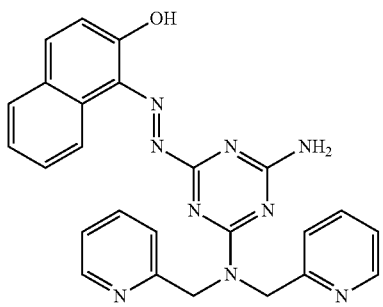
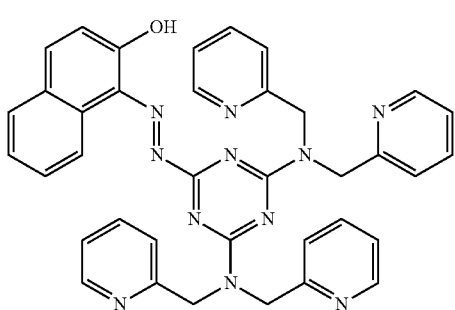
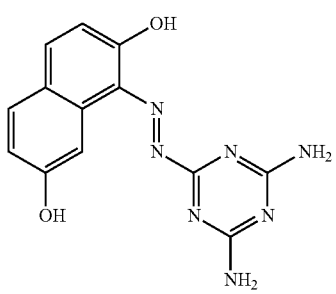
72
-continued
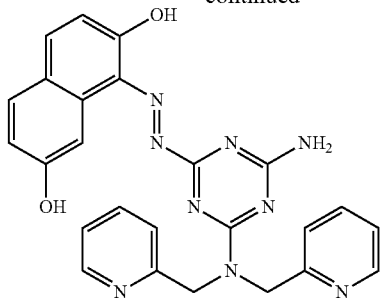
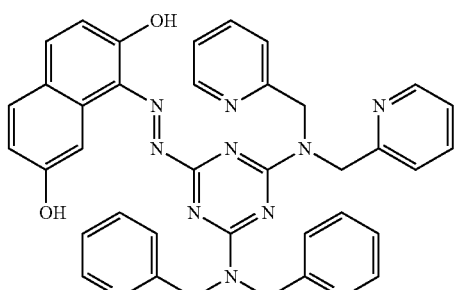
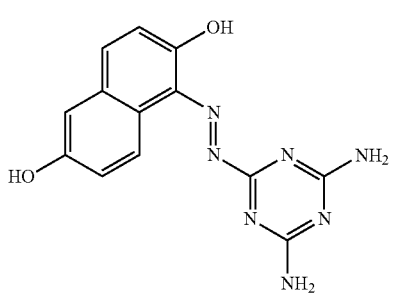
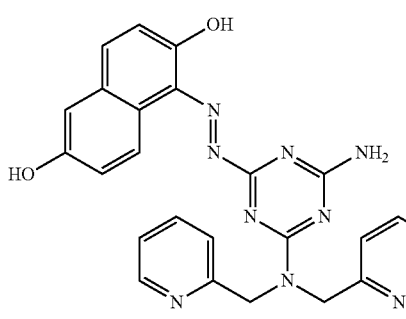
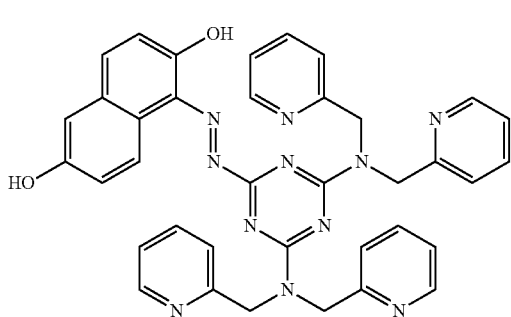

73
-continued
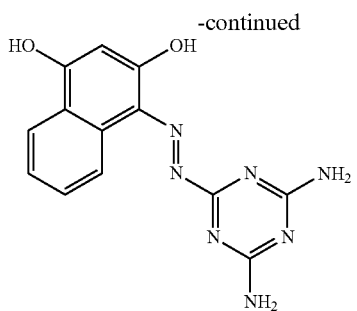
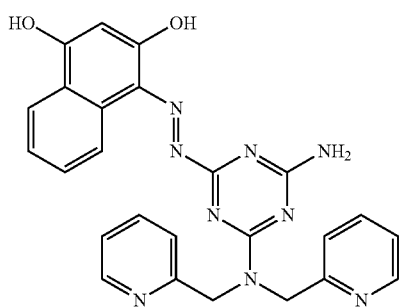
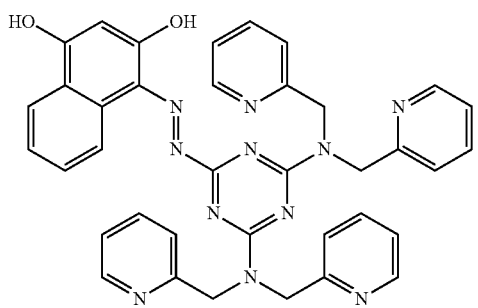
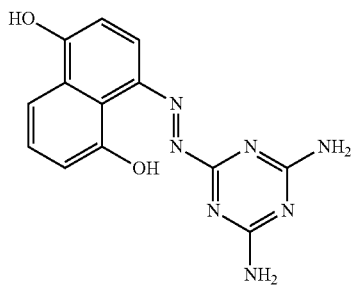
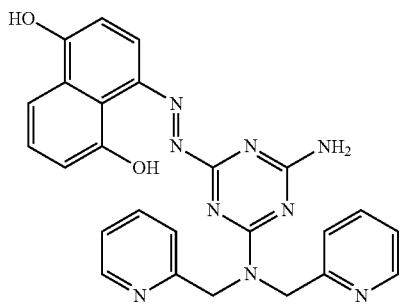
74
-continued
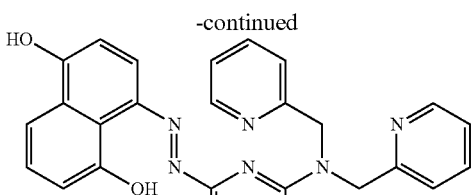
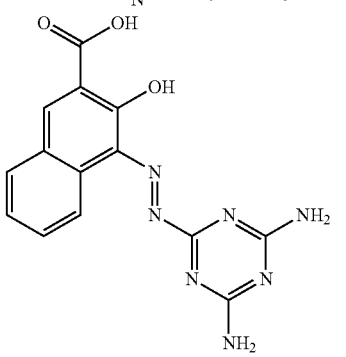
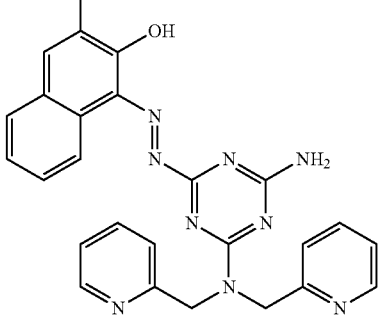
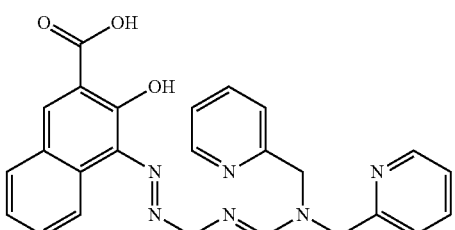
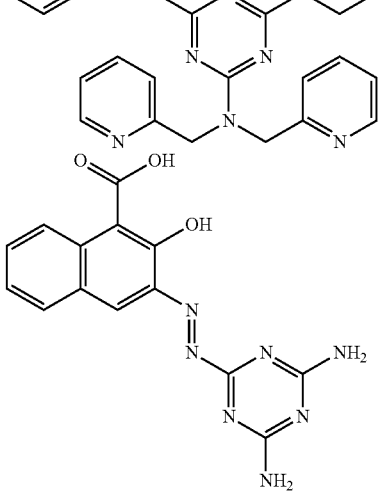

-continued

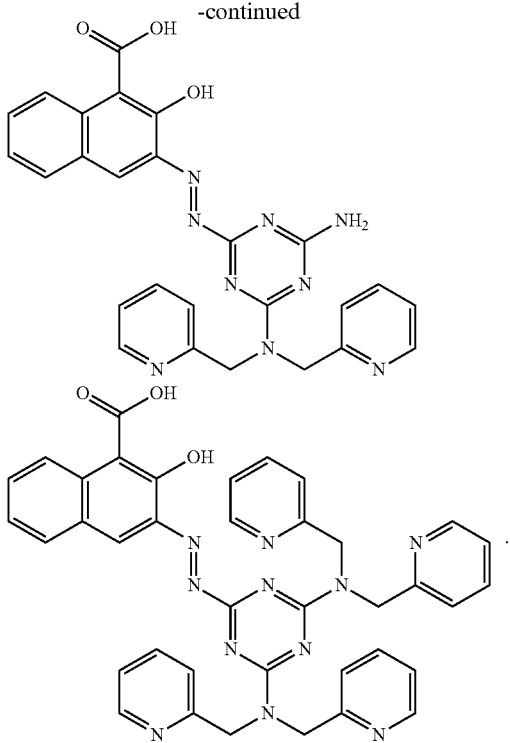

Other aspects of the disclosure will become apparent by consideration of the detailed description and accompanying drawings.

DETAILED DESCRIPTION

Figure 1A:
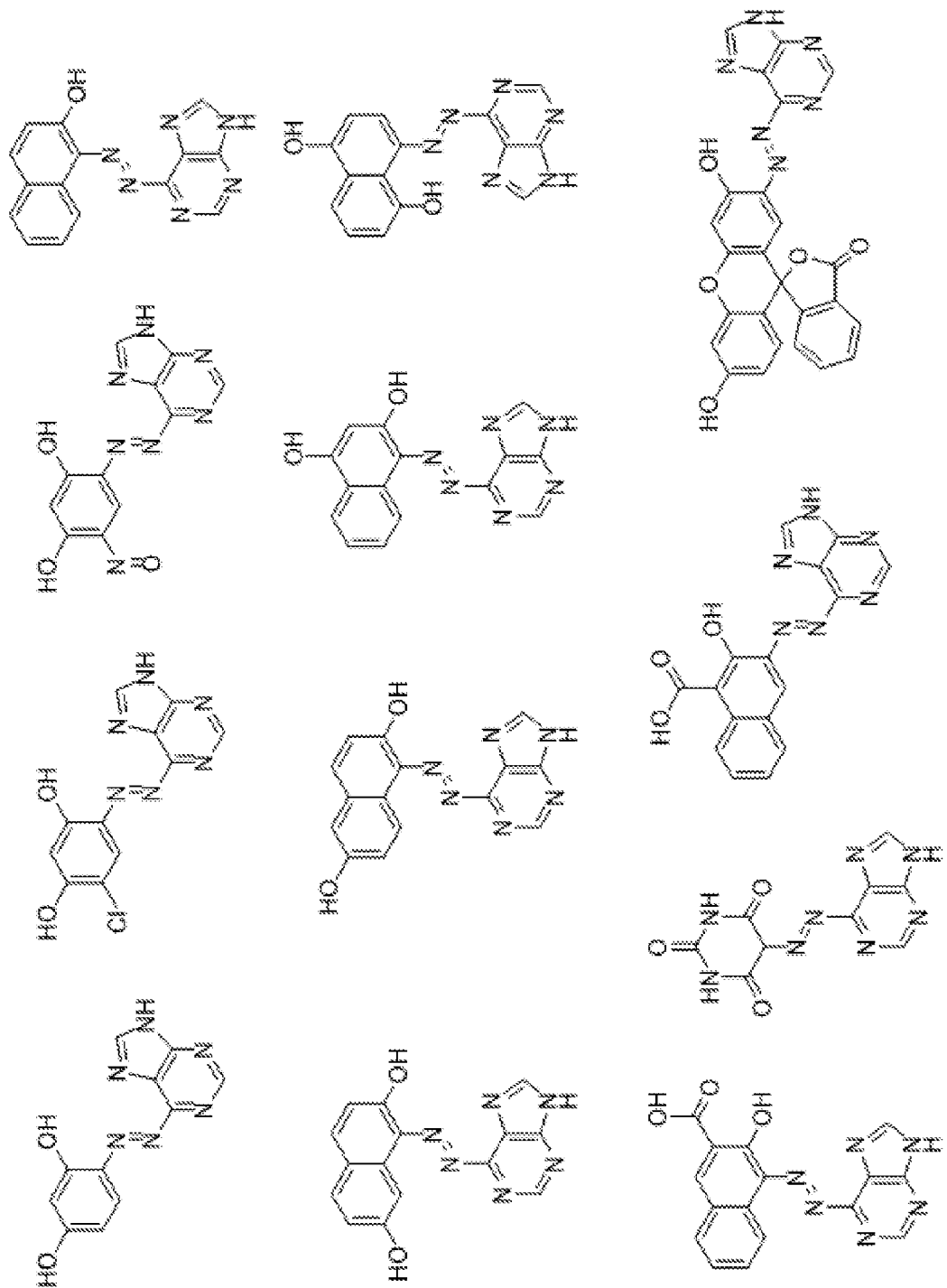
FIG. 1 are structures of various dyes.
Figure 1B:
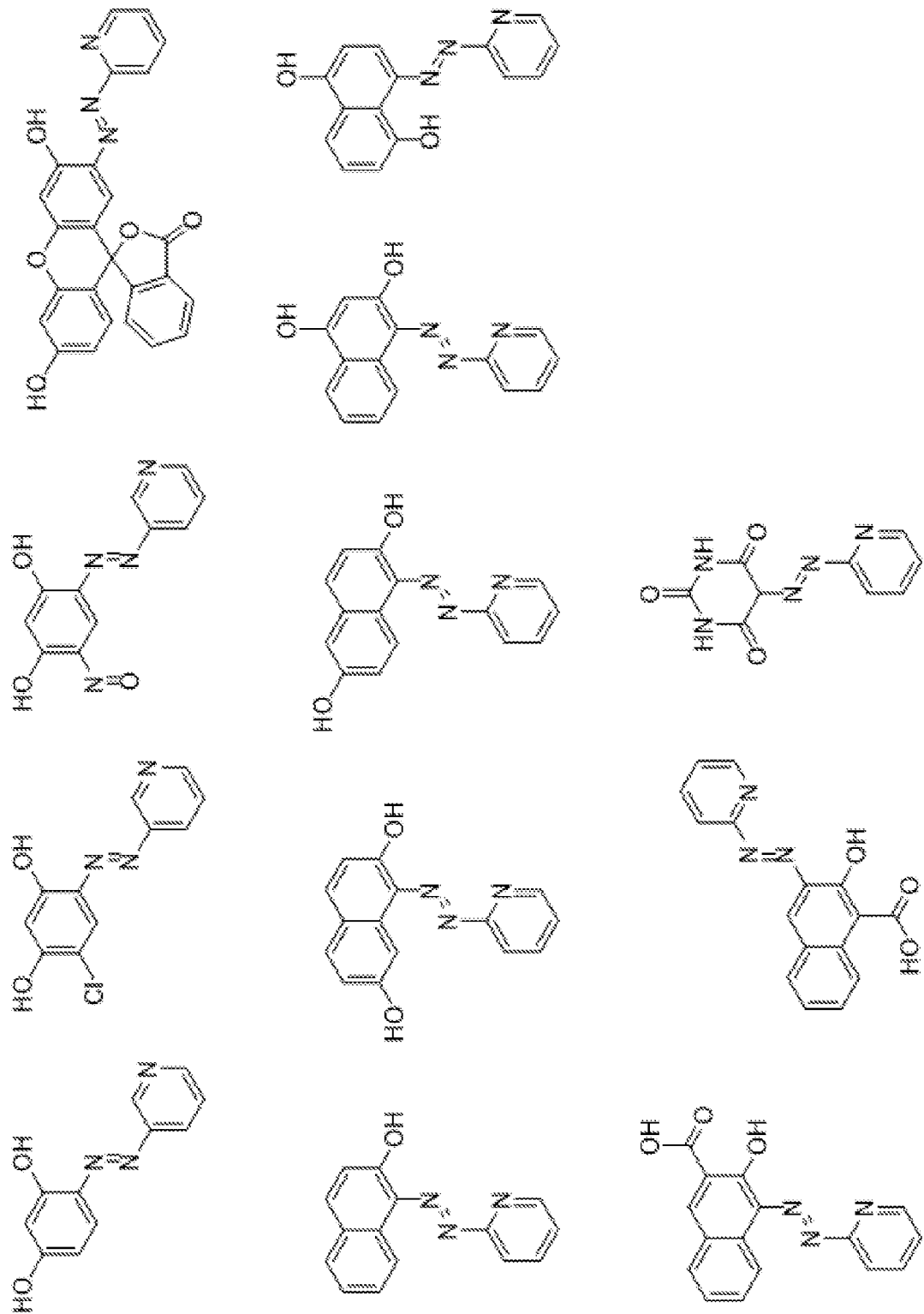
Figure 1C:
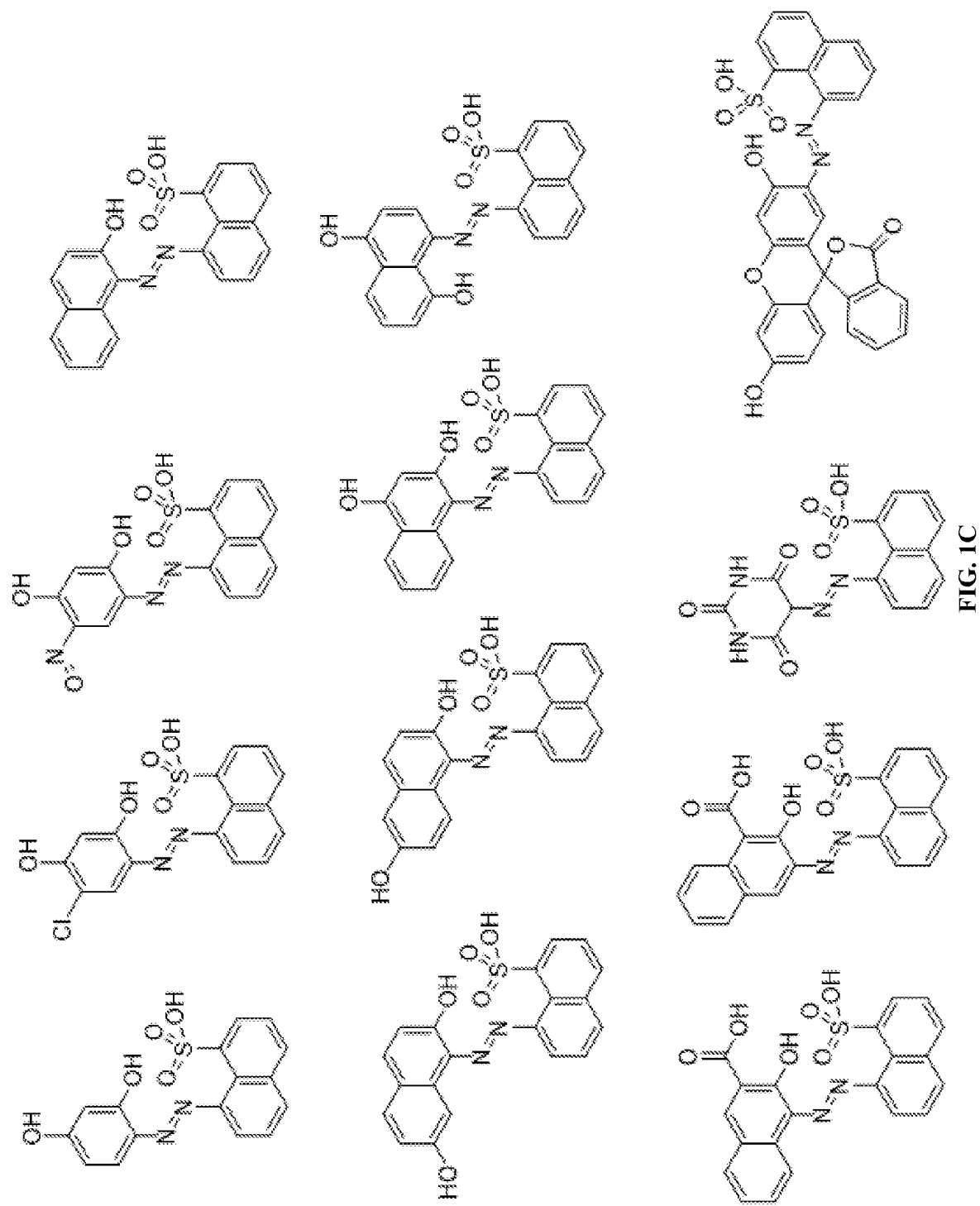
Figure 1D:
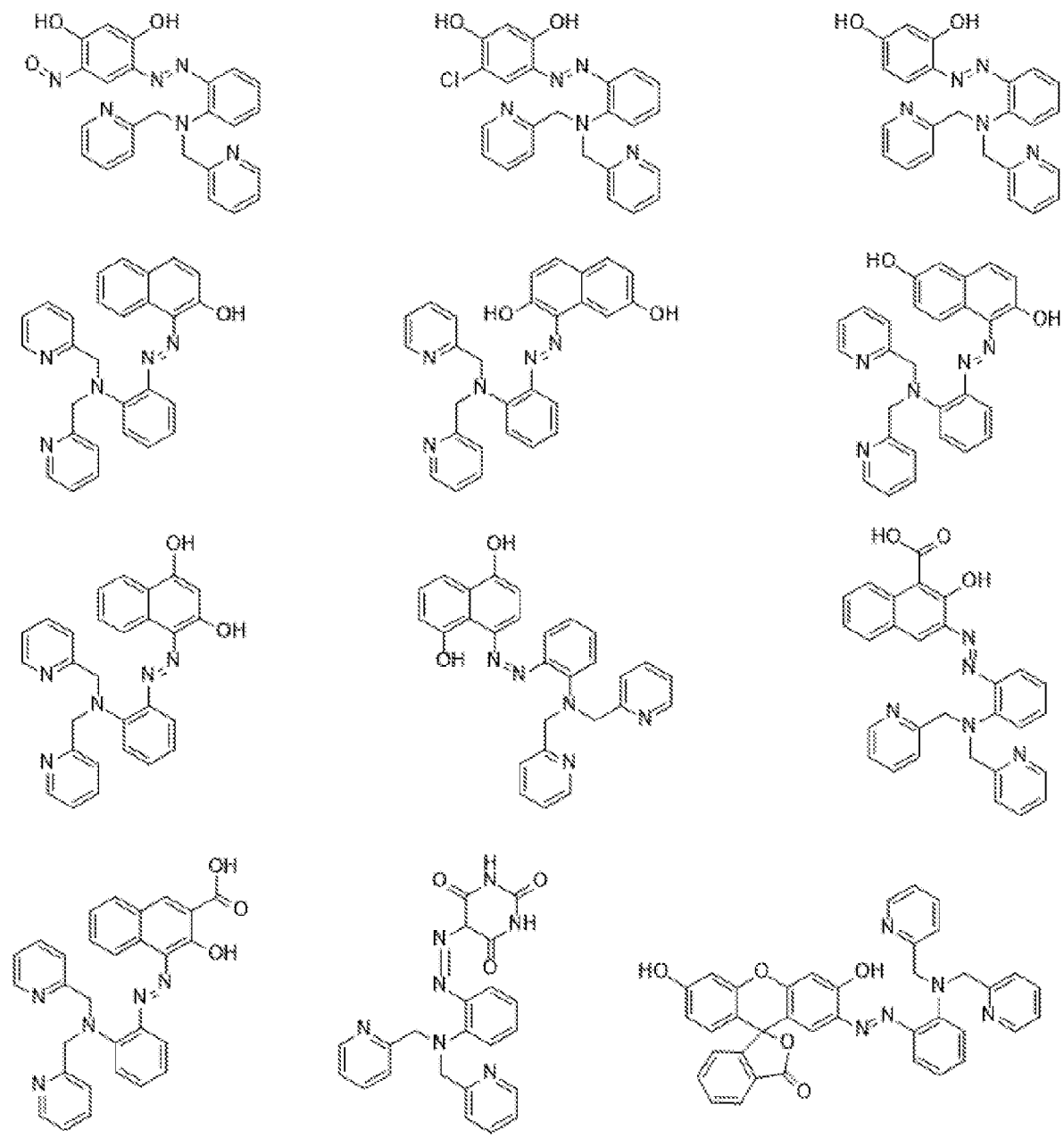
Figure 1E:
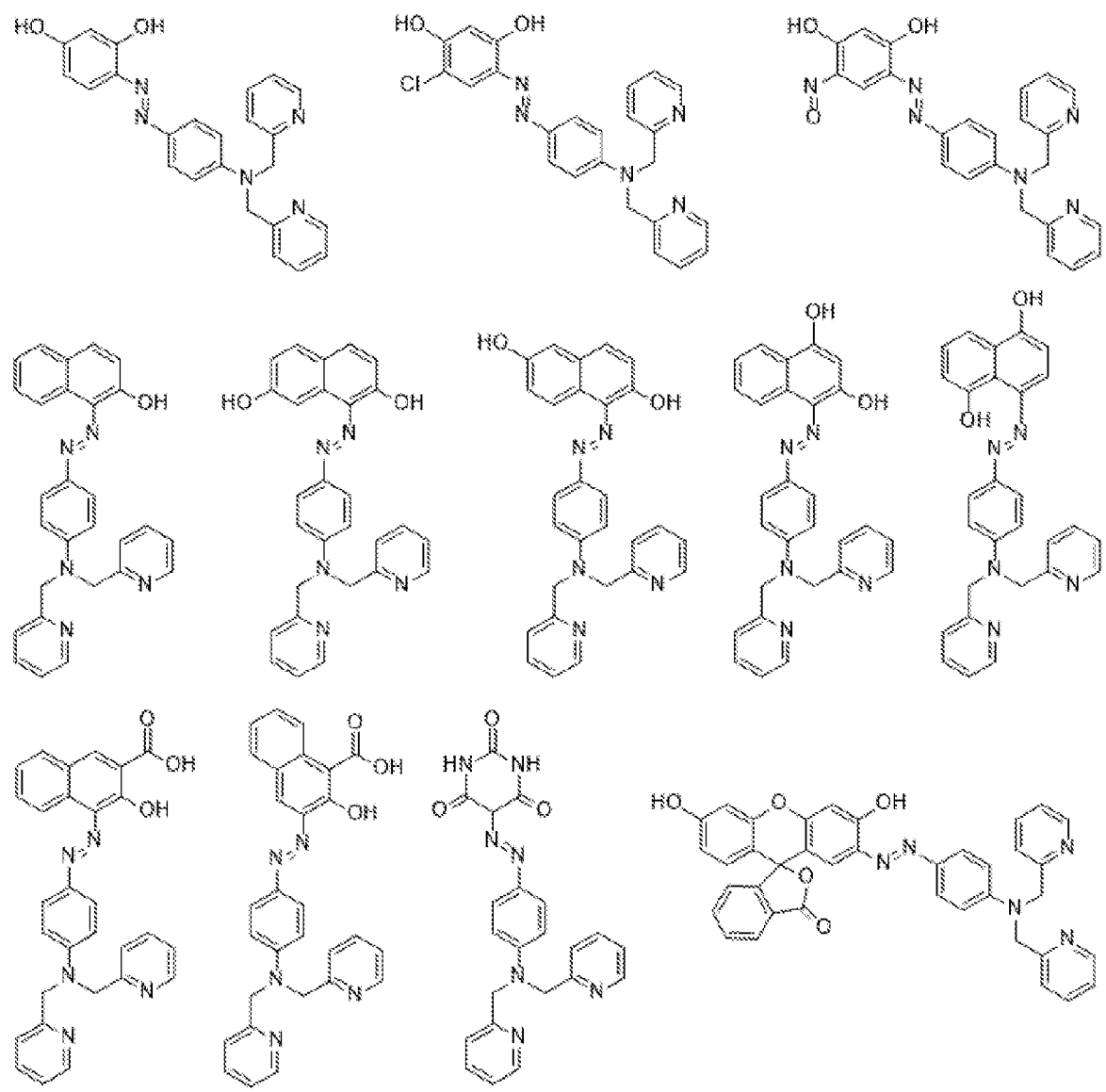
Figure 1F:
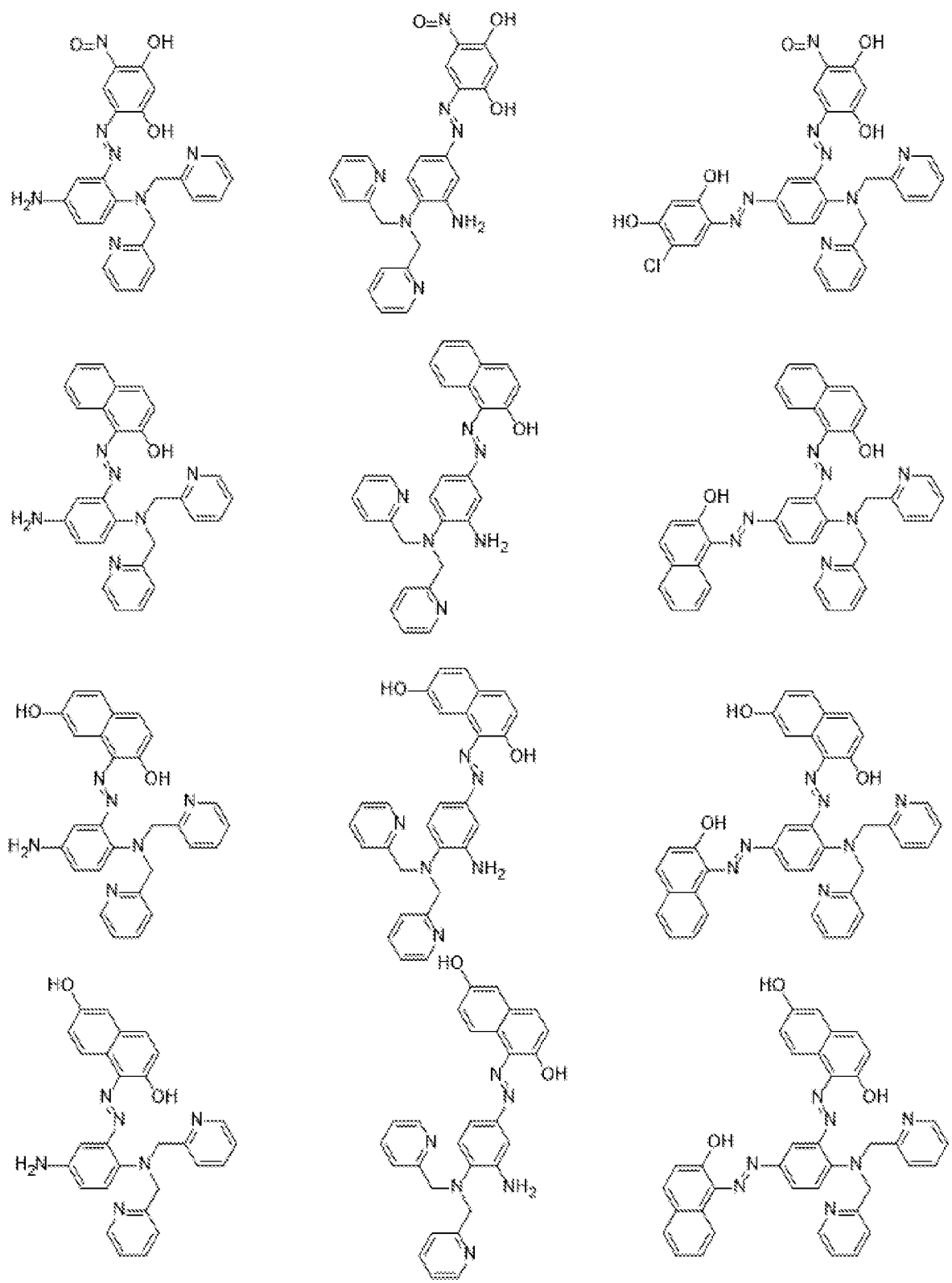
Figure 1G:
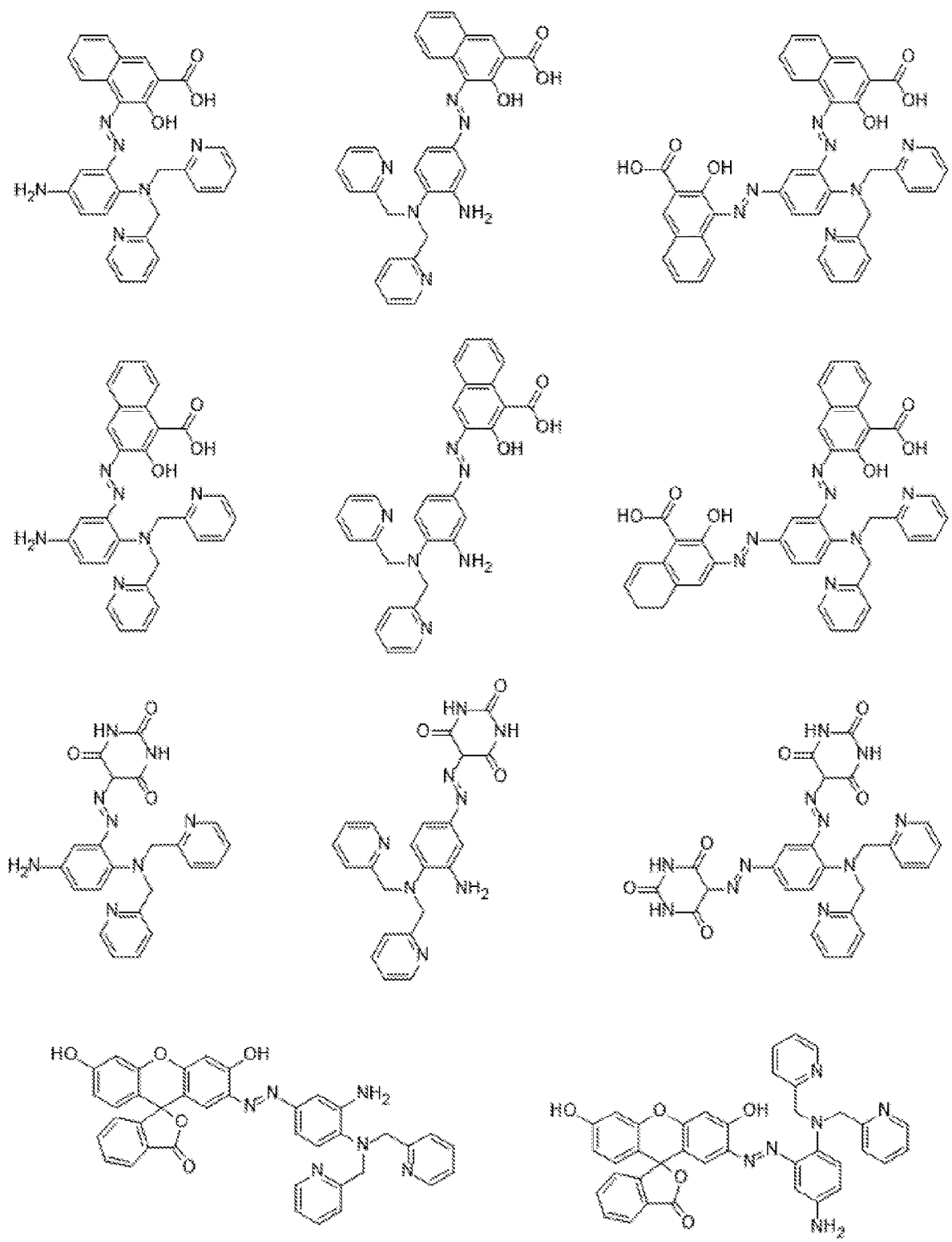
Figure 1H:
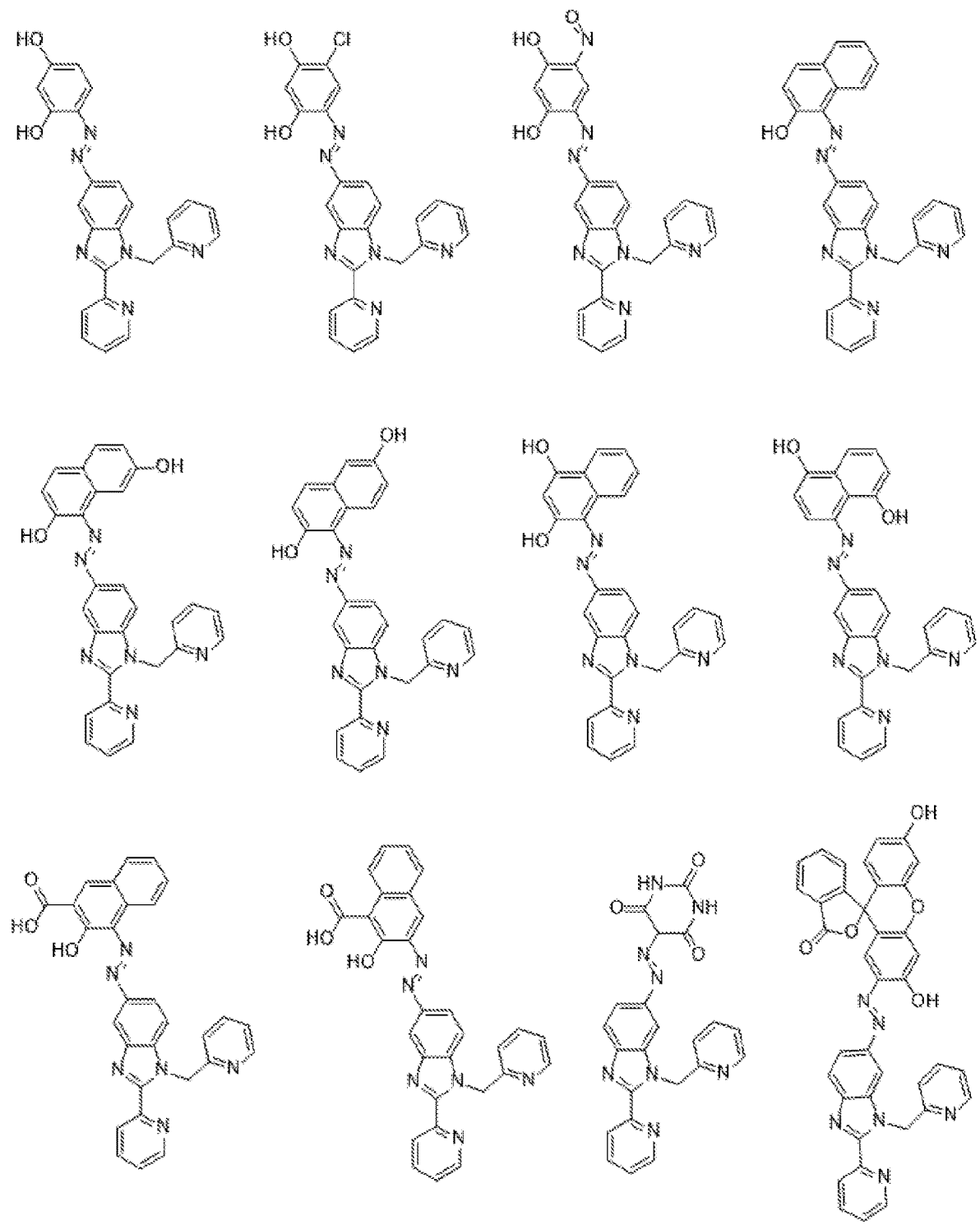
Figure 1I:
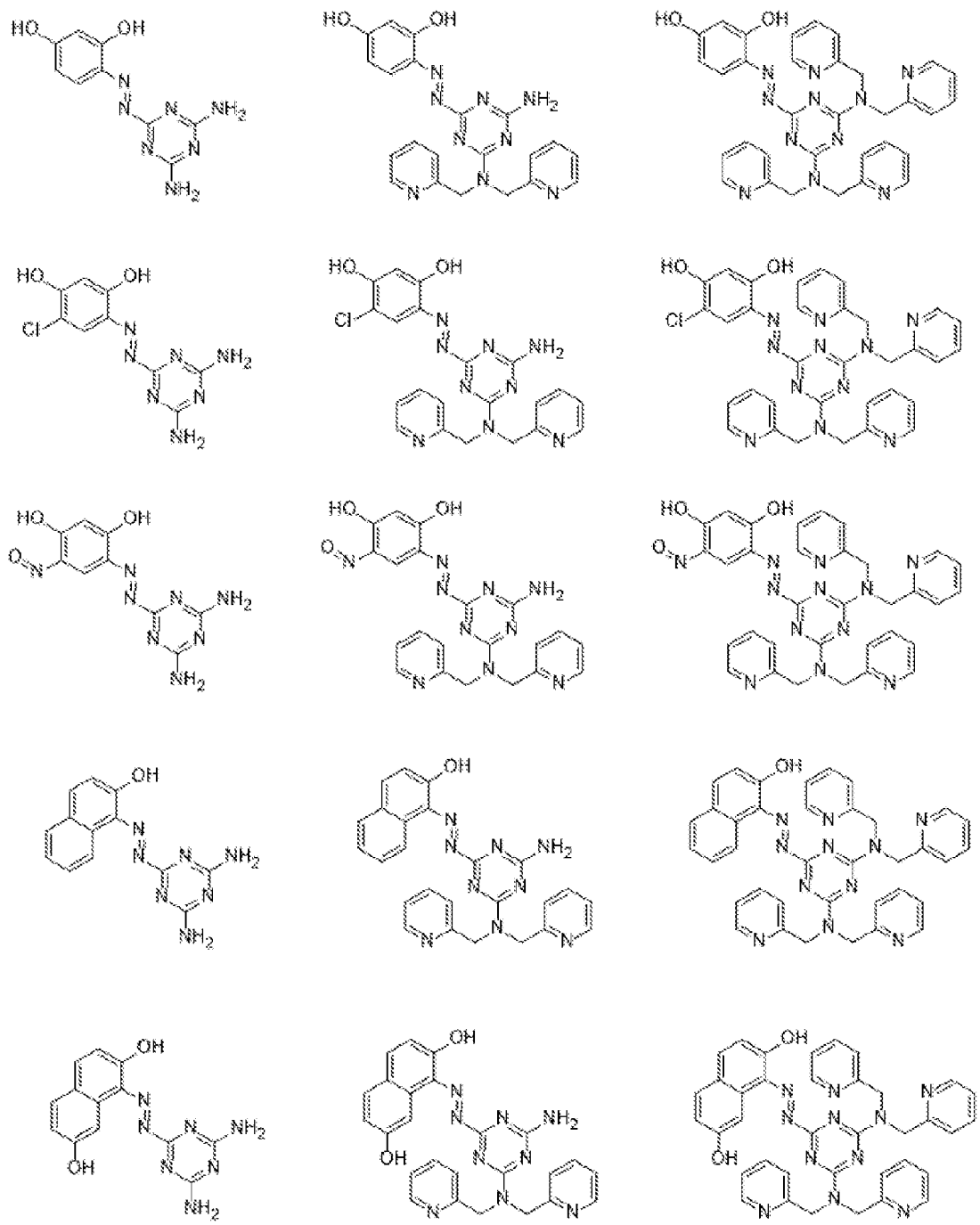
Figure 1J:
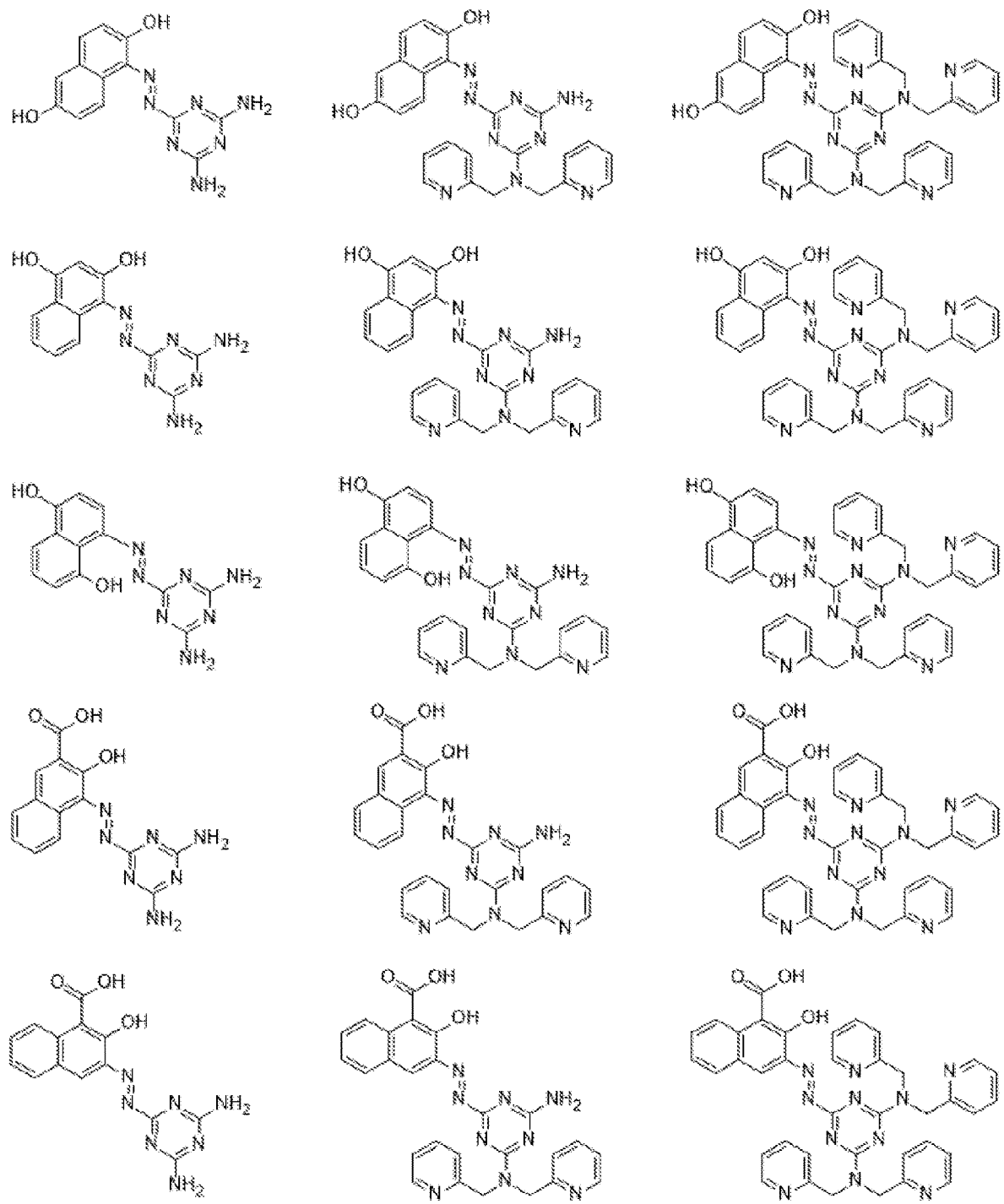

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

In one embodiment this disclosure describes the composition of a family of chemosensors that change optically in the presence of specific metal ions in aqueous or non-aqueous environments. In an embodiment this disclosure describes chemosensors for metal ions in aqueous or non-aqueous environments that are sensitive to changes in metal ion concentration, reusable, repeatable, and can be covalently attached to other materials. In an embodiment this disclosure describes methods of synthesizing a family of chemosensors for metal ions in aqueous environments. In an embodiment this disclosure describes a method comprising detecting metal ions in aqueous or non-aqueous solutions in real time. In an embodiment this disclosure describes a method for attaching chemosensors for metal ions to a substrate that fixes the sensor in space so that it is not dissolved or washed away and can be used for continuous measurement. In another embodiment this disclosure describes a method of templating in which polymerizable chemosensor molecules associate with their analyte before and during polymerization, followed by removal of analyte to provide proper geometric configuration for binding of analytes to be detected in samples. In an embodiment this disclosure describes a measurement platform that can detect multiple metal ions in analyte solution simultaneously in real time through any number of electronic apparatus that emit light of known wavelengths and measure optical absorption and/or emission changes from dyes bound to a semipermeable substrate. In so doing, said platform is capable of measuring the concentration of multiple metal ions continuously, with high precision and accuracy for months at a time. In an embodiment a chemosensor synthesized and used as described herein may have several behavioral improvements over the free dye analog including reduced light scatter and more stable response over a wider pH range. In an embodiment, this disclosure describes covalently-attached dyes that have enhanced metal-ion-binding properties compared to the same dyes in solution, showing that the novel structure of the covalently linked dye and substrate provides improved functionality.

The dyes and sensors detailed herein enable real-time monitoring of metal ions, creating a robust and portable measurement system for laboratory and field deployment that provides high precision and accuracy for multiple analytes with detection limits appropriate for the requirements of envisioned applications, while offering significant cost advantages compared to existing laboratory-based systems.

I. Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "acyl" or "carbonyl" refers to the group —C(O)R wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted, e.g., with one or more substituents. For example, when R is alkyl, such a group may be referred to as an alkylcarbonyl group.

The term "alkoxy" refers to the group —O—R wherein R is alkyl, alkenyl, alkynyl, cycloalkyl or heterocyclyl, any of which may be optionally substituted, e.g., with one or more substituents.

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "amino acid" refers to molecules containing an amine group, a carboxylic acid group and a side chain that varies between different amino acids. Amino acids are well known to those skilled in the art. Amino acids include alpha-amino acids of the general formula $H_2NCHRCOOH$, where R is an amino acid side chain comprising an organic substituent, as well as uniquely structured amino acids such as, for example, proline. Amino acids include, for example, isoleucine, leucine, alanine, asparagine, glutamine, lysine, aspartic acid, glutamic acid, methionine, cysteine, phenylalanine, threonine, tryptophan, glycine, valine, proline, serine, tyrosine, arginine, histidine, norleucine, ornithine, taurine, selenocysteine, selenomethionine, lanthionine, 2-aminoisobutyric acid, dehydroalanine, hypusine, citrulline, 3-aminopropanoic acid, gamma-aminobutryic acid, and the like. Accordingly, the term "amino acid side chain" refers to the various organic substituent groups (e.g., "R" in $H_2NCHRCOOH$) that differentiate one amino acid from another. A "derivative" of an amino acid side chain refers to an amino acid side chain that has been modified structurally (e.g., through chemical reaction to form new species, covalent linkage to another molecule, etc.). The terms "amino acid" and "amino acid side chain" refer to both natural and unnatural amino acids.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl. An aromatic amine is an aryl group substituted with one or more amino groups. An aromatic alcohol is an aryl group substituted with one or more hydroxyl groups. Both aromatic amines and aromatic alcohols may be further substituted with other substitutents.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "carboxyl" refers to the group —C(=O)OR, wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl any of which may be optionally substituted, e.g., with one or more substituents.

The term "carbonylamino" or "amido" refers to the group —C(O)NR'R" wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, or R' and R", together with the nitrogen to which they are attached, may form a ring. The groups R' and R" may be optionally substituted, e.g., with one or more substituents, or when R' and R" together with the nitrogen to which they are attached form a ring, the ring may be optionally substituted, e.g., with one or more substituents.

The term "cycloalkyl" as used herein refers to nonaromatic, saturated or partially unsaturated cyclic, bicyclic, tricyclic or polycyclic hydrocarbon groups having 3 to 12 carbons (e.g., 3, 4, 5, 6, or 7 carbon atoms). Any ring atom can be substituted (e.g., with one or more substituents). Cycloalkyl groups can contain fused rings. Fused rings are rings that share one or more common atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O— alkyl radical. The term "aryloxy" refers to an —O-aryl radical. The term "haloalkoxy" refers to an —O-haloalkyl radical.

The term "phosphonate" refers to the group —C(P=O)(OR')(OR") wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, or R' and R", together with the oxygens to which they are attached, may form a ring. The groups R' and R" may be optionally substituted, e.g., with one or more substituents, or when R' and R" together with the nitrogen to which they are attached form a ring, the ring may be optionally substituted, e.g., with one or more substituents.

The term "thioamido" refers to the group —C(S)NR'R" wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, or R' and R", together with the nitrogen to which they are attached, may form a ring. The groups R' and R" may be optionally substituted, e.g., with one or more substituents, or when R' and R" together with the nitrogen to which they are attached form a ring, the ring may be optionally substituted, e.g., with one or more substituents.

The term "linker" refers to a carbon chain that covalently attaches two chemical groups together and optionally can self-cleave, which chain is optionally interrupted by one or more nitrogen atoms, oxygen atoms, carbonyl groups, (substituted) aromatic rings, or peptide bonds. In some embodiments, the linker may be a chain of from 1 to 20 member atoms selected from carbon, oxygen, sulfur, nitrogen and phosphorus. In some embodiments, the linker contains a polyethylene glycol moiety. In some embodiments the linker is L is a divalent linker comprising 10 to 10 member atoms independently selected from carbon, nitrogen and oxygen, wherein at least one member atom is nitrogen or oxygen. In some embodiments, the linker has the formula, —OC(O)NH—$(CH_2CH_2O)_n$—$CH_2CH_2$—NH—C(O)—, wherein n is 2 to 4. The linker may be a straight chain or branched. In some embodiments, the linker is a free-radical polymerizable moiety.

The linker may also be substituted with one or more substituents including, but not limited to, halo groups, perfluoroalkyl groups, perfluoroalkoxy groups, alkyl groups, such $C_{1-4}$ alkyl, alkenyl groups, such as $C_{1-4}$ alkenyl, alkynyl groups, such as $C_{1-4}$ alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, —NH—$NH_2$; =N—H; =N-alkyl; —SH; —S-alkyl; —NH—C(O)—; —NH—C(=N)— and the like.

The term "substituent" refers to a group "substituted" on an alkyl, alkenyl, alkynyl, cycloalkyl, heterocyclyl, aryl, arylalkyl or heteroaryl group at any atom of that group. Suitable substituents include, without limitation: acyl, acylamido, acyloxy, alkoxy, alkyl, alkenyl, alkynyl, amido, amino, carboxy, carboxyamino, cyano, cycloalkyl, ester, halo, heterocyclyl, hydroxy, imino, nitro, oxo (e.g., C=O), phosphonate, sulfinyl, sulfonyl, sulfonate, sulfonamino, sulfonamido, thioamido, thiol, thioxo (e.g., C=S), aryl, heteroaryl, and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et, and Ph represent methyl, ethyl and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulas herein to depict the bond that is the point of attachment of the moiety or substituent to the core or backbone structure.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

The terms "control," "reference level," and "reference" are used herein interchangeably. The reference level may be a predetermined value or range, which is employed as a benchmark against which to assess the measured result. The predetermined level may be from a subject or a group or a composition of known metal ion concentration. "Control group" as used herein refers to a group of control samples. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (Time-dependent ROC curves for censored survival data and a diagnostic marker, Biometrics 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a metal ion may be defined in accordance with standard practice.

"Polymer" refers to a synthetic or natural polymer. Synthetic polymers include plastic. Examples of synthetic polymers include, for example, poly(lactide), poly(lactide-co-glycolide) (PLGA) of varying ratios, polystyrene, poly(glycolide), poly(acrylate)s, poly(methyl methacrylate), poly(hydroxyethyl methacrylate), poly(vinyl alcohol), poly(carbonate), poly(ethylene-co-vinyl acetate), poly(anhydride), poly(ethylene), poly(propylene), poly(hydroxybutyrate), poly(hydroxyvalerate), poly(urethane)s, poly(ether urethane), poly(ester urethane), poly(arylate), poly(imide), poly(anhydride-co-imide), poly(aminoacids) and poly(phosphazene). Examples of natural polymers include, for example, cellulose, polysaccharides, polypeptides, polynucleotides.

"Sample" or "test sample" as used herein can mean any sample in which the presence and/or level of a metal ion or metal ions is to be detected or determined. Samples may include liquids, solutions, emulsions, or suspensions in a fully contained vessel or in a flowing stream. Solutions may include aqueous or non-aqueous solutions. Samples may also include reactions. Examples of samples include environmental waters, untreated industrial waste water, treated industrial waste water, drinking water, municipal waste water or where ever liquids containing metal ions are present. Under the Clean Water Act of 1972, industrial waste water must be treated in such a way that metal concentrations are below regulated limits. Treated waste water is discharged from electroplaters, printing ink manufacturers, paint and coating manufacturers, textile and fabric finishers, iron and steel foundries, nonferrous foundries, leather tanning and finishing, petroleum refining, industrial launderers, battery manufacturers, pulp and paper mills, metal finishers and many other businesses called out in the Act.

II. Compounds

In an embodiment, the disclosure provides azo dyes, particularly those with much variation in the functional groups placed to ligate metals, the ring sizes of formed metallocycles, steric features restricting such ligation, extra ligating atoms, and substituents that vary pKa (electron donating and withdrawing groups, as well as solvating groups) and spectral effects (conjugation).

In one embodiment, the disclosure provides a compound according to Formula I:

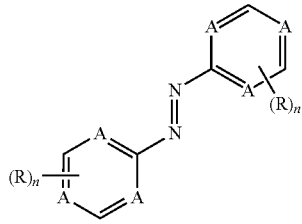

(I)

wherein each R is independently selected from the group consisting of OH, H, $OR_1$, $C_{1-4}$ alkyl, nitro, halo, and $NR_{N1}R_{N2}$, or two Rs may join together to form a 5, 6, or 7-membered ring, which may be aromatic or heteroaromatic;

each A is independently N or CH;

$R_{N1}$ and $R_{N2}$ are independently $C(O)R_2$, $C_{1-4}$ alkyl,

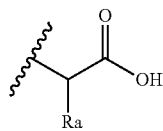

or H;

$R^a$ is an amino acid side chain;

$R_1$ is $C_{1-4}$ alkyl or $C_{2-4}$ alkenyl;

$R_2$ is $C_{1-4}$ alkyl or $C_{2-4}$ alkenyl; and each n is independently an integer from 1 to 5.

In one embodiment, the disclosure provides a compound according to Formula II:

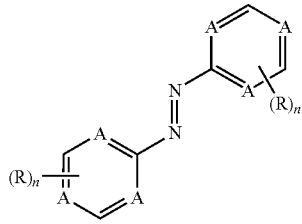

(II)

wherein each R is independently selected from the group consisting of OH, H, $OR_1$, $C_{1-4}$ alkyl, nitro, halo, $NR_{N1}R_{N2}$, $SO_3H$, $SO_2NHR_3$, $NHSO_2R_4$, carboxyl, amido, nitrile, —C(=N—OH)$R_3$, —C(=O)$NR_{N1}$OH, thioamido, phosphonate or two Rs may join together to form a 5, 6, or 7-membered ring, which may be aromatic or heteroaromatic, which may be substituted; each A is independently N, NO, CH, or $CR_5$;

$R_{N1}$ and $R_{N2}$ are independently $C(O)R_2$, heteroaryl, aryl, $C_{1-4}$ alkyl,

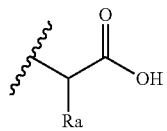

or H;

$R^a$ is an amino acid side chain;

each $R_1$ is independent $C_{1-4}$ alkyl, $C_{2-4}$ alkenyl, heteroaryl, or aryl;

each $R_2$ is independently $C_{1-4}$ alkyl, $C_{2-4}$ alkenyl, heteroaryl, or aryl;

each $R_3$ is independently H, $C_{1-4}$ alkyl, heteroaryl, aryl, cycloalkyl, or heterocyclyl;

each $R_4$ is independently H, $C_{1-4}$ alkyl, heteroaryl, aryl, cycloalkyl, or heterocyclyl;

each $R_5$ is independently H, $C_{1-4}$ alkyl, heteroaryl, aryl, cycloalkyl, or heterocyclyl; and each n is independently an integer from 1 to 5.

In one embodiment, the disclosure provides a compound according to Formula III:

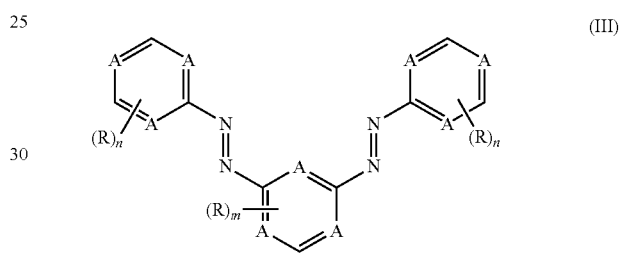

(III)

wherein each R is independently selected from the group consisting of OH, H, $OR_1$, $C_{1-4}$ alkyl, nitro, halo, $NR_{N1}R_{N2}$, $SO_3H$, $SO_2NHR_3$, $NHSO_2R_4$, carboxyl, amido, nitrile, —C(=N—OH)$R_3$, —C(=O)$NR_{N1}$OH, —$SR^5$, thioamido, phosphonate or two Rs may join together to form a 5, 6, or 7-membered ring, which may be aromatic or heteroaromatic, which may be substituted;

each A is independently N, NO, CH, or $CR_5$;

$R_{N1}$ and $R_{N2}$ are independently $C(O)R_2$, heteroaryl, aryl, $C_{1-4}$ alkyl,

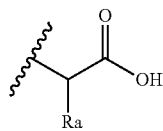

or H;

$R^a$ is an amino acid side chain;

each $R_1$ is independent $C_{1-4}$ alkyl, $C_{2-4}$ alkenyl, heteroaryl, or aryl;

each $R_2$ is independently $C_{1-4}$ alkyl, $C_{2-4}$ alkenyl, heteroaryl, or aryl;

each $R_3$ is independently H, $C_{1-4}$ alkyl, heteroaryl, aryl, cycloalkyl, or heterocyclyl;

each $R_4$ is independently H, $C_{1-4}$ alkyl, heteroaryl, aryl, cycloalkyl, or heterocyclyl;

each $R_5$ is independently H, $C_{1-4}$ alkyl, heteroaryl, aryl, cycloalkyl, or heterocyclyl;

each n is independently an integer from 1 to 5; and each m is independent an integer from 1 to 4.

In an embodiment, the compound of Formula (I), (II), (III), or (IV) is not 4-(2-pyridylazo)rescorinol (PAR). In an embodiment, the compound of Formula (I), (II), (III), or (IV) is not 4-(quinolin-8-yldiazenyl)benzene-1,3-diol (QAR).

In an embodiment, the disclosure provides a compound of Formula (IV),

A-B (IV)

wherein A is selected from the group consisting of:

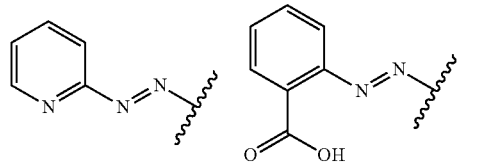

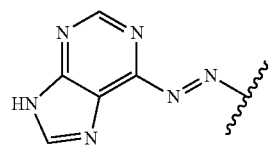

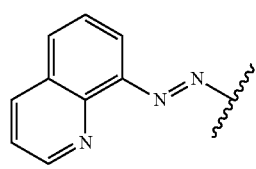

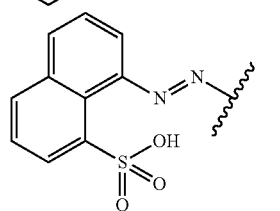

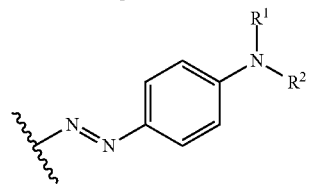

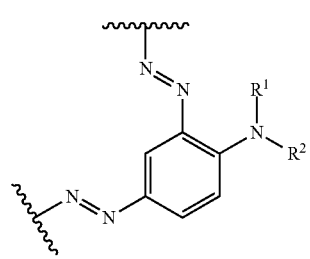

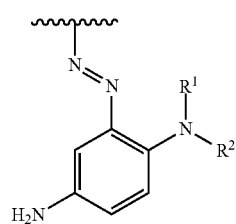

-continued

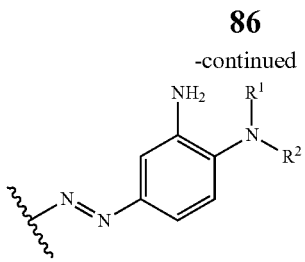

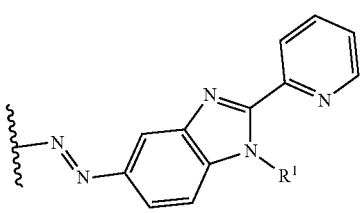

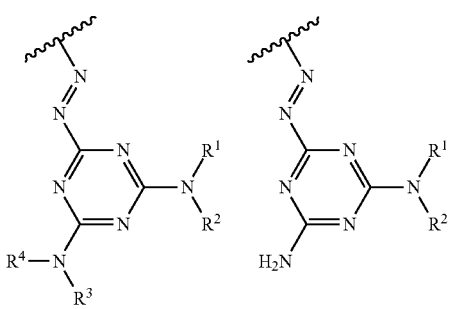

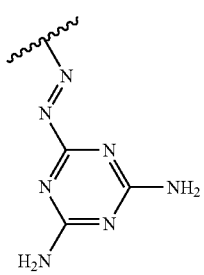

wherein $R^1$, $R^2$, $R^3$ and $R^4$ are independently selected from:

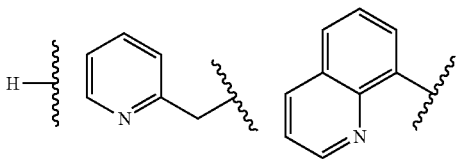

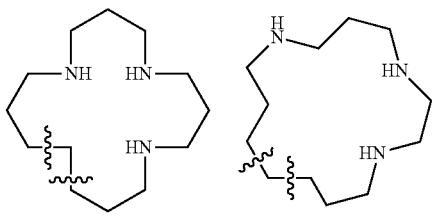

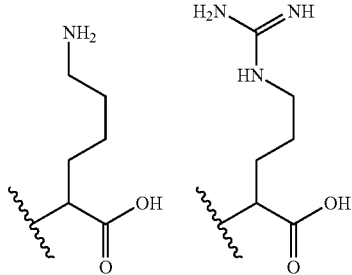
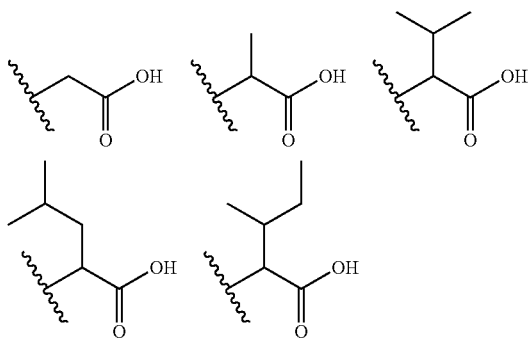
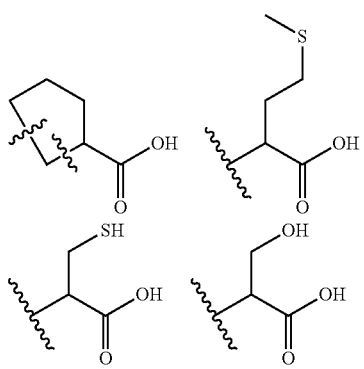
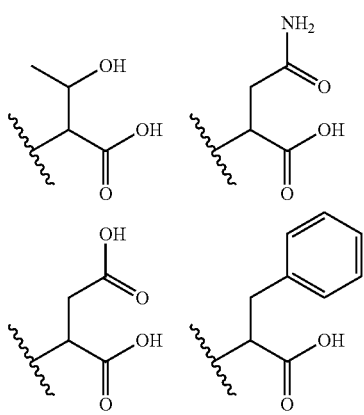
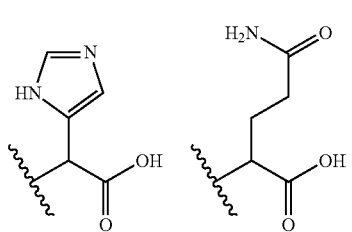
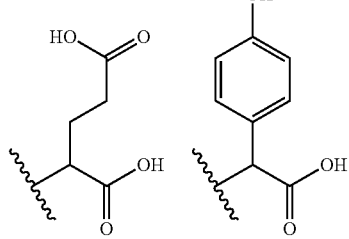
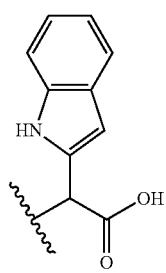
and B is selected from the group consisting of
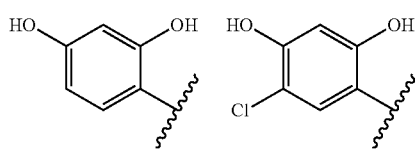
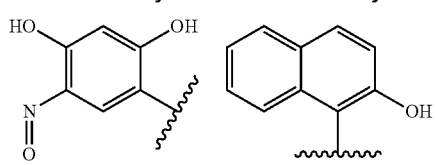
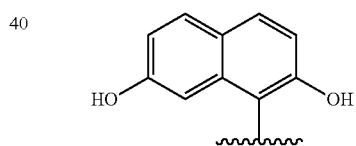
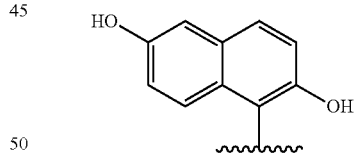
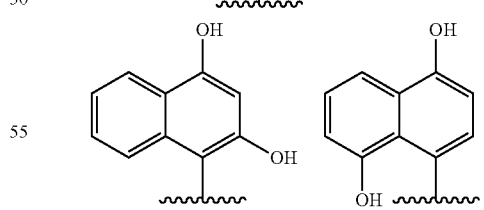
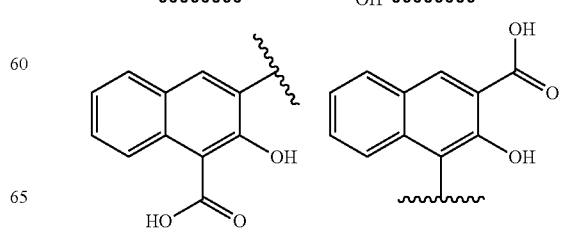

-continued

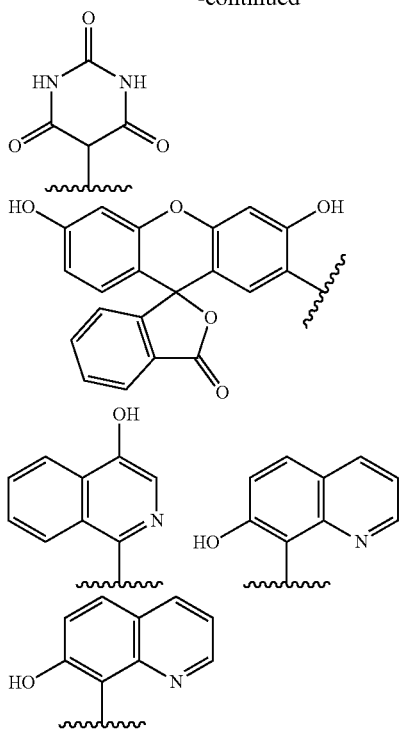

Suitable dyes include those shown in FIG. 1A-FIG. 1J.

In an embodiment, the disclosure provides a metal ion complex comprising a compound of Formula (I), (II), (III), or (IV) and a metal ion. In some embodiments, the metal ion is a heavy metal, zinc, chromium, cadmium, nickel, copper, arsenic, or mercury. In some embodiments, more than one compound of Formula (I), (II), (III), or (IV) is complexed to the metal ion.

In an embodiment, the present disclosure provides a compound of Formula (I), (II), (III), or (IV) or a metal ion complex comprising a compound of F Formula (I), (II), (III), or (IV) and a metal ion, wherein the compound or metal ion complex is further conjugated to a solid support, such as cellulose, film, optical fiber, polymethylmethacrylate, or microspheres. The compound may be conjugated via a linker.

In an embodiment, two Rs form a heteroaromatic ring, such as a nitrogen-containing heteroaromatic ring. In certain embodiment, the heteroaromatic ring may contain 6 member atoms and from 1-3 heteroatoms selected from nitrogen, sulfur and oxygen.

In an embodiment, at least one R is $NR_{N1}R_{N2}$. In certain embodiments, at least one of $R_{N1}$ and $R_{N2}$ is —($CH_2$)-heteroaryl. In certain embodiments, both of $R_{N1}$ and $R_{N2}$ are —($CH_2$)-heteroaryl. In certain embodiments, the heteroaryl is a nitrogen-containing heteroaryl, such as a 6-membered heteroaryl, such as pyridinyl, e.g. 2-pyridinyl.

In some embodiments, the compound has binding affinities to metal ions suitable for quantifying the metal ion concentration in the about 50 nano-molar to about 200 micro-molar range. In embodiments, the affinity may be at least about 50 nano-molar, at least about 75 nano-molar, at least about 100 nano-molar, at least about 250 nano-molar, at least about 500 nano-molar, at least about 750 nano-molar, at least about 1 micro-molar, at least about 25 micro-molar, at least about 50 micro-molar, or at least about 100 micro-molar. In embodiments, the affinity may be less than about 200 micro-molar, less than about 150 micro-molar, less than about 100 micro-molar, less than about 50 micro-molar, less than about 25 micro-molar, less than about 1 micro-molar, less than about 750 nano-molar, less than about 500 nano-molar, or less than about 250 nano-molar. Affinity of the compound for a metal ion may be determined by any means known by one of skill in the art. In some embodiments, the compound has a binding affinity for more than one metal ion.

In the compounds described herein, the metal ion-binding variability may derive from the substituents' interactions with metal ions.

A. Synthesis of Compounds

As would be readily understood by those of ordinary skill in the art, azobenzene derivatives that bind metal ions and change their absorbance are prepared in several ways.

Azo-dyes according to the present disclosure may be prepared by azo coupling reaction between a diazonium ion and an electron rich aromatic. The diazonium may be derived from substituted 2-aminopyridine, 8-aminoquinoline, adenine, melamine, other heterocycles (particularly those with fused rings and 5, 6, and 7 ring sizes), N,N-disubstituted o-aminoaniline (where the substituents on N are preferentially chosen from those that ligate metals), and other 2-aminoaryl substituted ligands including those with amines, carboxylates, sulfonates, amides, ethers, thioethers, sulfoxides, sulfones, N-oxides, amino acid derived groups, phosphonates, crown ethers, and cryptands. These groups are also useful in other presentations such as in the 8 position of a 1-naphthylamine. Substitution for property perturbation includes alkyl, aryl, halogen, nitro, acyl, sulfonyl, ether, cyano, aza substitution of carbon, and other common functional groups.

Electron rich aromatic groups appropriate to coupling with these diazonium ions include substituted resorcinols, naphthols, 3-substituted phenols, anilines, barbituric acids, ferrocenes, and these compounds substituted with the groups specified above.

Standard acid mediated diazotization works for many anilines, but diazonium salts from electron poor anilines like 2-aminopyridine are better prepared by alkaline treatment with nitrite esters. When neither aryl group of the azo dye is sufficiently electron rich to allow azo coupling to a diazonium ion, the desired substance can be prepared by other methods including oxidation of a diarylhydrazine derived from nucleophilic aromatic substitution, or N—N coupling of two distinct N-substituted aryl species.

For example, some azobenzene-based sensors have been prepared by diazotization of an aniline derivative such as 2-aminopyridine, and coupling to an electron-rich aromatic compound such as resorcinol or 2-naphthol, leading to PAR and PAN respectively. Other azobenzene-based sensors may be synthesized by diazotization of a suitable aniline derivative, followed by coupling to an electron-rich aromatic compound as is shown below in Schemes 1 and 2.

Scheme 1

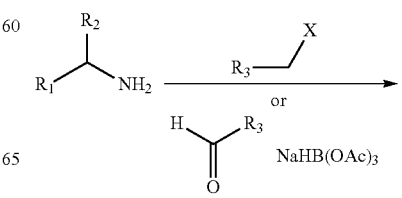

91

-continued

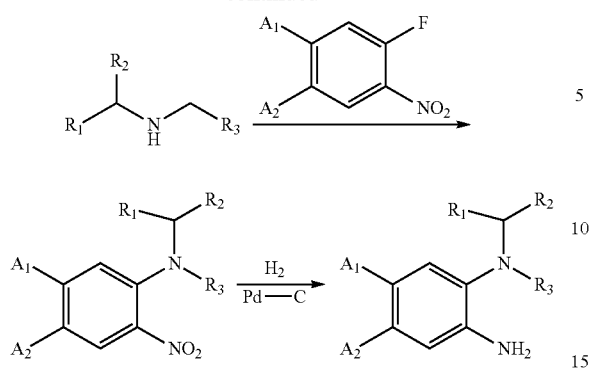

Scheme 2

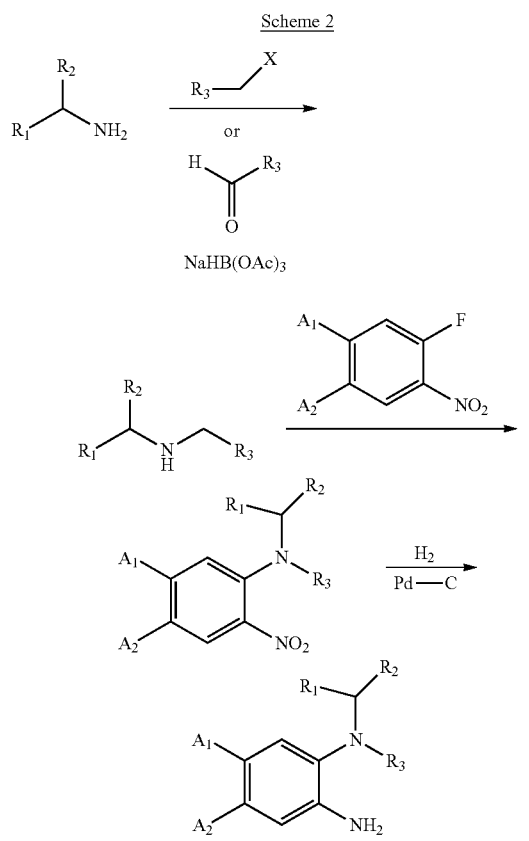

92

-continued

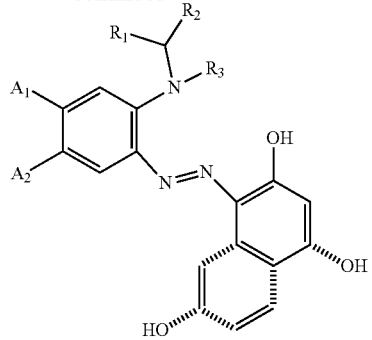

In Scheme 1, a versatile sequence leading to a new class of aniline derivatives begins by preparing a secondary amine by alkylation or reductive amination as shown. Alkylation or reductive amination provides to a secondary amine. Alternatively, nitrile or aldehyde hydrogenation in the presence of primary amine can also lead to the secondary amine product, incorporating multiple and varied ligands, in various positions and with varying steric interference to their access. Reaction of this secondary amine with an electron poor aromatic substance bearing a good leaving group attaches the amine to the aromatic substance. Reduction of the nitro group to amino forms the aniline.

Alternatively, the reaction of cyanuric chloride, for example, sequentially with a nucleophile, secondary amine, and then ammonia, also provides the aniline derivatives.

Standard diazotization and azo coupling of these anilines leads to metal ion-sensing azobenzene-based dyes.

Other methods for preparation of azobenzene derivatives remove the electron-rich limitation of azo coupling for azo dye formation. For example, condensation of a nitrosobenzene derivative with an aniline leads to an azobenzene. Another route to an azobenzene derivative is by direct nucleophilic attack of an arylhydrazine on an electron-poor aromatic bearing a good leaving group, followed by oxidation of the resulting hydrazobenzene derivative to an azobenzene.

Structural variation may result from using p-nitrofluorobenzene instead of the o-nitro, in that azobenzene would be attached at the position labelled $A_2$, rather than as shown. 2,4-dintrofluorobenzene also reacts, and allows azo coupling at both the position shown, and at $A_2$.

The azobenzene-based sensors may also be made from cyanuric chloride:

Scheme 3

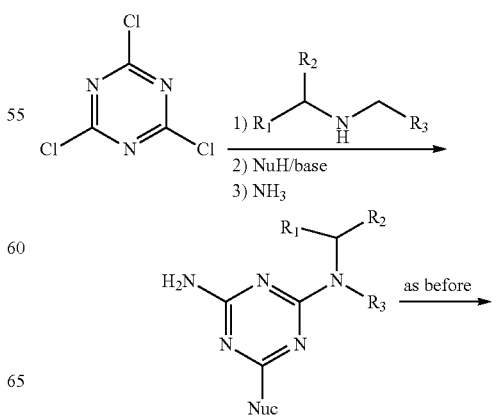

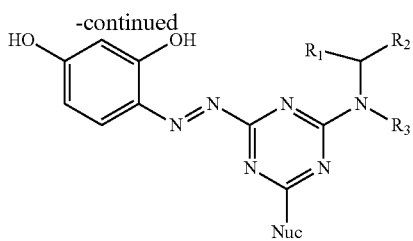

Azobenzene derivatives may also be prepared without the use of a phenol, or other electron-rich aromatic substrate. The oxidation step can be done by many different reagents; t-butyl hypochlorite as likely to be a good choice (J. Org. Chem. 1999, 64, 4976-4979).

Scheme 4

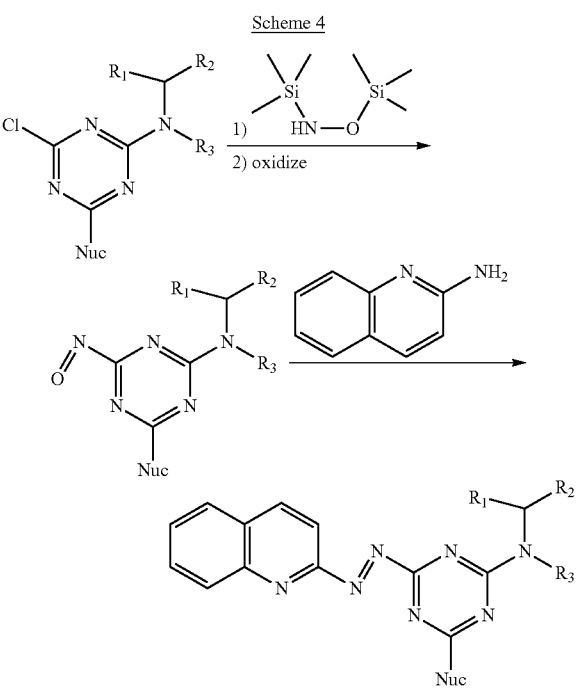

Other methods of synthesizing the compounds herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

B. Signal

Binding of metal ion to the dye may mediate a change in the dye-generated signal. That is, without metal ion bound, the dye generates a signal, and when metal ion is bound, the signal generated from the dye changes. The metal ion-bound dye results in a signal that is different from the signal of the unbound dye. In some embodiments, the signal is an optical signal.

In some embodiments, the change in signal may be an increase or decrease in the absorbance at a single wavelength or range of wavelengths. In some embodiments, the increase or decrease in the absorbance is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, or at least about 50%.

In some embodiments, the signal comprises the emission intensity of the dye recorded at a single wavelength or range of wavelengths. The change in signal may be a shift in the single wavelength or range of wavelengths. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, or at least about 100 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 100 nm.

In some embodiments, the signal is fluorescence. The change in signal may be an increase or decrease in the fluorescence intensity of the dye. In some embodiments, the increase or decrease in the fluorescence intensity is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, at least about 75% or at least about 100%.

In some embodiments, the signal is fluorescence. The change in signal may be an increase or decrease in the fluorescence of the dye. In some embodiments, the increase or decrease in the fluorescence is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, at least about 75% or at least about 100%.

The dye may bind one metal ion at a time. In some embodiments, the dye is able to bind multiple metal ions at separate times. In some embodiments, the dye generates a different signal when it binds a different metal ion.

In some embodiments, the dye detects a metal ion over a linear dynamic range of about 100 ppb to about 2000 ppb, about 150 ppb to about 1800 ppb, or about 200 ppb to about 1500 ppb. In embodiments, the dye detects a metal ion over a linear dynamic range of at least about 100 ppb, at least about 150 ppb, at least about 200 ppb, at least about 500 ppb, or at least about 1000 ppb. In embodiments, the dye detects a metal ion over a linear dynamic range of less than about 2000 ppb, less than about 1800 ppb, less than about 1500 ppb, or less than about 1000 ppb. In some embodiments, the dye detects a metal ion over a linear dynamic range of about 100 ng/mL to about 2000 ng/mL, about 150 ng/mL to about 1800 ng/mL, or about 200 ng/mL to about 1500 ng/mL. In embodiments, the dye detects a metal ion over a linear dynamic range of at least about 100 ng/mL, at least about 150 ng/mL, at least about 200 ng/mL, at least about 500 ng/mL, or at least about 1000 ng/mL. In embodiments, the dye detects a metal ion over a linear dynamic range of less than about 2000 ng/mL, less than about 1800 ng/mL, less than about 1500 ng/mL, or less than about 1000 ng/mL.

In some embodiments, the dye is reusable for metal ion detection, that is, the dye may be used multiple times to detect the same or different metal ions. After being used to detect a metal ion, the dye may be treated with a weak electrolyte solution, a dilute acid solution, or a solution containing a chelating agent. Examples of dilute acid solutions include 0.1 M hydrochloric acid and citric acid. An example of a weak electrolyte solution includes flowing water of the sensor material to release the metals from the sensor. Examples of chelating agents include trans-1,2-diaminocyclohexane-N,N,N',N'-tetraacetic acid (CyDTA), diethylenetriaminepentaacetic acid (DTPA), ethylenediaminetetraacetic acid (EDTA), ethyleneglycol bis(2-aminoethyl ether)-N,N,N',N' tetraacetic acid (EGTA), ethylenediamine (en), N-(2-hydroxyethyl)iminodiacetic acid (HIDA), iminodiacetic acid (IDA), nitrilotriacetic acid (NTA), nitrilotrimethylphosphonic acid (NTP), N,N,N',N'-tetrakis(2-pyridylmethyl)ethane-1,2-diamine (TPEN), and triethylenetetramine-N,N,N',N'',N''',N'''-hexaacetic acid (TTHA).

III. Sensor

Further provided herein are sensors for the detection of at least one metal ion in a sample. A sensor comprises at least one dye covalently attached to a substrate. A sensor may comprise more than one substrate with at least one dye attached thereto. A sensor may comprise a single dye or a panel of dyes. The dye may comprise a compound as detailed above.

The substrate is optically transparent and provides for sufficiently low light scattering. In embodiments, the optical density of the substrate is less than about 0.1 to about 1.0 absorbance units, less than about 0.05 to about 0.5 absorbance units, less than about 0.02 to about 0.2 absorbance units, less than about 0.01 to about 0.1 absorbance units, depending on scattering signal relative to sensor signal. In embodiments, the optical density is at least about 0.01 absorbance units, at least about 0.02 absorbance units, at least about 0.05 absorbance units, or at least about 0.1 absorbance units. In embodiments, the optical density is less than about 1.0 absorbance units, less than about 0.5 absorbance units, less than about 0.2 absorbance units, or less than about 0.1 absorbance units. Substrates may include hydrophilic polymers, hydrophobic polymers, cellulose, and gels. Suitable polymers include, but are not limited to, cellulose, a crosslinked polymethacrylate ester, polyacrylamide, and crosslinked polyethylene glycol. In embodiments, hydrophobic polymers can be made acceptable by hydrophilic substituents, as by anion (e.g. Sulfonate), cation (e.g. ammonium) or polar neutral (e.g. polyethylene glycol) substitution of polystyrene, and/or by polymerization with crosslinking in the presence of microspheres and subsequent dissolution of microspheres forming polymer microporosity.

In embodiments, the polymer may be cross-linked. Suitably, the crosslinker may be (poly(ethylene glycol) diacrylate or poly(ethylene glycol) dimethacrylate). In embodiments, the crosslinker is of suitable length (Avg MW>500) for the polymer to remain optically transparent when soaked in water.

In embodiments, the covalent attachment may be an ether bond, an amide bond, a sulfonamide bond, or an unsaturated bond.

In embodiments, the sensor further comprises perturbation moieties. The perturbation moiety allows for the adjustment of the affinity of the dye. The perturbation moiety may be a cation, an anion, or a zwitterion. In embodiments, the use of a cation perturbation moiety decreases the affinity of a dye for a cation. In embodiments, the use of a cation perturbation moiety increases the affinity of a dye for an anion. In embodiments, the use of an anion perturbation moiety decreases the affinity of a dye for an anion. In embodiments, the use of an anion perturbation moiety increases the affinity of a dye for a cation. In embodiments, the use of a zwitterion perturbation moiety decreases the affinity of a dye for a polar compound. In embodiments, the use of a zwitterion perturbation moiety increases the affinity of a dye for a non-polar compound. In embodiments, the perturbation moiety is covalently bound to the substrate. In embodiments, the perturbation moiety may be bound through a linker, such as that described below. In embodiments, the perturbation moiety alters the rate of binding and biocompatibility.

In embodiments, the sensor has the formula:

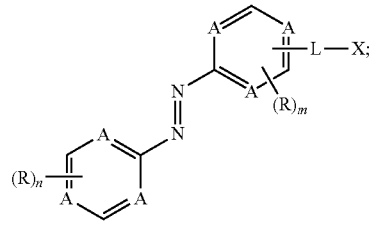

(V)

wherein each R is independently selected from the group consisting of OH, H, $OR_1$, $C_{1-4}$ alkyl, nitro, halo, $NR_{N1}R_{N2}$, $SO_3H$, $SO_2NHR_3$, $NHSO_2R_4$, carboxyl, amido, nitrile, —C(=N—OH)$R_3$, —C(=O)$NR_{N1}$OH, —$SR^5$, thioamido, phosphonate or two Rs may join together to form a 5, 6, or 7-membered ring, which may be aromatic or heteroaromatic, which may be substituted;

each A is independently N, NO, CH, or $CR_5$;

$R_{N1}$ and $R_{N2}$ are independently $C(O)R_2$, heteroaryl, aryl, $C_{1-4}$ alkyl,

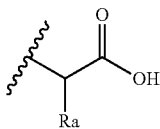

or H;
R$^a$ is an amino acid side chain;
each R$_1$ is independent C$_{1-4}$ alkyl, C$_{2-4}$ alkenyl, heteroaryl, or aryl;
each R$_2$ is independently C$_{1-4}$ alkyl, C$_{2-4}$ alkenyl, heteroaryl, or aryl;
each R$_3$ is independently H, C$_{1-4}$ alkyl, heteroaryl, aryl, cycloalkyl, or heterocyclyl;
each R$_4$ is independently H, C$_{1-4}$ alkyl, heteroaryl, aryl, cycloalkyl, or heterocyclyl;
each R$_5$ is independently H, C$_{1-4}$ alkyl, heteroaryl, aryl, cycloalkyl, or heterocyclyl;
each n is independently an integer from 1 to 5;
each me is independently an integer from 1 to 4
L is a linker; and
X is an optically transparent substrate.
In embodiments, the sensor has the formula:

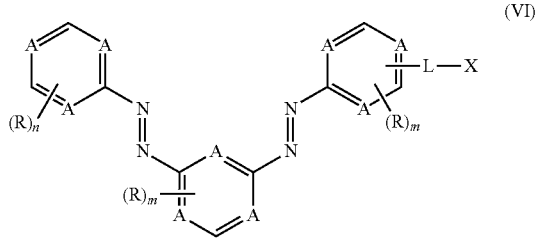

(VI)

wherein each R is independently selected from the group consisting of OH, H, OR$_1$, C$_{1-4}$ alkyl, nitro, halo, NR$_{N1}$R$_{N2}$, SO$_3$H, SO$_2$NHR$_3$, NHSO$_2$R$_4$, carboxyl, amido, nitrile, —C(═N—OH)R$_3$, —C(═O)NR$_{N1}$OH, —SR$^5$, thioamido, phosphonate or two Rs may join together to form a 5, 6, or 7-membered ring, which may be aromatic or heteroaromatic, which may be substituted;
each A is independently N, NO, CH, or CR$_5$;
R$_{N1}$ and R$_{N2}$ are independently C(O)R$_2$, heteroaryl, aryl, C$_{1-4}$ alkyl,

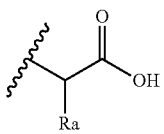

or H;
R$^a$ is an amino acid side chain;
each R$_1$ is independent C$_{1-4}$ alkyl, C$_{2-4}$ alkenyl, heteroaryl, or aryl;
each R$_2$ is independently C$_{1-4}$ alkyl, C$_{2-4}$ alkenyl, heteroaryl, or aryl;
each R$_3$ is independently H, C$_{1-4}$ alkyl, heteroaryl, aryl, cycloalkyl, or heterocyclyl;
each R$_4$ is independently H, C$_{1-4}$ alkyl, heteroaryl, aryl, cycloalkyl, or heterocyclyl;
each R$_5$ is independently H, C$_{1-4}$ alkyl, heteroaryl, aryl, cycloalkyl, or heterocyclyl;
each n is independently an integer from 1 to 5;
each m is independent an integer from 1 to 4;
L is a linker; and
X is an optically transparent substrate.
In embodiments, the linker may be —O—(CH$_2$)$_p$—C$_6$H$_4$—, wherein p is an integer from 1 to 4. In embodiments, the linker may be —OCH$_2$C(O)NH—(CH$_2$O)$_t$CH$_2$CH$_2$—NHC(O)—, wherein t is an integer from 1 to 10. In embodiments, the linker may be —O—(CH$_2$O)$_r$—C(O)NH—, wherein r is an integer from 1 to 10. In embodiments, the linker may be —C(O)NH—(CH$_2$O)$_q$—CH$_2$CH$_2$NHC(O)—(OCH$_2$)$_v$OC(O)—, wherein q and v are independently an integer from 1 to 10. In embodiments, the linker may be —O—(CH$_2$O)$_u$C(O)—, wherein u is an integer from 1 to 10.

A. Single Dye

In some embodiments, the sensor includes a single dye. In some embodiments, the sensor includes a plurality of a single dye.

B. Panel

In some embodiments, the sensor includes a plurality of different types of dyes. A plurality of these different types of dyes may be arranged or incorporated in a panel. As used herein, a "panel" refers to two or more different dyes. The panel may include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, or at least 100 different dyes.

The panel of dyes includes at least one sensor element. "Sensor element" refers to a single spot, site, location, or well for the at least one dye, to which a sample or aliquot thereof may be applied or administered. The panel may be arranged as a composite or an array.

i. Composite

In some embodiments, the panel is a composite. In a composite, each sensor element includes a mixture of two or more different dyes. In some embodiments, the composite includes one sensor element. In some embodiments, the composite includes two or more sensor elements. In some embodiments, signals are measured from a composite in which the signals arise from one or more dyes in the sensor element. For example, signals may be measured from a composite in which the signals arise from a subset of the total number of dyes in the sensor element. For example, signals may be measured from a composite in which the signals arise from two of five dyes in the sensor element.

ii. Array

In some embodiments, the panel is an array. In an array, each sensor element includes a single type of dye. An array comprises a plurality of individually and spatially localized sensor elements. Each sensor element includes a dye that is different than or the same as the dye of a different sensor element. In some embodiments, signals are measured from an array in which the signals arise separately from two or more selected dyes in separate sensor elements. An array may comprise a plurality of sensor elements of a variety of sizes and configurations. An array may comprise a plurality of sensor elements arranged linearly. For example, an array may comprise a plurality of micrometer-sized sensor elements arranged in a single row. An array may comprise a plurality of sensor elements arranged horizontally. An array may comprise a plurality of sensor elements arranged vertically. An array may comprise a plurality of sensor elements arranged in a grid. The grid may be two- or three-dimensional. In some embodiments, the grid is a spatially addressable grid. In some embodiments, the dyes are incorporated into an array, such as a multichannel or multiplexed array.

C. Synthesis of Sensor

In an embodiment, the sensor may be synthesized via a nucleophilic substitution reaction. The dye may be bound to the sensor before during or after the polymerization of the substrate. Suitably, the dye may be in the form of a soluble metal complex during the nucleophilic substitution.

In an embodiment, the sensor may be synthesized via an acylation reaction.

While many materials and covalent linking methods are possible, the sensors may be made via a particularly general approach that allows use of most of the dyes without the need to design in extra features for covalent attachment. For example, the dye may be made into a soluble metal complex, for instance by treatment with insoluble zinc salt. This serves to protect the phenol involved in metal binding, while leaving the second hydroxyl group available for alkylation. Exposure of this substance to $Cs_2CO_3$, p-chloromethylstyrene, a methacrylate monomer, a crosslinker of appropriate type, a radical initiator such as AIBN in a solvent such as NMP or DMF leads in one step to an optically transparent polymer with covalently attached sensor, with rapid water permeability. Extraction of the templating zinc ion with EDTA leaves the covalent sensor material.

Other methods of synthesizing the sensors herein will be evident to those of ordinary skill in the art. Synthetic chemistry transformations and protecting group methodologies (protection and deprotection) useful in synthesizing the sensors are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

IV. Methods of Use

Provided herein are methods of detecting the presence of a metal ion, methods of determining the concentration of a metal ion, and methods of monitoring the presence of a metal ion. In embodiments, the metal ion may be chromium, calcium, magnesium, copper, mercury, nickel, zinc, cobalt, manganese, cadmium, lead, tin, aluminum, potassium, sodium, or arsenic. Chromium may be chromium(III). Iron may be iron(II) or iron(III). Copper may be copper(I) or copper(II). Cobalt may be is cobalt(II). Nickel may be nickel(II). Zinc may be zinc(II). Mercury may be mercury (II). Calcium may be calcium(II). Magnesium may be magnesium(II). Aluminum may be aluminum(III). Cadmium may be cadmium(II). Potassium may be potassium(I). Sodium may be sodium(I). Lead may be lead(II). Manganese may be manganese (II). Tin may be tin(II). Arsenic may be arsenic(III) or arsenic(V).

Provided herein is a method of detecting the presence of a metal ion in a sample. The method may include contacting the sample with a sensor as detailed herein; measuring a signal from the sensor; and analyzing the signal. In some embodiments, analyzing the signal may include comparing the signal to a metal ion-free control, wherein a difference in signal indicates the presence of metal ion in the sample.

Also provided herein is a method of determining concentration of a metal ion in a sample. The method may include contacting the sample with a sensor as detailed herein; measuring a signal from the sensor; and analyzing the signal. In some embodiments, analyzing the signal may include comparing the signal to a standard calibration curve to determine the concentration of metal ion in the sample. The standard hyperbolic metal ion binding curve may be prepared by measuring the signal transduced by the sensor when contacted with control samples containing known concentrations and known types of metal ion.

Also provided herein is a method of determining the concentration of a metal ion in the range of 50 nano-molar to 200 micro-molar. This concentration range is relevant for detecting metal ions in water for real-time regulatory monitoring.

The present disclosure is also directed to a method of episodically or continuously monitoring the presence of a metal ion in a sample. In certain embodiments, the sensors may be used in episodic monitoring of sample aliquots. For example, aliquots of physiological, process, or industrial fluids can be analyzed on-site, point-of-care, or in a laboratory setting.

The method of episodically or continuously monitoring the presence of a metal ion in a sample may include contacting the sample with a sensor as detailed herein; maintaining the sample under conditions such that the sensor is capable of binding metal ion present in the sample; and episodically or continuously monitoring the signal from the sensor in the sample.

The method of episodically or continuously monitoring the presence of a metal ion in a sample may further include comparing the signal to a standard calibration curve to determine the concentration of metal ion in the test sample. The standard calibration curve may be prepared by measuring the signal transduced by the sensor when contacted with control samples containing known concentrations and known types of metal ion.

The method of episodically or continuously monitoring the presence of a metal ion in a sample may further include comparing the signal to a metal ion-free control, wherein a difference in signal indicates the presence of metal ion in the reaction.

The method of episodically or continuously monitoring the presence of a metal ion in a sample may further include washing the sensor to remove bound metal ions. In embodiments, the sensor may be washed with chelators, weak acids or electrolyte solutions such as CyDTA, DTPA, EDTA, EGTA, en, HIDA, IDA, NTA, NTP, TPEN, TTHA, 0.1 M HCl, citric acid, or flowing water respectively.

In embodiments, the present disclosure provides data unavailable from a single sensor molecule that is a component of the array. Such improved information includes, but is not limited to, greater selectivity of metal identification, larger dynamic range of measurement, and simultaneous measurement of multiple species and parameters.

Without wishing to be bound by theory, it is believed that each dye responds uniquely to a variety of metals but by analyzing multiple dyes together, greater specificity can be obtained, lowering the interference of one metal with another. For example, using one dye that responds well to lead, an accuracy error of approximately 20 ppb may be achieved When using two different dyes that respond differently to lead, an accuracy error of about 10 ppb may be achieved over the range of measurement from about 200 ppb to about 2,000 ppb. In another example, using one dye that responds to copper, nickel, and zinc, an accuracy error of about 10 ppb may be achieved for copper, an accuracy error of about 6 ppb may be achieved for nickel, and an accuracy error of about 10 ppb may be achieved for zinc simultaneously over the range of measurement from about 60 ppb to about 650 ppb. In an aspect, the use of multiple dyes provides the ability to report the concentration of multiple metal ions with much greater selectivity on the order of two times better with two dyes.

V. EXAMPLES

Example 1: Preparation of 4-(quinolin-8-yldiazenyl)benzene-1,3-diol (QAR)

Figure 2:
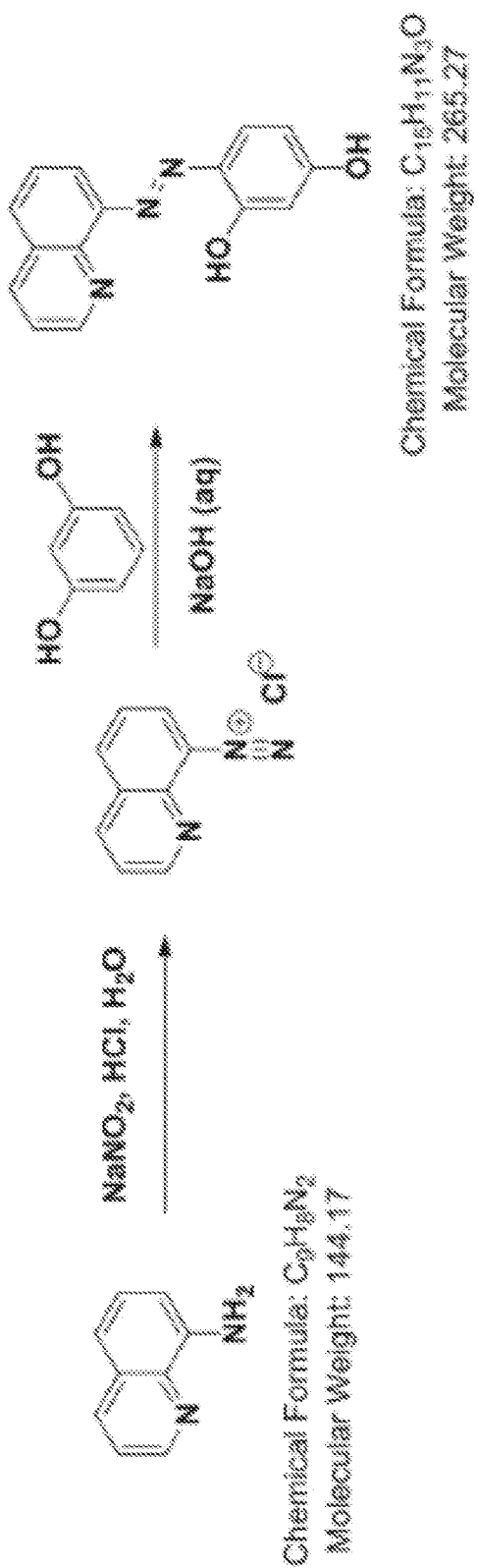
FIG. 2 is a scheme for the synthesis of QAR.

To a stirring solution of 8-aminoquinoline (2.0284 g, 14.07 mmol) in HCl (40 mL, 6 M) at 5° C. on an ice bath was added NaNO2 (1.0733 g in 2 mL cold $H_2O$) dropwise until the reaction mixture gave a positive test on KI-starch paper. The resulting mixture was added dropwise to a solution of 0.492 g resorcinol in 78.5 mL of 1 M NaOH stirring on an ice bath. After standing overnight, the solid was isolated by filtration, rinsed thoroughly with cold water, and dried in vacuo. Trituration in boiling methanol gave 0.984 g (77% yield) QAR as its mono-sodium salt, MP>320° C. (FIG. 2).

1H NMR (CD3OD): δ 8.866 (dd, j=1.8, 4.2; 1H) δ 8.250 (dd, j=1.8, 8.4, 1H) δ 7.989 (dd, 2.1, 6.6, 1H) δ 7.613 (m, 1H) δ 7.562 (m, 1H) δ 7.506 (dd, j=8.4, 4.2, 1H) δ 6.982 (d, j=9.6, 1H) δ 6.215 (d, j=9.6, 1H) δ 5.682 (d, j=2.1, 1H) 13C NMR (CD3OD): δ 148.72, 135.56, 134.83, 128.8, 126.91, 123.90, 121.62, 121.32, 116.72, 110.60, 106. Rf on TLC: 0.43, in 10% MeOH/CH2Cl2 MS: DUIS m/z 266.15[M+H]+; 264.05[M−H]−.

Figure 3:
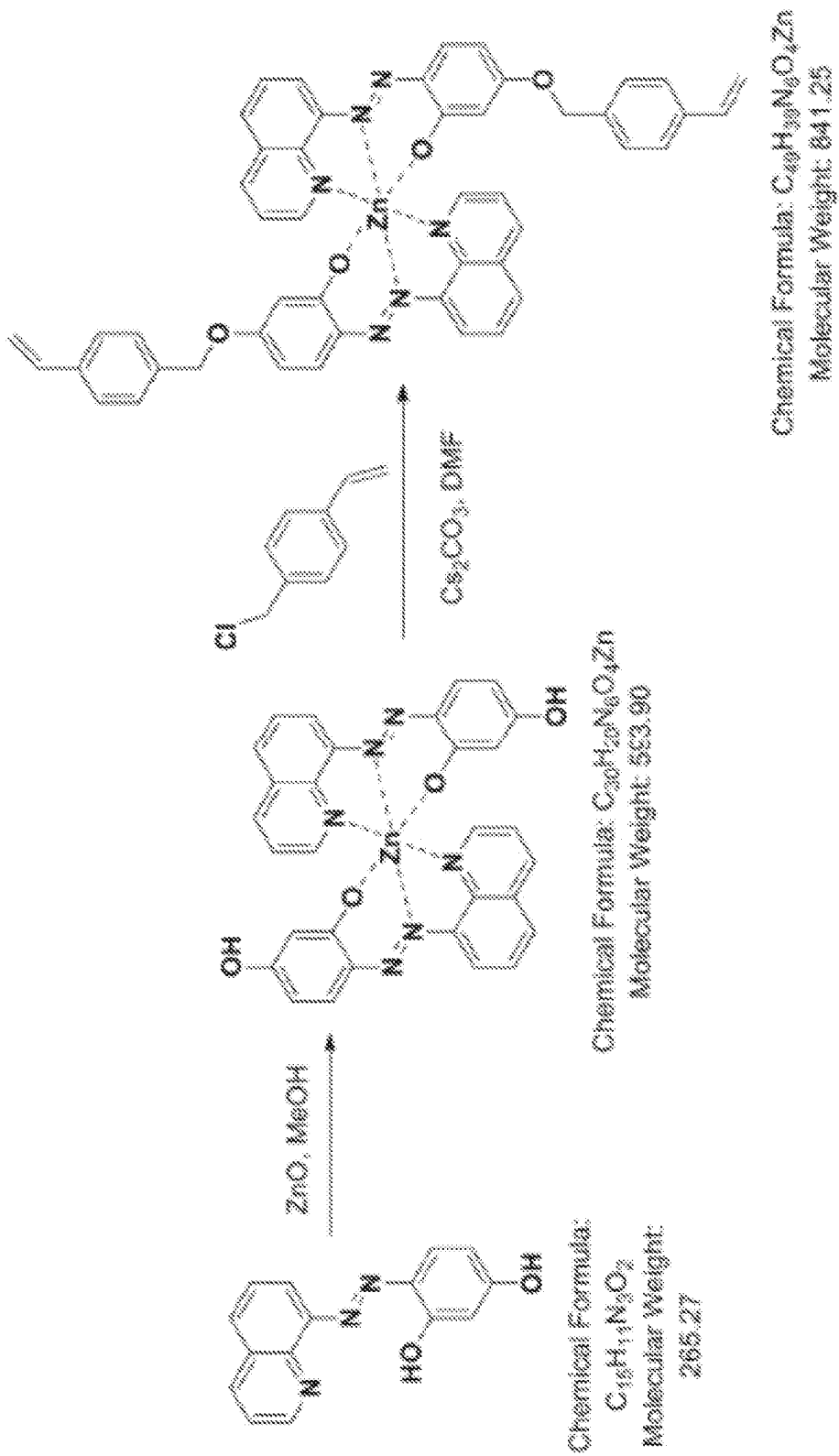
FIG. 3 is a scheme for the synthesis of the 4-(quinolin-8-yldiazenyl)benzene-3-ol-1-styrene-zinc complex.

Example 2: Preparation of 4-(quinolin-8-yldiazenyl)benzene-3-ol-1-styrene-zinc Complex A suspension of QAR (239.3 mg) and ZnO (36.7 mg) in 25 mL acetonitrile was heated at reflux for 24 hours; then the solvent was removed by rotary evaporation. To the solid, 0.2968 g Cs2CO3 is added followed by 11 mL dimethylformamide (DMF) and 0.14 mL chloro-methylstyrene. This is stirred under nitrogen at room temperature. After 3 hours a fine pale color precipitate is observed. The mixture was filtered and most of the solvent was removed by rotary evaporation followed by vacuum pumping. The reaction mixture was dissolved in 50 mL $CH_3CN$ and washed with 25 mL hexanes. The bright orange $CH_3CN$ solution was rotary evaporated to dryness to yield polymerizable sensor 4-(quinolin-8-yldiazenyl)benzene-3-ol-1-styrene-zinc complex (FIG. 3).

Example 3: Preparation of 2,2'-Dipicolylamine (DPA)

Synthesis of 2,2'-Dipicolylamine

To a round bottom flask equipped with a magnetic stir bar was added; 10.1015 g 2-cyanopyridine [96.05 mmol], 0.4966 g 5% (wt/wt) Palladium on Carbon and 16.5 mL of anhydrous ethanol stored over 4 Å molecular sieves. The reaction mixture was then slowly flushed with 3 L of H2(g) and once flushed, a vacuum was pulled on the reaction mixture before a balloon of hydrogen ~1 L was placed on top to incorporate overnight. The reaction vessel was flushed with a balloon of fresh hydrogen every day. Reaction progress was monitored by TLC [Eluent—20% CH3OH: 80% CH2Cl2] and visualized with acidic ninhydrin stain. The reaction occurred over 72 hours, after which TLC indicated the consumption of starting material.

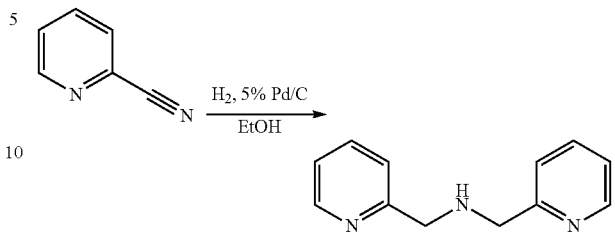

Isolation of 2,2'-Dipicolylamine

The reaction mixture was filtered through a 1 cm thick layer of packed celite by vacuum filtration. The celite was then washed with 50 mL of hot ethanol and the collected filtrates were combined and concentrated by rotary evaporation. The afforded 9.540 g [99.7% isolated] of transparent amber oil was verified by ESI-LCMS [M/Z+1: 200.1 positive ionization—M/Z−1: 198.95 negative ionization] and 1H NMR.

1H NMR 300 MHz [CD3Cl]: δ 3.97, s, H 4; 7.21, t (J c. 6.9 Hz), H 2; 7.38, d (J c. 8.7 Hz), H 2; 7.64, td c. 6.9 Hz) H 2; 8.55, d (J c. 7.2 Hz) H 2.

Example 4: Preparation of N,N'-di-[2-pyridylmethyl]-4-nitroaniline (PNI: Para Nitro Intermediate)

Synthesis of PNI.

To a clean and dry round bottom flask, under nitrogen, equipped with a magnetic stir bar was added 1.0506 g of 2,2'-dipicolylamine [5.28 mmol] and 0.8429 g of 1-fluoro-4-nitrobenzene [5.97 mmol]. The round bottom flask was attached to a reflux condenser and placed into an oil bath before flushing the system with nitrogen. Then 10.00 mL of toluene and 2 mL of diisopropylethylamine [11.78 mmol] were delivered via syringe while stirring vigorously. The reaction mixture was allowed to achieve reflux and reaction progress was determined by silica gel thin layer chromatography [10% MeOH: 90% DCM] and visualized by acidic ninhydrin stain. After 18 hours TLC indicated the total consumption of dipicolylamine and reflux was stopped.

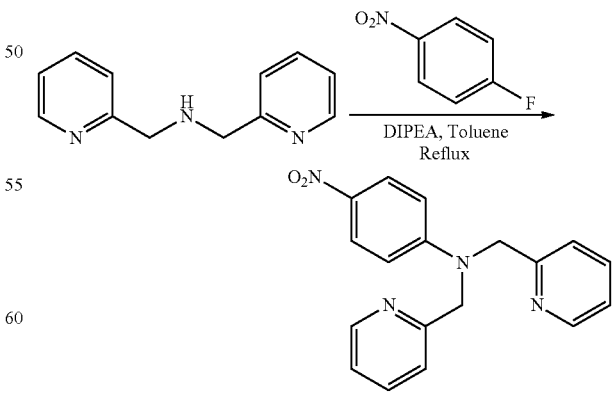

Isolation of PNI:

Once the reaction mixture had cooled to room temperature it was concentrated and excess DIPEA was removed by diluting the crude product into large volumes of toluene and methanol then concentrating by rotary evaporation. The crude product was then dissolved into 100 mL of EtOAc and extracted with three 25 mL additions of 0.5 M HCl. The aqueous acid layers were combined and basified with saturated K2CO3 while in the presence of 25 mL of DCM, the product was extracted further by three 25 mL additions of DCM. The organic extracts were combined, concentrated and placed into a vacuum desiccator to achieve constant mass. Yield: 1.037 g [61.4%] of a thick amber-red oil, this was stored at room temperature in a desiccator.

1H NMR 300 MHz [CD3OD]: δ 4.84, s, H 4; 6.64, d (J c. 9.3 Hz), H 2; 7.11, m (J c. 4.8, 9.3 Hz), H 4; 7.58, td (J c. 1.5 7.8 Hz) H 2; 7.97, d (J c. 9.6 Hz) H 2; 8.53, d (J c. 4.5 Hz) H 2.

Example 5: Preparation of N,N'-di-[2-pyridylmethyl]-2,4-dinitroaniline (DNI: Dinitro Intermediate)

Synthesis of DNI:

To a clean and dry round bottom flask, under nitrogen, equipped with a magnetic stir bar was added; 1.4622 g of 2,2'-dipicolylamine [7.34 mmol] and 1.5056 g of 2,4-dinitrofluorobenzene [8.09 mmol]. A syringe containing 10.0 mL of acetonitrile and 1.00 mL of triethylamine [7.17 mmol] was delivered to a vigorously stirring reaction mixture. Reaction progress was monitored by silica gel thin layer chromatography [20% MeOH: 80% DCM] and visualized by acidic ninhydrin stain. After 4 hours the total consumption of dipicolylamine was observed and the reaction was stopped.

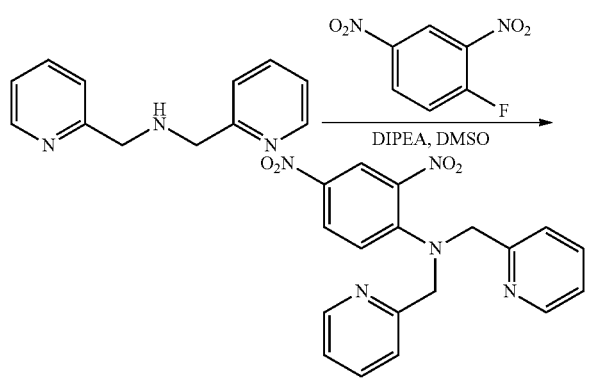

Isolation of DNI:

The reaction mixture was concentrated by rotary evaporation. Once constant mass was achieved, the crude product was dissolved into 20 mL of EtOAc and washed twice with 20 mL of 5%[wt/wt] sodium hydroxide solution. The organic layer was separated, concentrated and placed into a vacuum desiccator to fully dry. The crude product was dissolved into 50 mL of EtOAc and extracted with three 20 mL additions of 1 M HCl. The acid aqueous layers were combined and basified by the addition of saturated K2CO3 and the product extracted by three 20 mL additions of DCM. The organic extracts were then combined, concentrated and placed into a vacuum desiccator overnight. The concentrated extracts yielded 2.3788 g [89%] of a thick dark red oil.

Purification:

The extracted product was placed into the minimal amount of DCM necessary to completely dissolve. Once homogenous, hexanes were slowly added via syringe to the mixture, with stirring, until a precipitate could be observed. The reaction vessel was capped with a septa and flushed with nitrogen before being placed into the refrigerator to crystallize. Allowing crystallization to occur over multiple days in a cooled environment yielded transparent yellow crystals that grow into long needles or thick transparent orange bars. Melting Point: 98-99° C. (Sharp).

1H NMR 300 MHz [CD3OD]: δ 4.67, s, H 4; 7.21, m (J c. 4.2, 7.8 Hz), H 2; 7.26, d (J c. 6.6 Hz), H 1; 7.33, d (J c. 7.8 Hz) H 2; 7.65, t (J c. 7.5 Hz) H 2; 8.14, dd (J c. 2.1, 7.2 Hz) H 1; 8.53, d, (J c. 4.8 Hz) H 2; 8.66, d (J c. 2.1 Hz) H 1.

Example 6: Preparation of Ortho Nitro Intermediate (ONI)

Synthesis of ONI:

0.5123 g [2.5 mmol 1H NMR Det.] of 2,2'-dipicolylamine was placed into a clean round bottom flask with a magnetic stir bar. To this was added 0.3217 g [2.5 mmol] of diisopropylethylamine in 10 mL of DMSO. This was allowed to stir under a N2(g) atmosphere for a few minutes before a solution of 0.3567 g [2.5 mmol] of ortho-fluoronitrobenzene in 5 mL of DMSO was delivered to the rapid stirring reaction mixture via syringe. As a precaution, the reaction mixture was wrapped in paper towel to avoid direct sunlight and stirred at room temperature for multiple days. After 4 days, TLC had indicated the total consumption of 2,2'-dipicolylamine [Eluent—20% CH3OH: 80% CH2Cl2—visualized by acidic ninhydrin] and the reaction was stopped.

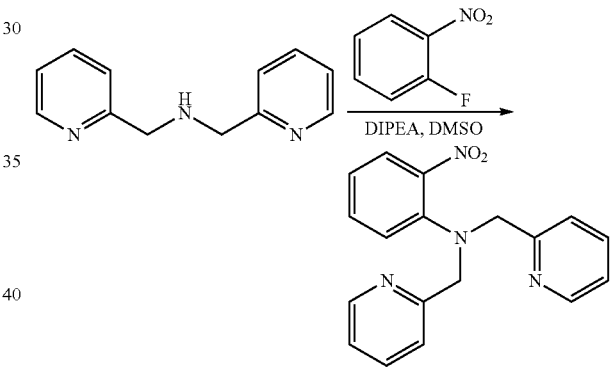

Isolation of ONI:

The reaction mixture was transferred to a separatory funnel containing 50 mL of 1 M NaOH and 25 mL of CH2Cl2. The product was further extracted with an additional 50 mL of CH2Cl2. The organic extracts were combined, dried over MgSO4 and concentrated by rotary evaporation. This was left on a vacuum line overnight to achieve constant mass. This afforded 0.5032 g [63% isolated] of a deep red-yellow oil that was verified by ESI-LCMS [M/Z+1: 321.2—positive ionization; M/Z−1: Not observed] and 1H NMR.

1H NMR 300 MHz [CD3Cl]: δ 4.48, s, H 4; 7.01, t (J c. 7.2 Hz), H 1; 7.15, td (J c. 8.1, 6.9 Hz), H 2; 7.22, d(J c. 8.1 Hz) H 1; 7.36, td (J c. 6.9, 1.5 Hz) H 1; 7.45, d (J c. 7.8 Hz), H 2; 7.62, td c. 7.8, 1.8 Hz), H 2; 7.72, dd c. 8.1, 1.2 Hz), H 1; 8.52, d (J c. 4.2 Hz), H 2.

Example 7: Preparation of N,N-bis(pyridin-2-ylmethyl)benzene-1,2,4-triamine (DAI: Diamino Intermediate)

Reduction:

To a small flask was added 0.3666 g [1.0 mmol] of DNI and 0.1783 g of 5% (wt/wt) palladium on carbon. Then 25 mL of anhydrous ethanol was delivered to the flask which was immediately capped with a septum. Hydrogen was slowly flushed through the reaction flask by placing the system under vacuum while ~1 L of H2 in a balloon was pulled through the flask. A balloon of H2(g) was placed on top of the reaction mixture to incorporate overnight. The following morning TLC had indicated the consumption of starting DNI and hydrogenation was stopped. The reaction mixture was vacuum filtered through a packed 1 cm thick layer of celite which was subsequently washed with ~50 mL of hot ethanol. The filtrate was collected, concentrated and placed into a vacuum desiccator overnight to achieve constant mass. This afforded 0.2850 g [90% isolated] of a deep green-black solid that was verified by ESI LCMS [M/Z+1: 306.20 positive ionization—M/Z−1: Not observed] and 1H NMR to be the desired diamino intermediate [DAI].

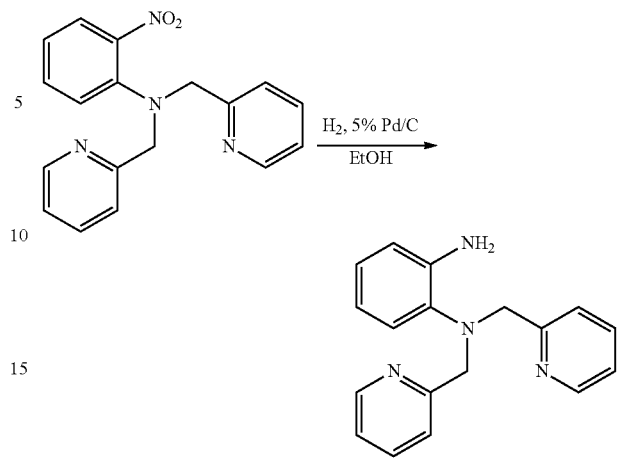

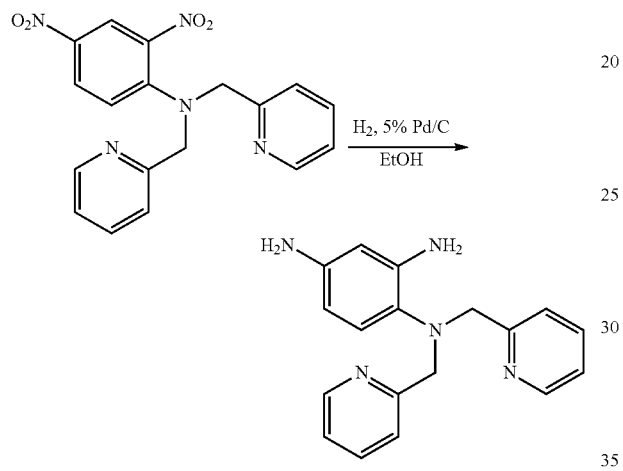

1H NMR 300 MHz [CD3Cl]: δ 2.63, sbroad, H 4; 4.24, s, H 4; 5.98, dd (J c. 2.4, 8.1 Hz), H 1; 6.09, d (J c. 2.4 Hz) H 1; 6.87, d (J c. 8.4 Hz) H 1; 7.09, t (J c. 7.5 Hz) H 2; 7.26, d (J c. 9.9 Hz) H 2; 7.53, td (J c. 1.5, 7.8 Hz) H 2; 8.52, d (J c. 4.8 Hz) H 2.

Example 8: Preparation of N,N-bis(pyridin-2-ylmethyl)benzene-1,2-diamine (OAI: Ortho Amino Intermediate)

Reduction:

To a small flask was added 0.3232 g [1.0 mmol] of DNI and 0.1430 g of 5% (wt/wt) palladium on carbon. Then 25 mL of anhydrous ethanol was delivered to the flask which was immediately capped with a septum. Hydrogen was slowly flushed through the reaction flask by placing the system under vacuum while ~1 L of H2 in a balloon was pulled through the flask. A balloon of H2(g) was placed on top of the reaction mixture to incorporate overnight. The following morning TLC had indicated the consumption of starting DNI and hydrogenation was stopped. The reaction mixture was vacuum filtered through a packed 1 cm thick layer of celite which was subsequently washed with ~50 mL of hot ethanol. The filtrate was collected, concentrated and placed into a vacuum desiccator overnight to achieve constant mass. This afforded 0.2850 g [97% isolated] of a deep red-black solid that was verified by ESI LCMS [M/Z+1: 291.10 positive ionization—M/Z−1: Not observed] and 1H NMR to be the desired ortho amino intermediate [OAI].

1H NMR 300 MHz [CD3Cl]: δ 2.69, sbroad, H 4; 4.72, sbroad, H 1; 7.16, t (J c. 6.6 Hz), H 2; 7.20, d (J c. 8.1 Hz) H 2; 7.35, m (J c. 8.7 Hz) H 2; 7.48, d (J c. 7.5 Hz) H 2; 7.63, t (J c. 8.1 Hz) H 2; 7.73, d (J c. 8.1 Hz) H 1; 8.52, t (J c. 7.5 Hz) H 2; 8.55, dbroad H 1.

Example 9: Preparation of o-Dipicolylamine Azo Resorcinol (DAR°)

Diazotization:

To a clean round bottom flask was added 0.4288 g [1.5 mmol] of OAI and 10 mL of chilled 1M HCl. The flask was then placed into an ice bath and cooled to 2° C., the reaction mixture was stirred until all of the OAI had dissolved. Then a chilled solution of 1M NaNO2(aq) was delivered to the stirring HCl solution dropwise and slowly until an instant positive KI-starch paper test was achieved. The solution was allowed to stir on ice at 2° C. for 30 minutes to ensure complete diazotization and reproducible instant positive KI-starch paper test.

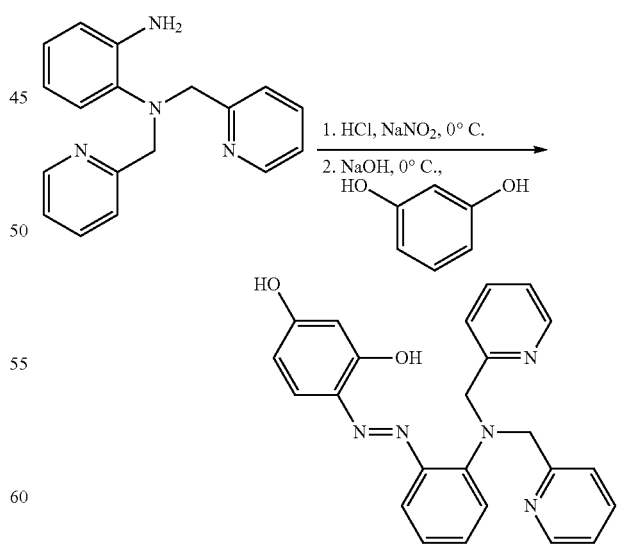

Azo Couple to Resorcinol:

While the diazotization solution was stirring on ice, a solution of 0.2201 g [2.0 mmol] of resorcinol in 22 mL of 1 M NaOH was prepared and placed into an ice bath. Once the temperature of the solution reached 2° C. and was homogenous, the diazotization solution was delivered to the resorcinol solution dropwise and very slowly. The solution was added over 20 minutes to mitigate any kind of exotherm that would raise the solution over 5° C. and destroy product. Once fully delivered, the reaction mixture was allowed to stir on ice and slowly reach room temperature overnight. The reaction mixture was then concentrated by rotary evaporation utilizing large volumes of toluene with some methanol to drive off residual H2O. This product was then suspended in 50 mL of methanol [stored over 3 Å molecular sieves] and brought to a boil for 30 minutes, acidified and then cooled in an acetone/dry ice bath to precipitate the product. The precipitate was filtered via vacuum filtration and washed with chilled $H_2O$ before being placed into a desiccator to achieve constant mass. This afforded 0.4718 g (78.0% crude mass) of a bright red-orange powder.

Isolation of DARo:

The 0.4718 g of crude DARo was combined with 25 mL of CH2Cl2 in an Erlenmeyer flask and heated while stirring. The mixture was allowed to boil but not concentrate for ~30 minutes before the flask was removed from the heat and allowed to cool to room temperature. The mixture was then filtered and washed with CH2Cl2 until the filtrate ran clear, the precipitate was then dried under vacuum for two hours. This afforded 0.2996 g of DARo as a deep orange-red powder.

Example 10: Preparation of Nitrosylated o-Dipicolylamine Azo Resorcinol (nDAR°)

Reduction:

To a small round bottom flask was added 0.8969 g [2.8 mmol] of ONI and 0.5302 g of 5% (wt/wt) 5% palladium on carbon. 15 mL of ethanol stored over 4 Å molecular sieves was delivered to the flask. Subsequently the flask was capped with a septum and flushed with hydrogen gas while vigorously stirring. A balloon of hydrogen was placed on top of the reaction flask to incorporate overnight. The following morning TLC indicated the consumption of starting material and hydrogenation was stopped. The reaction mixture was vacuum filtered through a 1 cm thick layer of packed celite which was washed with hot ethanol until the filtrate ran clear. The filtrates were collected, concentrated and placed into a vacuum dessicator to achieve constant mass. This afforded 0.7451 g (92%) of a deep red-black solid, OAI.

Diazonium:

the entirety of the reduced product was dissolved into 15 mL of 1 M HCl while stirring on an ice bath. Once the temperature of the acid solution fell below 5° C. a solution of 0.5304 g [7.7 mmol] of sodium nitrite in 10 mL of DI H2O was delivered dropwise to the acid solution. The diazonium solution was stirred on ice for 30 minutes and kept below 5° C. throughout.

Azo Couple:

in a large Erlenmeyer flask a solution of 0.3306 g [3.0 mmol] of resorcinol and 7.5 mL of 1 M NaOH was prepared in 10 mL of cold H2O. The flask was then placed into an ice bath and stirred. Once the hydroxide solution had become homogenous and reached 2° C., the chilled diazonium solution was added dropwise and slowly to maintain sub 5° C. temperatures while vigorously stirring. The reaction mixture was slowly warmed to room temperature over 2 hours, a bright orange-red precipitate was observed and subsequently vacuum filtered. The collected precipitate was placed into a vacuum desiccator overnight to achieve constant mass. This afforded 0.3134 g (28%) of an orange powder that was confirmed by ESI LCMS [M/Z+1: 441.20 positive ionization—M/Z−1: Not Observed] to be the nDAR°Sensor. M.P. 136° C.

Example 11: Preparation of Cyclized o-Dipicolylamine Azo Resorcinol (cDAR°)

Reduction:

To a small round bottom flask was added 0.2093 g [0.6 mmol] of cyclized dinitro intermediate and 0.2854 g of 5% (wt/wt) 5% palladium on carbon. 10 mL of ethanol stored over 4 Å molecular sieves was delivered to the flask. Subsequently the flask was capped with a septum and flushed with hydrogen gas while vigorously stirring. A balloon of hydrogen was placed on top of the reaction flask to incorporate overnight. The following morning TLC indicated the consumption of starting material and hydrogenation was stopped. The reaction mixture was vacuum filtered through a 1 cm thick layer of packed celite which was washed with hot ethanol until the filtrate ran clear. The filtrates were collected, concentrated and placed into a vacuum dessicator to achieve constant mass. This afforded 0.1788 g (94%) of a deep red sticky solid, cDAI°.

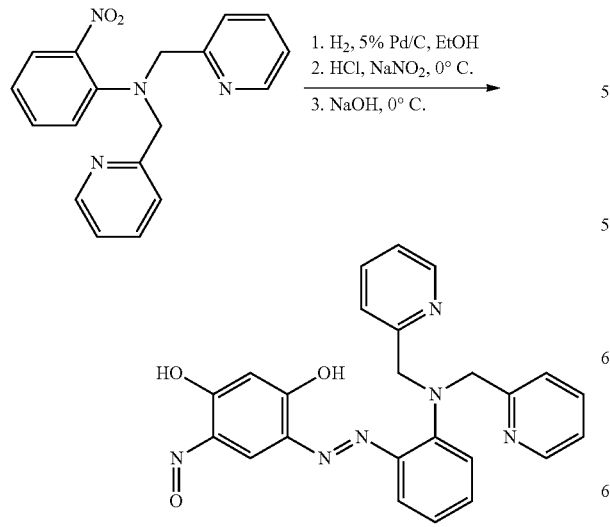

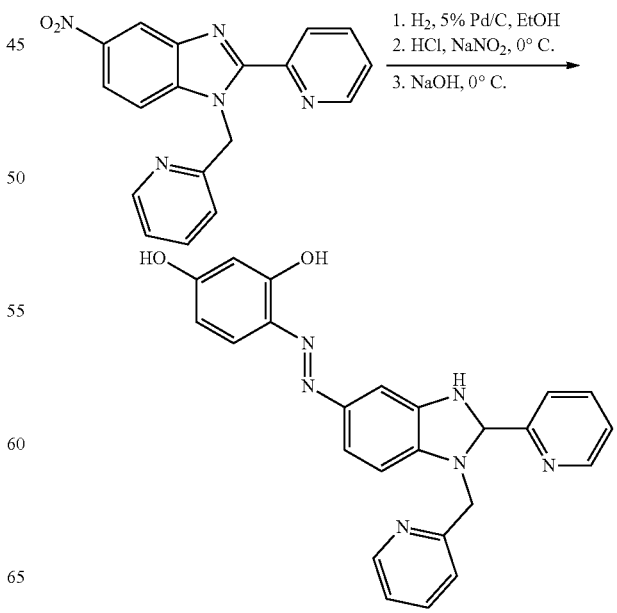

Diazonium:

the entirety of the reduced product was dissolved into 10 mL of 1 M HCl while stirring on an ice bath. Once the temperature of the acid solution fell below 5° C. a 1 M NaNO2 solution was delivered dropwise and slowly until KI-starch paper yielded an instant positive response. The diazonium solution was stirred on ice for 30 minutes and kept below 5° C. throughout.

Azo Couple:

in a large Erlenmeyer flask a solution of 0.1100 g [1 mmol] of resorcinol and 20 mL of 1 M NaOH was combined and cooled to sub 5° C. temperatures. Once the hydroxide solution had become homogenous and reached 2° C., the chilled diazonium solution was added dropwise and slowly to maintain sub-5° C. temperatures while vigorously stirring. The reaction mixture was stirred overnight, during which the reaction was slowly warmed to room temperature.

Isolation of cDAR°:

The reaction mixture was first concentrated by rotary evaporation and azeotroping residual water with large volumes of toluene. The product was then placed onto a vacuum line to achieve constant mass. The product was combined with 50 mL of anhydrous methanol and heated to a boil for 30 minutes and cooled to room temperature. The precipitate was separated by vacuum filtration and the filtrate was concentrated and placed into a vacuum desiccator to dry. The afforded 0.2158 g [86%] of a bright red powder was confirmed by ESI LCMS [M/Z+1: 423.25 Positive ionization—M/Z−1: 421.15 Negative ionization] to be the desired cDAR° sensor.

Example 12: Preparation of Pyridyl Azo 2,7-dihydroxy Naphthol (PAN-7OH)

Diazotate:

To a clean and dry round bottom flask equipped with a magnetic stir bar was added; 4.738 g [50.3 mmol] of 2-aminopyridine and 4.176 g [52.2 mmol] of lithium tert. butoxide while under a nitrogen stream. To the round bottom flask, 20 mL of THF was delivered via syringe, the reaction mixture was then flushed with nitrogen with vigorous stirring. Once everything had become dissolved, 6.65 mL [50 mmol] of (90%) tert-butyl nitrite was delivered via syringe. The reaction flask was placed on a warm heating mantle and stirred vigorously for 24 hours.

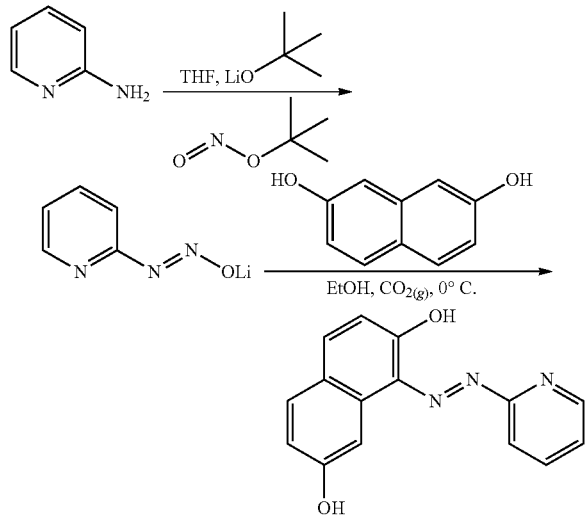

Isolation of Diazotate:

Once TLC indicated the consumption of 2-aminopyridine the reaction flask was removed from the heating mantle and allowed to cool to room temperature, the lithium diazotate salt was precipitated by the addition of 2 mL of diethyl ether to the reaction flask. The precipitate was collected via vacuum filtration and washed with 20 mL of diethyl ether until almost dry. The damp product was transferred to a vacuum desiccator to dry for 4 hours, affording 5.584 g [84.2% mass recovered] of a light yellow powder that is very hygroscopic.

Azo Couple:

Two solutions were prepared.

Solution A: a 20 mL vial placed in a cold H2O bath containing 1.2948 g [10.0 mmol] of lithium pyridine-2-diazotate under nitrogen had 10 mL of chilled anhydrous ethanol delivered to it via syringe. This mixture was stirred at 12° C. until the solution had become homogenous.

Solution B: A large pyrex test tube was submerged in a cold H2O bath, to the test tube was added, 1.6028 g [10.0 mmol] of 2,7-dihydroxynaphthalene and 10 mL of chilled anhydrous ethanol. This was allowed to fully dissolve before CO2 was bubbled into the solution via Teflon tubing.

Solution A was then delivered to solution B via syringe while the reaction had CO2 bubbling through it, this was maintained for 22 hours at 15° C. The resulting black solution had concentrated in volume by ½ before TLC had indicated the consumption of the naphthol and the reaction was stopped. The reaction mixture was brought to room temperature and concentrated by rotary evaporation, utilizing large volumes of toluene to azeotrope residual tert-butyl alcohol and H2O. The product was then dried in a vacuum desiccator to achieve constant mass.

Isolation of PAN-7OH Sensor:

The entirety of the crude material was then suspended in 50 mL of DI H2O and brought to a boil. Then 1 M HCl was delivered to the boiling solution dropwise until a pH of 2 was achieved. Then the water was concentrated by ½ to 25 mL, at which point the solution was removed from the heat and the reaction was allowed to cool to room temperature slowly. The reaction mixture was cooled to 5° C. for multiple hours to precipitate the free acid. The precipitate was filtered via vacuum filtration, the precipitate was washed with cold H2O and then placed into a desiccator overnight to achieve constant mass. This afforded 2.2150 g [84% crude mass] of a deep red fine powder that was verified by ESI-LCMS [M/Z+1: 226.15 positive ionization—M/Z−1: 264.10 negative ionization] and 1H NMR as the desired PAN-7OH sensor.

The PAN-7OH sensor can be recrystallized from methanol or ethanol utilizing large volumes. The best means of preparation of any diazotate based sensor is to freshly prepare the diazotate immediately before coupling to a phenol or naphthol.

1H NMR 300 MHz [CD3OD]: δ 6.41, d (J c. 9.6 Hz), H 1; 6.88, dd c. 8.4, 2.4 Hz), H 1; 7.22, td (J c. 6.3, 2.1 Hz), H 1; 7.42, d (J c. 8.4 Hz) H 1; 7.69, d (J c. 9.6 Hz) H1; 7.77, d (J c. 2.1 Hz) H 1; 7.92, s, H 1; 7.94, td (J c. 6.3, 1.8 Hz) H 1; 8.35, d (J c. 7.8 Hz) H 1.

Example 13: Preparation of Pyridyl Azo 1-Naphthoic Acid (PAN-1A)

Diazotate:

To a clean round bottom flask that has been thoroughly baked out in a 150° C. oven, 2.8261 g [30 mmol] of 2-aminopyridine and 2.5150 g [30 mmol] of lithium tert-butoxide were added. Then 50 mL of THF was delivered to the flask before being attached to a condenser and being flushed with nitrogen. This mixture was allowed to stir for 20 minutes at room temperature. Then 3.5984 g [30 mmol] of 90% tert-butyl nitrite in 10 mL of THF was delivered to the system via syringe and the reaction mixture was heated to ~40° C. for one hour before TLC [Eluent—5% AcOH: 10% CH3OH: 85% CH2Cl2] had indicated the total consumption of 2-aminopyridine. The reaction mixture was allowed to cool to room temperature, and the precipitate was subsequently filtered by vacuum filtration and washed with 25 mL of THF followed by 50 mL of diethyl ether. While the precipitate was still wet with ether the next step of the reaction was performed.

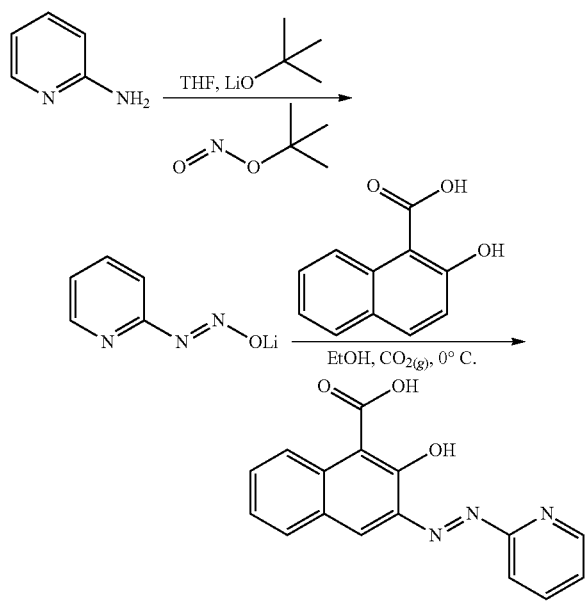

Azo Coupling:

The still wet lithium diazotate was immediately dissolved into 30 mL of anhydrous ethanol stirring over a dry ice bath. While the diazotate was dissolving, a second solution was prepared. 1.9122 g [10 mmol] of 2-hydroxy-1-Naphthoic Acid was dissolved into 50 mL of anhydrous ethanol stored over 4 Å molecular sieves and placed onto a dry ice bath. The naphthoic acid was dissolved while $CO_2(g)$ was bubbled through it and with stirring until both solutions achieved ~0° C. temperatures and became homogenous. Then, 10 mL of the diazotate solution was delivered to the naphthoic acid solution while $CO_2(g)$ was bubbling through it. Once fully delivered, $CO_2(g)$ was continually bubbled through the reaction mixture until consumed; 1 L of crushed dry ice was used. Additionally the sub 5° C. temperature was maintained for the first 12 hours of reacting and after 24 hours the reaction mixture had achieved room temperature and the reaction appeared complete by TLC.

Only ⅓ of the diazotate solution was used for this reaction. The diazotate synthesis can be adjusted down by ⅓ if not partitioning the diazotate solution among other naphthol solutions.

Isolation of PAN-1A:

Once the reaction was complete, the reaction mixture was placed into an acetone/dry ice bath to precipitate the product. The precipitate was then filtered via vacuum filtration and washed with chilled methanol. The precipitate was placed into a vacuum desiccator to achieve constant mass. The filtrate was brought to a boil and to it was added 1 M HCl until pH ~3 was observed, then the filtrate was concentrated to dryness, resuspended into 100 mL, and chilled in a freezer. The precipitate was filtered via vacuum filtration and combined with the first precipitate afforded 2.076 g (71% crude mass recovered) of a light brown powder. Characterization of this product indicated its isolation with ESI-LCM [M/Z+1: 294.3 positive ionization—M/Z−1: 292.3 negative ionization] and 1H NMR.

Purification of PAN-1A:

the entirety of the precipitates were dissolved into 100 mL of methanol stored over 3 Å molecular sieves and brought to a boil, 1 M HCl was delivered to the boiling solution until a pH of 3 was observed at which point the reaction mixture was allowed to concentrate by half. Once concentrated, the mixture was placed into an acetone/dry ice bath to precipitate the free acid product. The precipitate was filtered via vacuum filtration and washed with chilled methanol before being placed into a desiccator to achieve constant mass. This afforded 1.8030 g (61.5% isolated) of PAN-1A as the free acid with a melting point range of 230-232° C.

Derivatives have undergone decarboxylation when exposed to temperatures on the order of boiling $H_2O$ [100° C.]. Thus it is advisable to use methanol over ethanol over H2O when handling this product.

1H NMR 300 MHz [CD3OD]: δ 6.79, t (J c. 6.3 Hz), H 1; 6.87, d (J c. 8.7 Hz), H 1; 7.09, d (J c. 9.0 Hz), H 1; 7.29, t (J c. 7.5 Hz) H 1; 7.47, t (J c. 7.2 Hz) H 1; 7.74, t (J c. 7.2 Hz) H 1; 7.80, s, H 1; 7.85, d (J c. 8.7 Hz) H 1; 9.23, d (J c. 8.7 Hz) H 1.

Example 14: Preparation of Quinoline 1(3)-Azo Naphthol (QAN 1&3)

Three solutions were prepared.

Solution A—1.4418 g [10 mmol] of 8-aminoquinoline was dissolved into 2 mL of 6M HCl and 4 mL of H2O.

Solution B—0.7500 g [11 mmol] of sodium nitrite was dissolved into 4 mL of H2O.

Solution C—1.9015 g [10 mmol] of 2-hydroxy-1-naphthoic acid was dissolved into 15 mL of 1 M NaOH.

Each solution was placed into an ice bath and stirred while being cooled to −3° C. Once cooled and with stirring, solution B was delivered dropwise and slowly to solution A while maintaining ~3° C. temperatures throughout. KI-starch paper gave an instant positive result after complete delivery, this solution was allowed to stir on ice for 30 minutes. Once diazotization appeared complete, the combined A/B solution was delivered to solution C dropwise to avoid an exotherm and maintain sub 5° C. conditions. Once complete delivery was achieved the now very thick reaction mixture was stirred on ice for 2 hours and 20 mL of $H_2O$ was added to lessen the viscosity. Then the reaction mixture was filtered via vacuum filtration and rinsed with cold H2O. The precipitate was dried in a vacuum desiccator while the filtrate was extracted with 100 mL of EtOAc, dried over Na2SO4, concentrated and dried in a vacuum desiccator overnight. This afforded a combined mass of 1.7440 g (58.3%) of a very light powder with a deep red hue confirmed to be the QAN 1 product by ESI-LCMS [M/Z+1 300.3—positive ionization: M/Z−1 298.3—negative ionization].

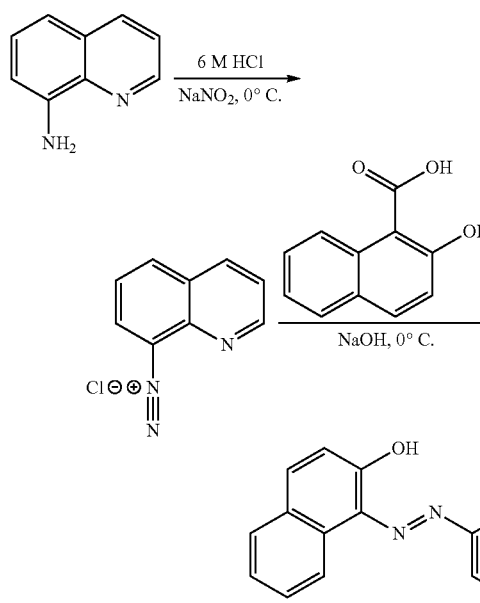

Current Understanding:

The 1H NMR of this product showed twice as many peaks in the aromatic region in a 1:2 ratio, indicating that the product obtained is likely a mixture of QAN isomers. Substitution may occur through an alternative and competing mechanism. The QAN 3 isomer was thought to be the major product of this reaction due to the carboxy group's positioning, however it appears as though the diazonium coupled ipso to the carboxy group generating the QAN 1 isomer as well.

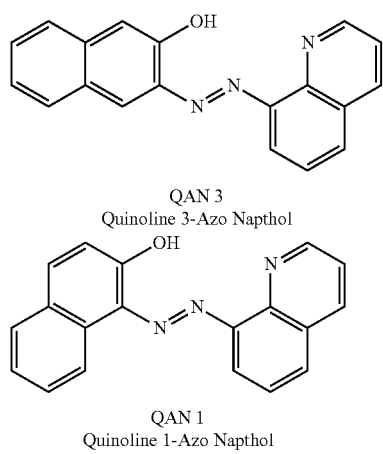

QAN 3
Quinoline 3-Azo Napthol

QAN 1
Quinoline 1-Azo Napthol

Example 15: Preparation of Quinoline Azo 3-Naphthoic Acid (QAN-3A)

Synthesis:
Three solutions were prepared.
Solution A—1.4418 g [10 mmol] of 8-aminoquinoline was dissolved into 2 mL of 6 M HCl and 4 mL of H2O.
Solution B—0.7420 g [11 mmol] of sodium nitrite was dissolved into 4 mL of H2O.
Solution C—1.9044 g [10 mmol] of 2-hydroxy-3-naphthoic acid was dissolved into 15 mL of 1 M NaOH.

Each solution was placed into an ice bath and stirred while being cooled to ~3° C. Once cooled and with stirring, solution B was delivered dropwise and slowly to solution A while maintaining ~3° C. temperatures throughout. KI-starch paper gave an instant positive result after complete delivery, this solution was allowed to stir on ice for 30 minutes. Once diazotization appeared complete, the combined A/B solution was delivered to solution C dropwise to avoid an exotherm and maintain sub 5° C. conditions. Once complete delivery was achieved the now very thick reaction mixture was stirred on ice for 2 hours and 20 mL of H2O was added to lessen the viscosity. Then the reaction mixture was filtered via vacuum filtration and rinsed with cold H2O. The precipitate was dried in a vacuum desiccator while the filtrate was extracted with 100 mL of EtOAc, dried over Na2SO4, concentrated and dried in a vacuum desiccator to afford a combined mass of 1.5540 g of a very light powder with a deep red hue.

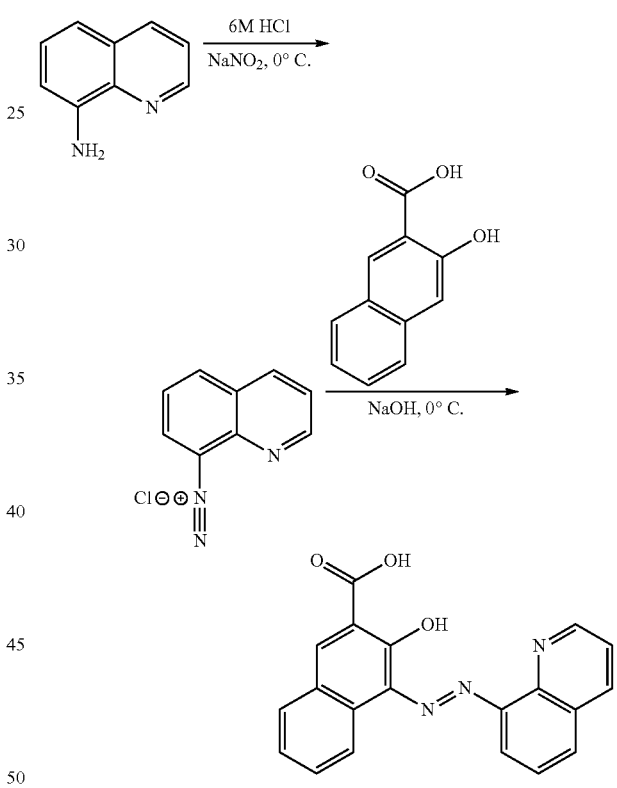

Isolation and Purification of QAN-3A:

From the crude product, 0.2860 g was suspended into 50 mL of CH2Cl2 and stirred, then the aqueous layer was washed with multiple 25 mL additions of 0.1 M HCl and separated. The organics were dried over Na2SO4, filtered and concentrated by rotary evaporation to afford a tick deep red paste. To the round bottom flask was added 150 mL of methanol stored over 3 Å molecular sieves, and brought to a boil. An inverted vial was placed on top of the flask to avoid concentration, this was continued for one hour. The flask was removed from heat and cooled to room temperature slowly, once cooled the flask was placed into an acetone/dry ice bath to precipitate more product. The precipitate was separated by vacuum filtration and dried in a desiccator overnight to achieve constant mass. The 0.2443 g of a fine red powder was confirmed to be the desired product by ESI-LCMS [M/Z+1 344.3—positive ionization: M/Z−1 342.3—negative ionization] and 1H NMR. Melting point, 124-125° C. (decomposition—loss of CO2).

1H NMR 300 MHz [CD3OD]: δ 6.38, dd (J c. 3.6, 9.6), H 1; 7.17, dd (J c. 1.5, 9.6 Hz), H 1; 7.28, td (J c. 2.7, 6.9 Hz), H 1; 7.39, m (J c. 4.5 Hz) H 5; 7.80, dd (J c. 2.7, 6.3 Hz) H 1; 8.17, td (J c. 1.5, 8.4 Hz) H 1; 8.71, dt (J c. 1.2, 4.2 Hz) H 1.

Example 16: Preparation of Quinoline Azo 1,3-dihydroxyNaphthol (QAN-1,3OH)

Diazonium Salt:

in a clean vial, a solution was prepared with 0.0466 g [0.3 mmol] of 8-aminoquinoline and ¼ mL of 6 M HCl in 5 mL of DI $H_2O$ while stirring in an ice bath. Once the temperature of the acidic solution fell below 5° C., a chilled solution of 0.0271 g [0.3 mmol] of sodium nitrite in 1½ mL of DI $H_2O$ was delivered to the quinoline solution dropwise and slowly. Once fully delivered, the solution was stirred on ice for 20 minutes, after which a KI-starch paper test indicated excess nitrite immediately upon spotting.

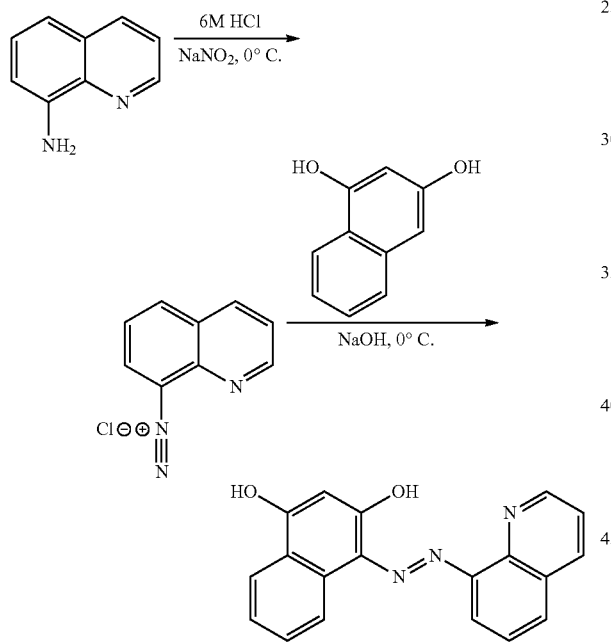

Azo Coupling:

While the diazonium salt was stirring on ice, a solution of 0.0495 g [0.3 mmol] of 1,3-dihydroxynaphthalene and ½ mL of 6 M sodium hydroxide in 5 mL of DI H2O was prepared in an ice bath. Once the naphthol solution became homogenous and its temperature fell below 5° C., the Diazonium solution was delivered to the naphthol solution dropwise and very slowly. Sub-5° C. temperatures were maintained through the complete delivery of the diazonium solution and thereafter for 2 hours. After 2 hours a precipitate was observed and the solution was filtered by vacuum and the precipitate was washed with cold H2O. The filtrate was concentrated by rotary evaporation and dried in a vacuum desiccator overnight with the precipitate to afford a combined mass of 0.0750 g (79.4% isolated) of QAN-1,3OH. The red-black solid was confirmed by ESI LCMS [M/Z+1: 316.2 positive ionization—M/Z−1: 314.1 negative ionization] and 1H NMR to be the desired QAN-1,3OH sensor. Melting Point: 275-277° C.

1H NMR 300 MHz [CD3OD]: δ 5.83, s, H 1; 7.36, t (J c. 7.2 Hz), H 1; 7.51, m (J c. 3.9, 7.2 Hz), H 3; 7.60, t (J c. 7.8 Hz) H 1; 8.07, m (J c. 7.8 Hz) H 2; 8.24, dd (J c. 1.5, 8.1 Hz) H 1; 8.45, d (J 8.1 Hz) H 1; 8.86, dd (J c. 1.5, 4.2 Hz) H 1.

Example 17: Preparation of Quinoline Azo 2,7-dihydroxyNaphthol (QAN-7OH)

Diazonium Salt:

in a clean Erlenmeyer flask, a solution was prepared with 0.7269 g [5 mmol] of 8-aminoquinoline and 2 mL of 6 M HCl in 20 mL of DI H2O while stirring in an ice bath. Once the temperature of the acidic solution fell below 5° C., a chilled solution of 0.3633 g [5 mmol] of sodium nitrite in 5 mL of DI H2O was delivered to the quinoline solution dropwise and slowly. Once fully delivered, the solution was stirred on ice for 20 minutes, after which a KI-starch paper test indicated excess nitrite immediately upon spotting.

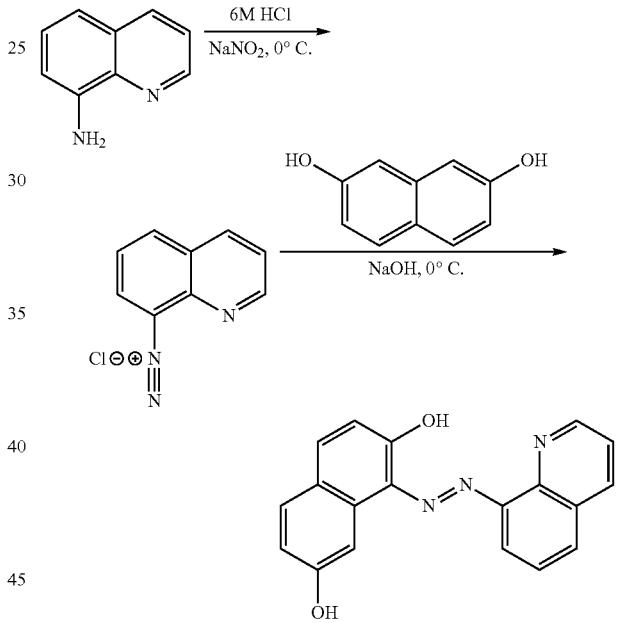

Azo Coupling:

While the diazonium salt was stirring on ice, a solution of 0.8027 g [5 mmol] of 2,7-dihydroxynaphthalene and 3 mL of 6 M sodium hydroxide in 20 mL of DI H2O was prepared in an ice bath. Once the naphthol solution became homogenous and its temperature fell below 5° C., the Diazonium solution was delivered to the naphthol solution dropwise and very slowly. Sub-5° C. temperatures were maintained through the complete delivery of the diazonium solution and thereafter for 2 hours. After 2 hours a precipitate was observed and the solution was filtered by vacuum and the precipitate was washed with cold H2O. The filtrate was concentrated by rotary evaporation and dried in a vacuum desiccator overnight with the precipitate to afford a combined mass of 1.3268 g (84.2% isolated) of QAN-7OH. The purple-black solid was confirmed by ESI LCMS [M/Z+1: 316.15 positive ionization—M/Z−1: 314.10 negative ionization] and 1H NMR to be the desired QAN-7OH sensor. Melting Point: 224° C. Decomposition.

1H NMR 300 MHz [CD3OD]: δ 6.27, d, (J c. 9.3 Hz) H 1; 6.74, dd (J c. 2.4, 8.7 Hz), H 1; 7.28, d (J c. 8.4 Hz), H 1; 7.57, t (J c. 4.5 Hz) H 1; 7.60, s, H 1; 7.71, m (J c. 3.3, 6.0 Hz) H 2; 8.34, t (J c. 8.1 Hz) H 1; 8.37, dd (J c. 2.7, 8.1 Hz) H 1; 8.95, d (J c. 3.9 Hz) H 1.

Example 18: Covalent Linkage

Figure 4:
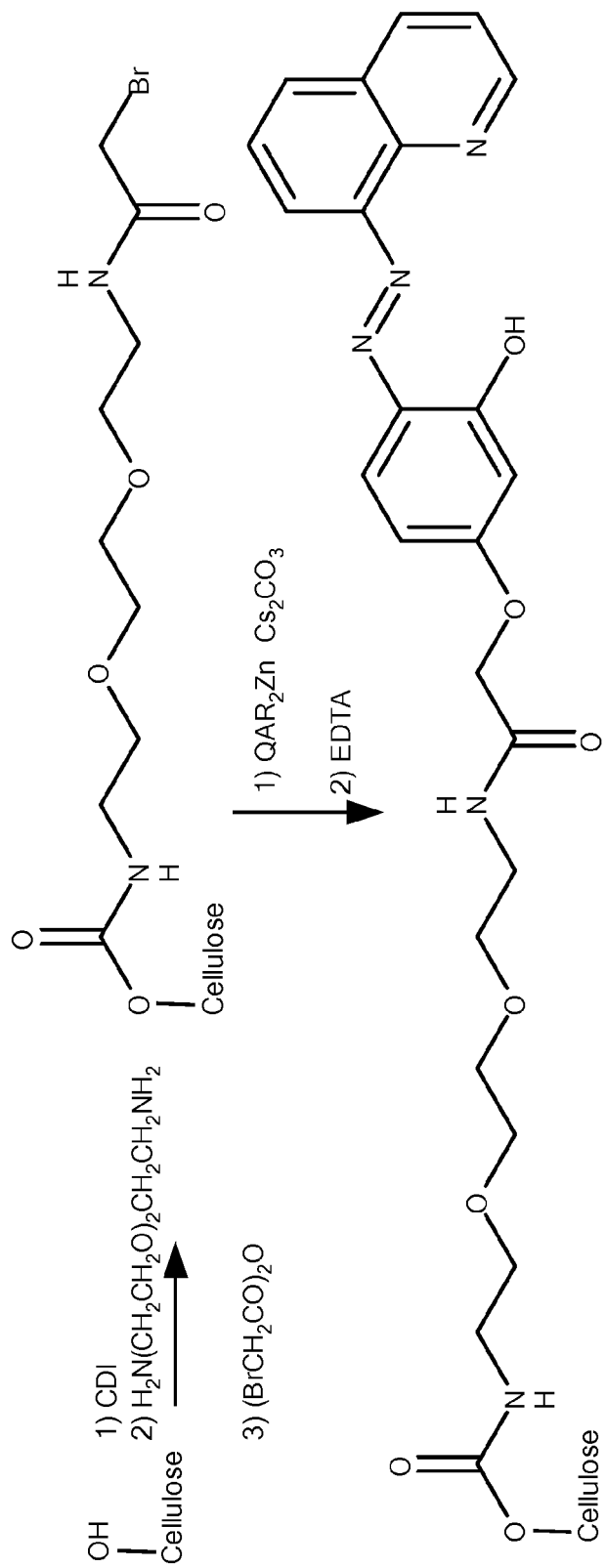
FIG. 4 is a scheme for the covalent attachment of a dye (QAR) to cellulose.

Covalent linkage without interference with metal binding properties depends on leaving the metal-interactive phenol alone. The general method for such linkage involves preforming a zinc complex, and then alkylating the remaining hydroxyl. The scheme has been demonstrated using a transparent cellulose membrane with a robust flexible non-interactive tether as shown in FIG. 4.

Cellulose dialysis membrane was dehydrated by rinsing with N-methyl-pyrrolidinone (NMP). The dried membrane was soaked in a solution of 1 g carbonyldiimidazole (CDI) 14 mL $CH_3CN$ for 4 hours, rinsed thoroughly with $CH_3CN$, and allowed to stand in 10% (v/v) triethyleneglycol diamine $CH_3CN$ for 24 hours. After thorough rinsing, the membrane was exposed to 1.5 mL solution of hydroxybenzotriazole/N,N-dicyclohexylcarbodiimide/bromoacetic acid (1M each in N-methyl-2-pyrrolidinone (NMP)). These films were washed 5× with dimethylformamide (DMF) and stored in DMF for further use. A mixture of 85 mg QAR and 13 mg ZnO (0.5 mol eq) was heated at reflux in 50 mL DMF, and then distilled to remove about half the solvent volume. $Cs_2CO_3$ (100 mg) was added to the remaining solution, and the prepared films were then submerged in vials containing the QAR solution. These were agitated with a vortex-genie and allowed to stand overnight. The intensely colored strips were removed from the QAR solution and rinsed with several portions of nanopure water. (Control strips of untreated tubing were placed in the QAR solution and did not take on the color of the dye). The treated strips were further treated with sodium ethylenediaminetetraacetate (EDTA) to remove $Zn^{2+}$ from the final template.

These covalent-linked films do not lose absorbance over several months exposed to water, air, and light, and retain their metal-responsive absorbance. This procedure will allow covalent linkage of any of the azo dyes that bears a nucleophilic group not involved in metal binding. A somewhat lower metal affinity, with lesser pH response, would result from the same procedure in the absence of the preformation of zinc complex: alkylation of phenolic groups in this case is not selective.

Example 19

For incorporation into other materials and surfaces, another covalent linkage method involves treatment of zinc complex of sensor with cesium carbonate and chloromethylstyrene. The product of this reaction can be incorporated by free radical polymerization into a wide range of materials, exemplified here by polyethyleneglycol diacrylate. The resulting hydrophilic gel, after removal of zinc ion by treatment with EDTA, is similarly stable and responsive to metals as the cellulose membrane. Note that these methods combine with standard silanization procedures to allow covalent linkage to a quartz, glass, silica, or other mineral surface, either as a monolayer, or as a covalently linked gel of controlled thickness, density, and porosity. Slight modifications allow linkage to other surfaces, including many plastics including PET and PMMA.

Example 20: Sensor pH Dependence

Figure 5A:
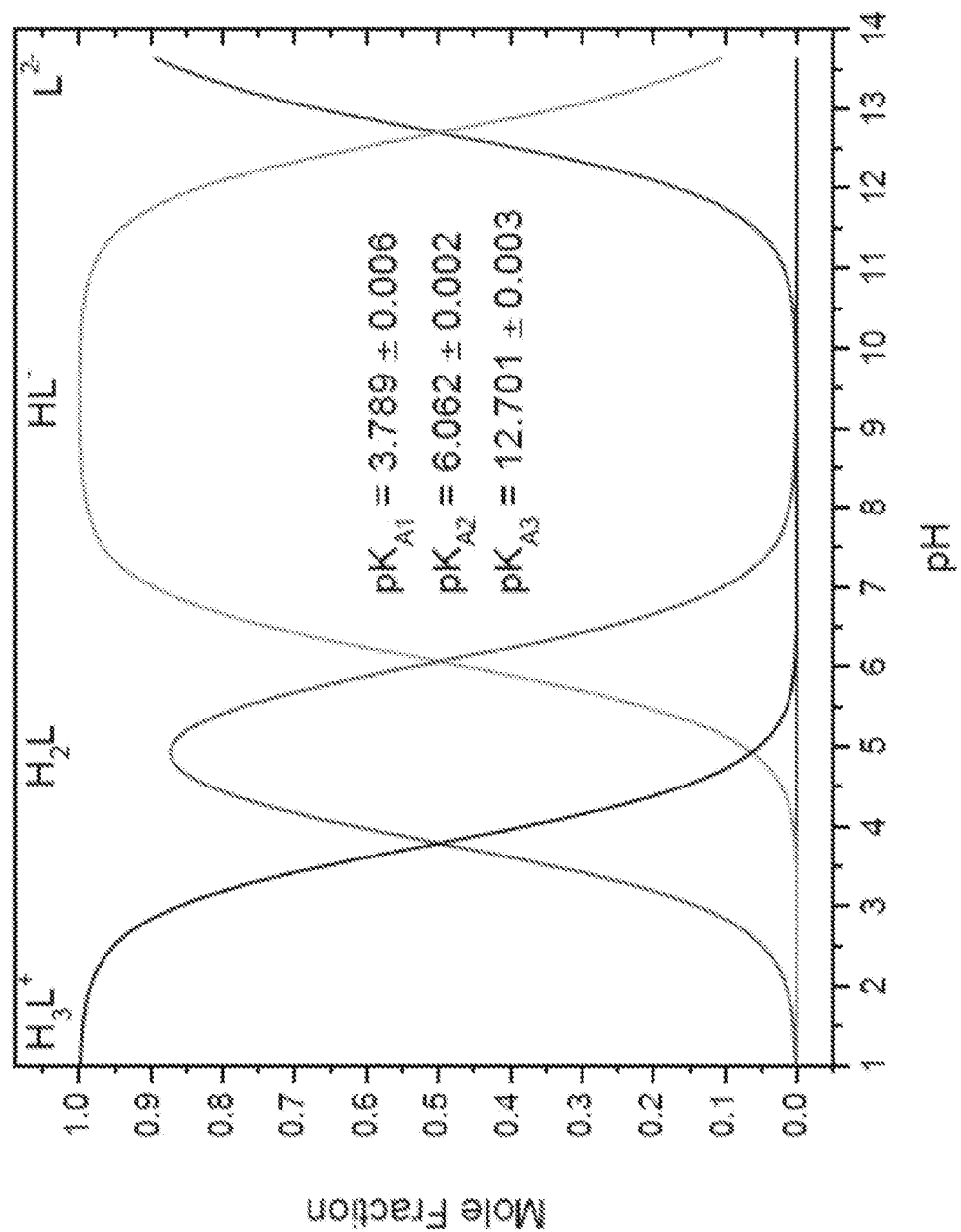
FIG. 5 are graphs showing the (A) protonation states of QAR (denoted as ligand "L" in the figures) as function of pH and the (B) corresponding pure component spectra.
Figure 5B:
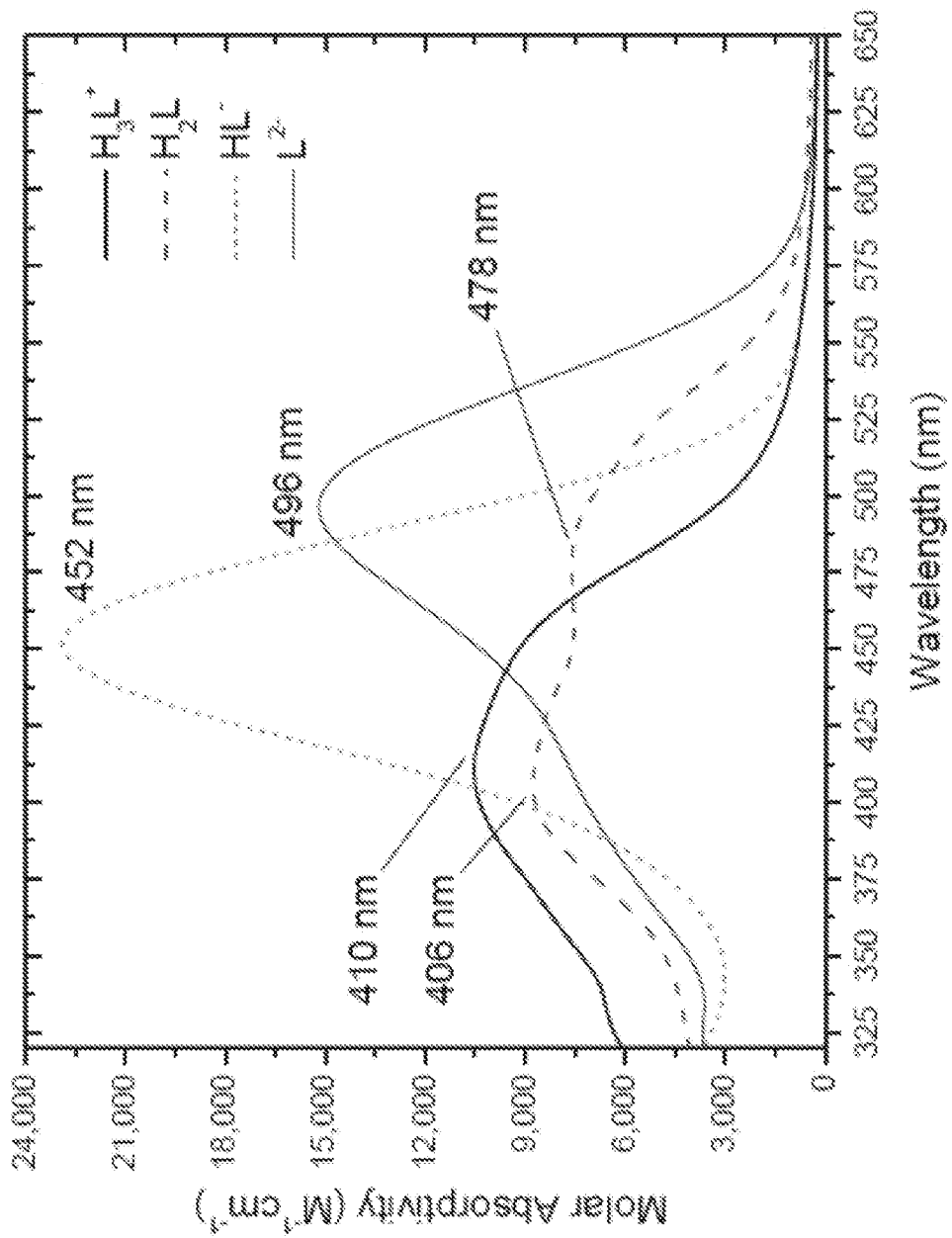

The pH dependent absorption spectra of QAR were measured to determine the acid-dissociation constants ($pK_A$) for use of the sensor for measuring metal-ion concentrations. The sensor was buffered over a pH range of one to fourteen, and the absorption spectra of each solution were recorded. The spectra were analyzed in ReactLab Equilibria to determine the $pK_A$ values and fraction of each protic species present at a given pH. The results are shown in FIG. 5A and FIG. 5B, where L represents the QAR molecule.

QAR has three $pK_A$ values at 3.8, 6.1, and 12.7. These values are similar to other sensor dyes with a similar structure. It was later determined that trace metal impurities were present in some of the buffer reagents used in this experiment, which generated an optical response with QAR and created an error source for the three $pK_A$ values. These impurities were later removed from the pH buffer reagents with an ion exchange resin.

Example 21: Response of QAR and PAR to Metal Ions at pH 7

Optical sensors typically contain a recognition site and chromophoric moiety where the sensor undergoes an optical change, such as a spectral shift or color change, when the target analyte binds to the recognition site. Ideally, a sensor should only respond to a single target analyte. However, many sensors do not have this high degree of selectivity to a single target analyte, and these chemical interferences can yield inaccurate results. Detection and quantification of metals in aqueous samples presents a challenge because many metals, especially d-block metals, have similar ionic radii and ionic charge. Therefore, multiple metals can bind to a particular recognition site to form a complex. In some cases, the sensor cannot differentiate two metal ions, and in other cases, each metal complex has a unique spectral change.

Figure 6:
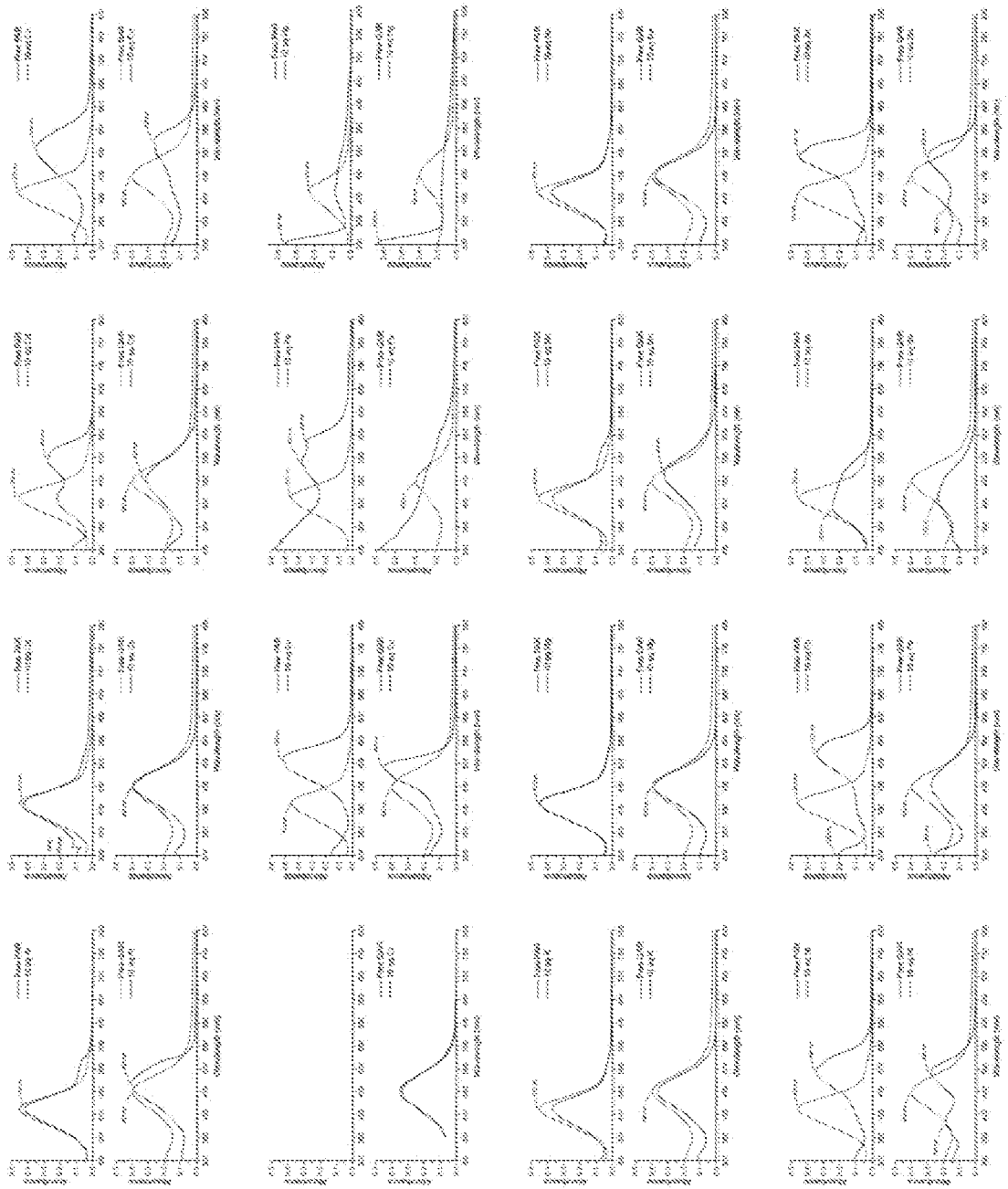
FIG. 6 are absorption spectra of PAR versus QAR in the presence of different metal ions, corresponding to the solutions shown in FIG. 7.
Figure 7:
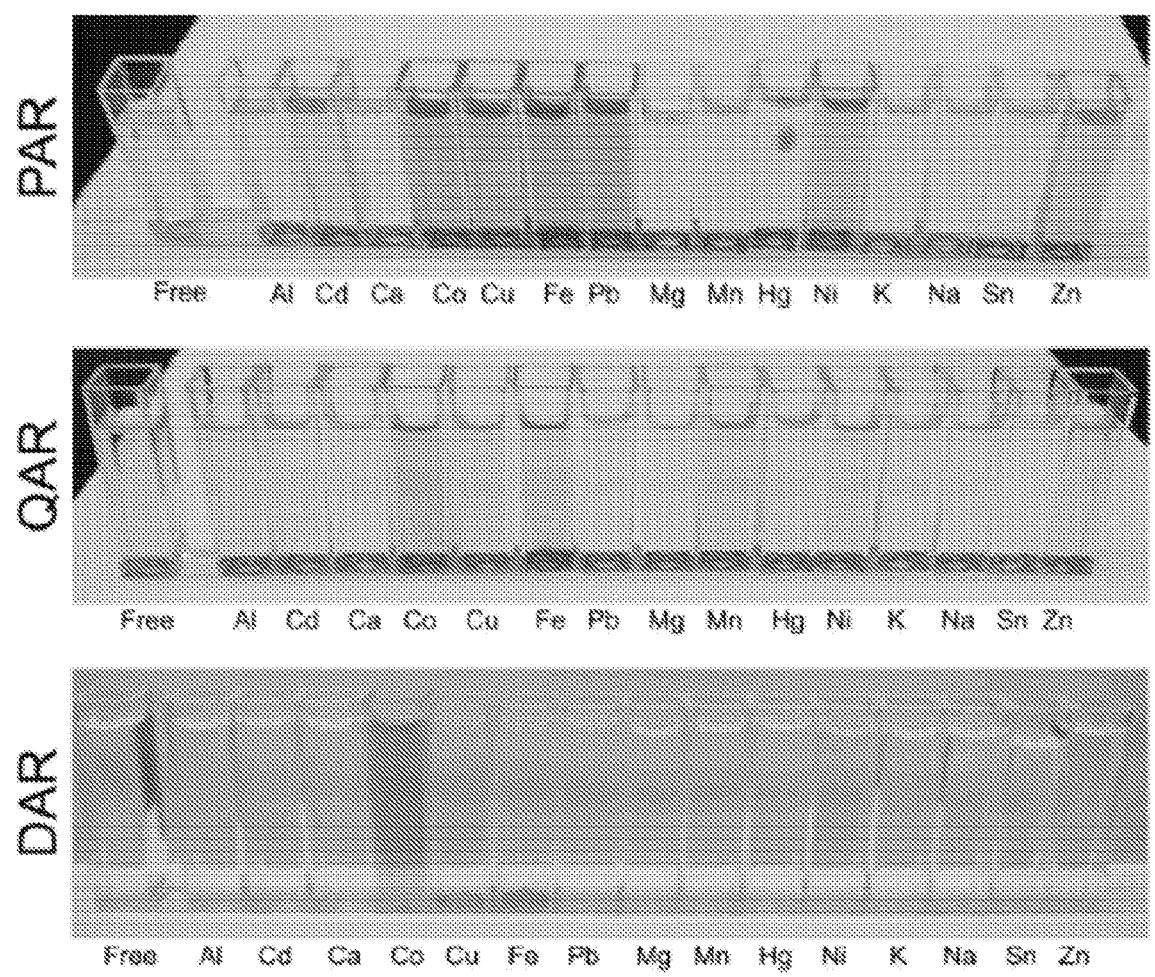
FIG. 7 shows the colorimetric response of PAR, QAR, and DAR to a variety of metal ions at pH 7.

The response of QAR to different metal ions was measured to determine its selectivity and compared to another sensor (PAR), which has a similar structure. Samples were prepared with different metal standards at pH 7, and the absorbance spectrum of each sample was recorded (FIG. 6). Also, photographs of the samples are provided below to allow for a visual comparison (FIG. 7).

The spectra of QAR were compared to the spectrum of the free dyes, and the general response of QAR at pH 7 can be described as follows:

Insensitive: Ca(II), Cr(III), K(I), Mg(II), Na(I), Pb(II), Sn(II).

Weakly Sensitive: Al(III), Cd(II), Mn(II).

Strongly Sensitive: Cu(II), Co(II), Ni(II), Zn(II).

Severe aggregation: Fe(III).

QAR has a higher binding selectivity and has a higher spectral sensitivity than PAR. Other general observations can be described as follows:

QAR, and PAR did not undergo a spectral change in the presence of the soft metals (Na(I), Ca(II), K(I), Mg(II)). This is important in biological applications where these ions are present at relatively high concentrations.

QAR forms a magenta complex with Co(II) while PAR forms a magenta complex with multiple metals, including Co(II), Cu(II), Fe(III), and Pb(II). QAR forms an orange complex with Cu(II), Ni(II), and Zn(II). PAR forms a magenta complex with Cu(II), and forms orange complexes with Cd(II), Ni(II), and Zn(II). So, QAR can differentiate Cd(II) from Zn(II), which are common interferents with colorimetric sensors.

QAR does not appreciably complex with Fe(III), Pb(II), Mn(II), and Sn(II).

Aggregation occurs with Fe(III) for both PAR and QAR, although a brown, globular suspension is clearly seen for QAR.

QAR forms a transparent complex with Hg(II) that does not strongly absorb in the visible and near-UV portions of the spectrum. A brown, globular suspension is observed with Hg(II) and PAR, which is attributed to aggregation.

Example 22: Evaluation of Covalently Attached QAR: Cellulose Substrate

Figure 8A:
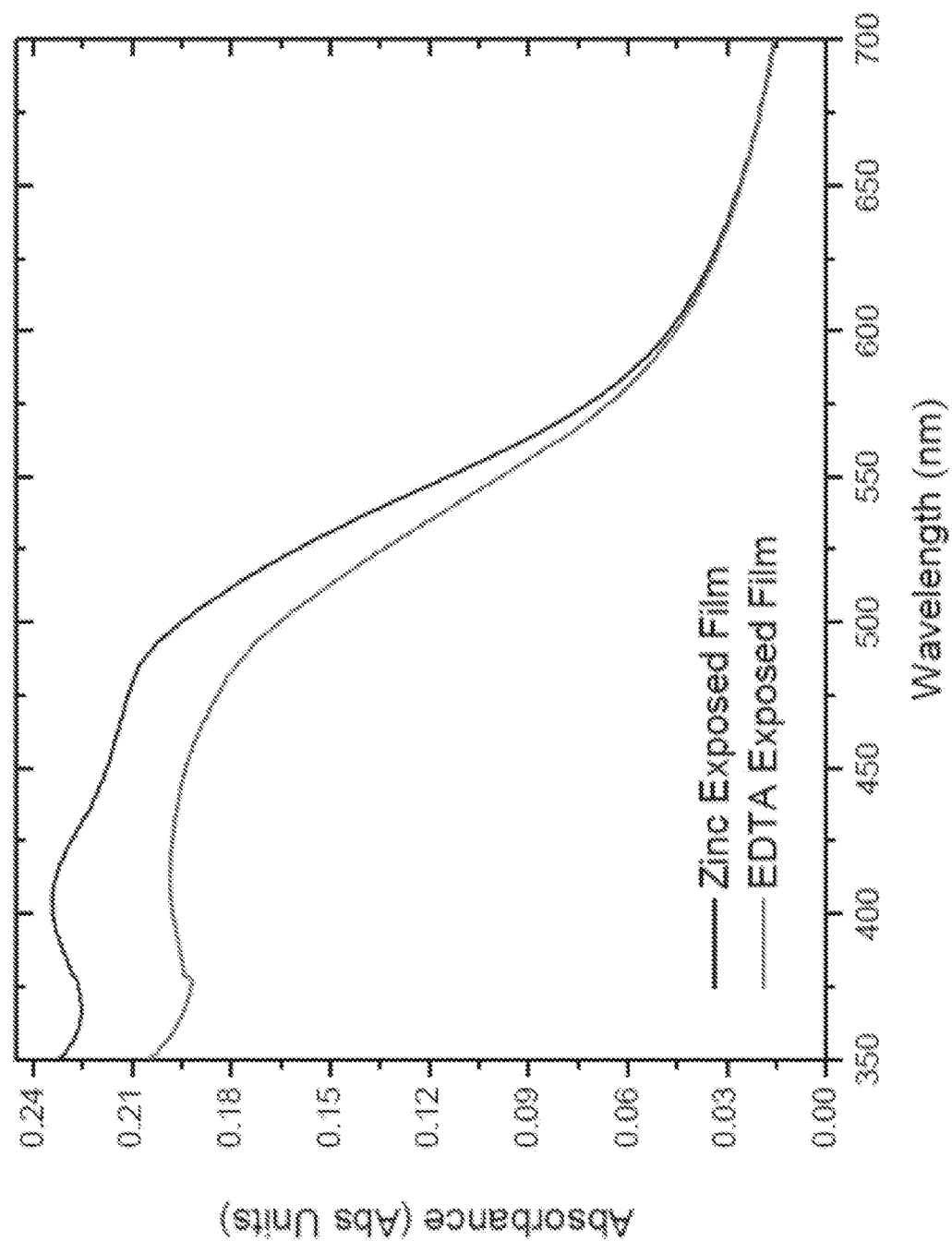
FIG. 8 are graphs showing the (A) absorbance spectra of cellulose film with the covalently attached QAR derivative after exposure to zinc and EDTA, and (B) the difference of the zinc from the EDTA film spectra showing the absorbance response to zinc.
Figure 8B:
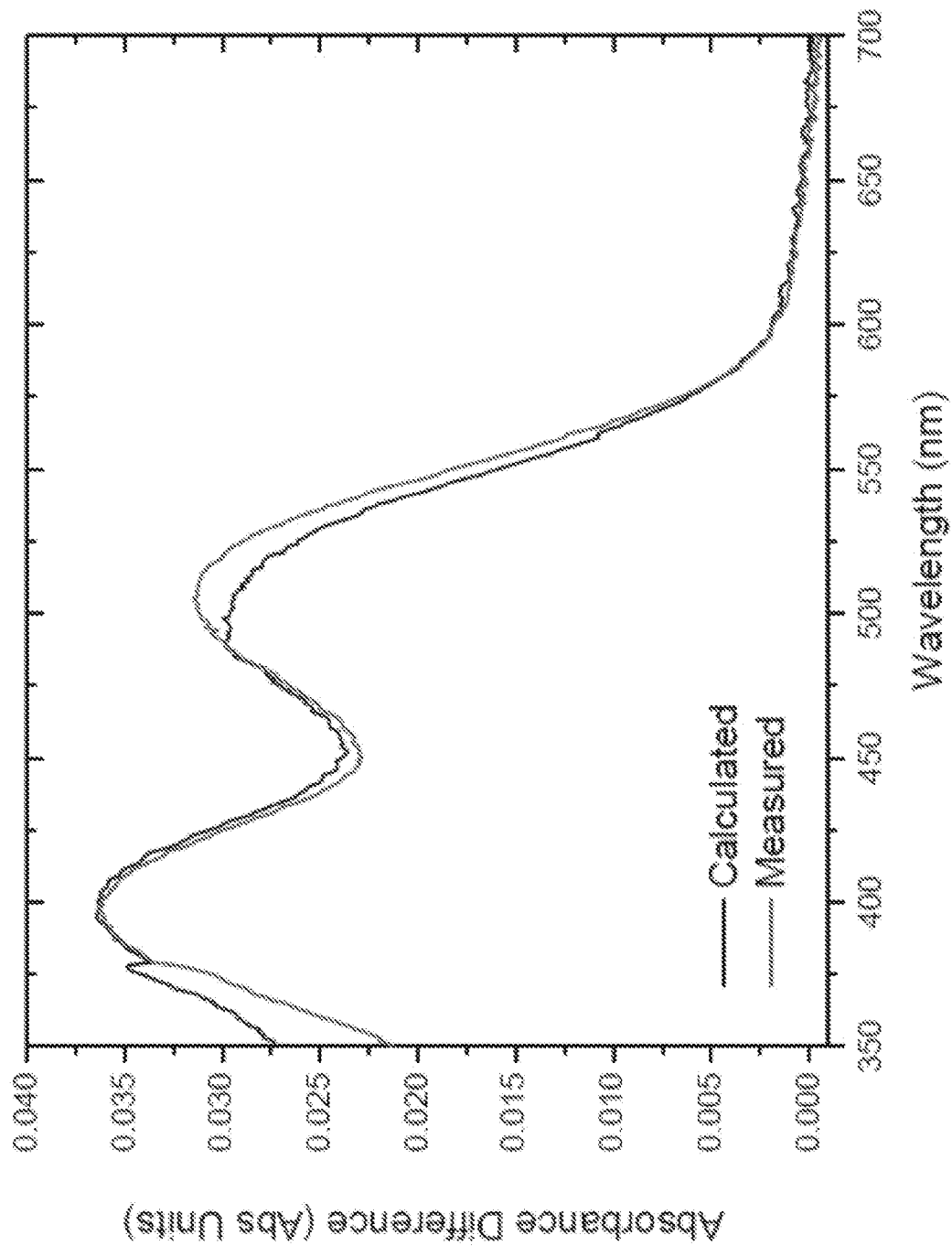

Next, QAR derivative was covalently attached to (1) a cellulose film and (2) to a porous polymer coating that was applied to an optical fiber. First, the QAR derivative was covalently attached to a modified cellulose film. The film was dehydrated, then activated and functionalized with a bromine-terminated poly(ethylene glycol). This readily reacted with a hydroxyl group on the QAR molecule to covalently attach the dye to the film. A portion of the film was divided and submerged into an EDTA solution to remove the complexed zinc from the attached dye. The films were placed between two microscope slides to create a flat surface in order to minimize unwanted optical scattering of the sample, and the absorbance spectra of the films was recorded with a spectrophotometer. The results are shown in FIG. 8A and FIG. 8B.

The free QAR derivative has a broad absorbance over 400 to 500 nm, and absorbance profile of the covalently-attached derivative is different than the unmodified QAR form. The absorbance of the zinc complex of the covalently-attached QAR derivative is larger than the unbound dye with a similar spectral profile.

The absorbance change upon complexation with zinc is not as dramatic as the absorbance change for the unmodified QAR molecule. A reduction or even the cessation of the sensor response is a common issue encountered when a sensor dye is modified for covalent attachment. Also, the value of the absorbance change is relatively small because the cellulose film only contains a monolayer of the QAR derivative. However, the high surface coverage of the dye provided sufficient optical density to obtain a spectrum within the instrumental limitations of the spectrophotometer.

The calculated difference spectrum, where the spectrum of the zinc complex was subtracted from the spectrum of the EDTA-washed film, reveals the absorbance change when zinc complexes with the covalently-attached QAR derivative. The measured difference spectrum was obtained by recording the absorbance of the zinc-complexed film using the EDTA-washed film as a blank, which is analogous to an "instrumental" subtraction. There is good agreement between the two curves. Also, the difference spectra resemble the spectrum of the MLH form of QAR. This is consistent because one of the protonation sites of the QAR molecule is modified with the covalent linker moiety.

Example 23: Evaluation of Covalently Attached QAR: Polyethylene Glycol Substrate Mounted to Optical Fibers for Measurement The QAR derivative was covalently attached to a polymer that replaced the cladding of the section of an optical fiber in contact with the analyte in a flow cell.

Figure 9:
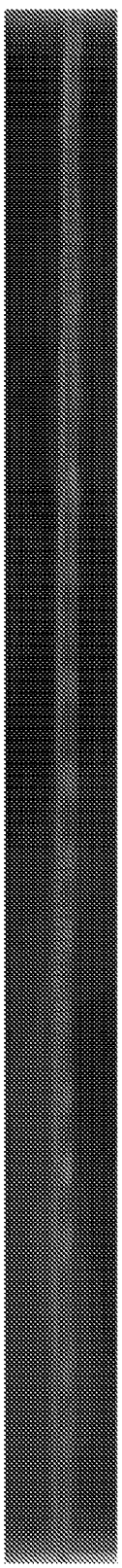
FIG. 9 is an image of the sensor coating curing under UV light where the fiber core has a violet hue and the sensor coating has a blue-green hue.

The buffer and cladding layers of an optical fiber were thermally removed from a section of optical fiber. Subsequently, the fiber was submerged in nitric acid to clean and protonate the surface. The surface was then functionalized with (trimethoxysilyl)propyl methacrylate, which will bond the polymer coating to the silica fiber during photopolymerization. A solution containing the QAR derivative, poly (ethylene glycol) diacrylate, photoinitiator, and PMMA microspheres was applied to the exposed fiber core and photopolymerized with UV light under an inert atmosphere (FIG. 9). The fiber sensor was then sealed into a glass flowcell. The cell was filled with acetone to dissolve the microspheres yielding a highly porous structure on the fiber core.

Figure 10:
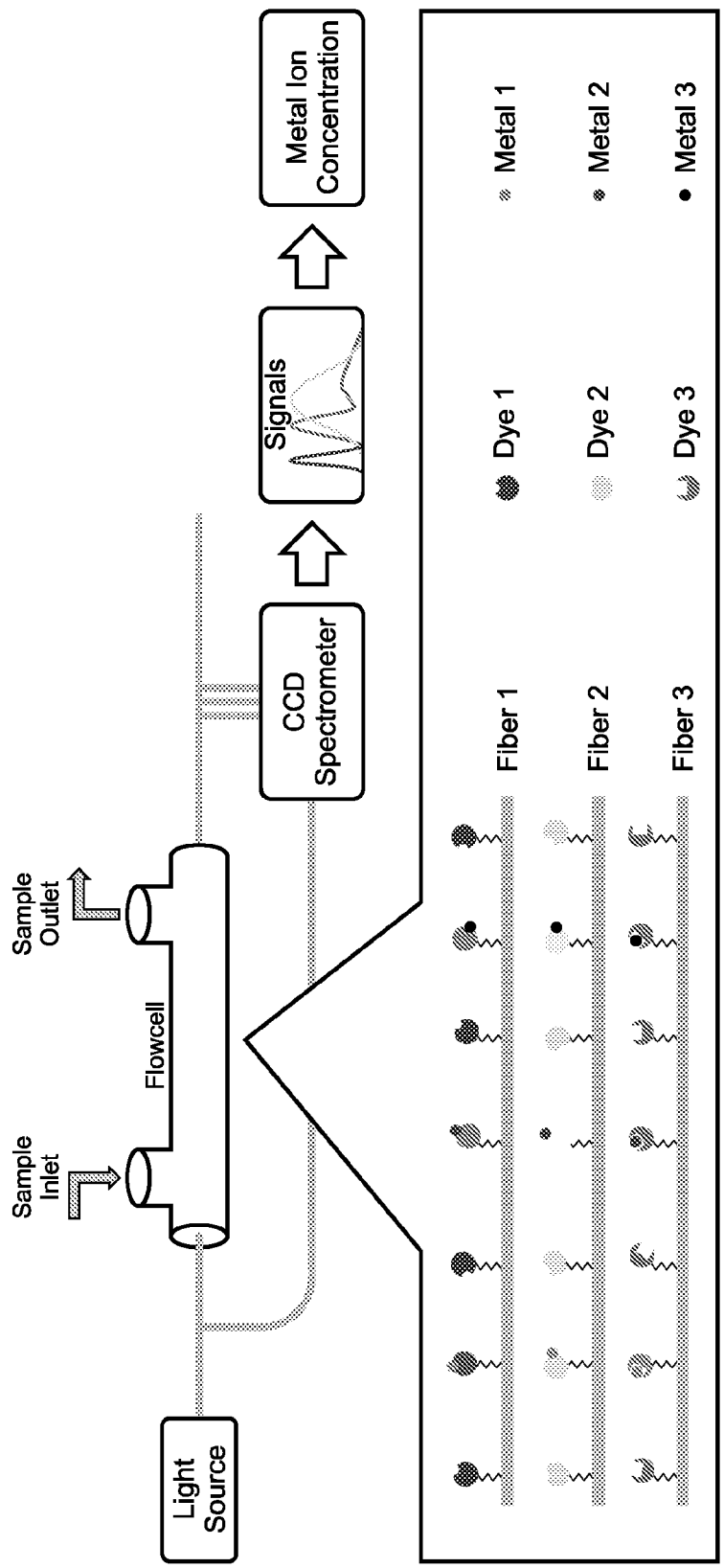
FIG. 10 is a schematic of the absorption-modulated luminescence setup to be used as detailed in Example 36.

Absorbance measurements through the fiber were carried out comparing the light intensity entering the flow cell and exiting the flow cell through the same fiber. Transmitted light intensities were determined by coupling light from fiber carrying in the QAR sensor polymer into orthogonally-crossing secondary optical fibers before and after the flow cell (FIG. 10). The orthogonal fiber measurement junctions were formed inserting a polymer between the fiber cores of the crossing fibers with a refractive index causing light to scatter and refract into the crossing fibers to generate an optical signal proportional to the light intensity in the fiber core.

Figure 11:
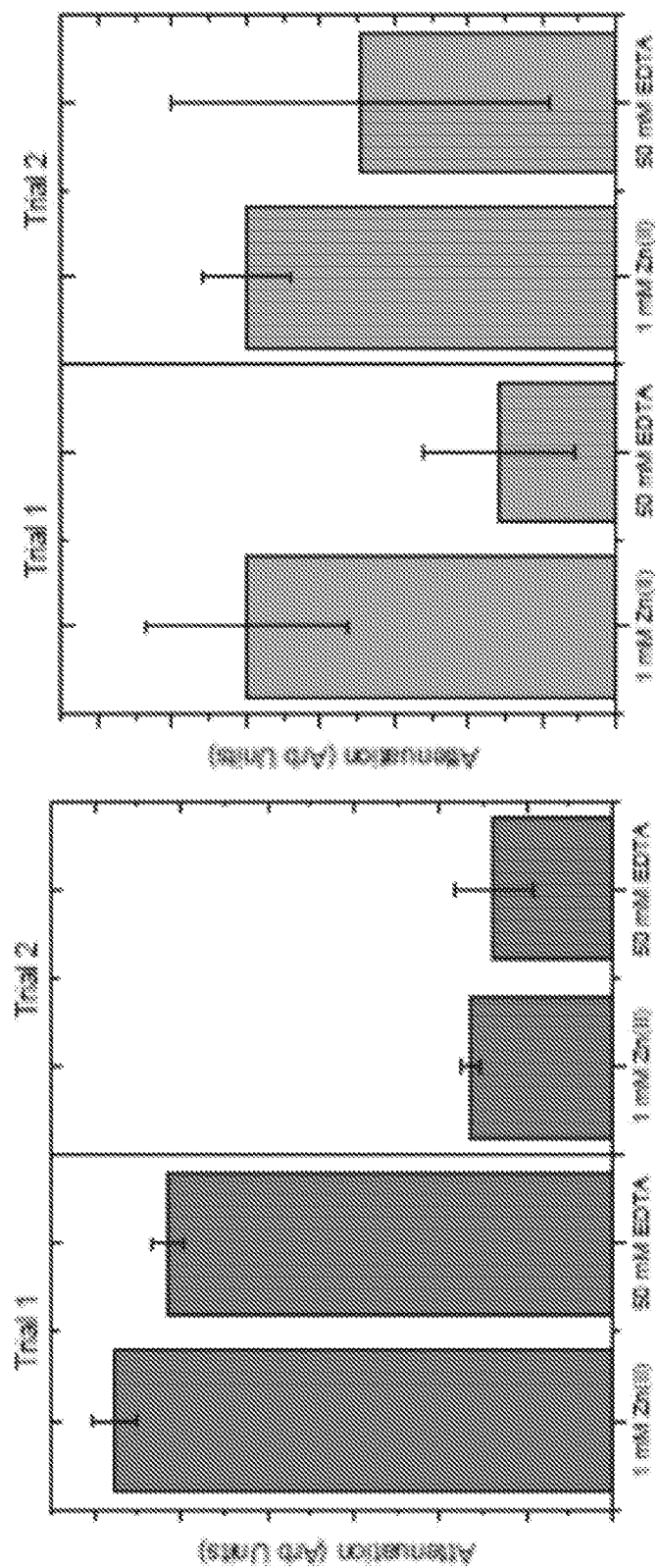
FIG. 11 are graphs showing the results from the fiber absorbance sensor containing QAR derivative showing the standard attenuation directly as measured (left) and normalized attenuation (right) after exposure to zinc and then EDTA. The error bars represent the 95% confidence interval with five replicate measurements.

The porous sensor layer was tested by exposure to zinc and EDTA in an alternating fashion and recording the intensities of both reference regions. The fiber was illuminated with 505-nm light, where the absorbance change is indicative of zinc complexation. The absorbance change of the zinc complex is greatest at 396 nm. However, the fiber has high intrinsic loss at these shorter wavelengths, so the fiber was illuminated at the next largest absorbance change for zinc complex (505 nm). Five replicate measurements were recorded and averaged for each sample, and two trials were performed (FIG. 11). The attenuation was calculated using the integrated intensity values from both reference regions. The attenuation change when the complexed zinc is removed from the sensor layer is consistent with the absorbance change observed with the cellulose film.

Example 24: pH Measurement from the Spectra of QAR Using Multivariate Analysis

Figure 12:
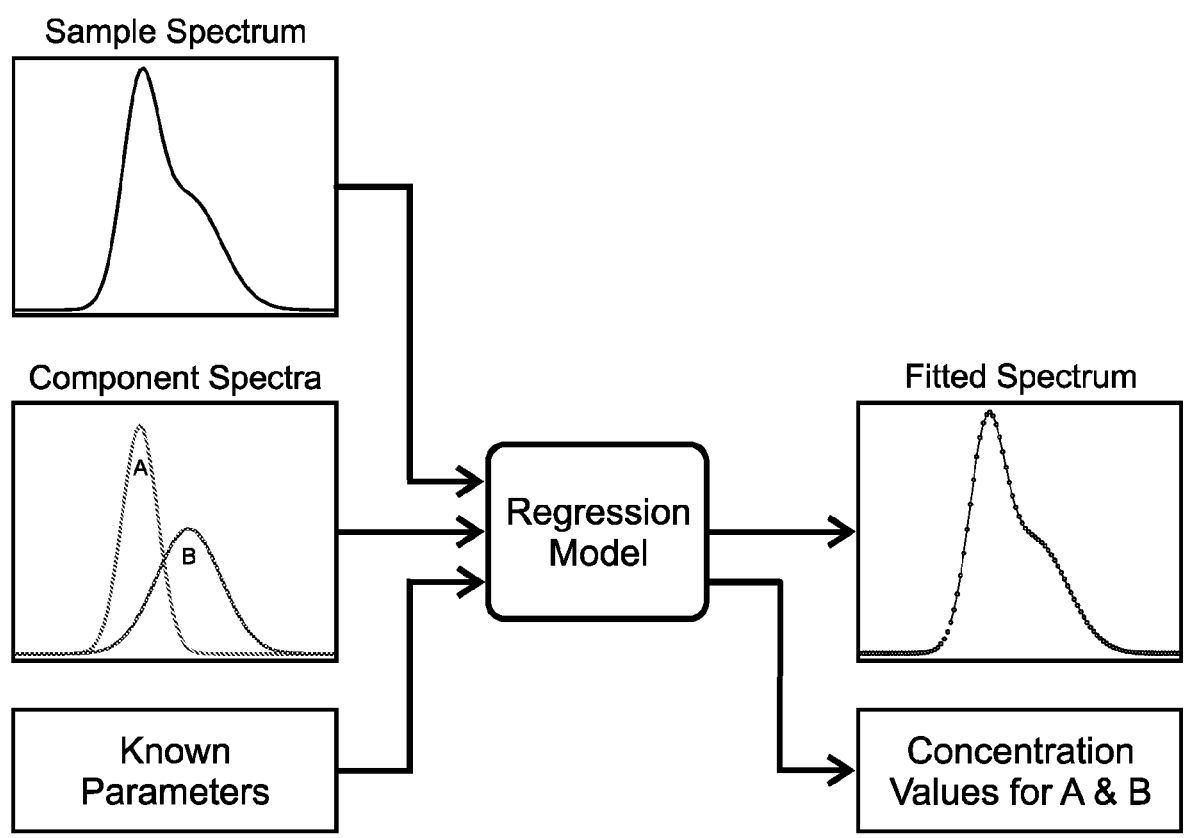
FIG. 12 is a schematic of the decomposition process of aggregate array response data.

Several multivariate approaches are available for determining analyte concentration from an optical spectrum. These include Multiple Linear Regression (MLR), Inverse Least Squares (ILS), Principal Component Analysis (PCA), Principal Component Regression (PCR), and Partial Least Squares, which is also known as Projection of Latent Structures, (PLS). FIG. 12 is a general diagram for these multivariate analysis techniques, although the pure component spectra are not required for some of the methods in the above list.

Figure 13:
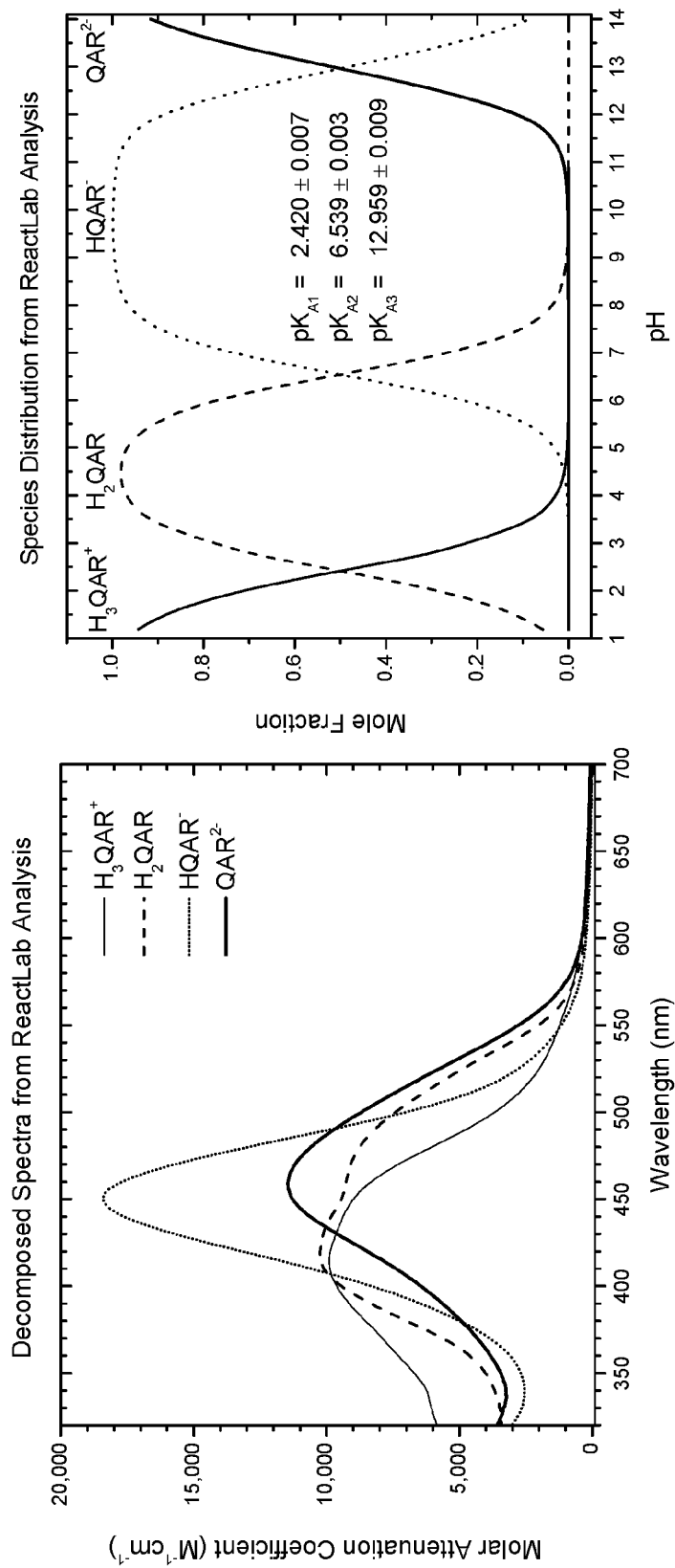
FIG. 13 are graphs showing the decomposed spectra and species distribution for the protonation states of free QAR.

MLR was demonstrated by determining the pH of a solution containing a known amount of QAR. QAR has three pKA values and four colored species (FIG. 13). The concentration of each protonated species is related to pH by the Henderson-Hasselbalch equation. Each species has a unique contribution to the absorbance spectrum at a given pH.

A series of validation samples was prepared with a pH ranging from two to twelve. The pH of each solution was measured with a conventional pH probe and meter, and the absorbance spectrum of each solution was recorded with a spectrometer.

MLR regression was performed using a model that incorporated the component spectra (spectral profiles) and the acid dissociation equilibria of QAR to calculate the concentration of each species in solution. More specifically, the regression model used a single concentration parameter related the known pKA values.

The pH error was calculated using the measurement with the conventional pH probe and the value determined by MLR. The relative errors were less than 1.5% for a majority of the samples, and the error increased proportionately as the single concentration parameter in the MLR model decreased below one-millionth of the total QAR concentration.

The validation samples in this example were free of any detectable metal ions. QAR forms complexes with several metal ions, and these complexes have spectral profiles that differ from the free sensor. Therefore, these metal ions are classified as interferences for measuring pH with QAR. Although not practical, a more complex approach could be implemented if metal ion concentrations and component spectra for the metal complexes are known.

Example 25: Determination of Three Metal Ion Concentrations from the Spectra of PAR Using Multivariate Analysis PLS is a soft model method used for building predictive models without the requirement for strict understanding of the relationships between variables. Although the relationship between concentration (dose) and absorbance (response) is well-understood, PLS has several advantages to MLR. PLS does not require component spectra for analysis, it is less prone to overfitting the response data and yielding erroneous results, is compatible with highly collinear (redundant) data, and can efficiently cope with a large datasets. In this example, PLS was demonstrated by determining the concentrations of copper, nickel, and zinc at pH 7 using PAR as the sensor.

A set of samples was prepared using 20.0 micro-molar of PAR so that the absorbance values would be in the range of 0.05 to 1.0 absorbance units. Also, the initial dye concentration exceeds the $K_D$ of the metal complexes, so the sensor was operating in saturation mode where the metal was "driven by equilibrium" to form the complex with the sensor. Therefore, a negligible amount of free metal was present in solution.

Similarly, the samples were prepared so the total metal ion concentrations did not exceed 10.0 micro-molar. PAR forms 1:2 M:L complexes with the copper, nickel, and zinc. Therefore, the total metal concentration was constrained to a maximum 10.0 micro-molar to ensure that the absorbance response was a linear for the PLS model.

A 20.0 micro-molar stock PAR solution was prepared with 0.1 M MOPS buffer at pH 7.0 and 0.500 mM Triton X-100, a surfactant that prevents aggregation. Metal ion standards were prepared containing 100. ppm copper, nickel, or zinc by dilution of an atomic absorption standard with ultrapure water. A set of 64 calibration solutions and seven pseudo-unknown samples were prepared.

The absorption spectrum of each sample was recorded with Stellarnet Black Comet compact spectrometer with thermo-electrically cooled CCD detector and a Stellarnet SL1 tungsten-halogen lamp containing a color-balance filter. The absorption spectrum range was 350 to 843 nm in 0.5 nm increments. A total of 100 acquisitions were recorded and averaged to improve SNR. No digital smoothing, baselining, or pre-processing of the spectra was performed.

The PLS model was built using the calibration data in OriginPro 2016. Then, the predicted metal ion concentrations in the pseudo-unknown samples were calculated from the spectra using the model. The concentration error in the pseudo-unknowns was calculated to estimate the accuracy of the model. The results are given in the following table where the "Prepared Concentration" is concentration of the metals used to prepare the pseudo-unknown samples. The "Model Predicted Concentration" is the metal ion concentration computed by the PLS model. The absolute error was calculated for each sample. RMSE is the root-mean-square of the individual errors. All of the concentration values are given in micro-molar units. Negative concentration values are nonsensical and an artifact of the PLS model, which could not be constrained to positive values (TABLE 1).

TABLE 1

| Unknown Index | Cu | Ni | Zn |
|---|---|---|---|
| Prepared Concentration (µM) | | | |
| 1 | 0.00 | 2.73 | 0.00 |
| 2 | 3.78 | 2.04 | 1.84 |
| 3 | 1.89 | 2.11 | 2.20 |
| 4 | 1.95 | 2.73 | 2.14 |
| 5 | 1.51 | 2.52 | 2.81 |
| 6 | 3.15 | 3.41 | 0.61 |
| 7 | 2.14 | 2.45 | 1.71 |
| Model Predicted Concentration (µM) | | | |
| 1 | −0.06 | 2.76 | −0.07 |
| 2 | 3.64 | 1.96 | 1.77 |
| 3 | 2.00 | 2.26 | 2.24 |
| 4 | 2.03 | 2.70 | 2.07 |
| 5 | 1.69 | 2.53 | 2.56 |
| 6 | 3.04 | 3.31 | 0.65 |
| 7 | 2.06 | 2.38 | 1.80 |
| Error (µM) | | | |
| 1 | −0.06 | 0.04 | −0.07 |
| 2 | −0.14 | −0.09 | −0.06 |
| 3 | 0.11 | 0.15 | 0.04 |
| 4 | 0.08 | −0.03 | −0.07 |
| 5 | 0.18 | 0.01 | −0.26 |
| 6 | −0.11 | −0.10 | 0.03 |
| 7 | −0.08 | −0.07 | 0.09 |
| RMSE (µM) | | | |
| 1 | 0.10 | | |
| 2 | 0.18 | | |
| 3 | 0.19 | | |
| 4 | 0.11 | | |
| 5 | 0.31 | | |
| 6 | 0.15 | | |
| 7 | 0.14 | | |

Metal ion concentrations in water are often specified in parts-per-million (ppm) or parts-per-billion (ppb). Molar units allow the side-by-side comparison of the concentration of two different metals, while 1 ppm zinc is not equal to the same amount copper. A conversion table is given below (TABLE 2).

TABLE 2

Conversion table.

| Metal µM | Cu ppb | Ni ppb | Zn ppb | Pb ppb |
|---|---|---|---|---|
| 1 | 63.5 | 58.7 | 65.4 | 207.2 |
| 0.5 | 31.8 | 29.3 | 32.7 | 103.6 |
| 0.4 | 25.4 | 23.5 | 26.2 | 82.9 |
| 0.3 | 19.1 | 17.6 | 19.6 | 62.2 |
| 0.2 | 12.7 | 11.7 | 13.1 | 41.4 |
| 0.1 | 6.4 | 5.9 | 6.5 | 20.7 |
| 0.05 | 3.2 | 2.9 | 3.3 | 10.4 |

In this example, the predictive PLS model performed well for quantifying the concentrations of three metal ions simultaneously using a single absorbance spectrum. The RMSE value for most samples was within 0.20 µM, which is approximately 13 ppb. Pseudo-unknown 5 has an RMSE of 0.31 µM, which is slightly less than 20 ppb. Two of the predicted concentration values were negative for Pseudo-unknown 1, but these errors are small (less than 5 ppb).

It is worth noting that PAR binds to many other metal ions not included in this example, which may have spectral overlap with each other. If the responses from other metal ions are used to build a more complex PLS model with a single sensor, then the predictive error is also expected to increase. However, the responses from an array containing two-or-more sensors can be also be used to build a more complex PLS model to improve the accuracy when quantifying an increased number of metal ion species.

Example 26: Determination of Four Metal Ion Concentrations from the Spectra of QAR and PAR Using Multivariate Analysis In this example, PLS was demonstrated by determining the concentrations of copper, lead, nickel, and zinc at pH 7 using two sensors: PAR that has a response for lead and QAR that does not. The individual responses from PAR and QAR were combined into a single PLS model to improve quantification of lead in the mixture.

The calibration solutions and pseudo-unknowns were prepared, and the absorbance spectra were recorded and analyzed in a similar manner to the previous example. Here, 200 calibration solutions were used to build the predictive PLS model and eight pseudo-unknown samples were prepared to estimate the accuracy of the model.

A PLS model was built for the four metals using a single sensor, PAR, which has a spectral response for copper, lead, nickel, and zinc. A second PLS model was built using the combined response from each sensor to these four metal ion species. The errors in the metal ion concentration were calculated for both models. This allowed comparison of performance of a single sensor and a two-element sensor array. Results are shown in TABLE 3.

TABLE 3

| Unknown Index | Cu | Ni | Zn | Pb |
|---|---|---|---|---|
| PAR: Prepared Concentration (µM) | | | | |
| 8 | 1.83 | 2.11 | 1.77 | 1.74 |
| 9 | 1.76 | 1.98 | 1.65 | 2.32 |
| 10 | 1.57 | 1.70 | 1.53 | 3.07 |
| 11 | 1.32 | 1.43 | 1.28 | 3.59 |
| 12 | 0.94 | 1.02 | 0.92 | 4.11 |
| 13 | 2.33 | 1.43 | 2.08 | 0.64 |
| 14 | 2.14 | 2.79 | 0.67 | 0.93 |
| 15 | 2.14 | 1.16 | 2.51 | 1.27 |
| PAR: Model Predicted Concentration (µM) | | | | |
| 8 | 1.72 | 2.25 | 1.56 | 1.85 |
| 9 | 1.73 | 2.06 | 1.65 | 2.47 |
| 10 | 1.60 | 2.09 | 1.51 | 3.14 |
| 11 | 1.32 | 1.54 | 1.04 | 3.42 |
| 12 | 0.96 | 1.43 | 0.67 | 4.24 |
| 13 | 2.24 | 1.56 | 1.95 | 0.75 |
| 14 | 2.08 | 3.00 | 0.60 | 1.00 |
| 15 | 2.11 | 1.30 | 2.20 | 1.49 |
| PAR: Error (µM) | | | | |
| 8 | −0.10 | 0.13 | −0.21 | 0.11 |
| 9 | −0.03 | 0.08 | 0.00 | 0.15 |
| 10 | 0.03 | 0.38 | −0.02 | 0.07 |
| 11 | 0.00 | 0.11 | −0.25 | −0.17 |
| 12 | 0.01 | 0.41 | −0.25 | 0.12 |
| 13 | −0.09 | 0.13 | −0.13 | 0.11 |
| 14 | −0.06 | 0.20 | −0.08 | 0.07 |
| 15 | −0.03 | 0.14 | −0.31 | 0.21 |
| PAR + QAR: Prepared Concentration (µM) | | | | |
| 8 | 1.83 | 2.11 | 1.77 | 1.74 |
| 9 | 1.76 | 1.98 | 1.65 | 2.32 |
| 10 | 1.57 | 1.70 | 1.53 | 3.07 |
| 11 | 1.32 | 1.43 | 1.28 | 3.59 |
| 12 | 0.94 | 1.02 | 0.92 | 4.11 |
| 13 | 2.33 | 1.43 | 2.08 | 0.64 |
| 14 | 2.14 | 2.79 | 0.67 | 0.93 |
| 15 | 2.14 | 1.16 | 2.51 | 1.27 |
| PAR + QAR: Model Predicted Concentration (µM) | | | | |
| 8 | 1.90 | 2.30 | 1.45 | 1.76 |
| 9 | 1.95 | 2.21 | 1.52 | 2.42 |
| 10 | 1.71 | 2.11 | 1.37 | 3.09 |
| 11 | 1.47 | 1.66 | 1.01 | 3.37 |
| 12 | 1.01 | 1.52 | 0.72 | 4.16 |
| 13 | 2.46 | 1.68 | 1.71 | 0.67 |
| 14 | 2.32 | 3.07 | 0.49 | 0.94 |
| 15 | 2.24 | 1.41 | 2.10 | 1.40 |
| PAR + QAR: Error (µM) | | | | |
| 8 | 0.07 | 0.19 | −0.32 | 0.02 |
| 9 | 0.19 | 0.24 | −0.14 | 0.10 |
| 10 | 0.14 | 0.41 | −0.16 | 0.02 |
| 11 | 0.15 | 0.23 | −0.27 | −0.22 |
| 12 | 0.07 | 0.50 | −0.20 | 0.05 |
| 13 | 0.13 | 0.24 | −0.37 | 0.03 |
| 14 | 0.18 | 0.28 | −0.18 | 0.01 |
| 15 | 0.10 | 0.25 | −0.41 | 0.12 |

Figure 14:
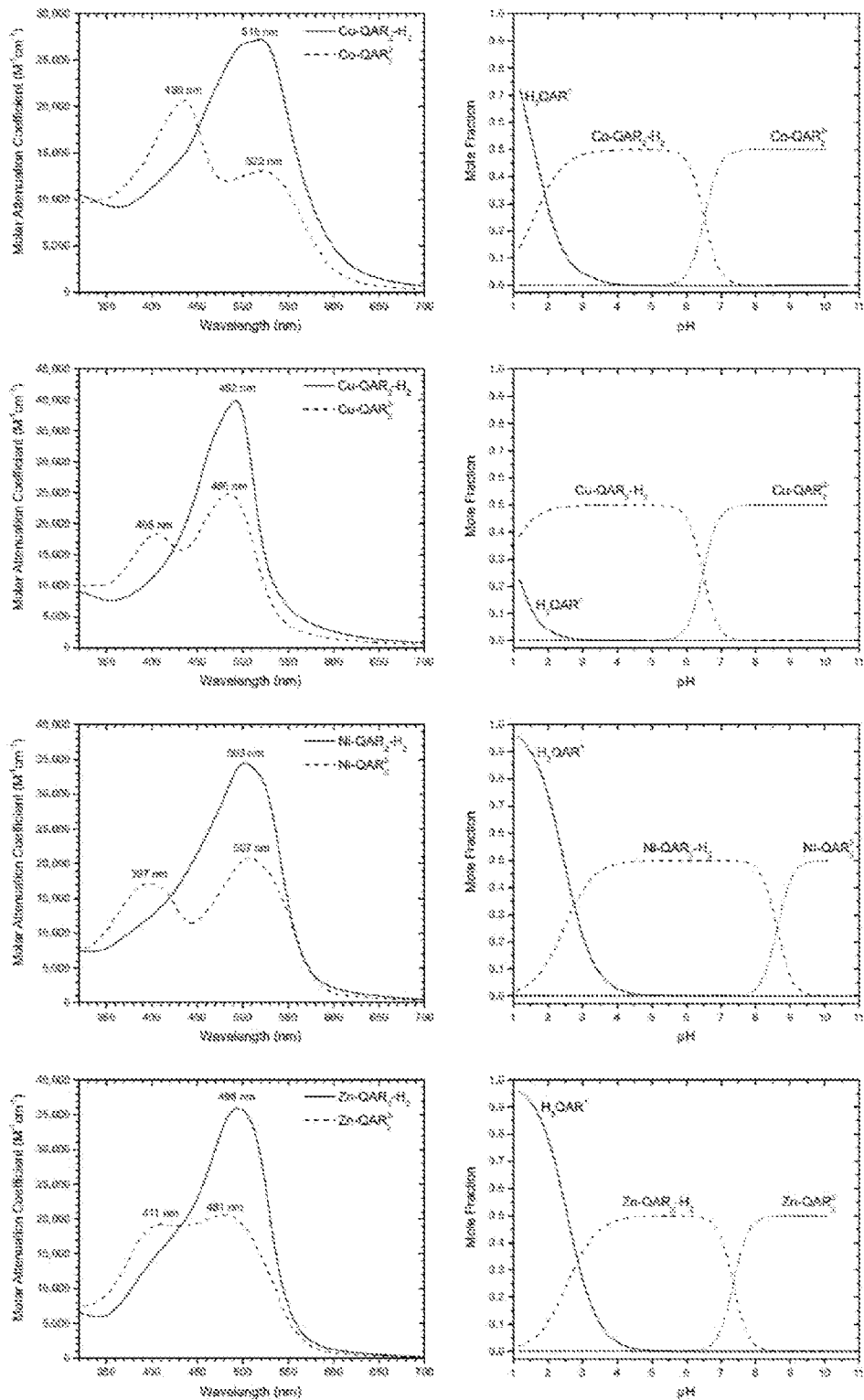
FIG. 14 are graphs for the protonation states of metal-QAR complexes.

An examination of the errors for lead show an improved accuracy for the PLS model with the two-sensor array compared to the single sensor, with an exception for pseudo-unknown 11. This is reasonable because PAR has a spectral response for lead while QAR does not. Also, a comparison of the errors decreased accuracy in most cases for copper, nickel, and zinc with the two-sensor array. This can be partially explained by the less than optimal response of QAR at pH 7 where a mixture of protonated species exist for the metal-QAR$_2$ complexes. For example, the spectral profiles are similar for the Cu-QAR$_2$-H$_2$, Ni-QAR$_2$-H$_2$, and Zn-QAR$_2$-H$_2$ complexes, as shown in FIG. 14. This analysis demonstrates that a PLS model can be constructed using the responses from an array containing two-or-more sensors. Also, it illustrates that PLS can be used with sensors under non-optimal conditions, and PLS performs satisfactorily when spectral overlap is present for two metals.

In another analysis, which is not shown here, the spectra were preprocessed to remove any baseline offset. A baseline value was calculated from the average absorbance from 750 to 840 nm where the sensors do not absorb light. This value was subtracted from the raw spectra. The PLS analysis was then performed with the baselined data. There was no significant improvement for the accuracy of any metals, which suggests that the PLS analysis technique is not overly sensitive to baseline effects in absorption spectra.

Example 27: Determination of Four Metal Ion Concentrations from Replicate Measurements with the Spectra of QAR and PAR Using Multivariate Analysis In this example, PLS models were used with replicate measurements. This secondary validation method was used to obtain error distributions for each metal.

Figure 15:
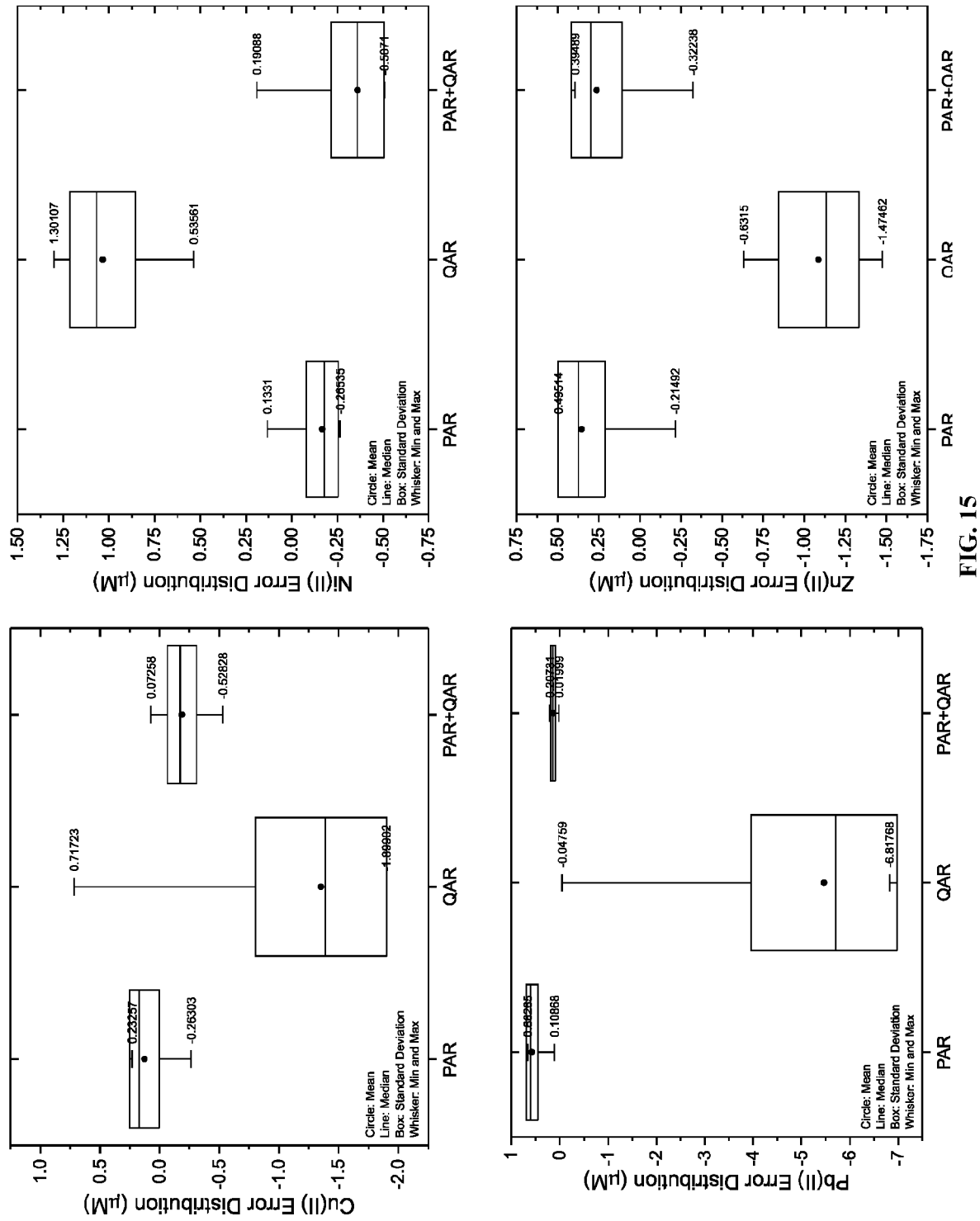
FIG. 15 are graphs of the error distribution for PAR, QAR, and PAR+QAR binding to Cu, Ni, Pb, and Zn.

A set of eighteen replicate samples was prepared with each sensor. Pseudo-unknown 8 was selected because it has approximately the same amount of each metal in the mixture, and hence should have a muddled response. The absorbance spectrum of each replicate was recorded in the same manner as in the previous examples. The PLS model used here was constructed on a previous day to further test the limits of the analysis procedure. The errors were computed in the same manner as previous examples. Also, the distribution of errors was plotted for each metal for visual comparison. Results are shown in FIG. 15 and TABLE 4.

TABLE 4

| Replicate Index | Cu | Ni | Zn | Pb |
|---|---|---|---|---|
| Prepared Concentration (μM) | | | | |
| 1 | 1.83 | 2.11 | 1.77 | 1.74 |
| 2 | 1.83 | 2.11 | 1.77 | 1.74 |
| 3 | 1.83 | 2.11 | 1.77 | 1.74 |
| 4 | 1.83 | 2.11 | 1.77 | 1.74 |
| 5 | 1.83 | 2.11 | 1.77 | 1.74 |
| 6 | 1.83 | 2.11 | 1.77 | 1.74 |
| 7 | 1.83 | 2.11 | 1.77 | 1.74 |
| 8 | 1.83 | 2.11 | 1.77 | 1.74 |
| 9 | 1.83 | 2.11 | 1.77 | 1.74 |
| 10 | 1.83 | 2.11 | 1.77 | 1.74 |
| 11 | 1.83 | 2.11 | 1.77 | 1.74 |
| 12 | 1.83 | 2.11 | 1.77 | 1.74 |
| 13 | 1.83 | 2.11 | 1.77 | 1.74 |
| 14 | 1.83 | 2.11 | 1.77 | 1.74 |
| 15 | 1.83 | 2.11 | 1.77 | 1.74 |
| 16 | 1.83 | 2.11 | 1.77 | 1.74 |
| 17 | 1.83 | 2.11 | 1.77 | 1.74 |
| 18 | 1.83 | 2.11 | 1.77 | 1.74 |
| Model Predicted Concentration (μM) | | | | |
| 1 | 1.63 | 1.65 | 2.08 | 1.79 |
| 2 | 1.53 | 1.61 | 2.15 | 1.94 |
| 3 | 1.60 | 1.62 | 2.07 | 1.83 |
| 4 | 1.67 | 1.71 | 1.99 | 1.88 |
| 5 | 1.30 | 1.77 | 2.17 | 1.91 |
| 6 | 1.69 | 1.75 | 2.12 | 1.89 |
| 7 | 1.59 | 1.67 | 2.11 | 1.91 |
| 8 | 1.76 | 1.75 | 2.03 | 1.90 |
| 9 | 1.68 | 1.74 | 2.04 | 1.87 |
| 10 | 1.71 | 1.74 | 2.16 | 1.92 |
| 11 | 1.56 | 1.69 | 2.08 | 1.88 |
| 12 | 1.57 | 1.76 | 2.12 | 1.85 |
| 13 | 1.71 | 1.79 | 1.99 | 1.91 |
| 14 | 1.71 | 1.76 | 2.02 | 1.89 |
| 15 | 1.65 | 1.67 | 2.08 | 1.88 |
| 16 | 1.58 | 1.79 | 1.97 | 1.89 |
| 17 | 1.57 | 1.76 | 2.04 | 1.92 |
| 18 | 1.77 | 1.76 | 2.02 | 1.88 |
| Error (μM) | | | | |
| 1 | −0.20 | −0.46 | 0.31 | 0.06 |
| 2 | −0.30 | −0.51 | 0.38 | 0.21 |
| 3 | −0.22 | −0.49 | 0.30 | 0.09 |
| 4 | −0.16 | −0.41 | 0.21 | 0.15 |
| 5 | −0.53 | −0.34 | 0.39 | 0.17 |
| 6 | −0.14 | −0.36 | 0.35 | 0.15 |
| 7 | −0.23 | −0.44 | 0.34 | 0.17 |
| 8 | −0.07 | −0.36 | 0.26 | 0.16 |
| 9 | −0.15 | −0.38 | 0.26 | 0.13 |
| 10 | −0.11 | −0.37 | 0.38 | 0.18 |
| 11 | −0.27 | −0.43 | 0.30 | 0.15 |
| 12 | −0.26 | −0.35 | 0.35 | 0.11 |
| 13 | −0.11 | −0.33 | 0.21 | 0.17 |
| 14 | −0.12 | −0.36 | 0.25 | 0.15 |
| 15 | −0.17 | −0.44 | 0.30 | 0.14 |
| 16 | −0.25 | −0.32 | 0.20 | 0.15 |
| 17 | −0.26 | −0.35 | 0.27 | 0.18 |
| 18 | −0.06 | −0.35 | 0.25 | 0.14 |

The error distributions for QAR PLS model are larger than those for the PAR model, which is consistent with the above data. Also, there is a significant error and broad distribution for lead with QAR only, which is expected as QAR has no response to lead. Lead has dramatic improvement and copper has a slight improvement for the model with the combined responses of PAR and QAR. Also, there is no significant change for nickel and zinc (compared to PAR model). This suggests that the combination of two sensors can yield increased selectivity when one sensor exhibits a response to a particular metal while the other does not.

Also, the magnitude of the absorbance values was different between the old and new data, and it appears as the PLS model was not terribly affected by these discrepancies. PLS is a statistical tool, and the algorithm may be designed to cope and tolerate with these effects.

It is possible that PLS tolerates random error, including variations in sample preparation and spectra baselines.

Example 28: Analysis of a Library of Sensor Compounds

Figure 16:
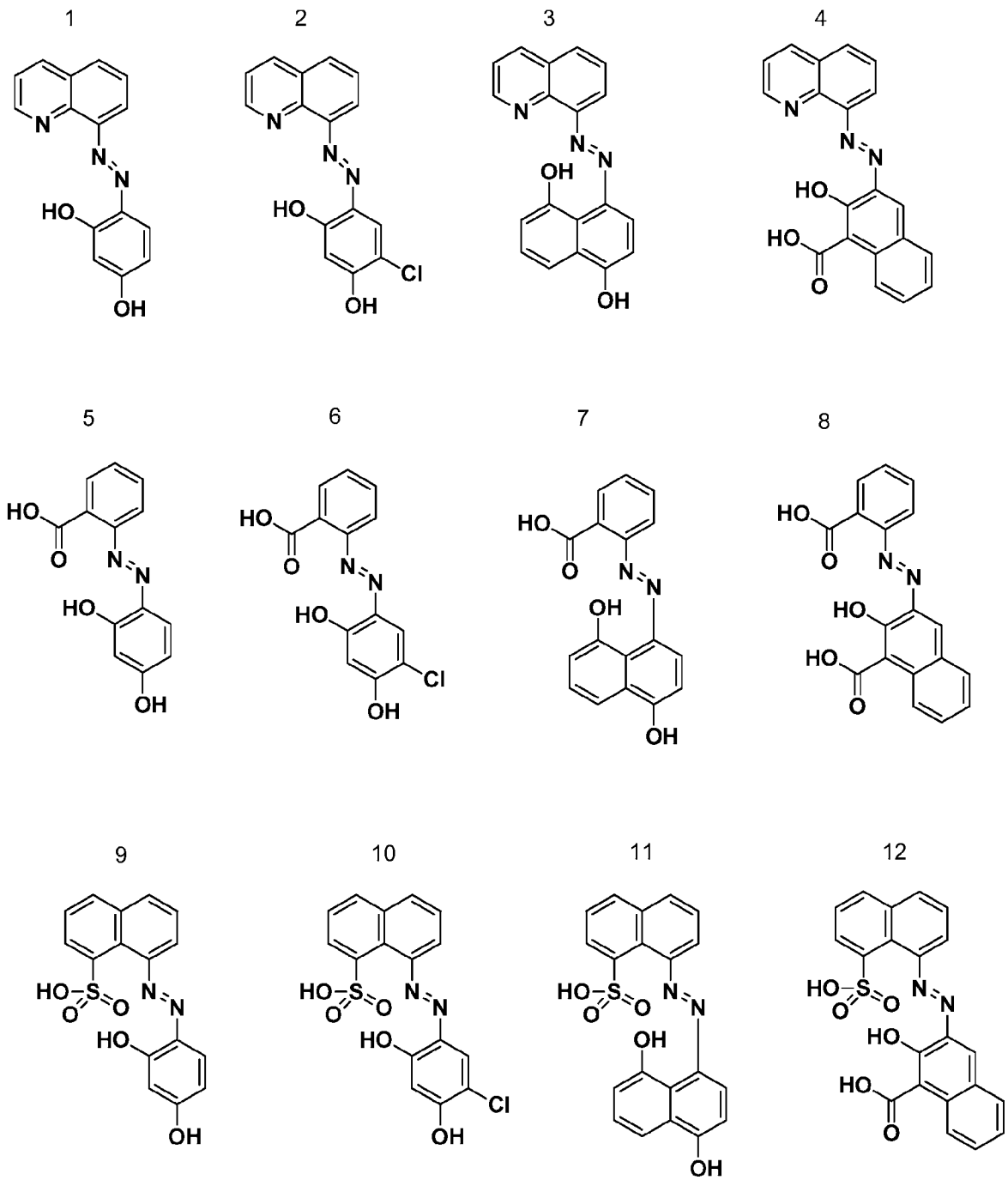
FIG. 16 structures of various dyes as detailed herein.

Compounds with structures shown in FIG. 16 were synthesized in parallel by the following method: 0.1 mmol of each aniline (8-amino quinolone, Anthranilic acid, 8-amino-1-naphthalene sulfonic acid) is dissolved in 1 mL of 0.5 M HCl and cooled in an ice bath, to which 1 mL 0.12 M NaNO2 was added, forming the corresponding diazonium salts. Each phenol (0.1 mmol of resorcinol, 4-chlororesorcinol, 1,5-dihydroxy-naphthalene, 2-hydroxy-1-naphthoic acid) was dissolved separately in 5 mL of 80 mM NaOH and charged with the diazonium salts.

Figure 17:
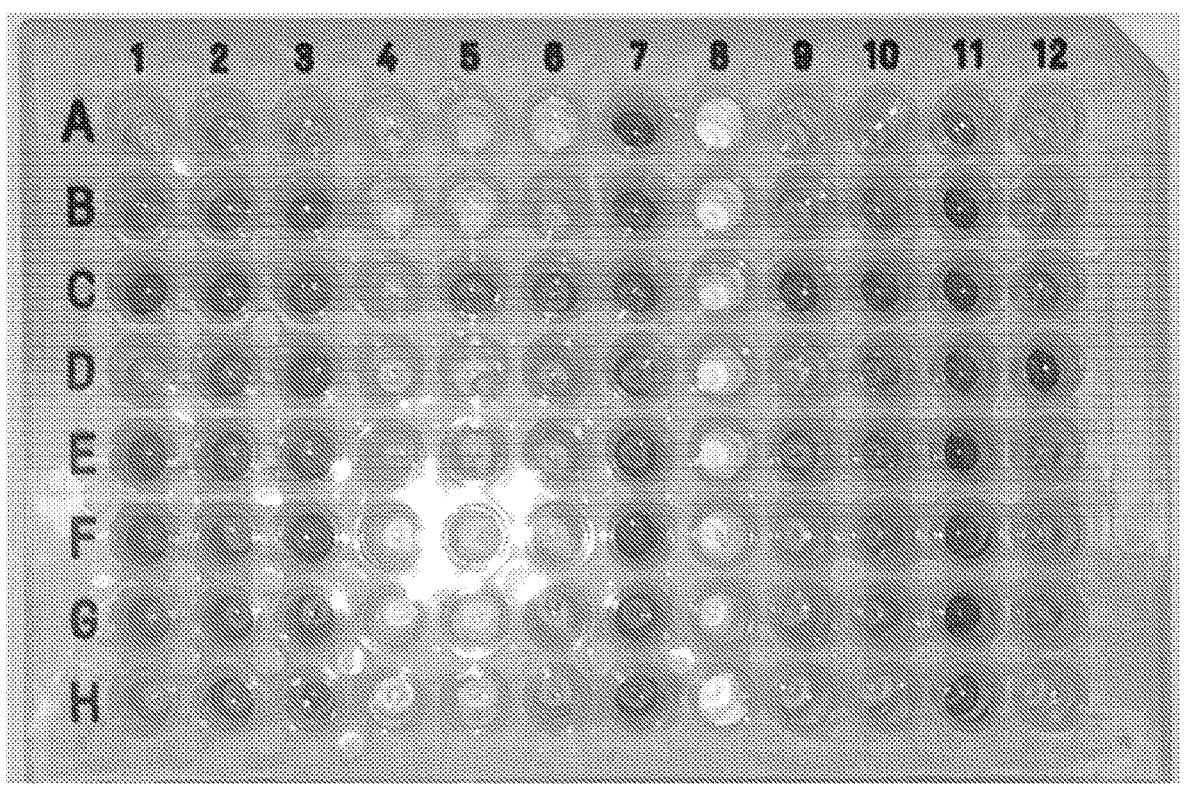
FIG. 17 shows the binding of the various dyes shown in FIG. 16 to metal ions (A=free dye, B=Zn, C=Co, D=Hg, E=Ni, F=Cd, G=Pb, H=Mg).

The compounds was screened for activity with metals, with results shown in FIG. 17 (A=free dye, B=Zn, C=Co, D=Hg, E=Ni, F=Cd, G=Pb, H=Mg). Dye solutions were prepared from crude reaction mixtures such that the maximum concentration of any dye would be 0.0286 mM in pH 7.7 MOPS buffer each dye was placed in one of 12 rows of a 96-well plate. To each well, 104, of 1000 ppm atomic absorption standard solutions were added across the columns of the 96-well plate, such that a minimum of 0.0396M concentration of zinc, cobalt, mercury, nickel, cadmium, lead, and magnesium was added individually to each dye.

Example 29: Protonation States of Free QAR

QAR has three protonation sites: The heterocyclic nitrogen in the quinoline moiety, and the para-hydroxyl group and the ortho-hydroxyl group in the resorcinol ring. The ortho-hydroxyl group is involved in binding with the metal.

The acid dissociation constants ($pK_A$) and spectral profiles were determined for QAR. Absorption measurements were made with the Perkin-Elmer Lambda 650 spectrophotometer with 1-cm cuvettes. The data was analyzed using ReactLab Equilibria (JPlus Consulting Pty Ltd, Australia) to determine the resulting $pK_A$ values. QAR has three protonation sites, so four species were used for the analysis model. The $pK_A$ values were assigned using values from well-known molecules with a similar structure.

Error analysis was performed using the measurement uncertainties (pH meter and probe, temperature, etc.) and the conventional rules of error propagation. The standard error is the uncertainty determined from regression during the analysis. The total uncertainty was estimated from the error analysis (TABLE 5).

TABLE 5

| Site | $pK_A$ | Standard Error | Total Uncertainty |
|---|---|---|---|
| Quinoline N | 2.420 | ±0.007 | ±0.170 |
| p-OH | 6.539 | ±0.003 | ±0.134 |
| o-OH | 12.959 | ±0.009 | ±0.123 |

Results are shown in FIG. 13. The analysis yielded the mole fractions of each species present at a specified pH and spectral profile (molar attenuation coefficients) of each species. $H_3QAR^+$ exists under acidic conditions and has a broad absorption in the 400 to 500 nm region. The absorbance spectrum $H_2QAR$ is red shifted relative to $H_3QAR^+$. $HQAR^-$ exists under circum-neutral conditions and as a strong absorbance band centered at 450 nm. $QAR^{2-}$ exists under strong alkaline conditions and has a broad absorbance band at 459 nm.

Example 30: Formation and Dissociation Constants of QAR

The formation constants ($K_F$) were determined for QAR and different metals. The relative binding affinities characterized the selectivity of the sensor, i.e. the sensor's preference for binding one metal over another. Also, the corresponding dissociation constants ($K_D$) were computed from the formation constants. This metric yielded the lower performance limit of the sensor that is thermodynamically possible (for a given set of conditions), and it can provide the practical operating range of the sensor.

The absorbance spectra were recorded using a Perkin-Elmer Lambda 650 spectrophotometer while a QAR solution was titrated with a metal ion standard. Scout titrations were performed to obtain an estimate range for the $K_D$. Then, the titration was performed with a sufficiently low initial dye concentration (approximately equal to the $K_D$) for proper determination. Also, measurements were made using 10 cm longpath cuvettes. The increased pathlength compensated for the reduced dye concentration so measurements were made within the instrumental limitations (i.e. absorbance values greater than 0.05 absorbance units).

The dye solution was pH-buffered at such that only one protonated form of the free dye and complex is present. Also, the pH was chosen where metal hydroxides do not form, which would can precipitate out from solution and generate errors in the measured values. At pH 8.8, the following expression describes the metal-dye complex formation where $HQAR^-$ predominates as the free dye and $M(QAR)_2^2$ predominates as the metal complex, and minimal formation of metal hydroxides is expected.

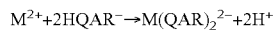

The data was analyzed in ReactLab Equilibria to determine the formation constant using the above model, and initial concentrations of HQAR and the respective metal. This software performs regression with the entire spectrum to calculate the formation constants specified in the model. Analysis was performed several times with different initial "guesses" for parameter values to ensure the algorithm yielded reproducible results.

The corresponding K values were calculated and are shown in the table below where the standard error from regression is given as the uncertainty values. The accuracy of the values is limited for cobalt and copper because the absorbance changes were too steep to properly capture the hyperbolic nature of the curve. And, the experimental conditions could not be adjusted to yield the same level of instrumental sensitivity and accuracy as the other metals. However, a relative comparison of the binding affinities is valid. Therefore, the binding affinity rank of QAR at pH 8.8 is shown in the table below (TABLE 6).

TABLE 6

| Metal Ion | $\log K_F$ | $K_F$ | $K_D$ | $\sqrt{K_D}$ | Note |
|---|---|---|---|---|---|
| Co(II) | 13.276 ± 0.008 $M^{-2}$ | (1.86 ± 0.03) × $10^{13}$ $M^{-2}$ | (5.30 ± 0.10) × $10^{-14}$ $M^2$ | 230. ± 2 nM | Accuracy limited. |
| Cu(II) | 16.268 ± 0.092 $M^{-2}$ | (1.85 ± 0.40) × $10^{16}$ $M^{-2}$ | (5.40 ± 1.15) × $10^{-17}$ $M^2$ | 7.35 ± 0.78 nM | Accuracy limited. |
| Hg(II) | 12.986 ± 0.020 $M^{-2}$ | (9.68 ± 0.45) × $10^{12}$ $M^{-2}$ | (1.03 ± 0.04) × $10^{-13}$ $M^2$ | 321 ± 7 nM | |
| Ni(II) | 12.575 ± 0.010 $M^{-2}$ | (3.76 ± 0.09) × $10^{12}$ $M^{-2}$ | (2.66 ± 0.06) × $10^{-13}$ $M^2$ | 516 ± 6 nM | |
| Zn(II) | 12.490 ± 0.007 $M^{-2}$ | (3.09 ± 0.05) × $10^{12}$ $M^{-2}$ | (3.24 ± 0.03) × $10^{-13}$ $M^2$ | 569 ± 5 nM | |

Cu(II) > Co(II) > Hg(II) > Ni(II) > Zn(II)

Figure 18:
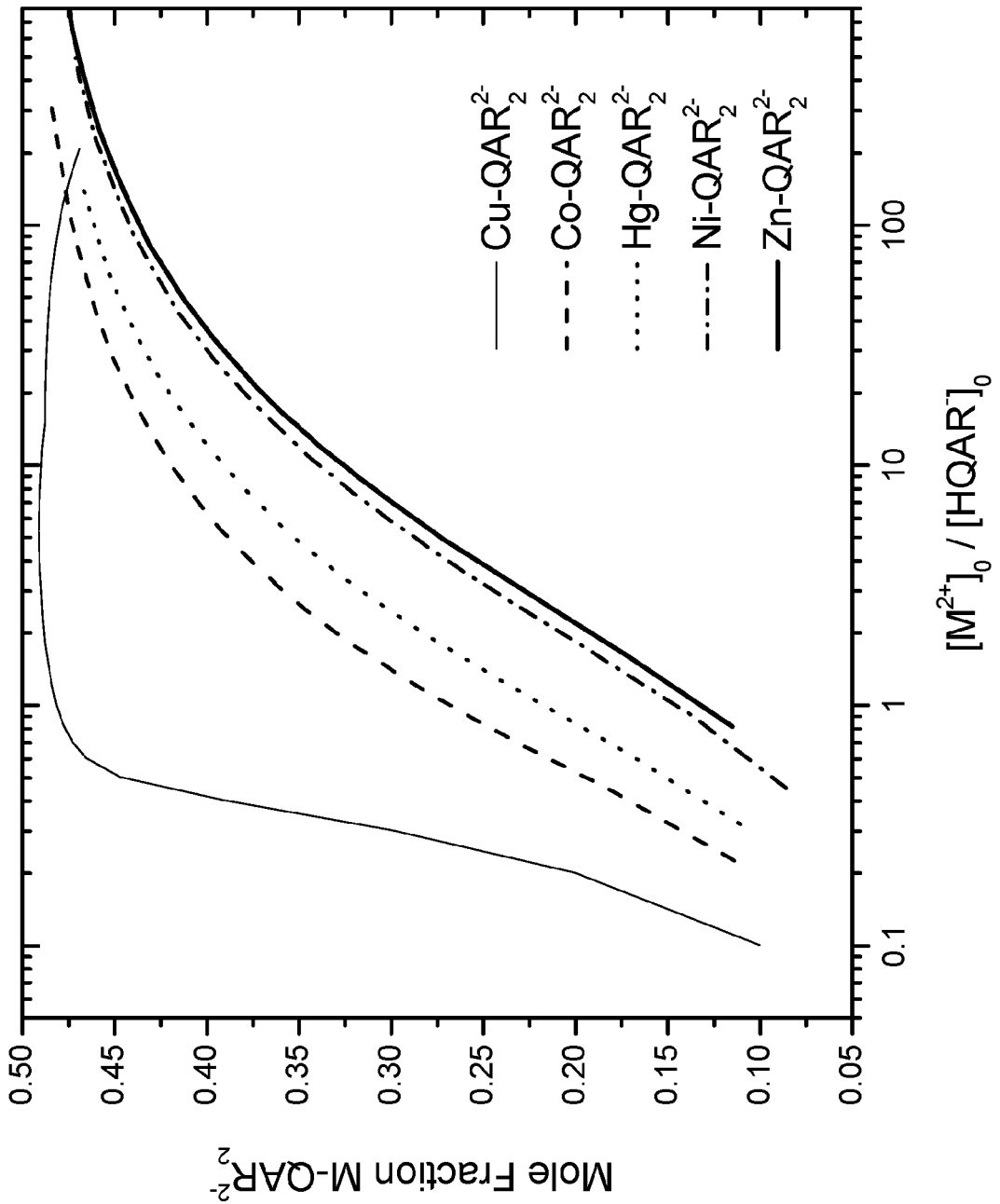
FIG. 18 is a graph showing the binding affinities of QAR to different metals at pH 8.8.
Figure 19:
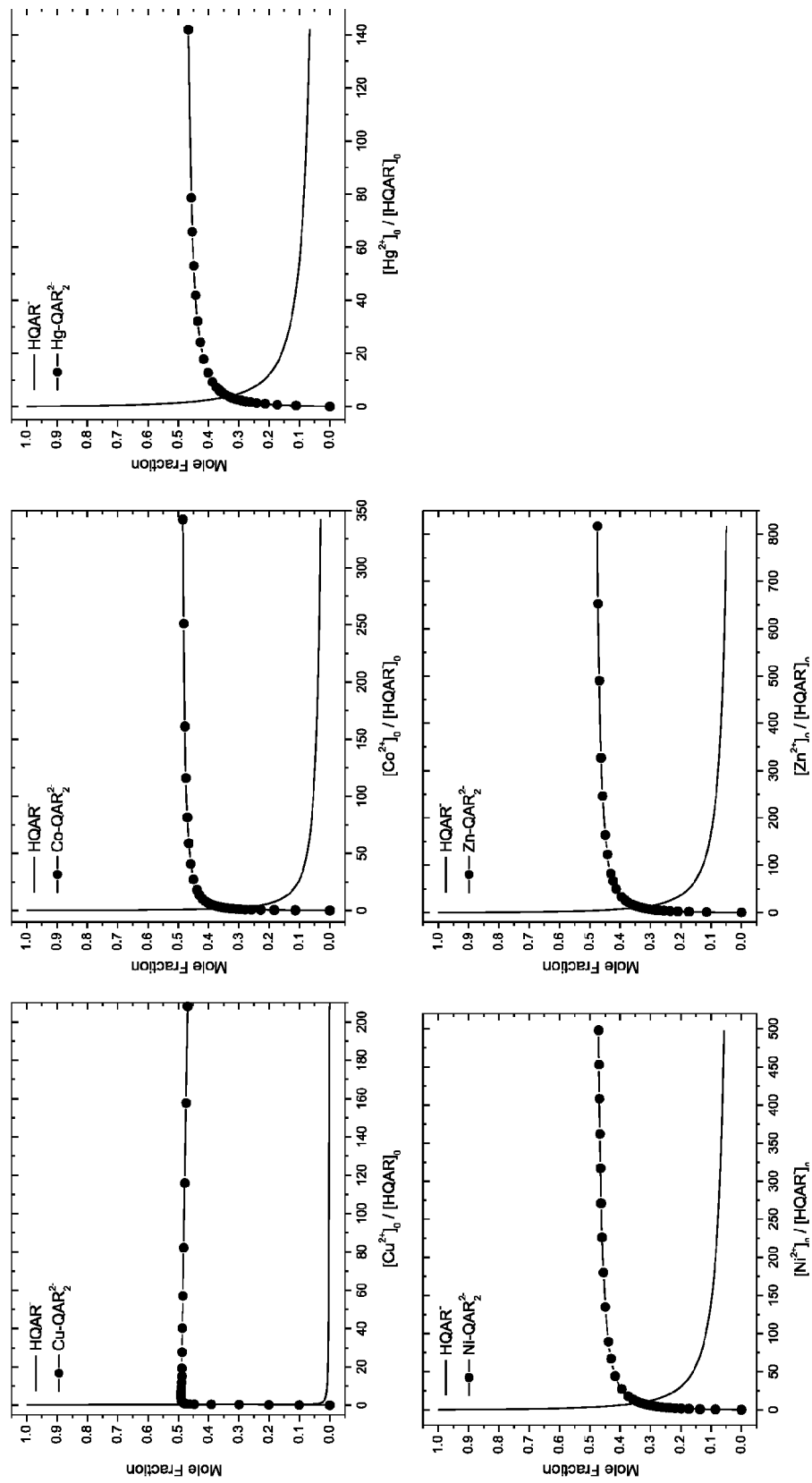
FIG. 19 are the individual graphs used to construct FIG. 18.

The binding curves were combined into a single semi-logarithmic plot to provide a relative comparison of the binding affinities of QAR to different metals at pH 8.8 (FIG. 18). Copper had the highest affinity (left side of the plot). Similarly, zinc had the lowest affinity (right side of the plot). The individual curves used to construct the plot in FIG. 18 are shown in FIG. 19.

Example 31: Protonation States of Metal-QAR Complexes

The $pK_A$ of the para-hydroxy group on QAR was determined to be 6.5 for the free dye. Although this group is not involved in complex formation with the metal, the absorbance spectra of metal-QAR complexes exhibited a pH dependency under circum-neutral conditions. (Note that one scheme for covalent attachment modifies this group and should remove this pH dependency).

Similarly, the nitrogen atom in the quinolone ring also exhibits a pH dependency. The absorption spectrum resembled free $H_3QAR^+$, so protonation of this nitrogen under acidic conditions prevented formation of the metal complex.

The dissociation constant under acidic conditions and the $pK_A$ for the para-hydroxy group on the metal-QAR complexes was determined. A set of samples containing QAR and a single metal standard, were prepared in a pH buffer containing 2 mM Triton X-100 surfactant. The pH of the buffer was measured with a convention pH probe and meter, and the buffer reagents were pre-treated with Chelex-100 to remove any trace metal impurities. The absorption spectrum of each sample was recorded with the Perkin-Elmer Lambda 650 spectrophotometer.

Analysis was performed in ReactLab Equilibria. The protonation of the para-hydroxy groups was modelled using the first reaction. Here, the pH micro-constants (stepwise protonation of each dye molecule in the complex) could not be resolved, so the two para-hydroxy groups in the complex were treated as both protonated or both deprotonated in the model. The decomposition of the complex under acidic conditions was modelled using the second reaction.

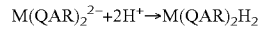

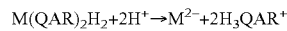

The results of the analysis are given in the following table. The standard error is the uncertainty determined from regression analysis. The total uncertainty was estimated from the measurements involved in the experiment using rules of conventional error propagation (TABLE 7).

TABLE 7

| Metal | Acidic Dissociation | Standard Error | Total Uncertainty | $pK_A$ | Standard Error | Total Uncertainty |
|---|---|---|---|---|---|---|
| Co(II) | 1.593 | ±0.009 | ±0.077 | 6.518 | ±0.009 | ±0.078 |
| Cu(II) | 0.635 | ±0.015 | ±0.062 | 6.479 | ±0.009 | ±0.062 |
| Ni(II) | 2.455 | ±0.008 | ±0.070 | 8.625 | ±0.008 | ±0.071 |
| Zn(II) | 2.558 | ±0.010 | ±0.070 | 7.354 | ±0.011 | ±0.071 |

Decomposition of the metal-QAR complexes occurs below pH 3. The dissociation constant is different for each metal. For example, copper has the highest resistance and zinc has the lowest resistance to decomplexation under acidic conditions. Also, this trend [Cu(II)>Co(II)>Ni(II)>Zn(II)] matches the trend in the binding affinities, and the two effects may be related to the specific interactions that occur in the binding of each metal. Also, this presents a potential method for reversing the sensor attached to a substrate by stripping the metal with an acid wash (e.g. hydrochloric acid).

The spectral profile of each species and the species distribution as a function of pH are generated during analysis. The protonatated metal-QAR complex (M-QAR$_2$-H$_2$) has two absorption bands and the deprononated metal-QAR complex (M-QAR$_2$) has a single, but more intense, absorption band. The metal-QAR complexes have a unique spectral profile for each metal, as evident by the peak absorption wavelengths and the shapes of each curve.

The metal-QAR complexes were protonated under circum-neutral pH conditions, as shown in FIG. 14. Again, the decomposition of the metal-QAR complexes under acidic conditions is unique for each metal, although decomposition begins to occur around pH 3 for most of the complexes. (Note: The K values listed in Table 7 correspond to the midpoint of curves in the species distribution plots of FIG. 14).

Example 32: Metal Response of PAN-7011

Figure 20:
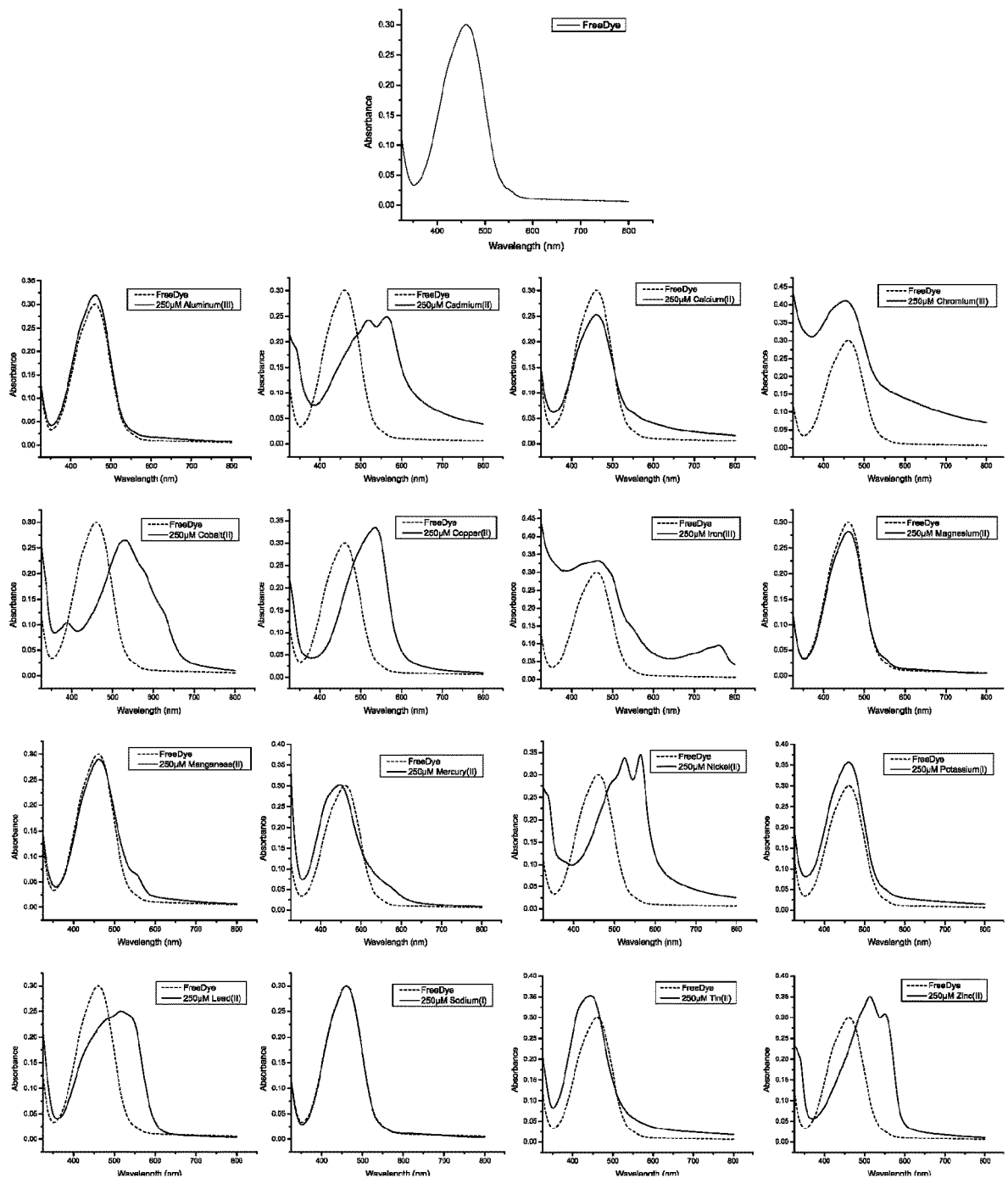
FIG. 20 are graphs showing the metal response of PAN-7OH.

Solutions were made containing 25 µM PAN-7OH and 250 µM metal ion (excess amount) in pH 7 buffer containing 2 mM Triton X-100. Absorption measurements were made with the Perkin-Elmer Lambda 650 spectrophotometer with 1 cm length cuvettes. Results are shown in FIG. 20.

Cadmium, cobalt, copper, lead, manganese (minor), nickel, and zinc produced a red-shifted absorbance relative to the free dye. The absorbance profile of these complexes is unique for each metal, although cadmium, nickel, and zinc produced similar absorbance profiles.

Mercury and tin produced a blue-shifted absorbance relative to the free dye, and the spectral profiles are unique for these complexes.

Aluminum, calcium, magnesium, potassium, and sodium did not exhibit an appreciable absorbance change relative to the free dye. Therefore, PAN-7OH is not considered to be sensitive to these metal ions.

Example 33: Protonation States of Free PAN-7OH

The acid dissociation constants ($pK_A$) and spectral profiles were determined for PAN-70H. PAN-7OH has three protonation sites: The heterocyclic nitrogen in the pyridyl moiety, and the two hydroxyl groups on the naphthalene ring. The hydroxyl group in the 1-position binds to the metal while the hydroxyl group in the 7-position does not bind to the metal. The latter group can potentially be used for covalent attachment of the sensor to a substrate.

The buffer reagents were treated with Chelex-100 to remove trace metal impurities. The samples were prepared containing 25 µM PAN-7OH in a 0.1 M pH buffer containing 2 mM Triton X-100 surfactant. The pH of the buffer was measured with a convention pH probe and meter. Absorption measurements were made with the Perkin-Elmer Lambda 650 spectrophotometer with 1-cm length cuvettes.

The data was analyzed using ReactLab Equilibria to determine the resulting $pK_A$ values. PAN-7OH has three protonation sites, so four species were used for the analysis model. The $pK_A$ values were assigned using values from well-known molecules with a similar structure. The results are given in the table below. The standard error is the uncertainty determined from regression analysis. No error propagation calculations were performed here.

The acidic dissociation constant of the non-binding hydroxyl group (7-position) in PAN-7OH occurs around pH 2.7. The acidic dissociation constant of the binding hydroxyl group (1-position) in PAN-7OH occurs around pH 12.3. The acidic dissociation constant of the heterocyclic nitrogen atom in the pyridyl group, which is involved with binding to metals with PAN-7OH, occurs around pH 9.1 (TABLE 8).

TABLE 8

| Site | $pK_A$ | Standard Error |
|---|---|---|
| Pyridyl N | 2.702 | ±0.022 |
| 1-OH (Metal Binding) | 12.258 | ±0.017 |
| 7-OH (Non-Binding) | 9.143 | ±0.011 |

Figure 21:
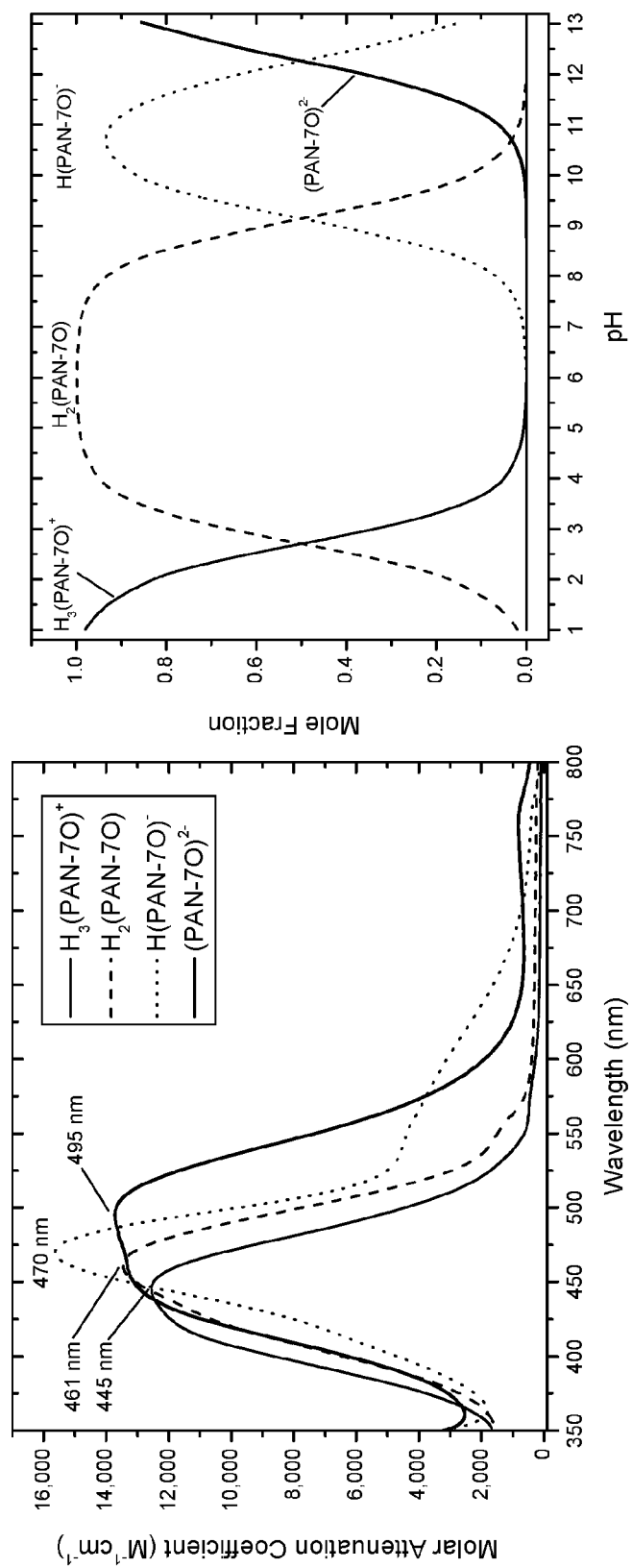
FIG. 21 are graphs showing the protonation stats of free PAN-7OH.

The spectral profile of each species and the species distribution as a function of pH were generated during analysis and are shown in FIG. 21. The different protonated forms of PAN-7OH have semi-unique spectral profiles. H$_3$(PAN-7OH)$^+$ has a relatively broad absorption band at 445 nm and predominates under acidic conditions. H$_2$(PAN-7OH) has a absorption band centered at 460 nm and predominates between pH 4 and 8.5. H(PAN-7OH)$^-$ has a absorption band centered at 470 nm and predominates at pH 10.5. Finally, (PAN-7OH)$^{2-}$ has two overlapping absorption bands with a maximum at 495 nm and predominates under strongly alkaline conditions.

Example 34: Formation and Dissociation Constants of Zn-(PAN-7OH)$_2$ Complex

The formation constants ($K_F$) were determined for zinc and PAN-7OH. Also, the corresponding dissociation constant ($K_D$) were computed from the formation constant. This metric yields the lower performance limit of the sensor that is thermodynamically possible (for a given set of conditions), and it can provide the practical operating range of the sensor.

Figure 22:
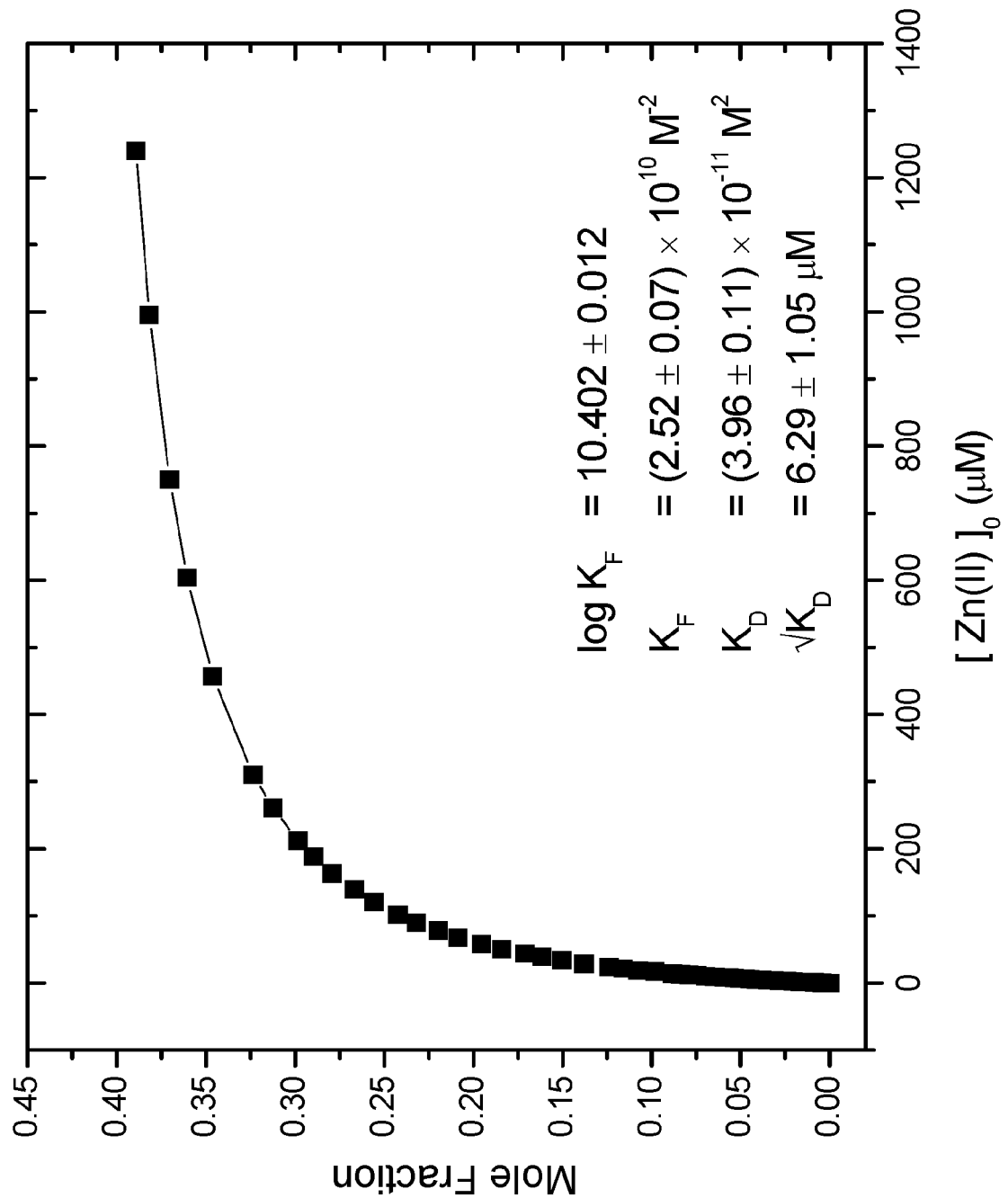
FIG. 22 is a graph for the formation and dissociation constants of the Zn-(PAN-7OH)$_2$ complex.

The absorbance spectra were recorded using a Perkin-Elmer Lambda 650 spectrophotometer while a 0.5 µM PAN-7OH solution was titrated with a metal ion standard. Scout titrations were performed to obtain an estimate range for the $K_D$. Then, the titration was performed with a sufficiently low initial dye concentration (approximately equal to the $K_D$) for proper determination. Also, measurements were made using 10-cm longpath cuvettes. The increased pathlength compensated for the reduced dye concentration so measurements were made within the instrumental limitations (i.e. absorbance values greater than 0.05 absorbance units). Results are shown in FIG. 22.

The dye solution was pH-buffered at such that only one protonated form of the free dye and complex is present. Also, the pH was chosen where metal hydroxides do not form, which would can precipitate out from solution and generate errors in the measured values. At pH 7.2, the following expression describes the metal-dye complex formation where $H_2PAN$-7OH predominates as the free dye and $M(QAR)_2^{2-}$ predominates as the metal complex, and minimal formation of metal hydroxides is expected.

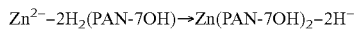

$$Zn^{2+} - 2H_2(PAN\text{-}7OH) \rightarrow Zn(PAN\text{-}7OH)_2 - 2H^-$$

The data was analyzed in ReactLab Equilibria to determine the formation constant using the above model, and initial concentrations of $H_2(PAN$-7OH$)$ and zinc. This software performs regression with the entire spectrum to calculate the formation constants specified in the model. Analysis was performed several times with different initial "guesses" for parameter values to ensure the algorithm yielded reproducible results. The corresponding K values were calculated and are shown in the plot below where the standard error from regression is given as the uncertainty values.

Example 35: Protonation States of Zn-(PAN-7OH) Complexes

PAN-7OH contains two hydroxyl groups where one is involved with binding to the metal. Also, the non-binding hydroxyl group is responsible for pH dependent absorption of the Zn-(PAN-7OH)$_2$ complex in solution.

Buffer reagents were pre-treated with Chelex-100 to remove any trace metal impurities. A set of samples containing 20 μM PAN-7OH and 20 μM zinc were prepared in a pH buffer containing 2 mM Triton X-100 surfactant. The pH of the buffer was measured with a convention pH probe and meter. Absorption measurements were made with the Perkin-Elmer Lambda 650 spectrophotometer with 1-cm length cuvettes.

Analysis was performed in ReactLab Equilibria using the following model. The first reaction was used to model protonation of the hydroxyl group that is not involved in binding. Again, the micro-constants cannot be resolved here. Also, decomposition of the Zn-(PAN-7OH) complexes was observed under acidic and strongly alkaline conditions where the spectra resembled that of the respective free dye. The second reaction was used to model the decomposition of the protonated complex under acidic conditions. The third reaction was used to model the decomposition of the deprotonated complex and formation of zinc hydroxide under strongly alkaline conditions.

$$Zn(PAN\text{-}7OH)_2^{2-} - 2H^- \rightarrow Zn(PAN\text{-}7OH)_2H_2$$

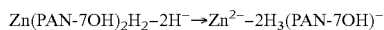

$$Zn(PAN\text{-}7OH)_2H_2 - 2H^- \rightarrow Zn^{2+} - 2H_3(PAN\text{-}7OH)^-$$

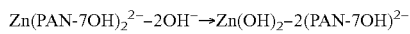

$$Zn(PAN\text{-}7OH)_2^{2-} - 2OH^- \rightarrow Zn(OH)_2 - 2(PAN\text{-}7OH)^{2-}$$

The results are given in the table below (TABLE 9). The standard error is the uncertainty determined from regression analysis. No error propagation calculations were performed here. The acidic dissociation constant of the non-binding hydroxyl group in the Zn-(PAN-7OH) complex occurs around pH 10.5. Decomposition of the Zn-(PAN-7OH) complex occurred under weakly acidic conditions and was attributed to the protonation of the heterocyclic nitrogen atom in the pyridyl group, which is involved in binding to zinc. Decomposition of the Zn-(PAN-7OH) complex also occurred under strongly alkaline conditions. One possible explanation is: the formation of zinc hydroxide is favorable to binding with PAN-7OH.

TABLE 9

| Complex $pK_A$ | Standard Error | Acidic Dissociation | Standard Error | Alkaline Dissociation | Standard Error |
|---|---|---|---|---|---|
| 10.449 | ±0.018 | 5.272 | ±0.008 | 13.164 | ±0.011 |

The spectral profile of each species and the species distribution as a function of pH were generated during analysis. The protonated and deprononated forms of the Zn-(PAN-7OH) complex had unique spectral profiles. The protonatated complex, Zn-(PAN-7OH)$_2$H$_2$, had two overlapping absorption bands at 514 nm and 552 nm. The deprotonatated complex, Zn-(PAN-7OH)$_2^{2-}$, had two overlapping absorption bands with a maximum at 529 nm.

Figure 23:
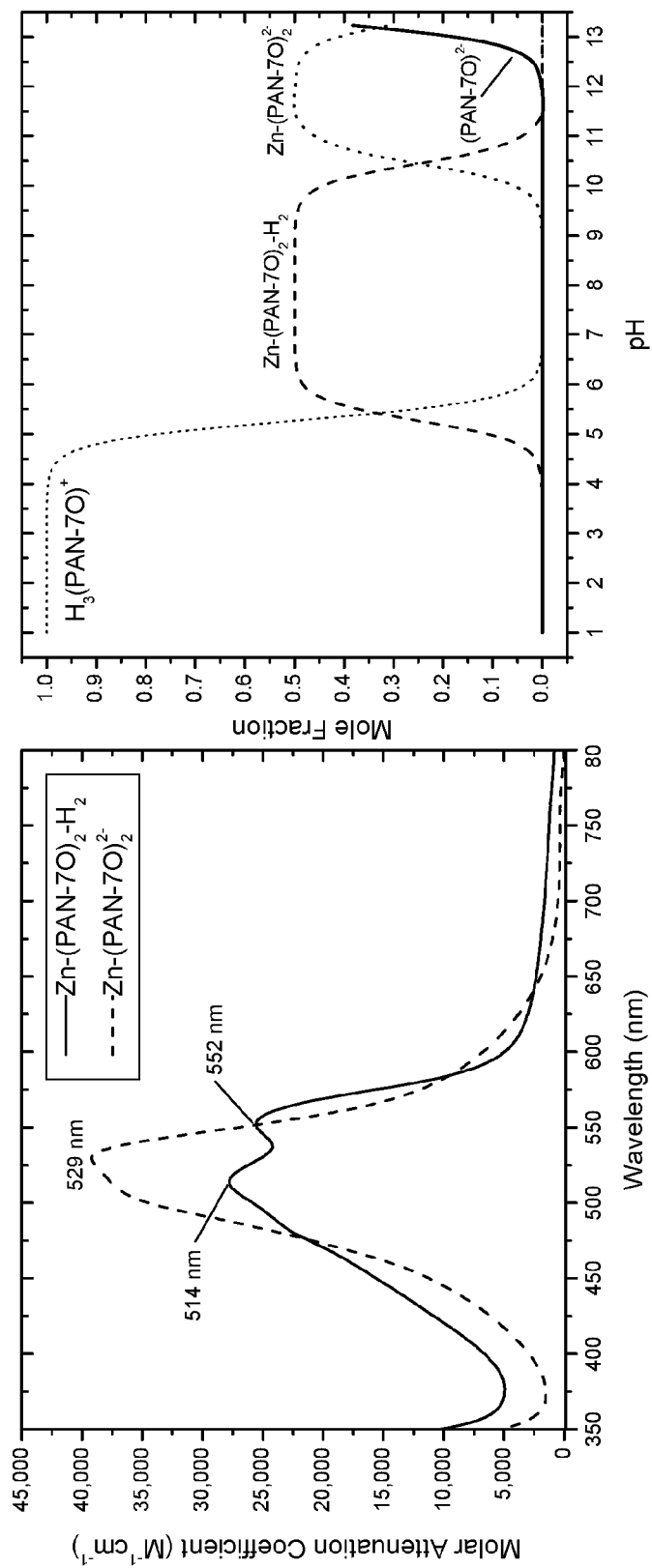
FIG. 23 are graphs showing the protonation states of Zn-(PAN-7OH) complexes.

The Zn-(PAN-7OH) complexes decomposed under weakly acidic (below pH 6) and strongly alkaline conditions (above pH 12). Protonation of Zn-(PAN-7OH)$_2$ occurred under alkaline conditions (around pH 10.5). The K values listed in the above table correspond to the midpoint of curves in the species distribution plots shown in FIG. 23.

Example 36: Silanization of Glass Surfaces

A glass slide was cleaned and prepped by soaking in MeOH:HCl bath for 30 minutes, rinsed with DI water and then soaked in a sulfuric acid bath for 30 minutes, rinsed with DI water and then rinsed with toluene. The slide was then submerged in a 2% (v/v) solution of methacryloxypropyltrimethoxysilane in toluene for 30 minutes. Slide was rinsed with toluene and then dried under a stream of nitrogen. Alternatively, the glass slide can be silanized with octadecyltrichlorosilane by soaking the acid treated slide in a 2% (v/v) solution of octadecyltrichlorosilane in methylene chloride for 1 hour. This produces a hydrophobic glass surface that the polymerized hydrogel will not adhere to.

Example 37: A One Step Preparation of QAR Alkylated Hydrogel Polymers

A sensor film was prepared in one step. To 0.6 mL of a solution of 45 mg QAR$_2$Zn, 50 mg Cs2CO3 in 7.0 mL DMF, was added 0.6033 g 2-(2-methoxyethoxy)ethyl methacrylate, 63.0 mg polyethyleneglycol diacrylate (Avg. MW=575), 0.04 mL chloromethylstyrene, and 12 mg AIBN. This mixture was heated under N$_2$ for 1 hour at 80° C., in the thin space between two optically smooth glass surfaces, one silanized with octadecyltrichlorosilane, and the other with methacryloxypropyltrimethoxysilane. The octadecyl surface was removed and the film submerged in neat trimethylamine for 24 hours. After a 30 min soak in CH$_3$OH, the sensor film was stored in pure H$_2$O. The scheme for the polymerization and covalent attachment of a sensor dye (QAR is this case) is shown below.

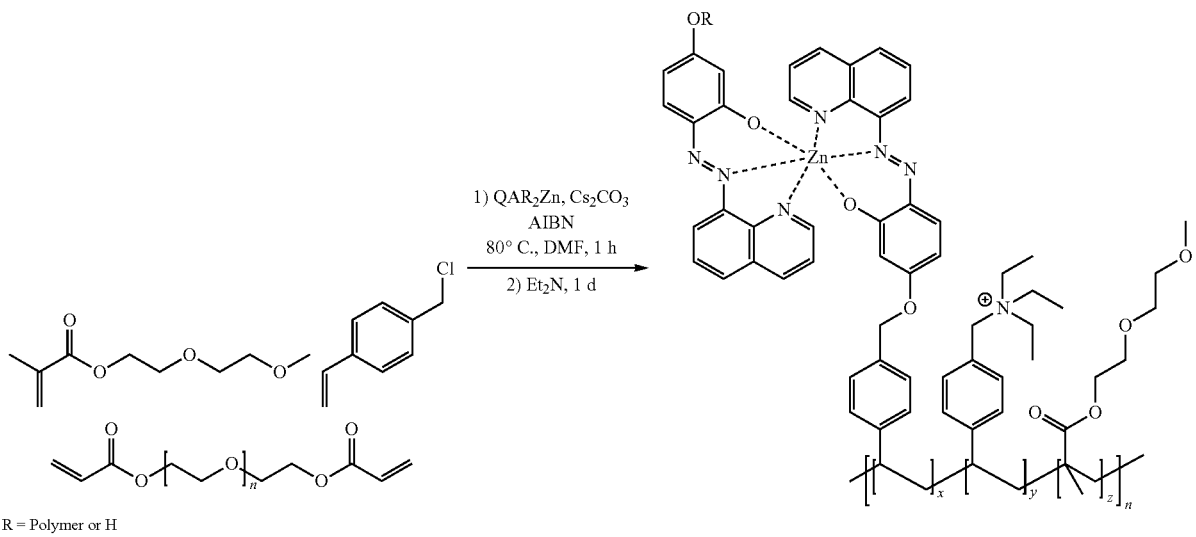

The scheme for the removal of the metal ion used for templating the polymer is shown below.

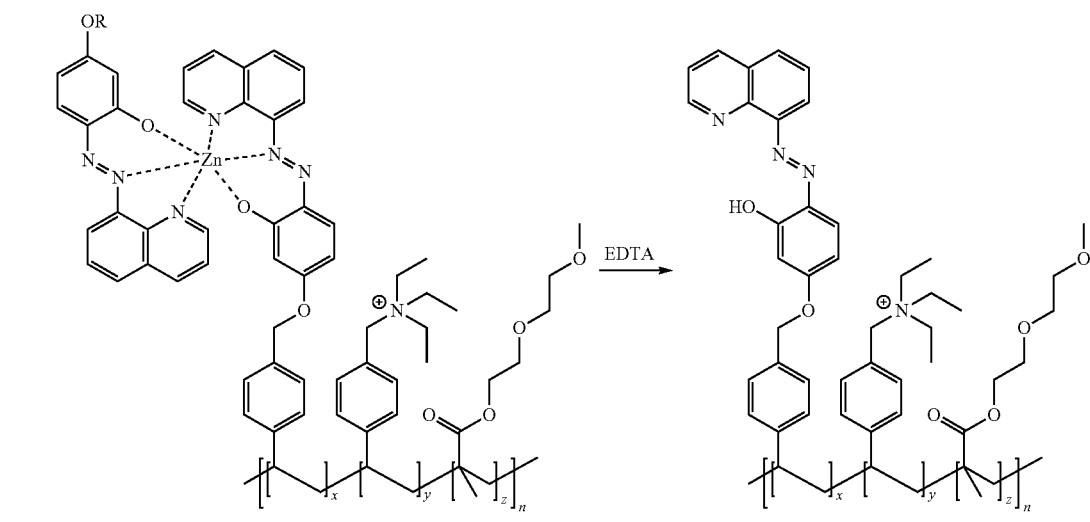

The zinc templated film was analyzed for its response to metal ions by UV/Vis Spectroscopy. These spectra were obtained after removing sensor film for aqueous exposure, and replacing the film in the spectrometer. Variation in film position during spectral measurements caused scatter in signal.

Figure 24:
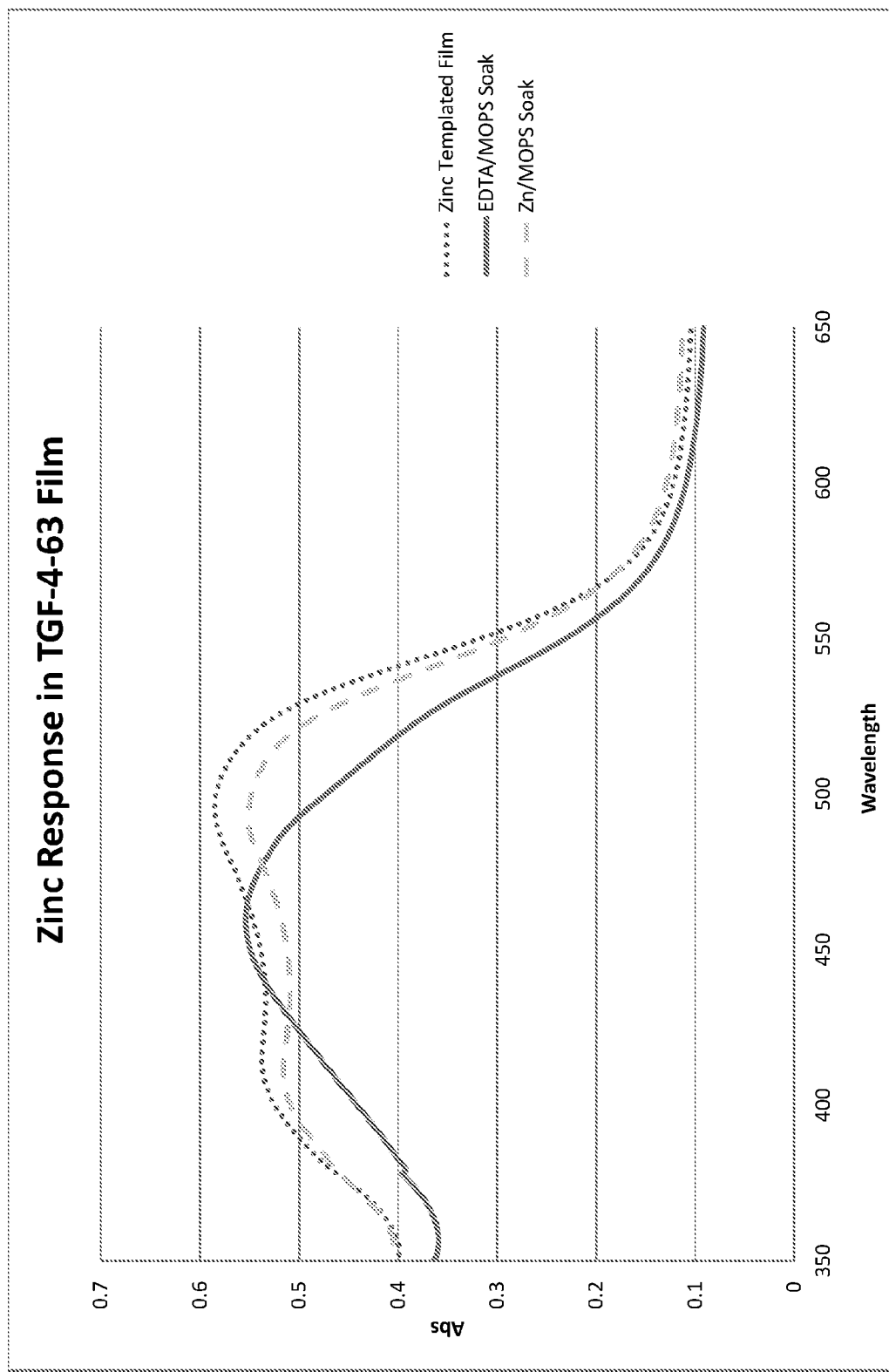
FIG. 24 is a graph of absorbance versus wavelength for the zinc template film described in Example 37.
Figure 25:
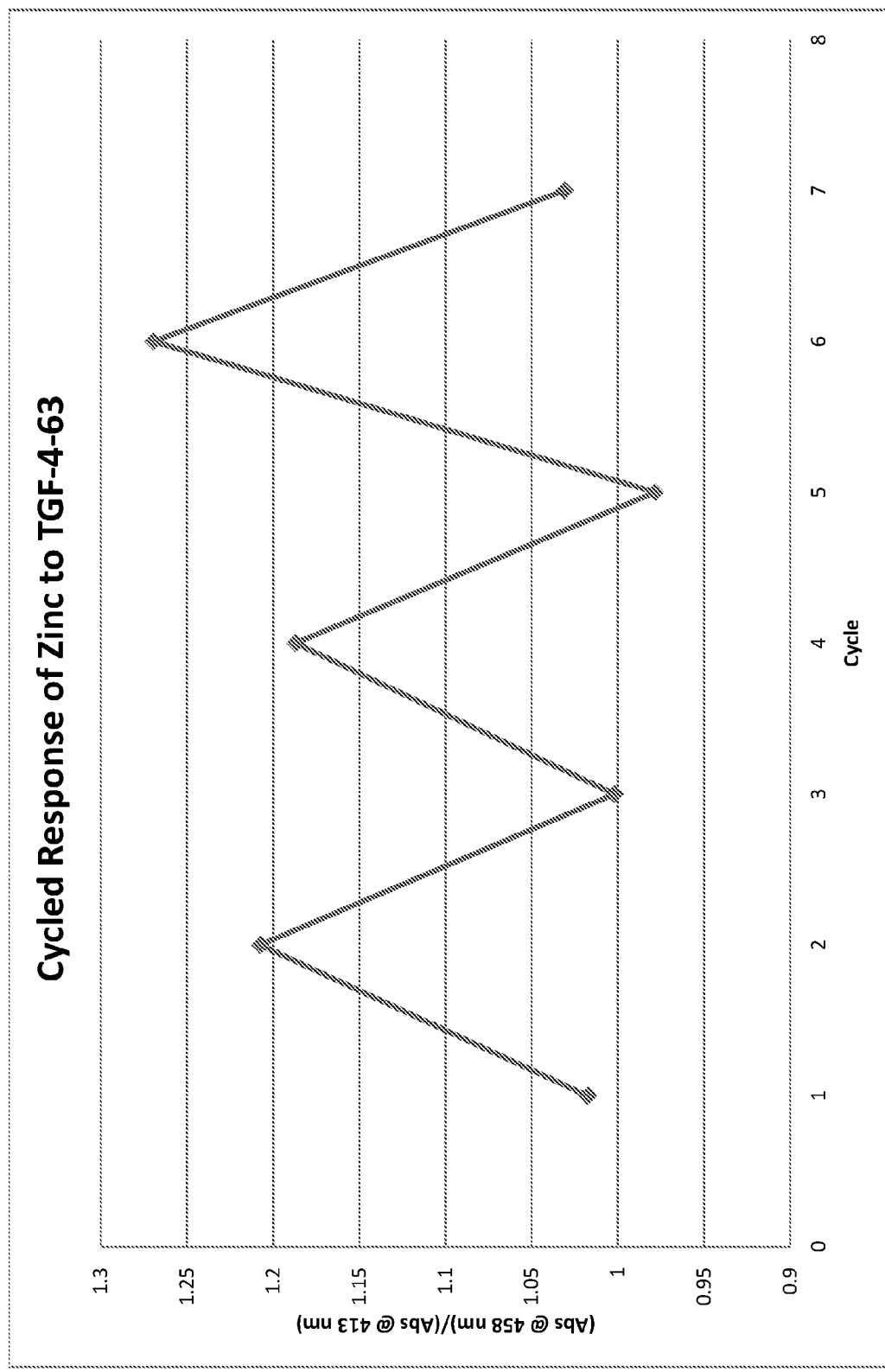
FIG. 25 is a graph showing the reversibility in sensing by the zinc template film described in Example 37 after alternate exposure to zinc ion and EDTA.

Spectrum of the zinc template film as prepared differed from that obtained after EDTA exposure to remove zinc ion (FIG. 24). Subsequent exposure to zinc ion returned the film to its zinc-bound state. Alternant exposure to zinc ion and EDTA demonstrated reversibility in sensing by these stable films (FIG. 25).

Figure 26:
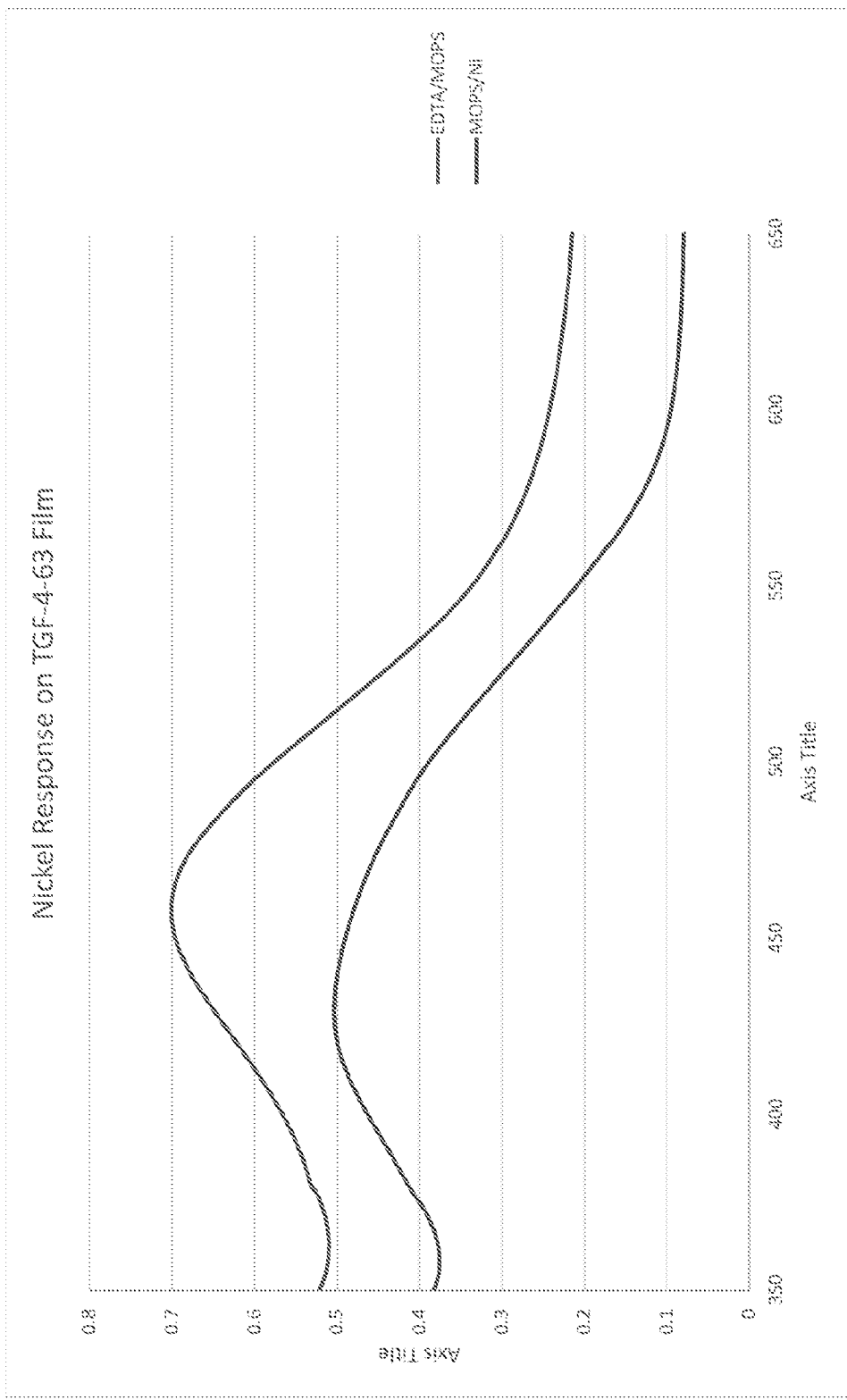
FIG. 26 is a graph of absorbance versus wavelength for the sensor described in Example 37 in response to nickel.
Figure 27:
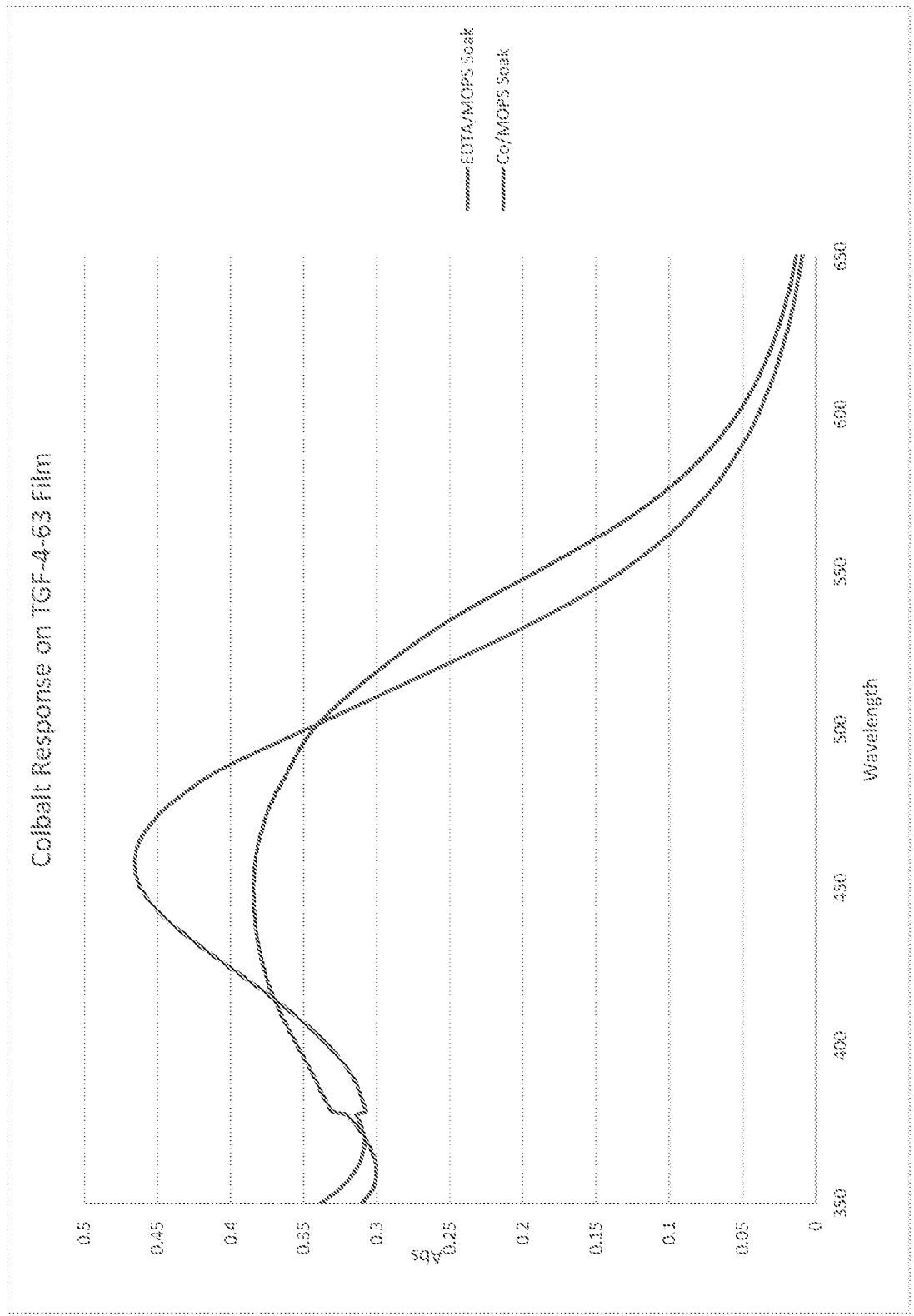
FIG. 27 is a graph of absorbance versus wavelength for the sensor described in Example 37 in response to cobalt.

Cobalt and nickel ions also caused characteristic spectral changes that were reversed by EDTA treatment (FIG. 26 and FIG. 27).

This one-step preparation demonstrated several features:

1. A general approach to covalent attachment of sensor to polymer by alkylation of a zinc complex of sensor. This allows alkylation only of the phenol not required for sensing.

2. Modification of sensor behavior by incorporation of cations into the polymer structure to raise the concentration range for sensing without changing absorption spectrum. These are triethylammonium groups formed by reaction of trimethylamine with the excess of chloromethyl groups beyond those needed for sensor incorporation.

3. High quality absorbance spectra of polymer film in contact with water.

4. Reversible and characteristic spectral response to metal. Seven cycles of alternating exposure to zinc ion and EDTA solution (which removes zinc ion) provides evidence both of specific sensing by these films, and the reversibility of that sensing.

5. Cobalt and nickel responses are distinct and reversible.

Example 38: Selective Alkylation of PAR Using Zn-Templating

PAR$_2$Zn was prepared and isolated by adding 0.2197 g PAR to 4 mL ethanol and 10 mL and refluxing until dissolved. ZnO (0.0421 g, 1.008 mol eq) is added and refluxed for 2 hours and allowed to stand overnight before solvent was removed. This was recrystallized from 25 mL CH$_3$CN and 0.0292 g used for alkylation with tert-butyl bromoacetate (17.4 µL) using Cs$_2$CO$_3$ (3.84 mg) in 3 mL CH$_3$CN. This yielded the desired mono-alkylated product as the major product. A similar reaction was carried out with the free dye, and resulted in a mixture with alkylation of both hydroxyl groups of PAR.

Example 39: QAR as a pH Sensor on Cellulose

Figure 28:
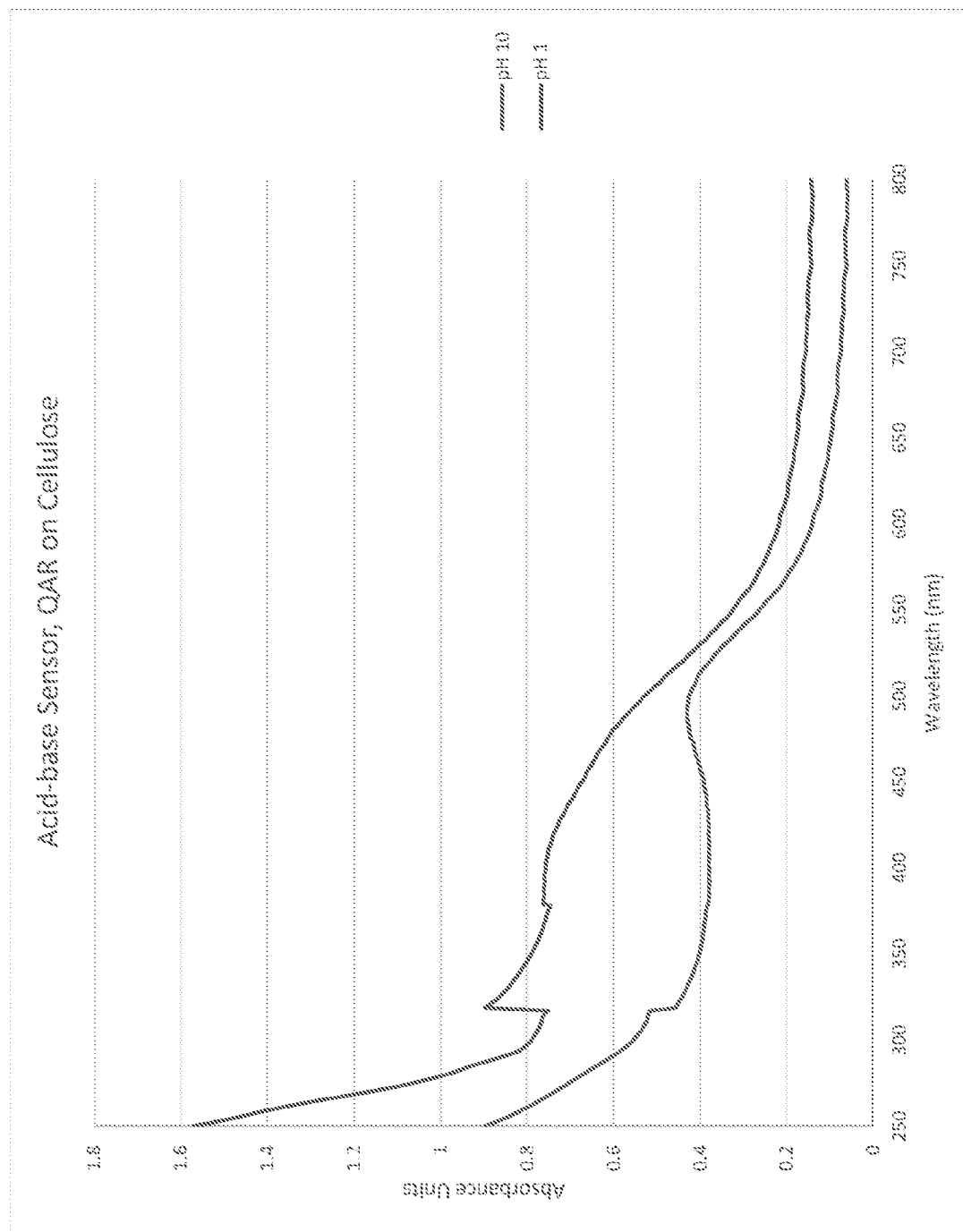
FIG. 28 is a graph of absorbance versus wavelength for QAR was covalently attached to cellulose, a pH 1 or pH 10.

QAR was covalently attached to cellulose by a covalent alkylation as described above. The cellulose was allowed to stand in a solution of pH 1 and then a separate solution of pH 10 before obtaining UV-VIS spectra, shown in FIG. 28.

Example 40: QAN-3A Solution Studies

Several attempts were made at obtaining solution spectra of the metal response of QAN-3A. A stock solution was made in a 10 mL volumetric flask using DMSO. Dye was weighed by difference into the flask and an 11.5339 mM solution (stock A) was made. This solution was diluted to 3.4602 mM (Stock B) in another 10 mL glass volumetric flask. 60 µM samples of the dye solution were made by pipetting 52.5 µL of stock B into a PMMA cuvette, adding 0.5 mole equivalents of metal, and enough 0.1 M MOPS buffer, with 2 mM Triton X-100, to obtain a final volume of 3 mL. Upon inspection, the solutions appeared cloudy and aggregation was seen.

Additionally, spectral data was obtained with the stellarnet black comet. None of the spectra taken were useful as they all scattered too much light leading to unresolved peaks. Several attempts were made to fix the aggregation problem. All of the alterations to the procedure were attempted with Zinc first to see if any of the scattering was reduced. The Triton X-100 concentration was first switched to 0 µM and then 200 µM. In another cuvette, small amounts of DMSO were add as a cosolvent. Additionally, the order of addition to the cuvettes was also altered. All of these modifications to the procedure were attempted with Zinc first to see if any of the scattering was reduced. None of these methods produced a useable spectrum for the solution metal response of QAN-3A.

Example 41: Derivatization of Hydrogel Polymer with Sensor Dye after Polymerization A stock solution of monomers was pre-made (with inhibitors) by combining 2-hydroxyethyl methacrylate (8.678 g, 8.0 mL), methoxy(ethoxy)ethyl methacrylate (12.323 g, 12.0 mL) and poly(ethylene glycol) dimethacrylate (Avg. MW=750, 2.741 g, 2.50 mL). 1.0 mL of this stock solution was then combined with 10 mL toluene and passed through a basic alumina resin to remove any inhibitors present. This solution was then concentrated under reduced pressure to remove any toluene. To this, 34.0 mg of AIBN was added along with 1.2 mL of DMF. This degassed mixture was heated under N$_2$ for 1 hour at 80° C. in the thin space between two optically smooth glass surfaces, one silanized with octadecyltrichlorosilane, and the other with methacryloxypropyltrimethoxysilane. The octadecyl surface was removed leaving the polymerized film attached to the other glass surface.

Acylation of Hydrogel Film:

A glass slide with covalently linked hydrogel polymer with hydroxyl functional groups was acylated with QAN-3A and its response to zinc has been measured. The glass slide was polymerized as described above, and subsequently activated with carbonyldiimidazole by allowing the slide to stand for 24 h in a 0.10 M solution of carbonyldiimidazole in N-methyl-pyrrolidinone. The plate was then placed in a 10% (v/v) triethyleneglycol diamine in N-methyl-pyrrolidinone solution and allowed to stand for 24 h and subsequently acylated. A second plate was prepared similarly, but rather than standing in the solutions for 24 h, it was submerged in each solution for 5 minutes and allowed to cure for 24 h before acylation.

Figure 29:
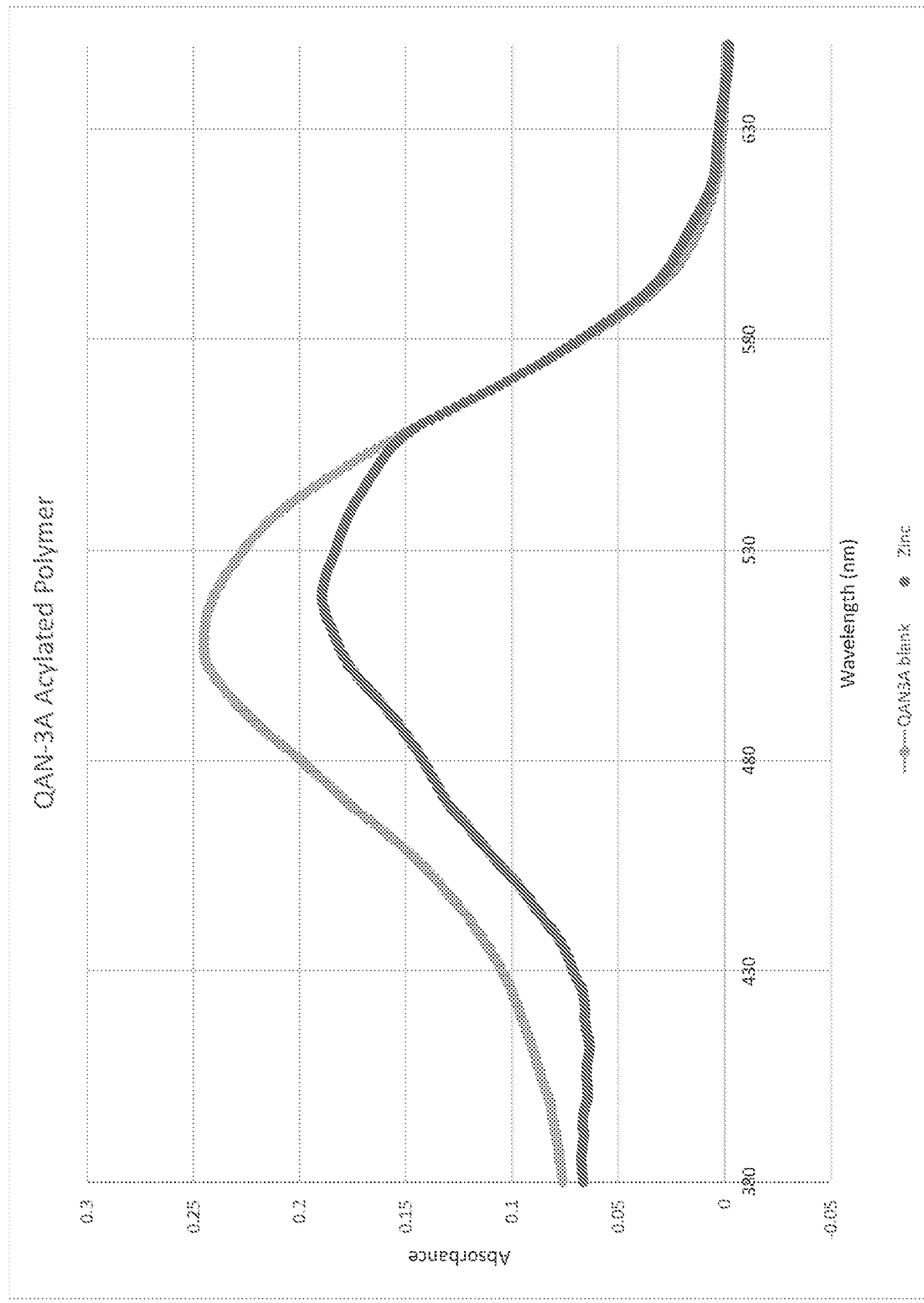
FIG. 29 is a graph of absorbance versus wavelength for a QAN-3A acylated polymer.

Acylation Procedure:

Azo dye with a carboxylic acid functionality, can be acylated to amine polymer following a general procedure of preparing the carboxylic acid with diisopropylcarbodiimide and hydroxybenzotriazole in 1:1:1 molar ratio in N-methyl-pyrrolidinone so that the final solution is 0.5 M in each reactant and adding the solution to the amine polymer. QAN-3A was used to acylate amine-functionalized hydrogel by making a solution of QAN-3A (0.0082 g, 0.024 mmol) dissolved in 0.48 mL N-methyl-pyrrolidinone (NMP), this was charged with diisopropylcarbodiimide (0.024 mmol) and hydroxybenzotriazole (0.024 mmol). The solution was applied to the amine polymer and allowed to react for 5 minutes before washing with NMP and several portions of nanopure water. UV-VIS spectra of the QAN-3A acylated polymer was collect in the presence and absence of zinc. Results are shown in FIG. 29, and the scheme is shown below.

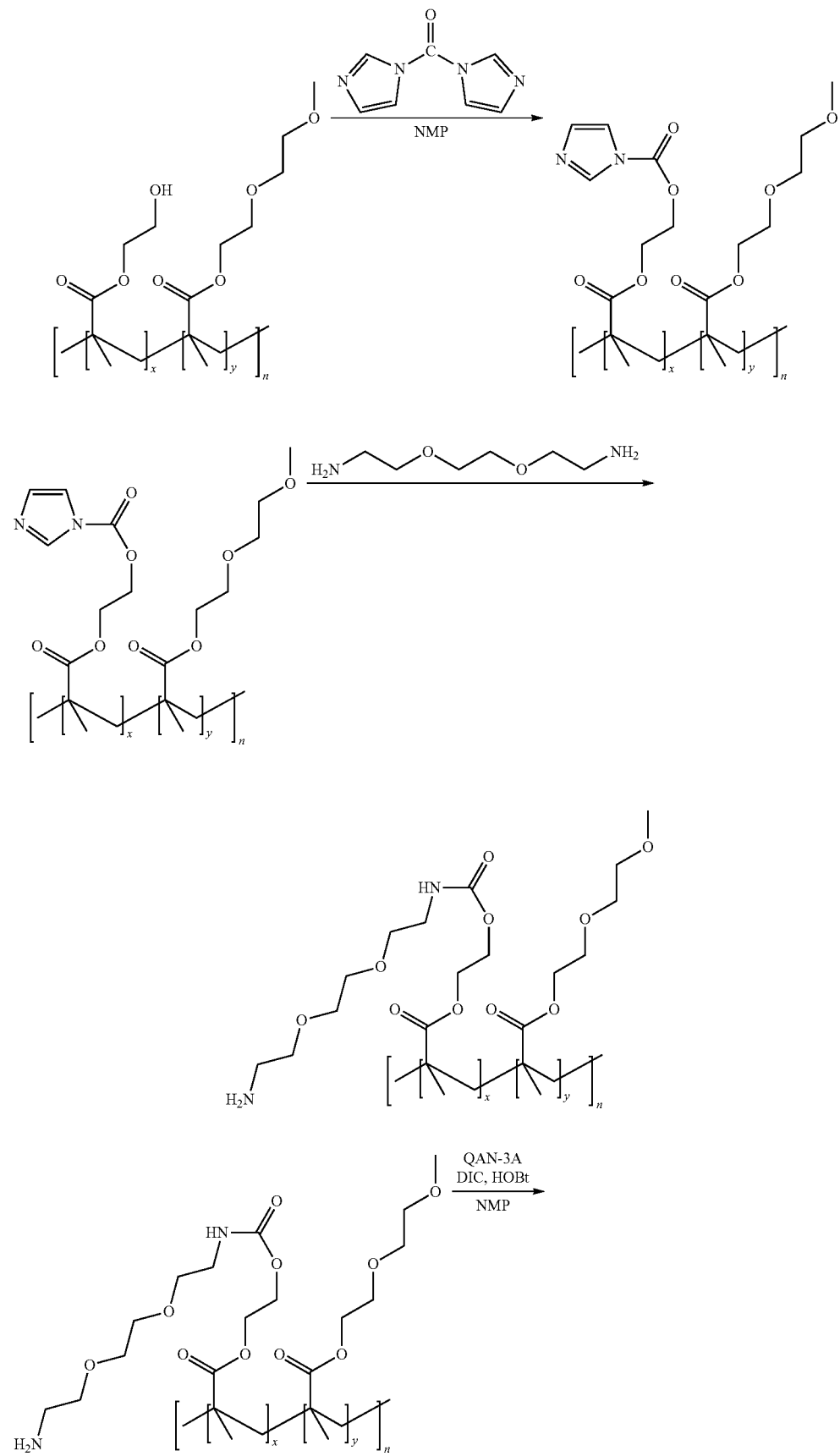

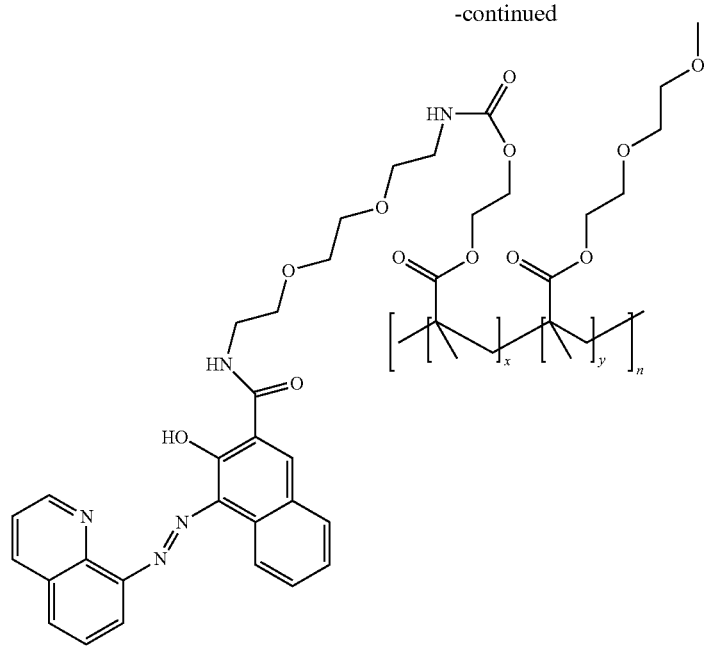

Mesylation and Alkylation of Hydrogel with QAR: A hydrogel film with available hydroxyl functional groups was submerged in dry THF (60 mL) and cooled to 0° C. To this methanesulfonyl chloride was added (1.0 mL). Triethylamine (1.0 mL) was then added. Solution was allowed to sit for one day before removing the polymer and rinsing with CH$_3$CN. This mesylated film was then submerged in DMF (60 mL) and 0.1 mL of a previously prepared alkylation solution was added (45 mg QAR$_2$Zn, 50 mg Cs$_2$CO$_3$, 7.0 mL DMF). This was allowed to sit for 24 hours before removing the polymer and rinsing with CH$_3$CN.

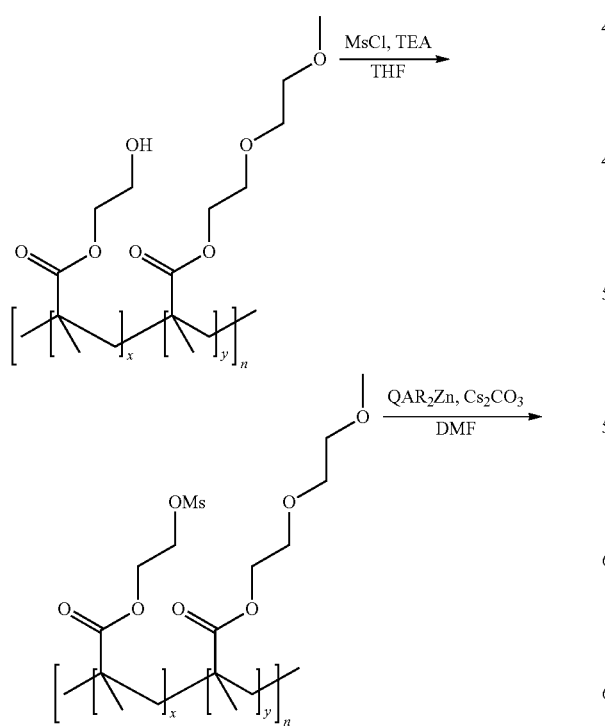

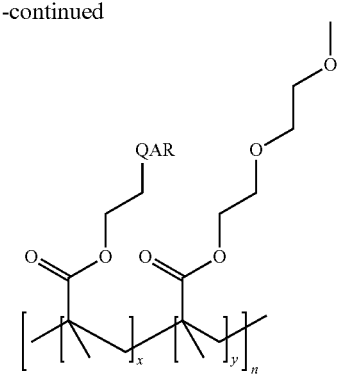

Example 42: Metal Response to a Hydrogel that has been Derivatized with QAN-4011

The metal response to a hydrogel that has been derivatized with QAN-4OH was analyzed by UV/Vis Spectroscopy.

A solution was prepared by combining methoxy(ethoxy)ethyl methacrylate (0.50 mL, 0.5468 g), p-chloromethylstyrene (0.04 mL, 0.0452 g), poly(ethylene glycol) dimethacrylate (0.0534 mg) and AIBN (21.7 mg). To this, 0.6 mL of an alkylation solution was added (6.0 mg (QAN-4OH)$_2$Zn, 8.4 mg Cs$_2$CO$_3$, in 3.0 mL DMF). This degassed mixture was heated under Na for 1 hour at 80° C. in the thin space between two optically smooth glass surfaces, one silanized with octadecyltrichlorosilane, and the other with methacryloxypropyltrimethoxysilane. The octadecyl surface was removed and the film submerged in neat trimethylamine for 24 h. After a 30 min soak in CH$_3$OH, the sensor film was stored in pure H$_2$O.

Figure 30:
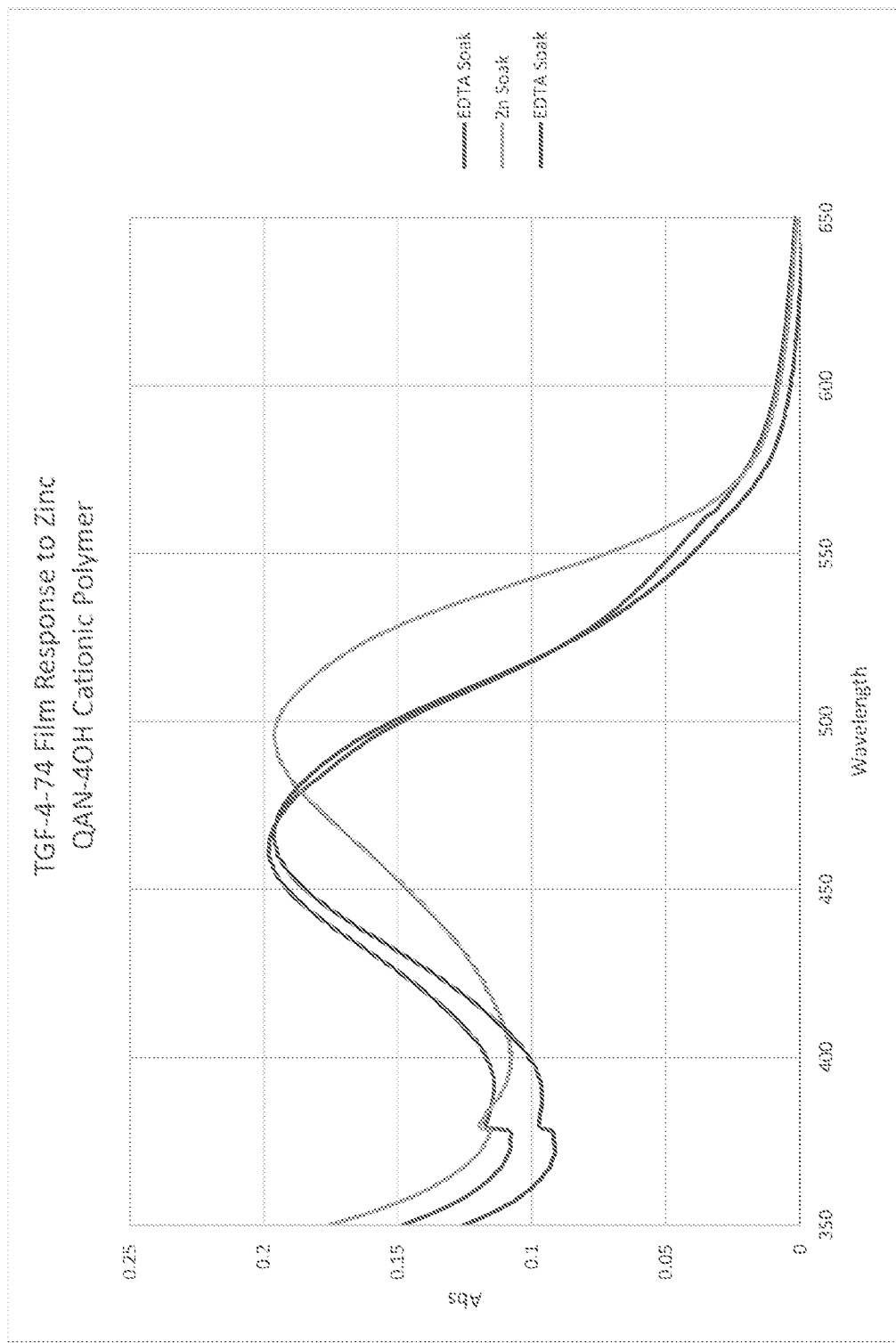
FIG. 30 is a graph of absorbance versus wavelength for a QAN-4OH cationic polymer film in response to zinc.
Figure 31:
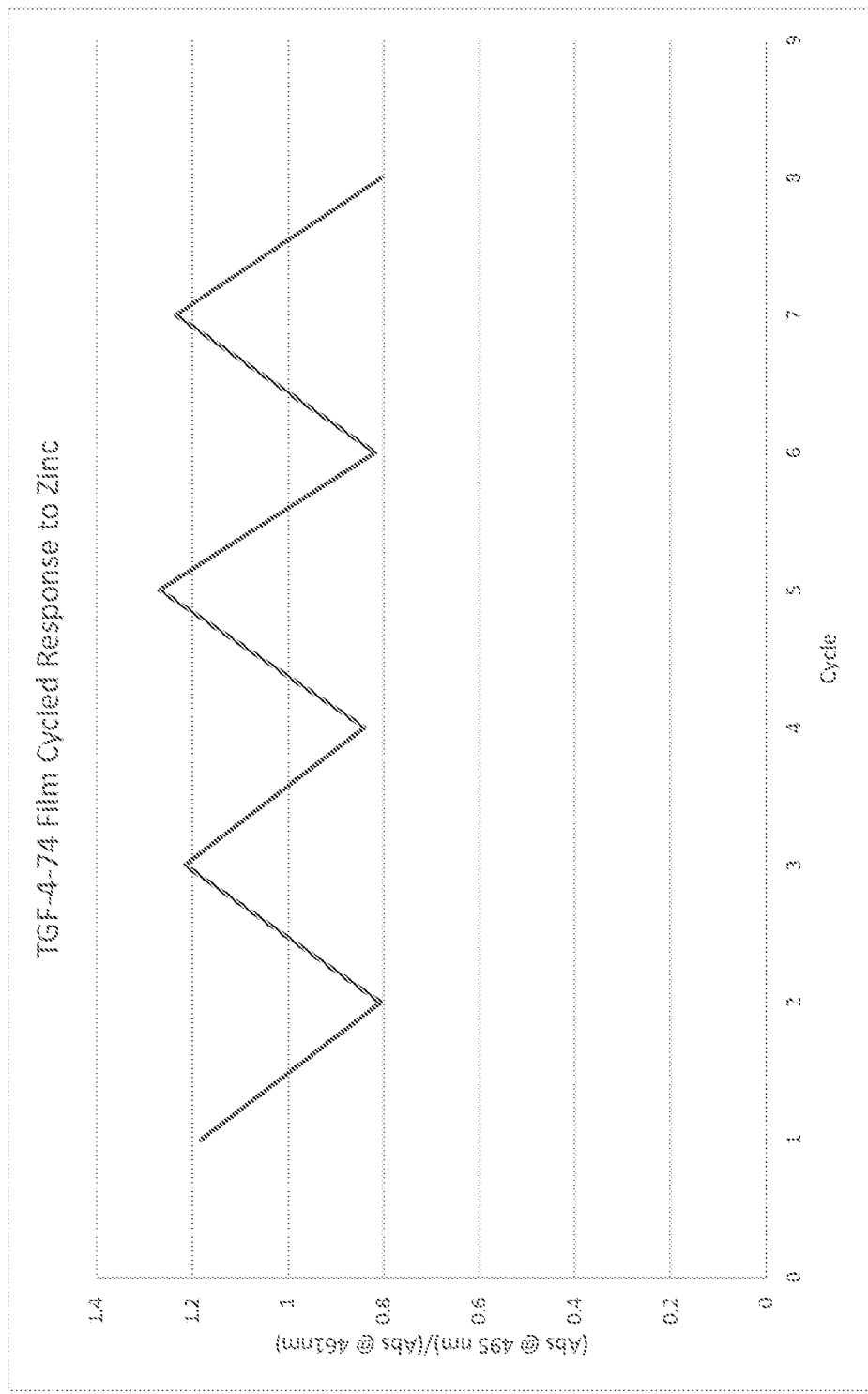
FIG. 31 is a graph of absorbance when a hydrogel that has been derivatized with QAN-4OH was soaked in a solution containing zinc ions (unknown concentration) and switched to an EDTA solution (unknown concentration), and repeated multiple times.

There is a significant shift in the absorbance profile demonstrated when the polymer is soaked in a solution containing zinc ions (unknown concentration) and an EDTA solution (unknown concentration). This response was repeated multiple times to demonstrate its reversibility. Results are shown in FIG. 30 and FIG. 31.

Example 43: Acylation of QAN-3A to Amine-Terminated Cellulose

Acylation Procedure:

Cellulose dialysis membrane was dehydrated by rinsing with N-methyl-pyrrolidinone (NMP). The dried membrane was soaked in a solution of 1 g carbonyldiimidazole (CDI) 14 mL $CH_3CN$ for 4 hours, rinsed thoroughly with $CH_3CN$, and allowed to stand in 10% (v/v) triethyleneglycol diamine $CH_3CN$ for 24 hours. Azo dye with a carboxylic acid functionality can be acylated to amine-terminated cellulose, in this example QAN-3A was used. A solution of QAN-3A with diisopropylcarbodiimide and hydroxybenzotriazole was combined in a 1:1:1 molar ratio in N-methyl-pyrrolidinone so that the final solution is 0.5 M in each reactant and adding the solution to the amine-terminated cellulose. QAN-3A was used to acylate amine-terminated cellulose by making a solution of QAN-3A (0.0082 g, 0.024 mmol) dissolved in 0.48 mL N-methyl-pyrrolidinone (NMP), this was charged with diisopropylcarbodiimide (0.024 mmol) and hydroxybenzotriazole (0.024 mmol). The solution was applied to the amine-terminated cellulose and allowed to react for 5 minutes before washing with NMP and several portions of nanopure water.

Example 44: Alkylation of Sensor Dye to Form Functional Monomer and its Incorporation into a Hydrogel Polymer This example demonstrates an alternative method of covalently attaching a sensor dye to a hydrogel polymer.

Alkylation of QAR: $QAR_2Zn$ (44.8 mg, 1 eq.) and $Cs_2CO_3$ (63.6 mg, 2.6 eq.) were combined. To this a solution of p-chloromethyl styrene (0.0649 M in DMF, 2.5 mL, 2.2 eq) was added. This was stirred at RT for 4 days. Reaction mixture was concentrated to dryness and the crude residue was purified by step gradient silica chromatography. First a solution of 10% ethyl acetate in hexanes was used to move the di-alkylated product off the column and then neat ethanol was used to move the mono-alkylated product off the column.

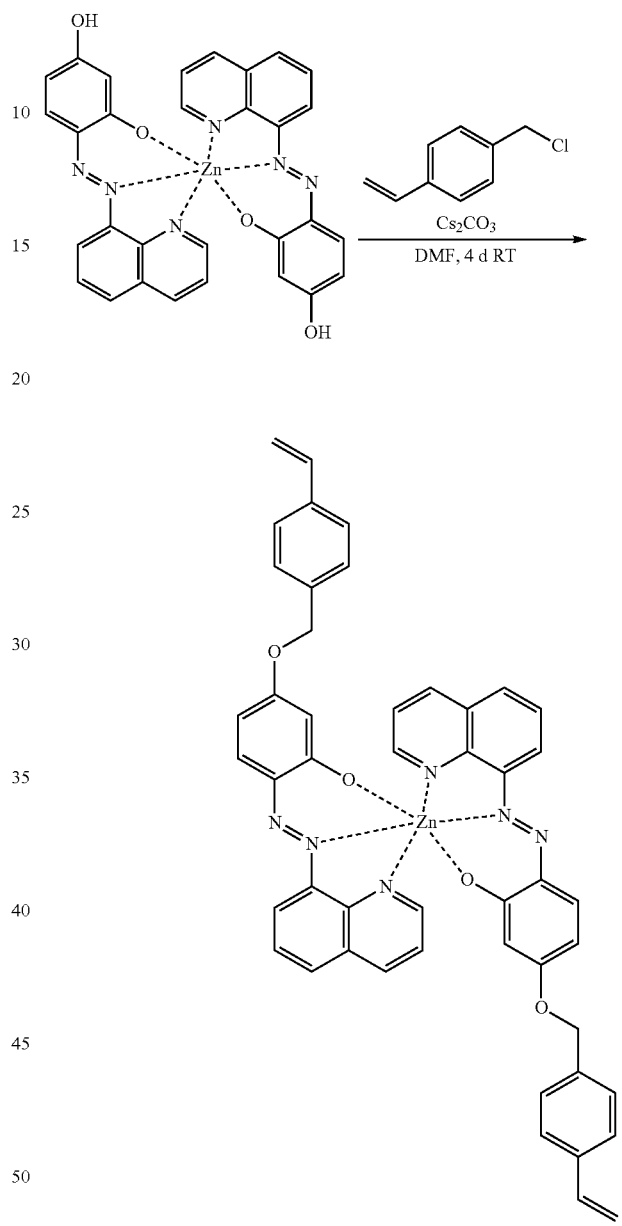

Polymerization of Hydrogel with Functional Monomer: The di-alkylated $QAR_2Zn$ (unknown mass) was then dissolved in DMF (0.5 mL) and combined with methoxyethoxyethyl methacrylate, poly(ethylene glycol) diacrylate (7 mg, Avg. MW=575) and AIBN (10 mg). This degassed This degassed mixture was heated under Na for 1 hour at 80° C. in the thin space between two optically smooth glass surfaces, one silanized with octadecyltrichlorosilane, and the other with methacryloxypropyltrimethoxysilane. The octadecyl surface was removed and the film submerged in $CH_3OH$ for 30 minutes. The sensor film was stored in pure $H_2O$.

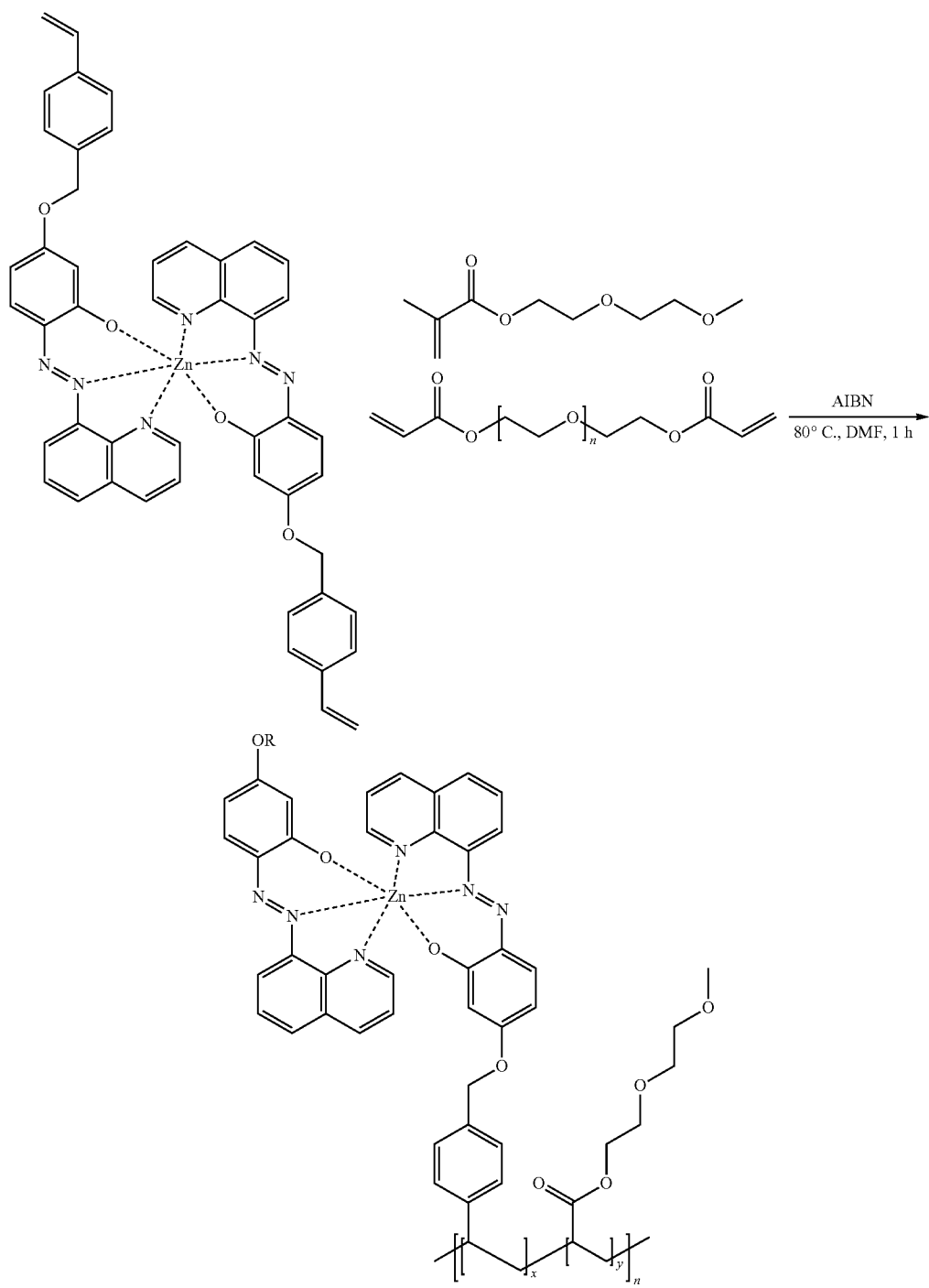

Figure 32:
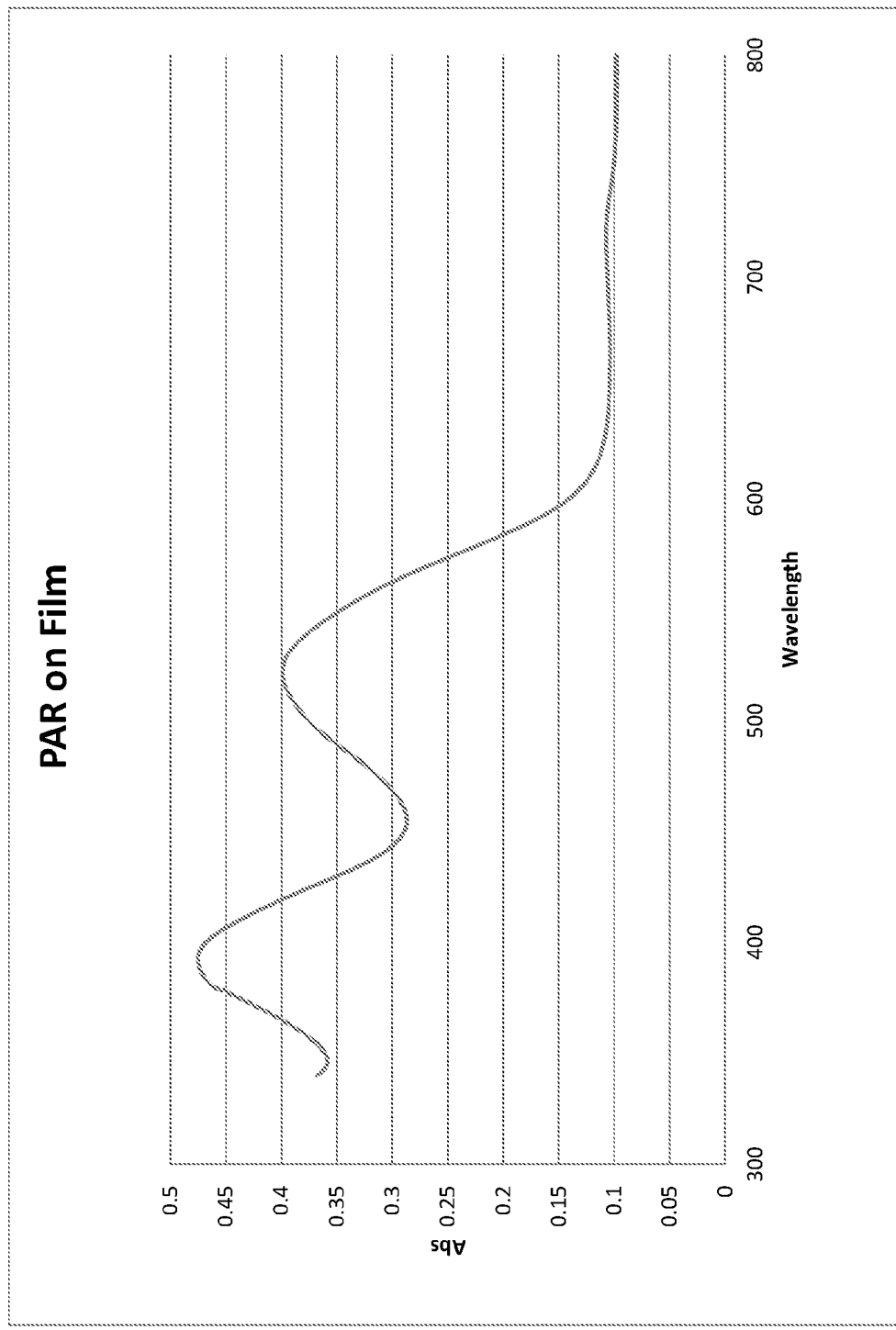
FIG. 32 is a graph of absorbance versus wavelength for PAR on film.

Absorbance spectrum of the resulting film is shown in FIG. 32.

Thus, the disclosure provides, among other things, a sensor for the detection of at least one metal in a sample. Various features and advantages of the disclosure are set forth in the following claims.

What is claimed is:

1. A sensor comprising a panel, the panel comprising an optically transparent substrate and more than one dye of formula (IV) bound to the optically transparent substrate by a covalent linkage alkylated on a phenol group of the more than one dye of formula (IV), wherein each phenol group of the more than one dye of formula (IV) has a hydroxy involved in metal binding and a second hydroxy and is alkylated on the second hydroxy; wherein the dye of formula (IV) reversibly binds at least one metal ion;

A-B (IV)

wherein A is selected from the group consisting of:

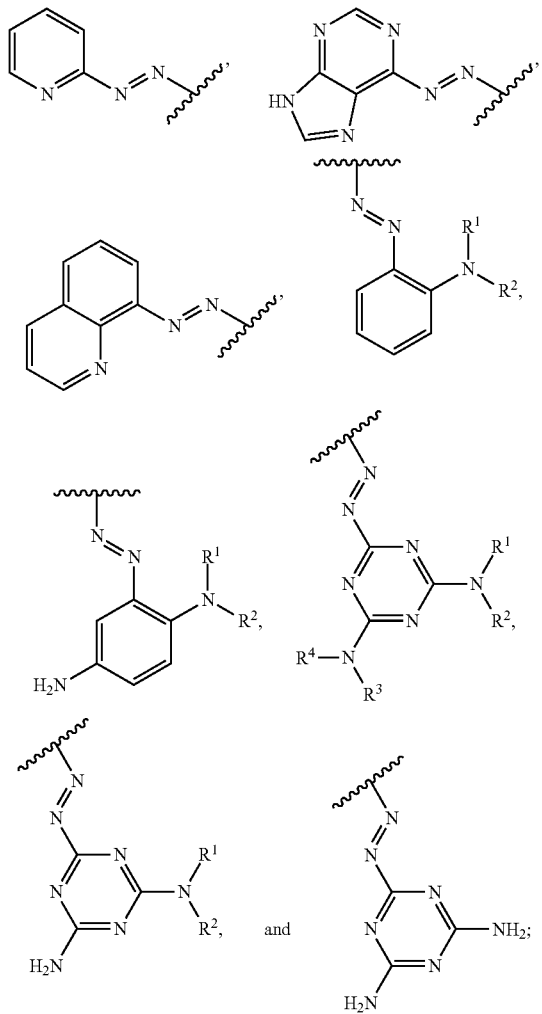

B is selected from the group consisting of:

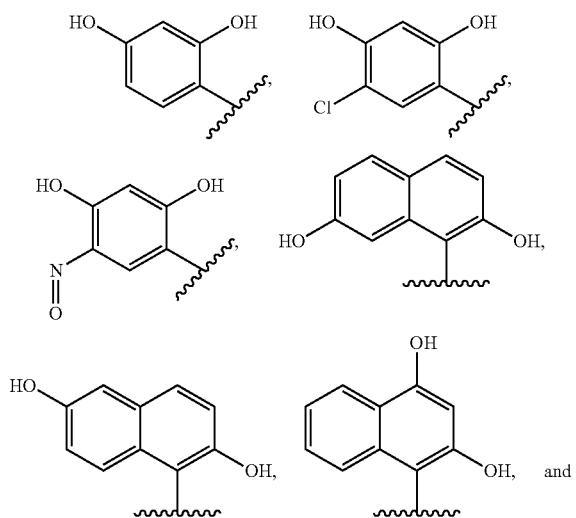

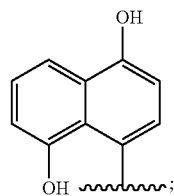

and $R^1$, $R^2$, $R^3$, and $R^4$ are independently selected from the group consisting of:

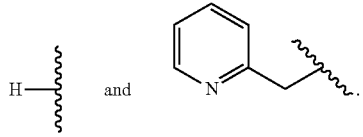

2. The sensor of claim 1, wherein the more than one dye of formula (IV) are different.

3. The sensor of claim 1, wherein the panel is an array comprising more than one optically transparent substrate; wherein each optically transparent substrate is covalently bound to a dye capable of sensing more than one metal covalently bound to the substrate.

4. The sensor of claim 1, wherein the more than one dye of formula (IV) is selected from the group consisting of 4-(2-pyridylazo)resorcinol (PAR), 4-(quinolin-8-yldiazenyl)benzene-1,3-diol (QAR),

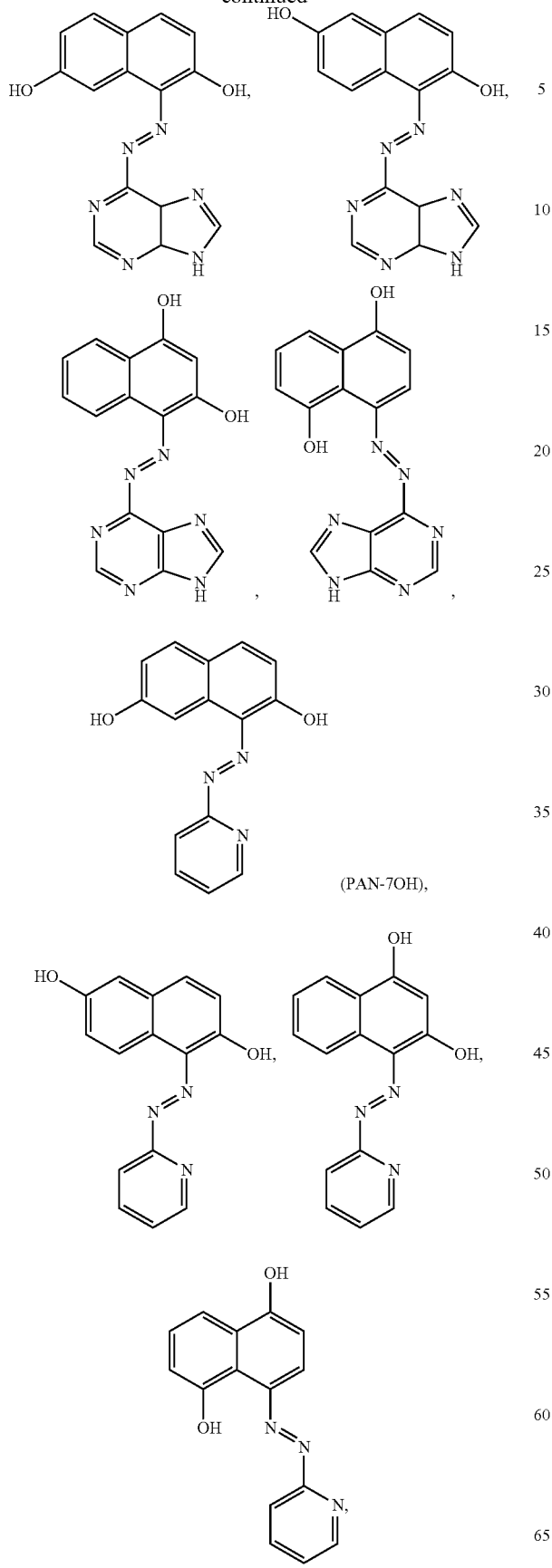
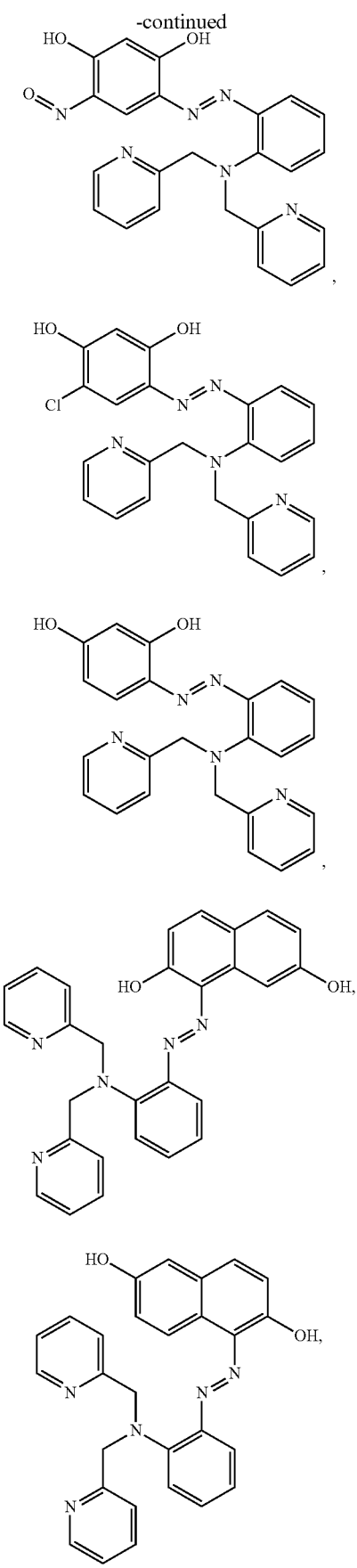

149
-continued
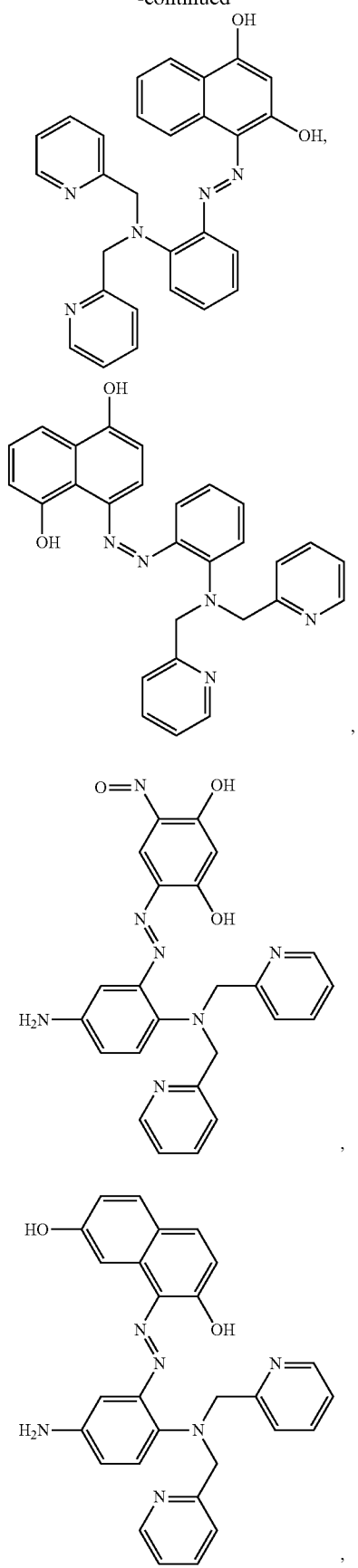
150
-continued
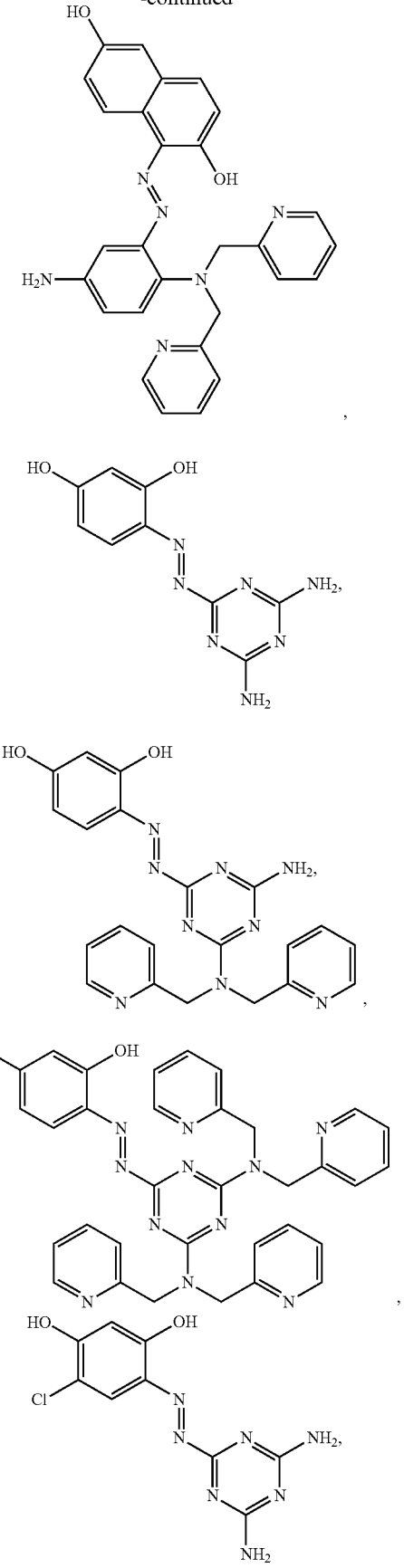

151
-continued
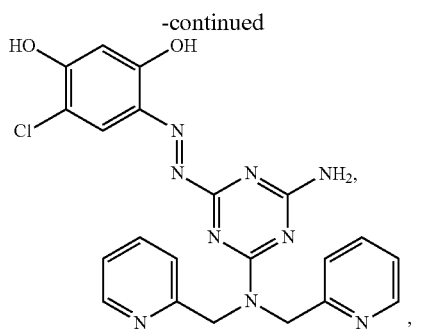
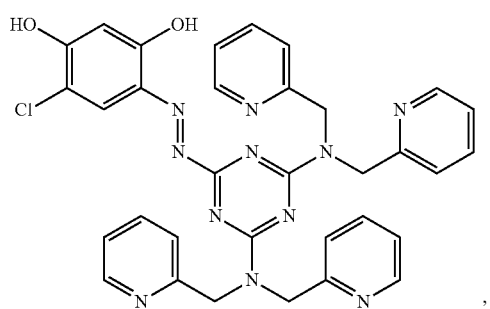
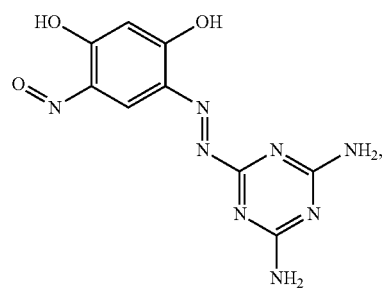
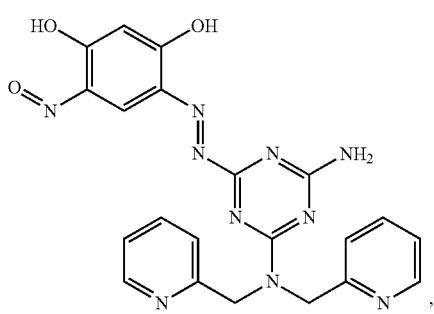
152
-continued
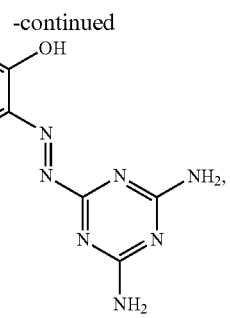
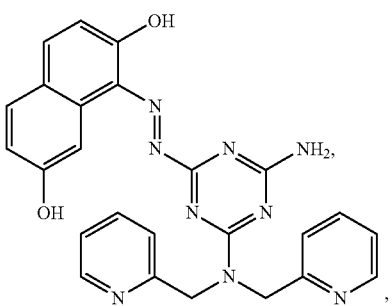
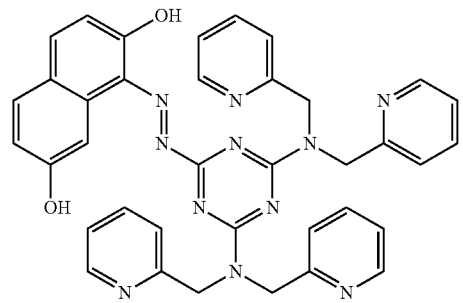
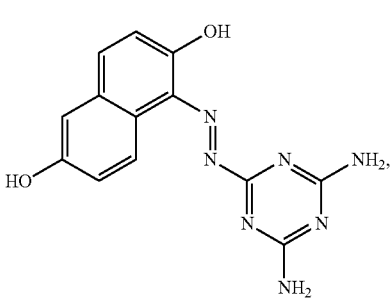
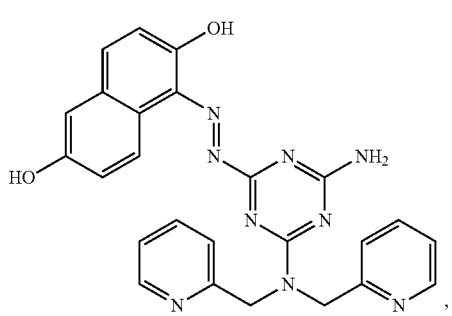

-continued

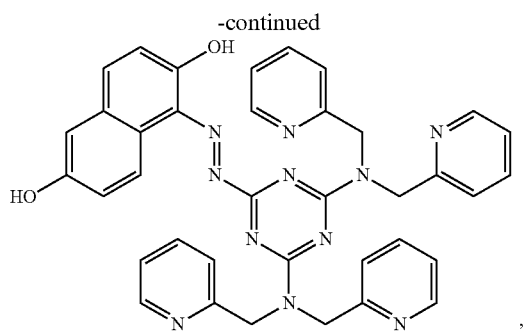

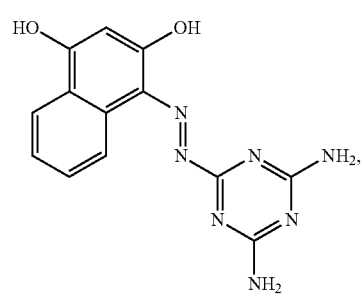

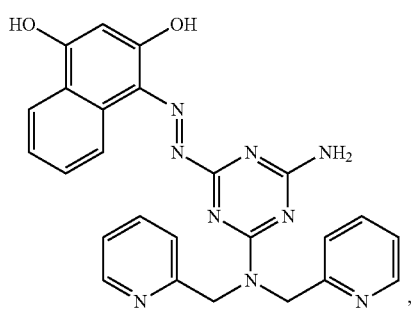

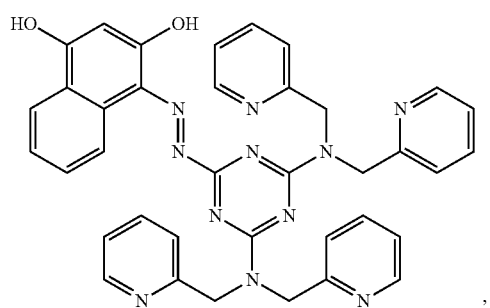 [SMILES: Oc1ccc(/N=N/c2nc(N(Cc3ccccn3)Cc3ccccn3)nc(N(Cc3ccccn3)Cc3ccccn3)n2)c2c(O)cccc12]

-continued

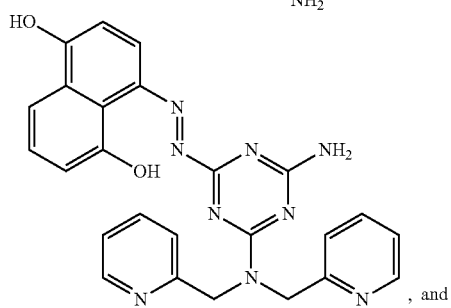

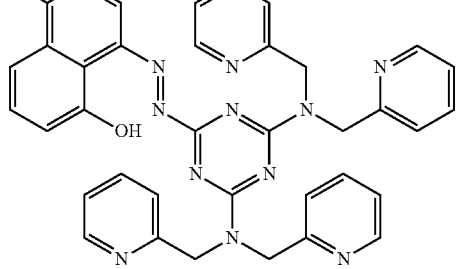
, and

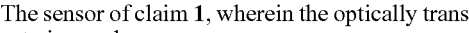

5. The sensor of claim 1, wherein the optically transparent substrate is a polymer.

6. The sensor of claim 5, wherein the polymer comprises cellulose, crosslinked polymethacrylate ester, polyacrylamide, or crosslinked polyethylene glycol.

7. The sensor of claim 5, wherein the polymer is a synthetic polymer.

8. The sensor of claim 7, wherein the polymer comprises crosslinked polymethacrylate ester, polyacrylamide, or crosslinked polyethylene glycol.

9. The sensor of claim 7, wherein the polymer comprises poly(acrylate)s, poly(methylmethacrylate), or poly(hydroxyethylmethacrylate).

10. The sensor of claim 1, wherein the optically transparent substrate further comprises a perturbation moiety.

11. The sensor of claim 10, wherein the perturbation moiety is a cation, an anion or a zwitterion or a neutral species.

12. The sensor of claim 11, wherein the cation comprises trialkylammonium groups.

* * * * *